United States Patent
Prakash et al.

(10) Patent No.: US 10,023,861 B2
(45) Date of Patent: Jul. 17, 2018

(54) OLIGOMER-CONJUGATE COMPLEXES AND THEIR USE

(75) Inventors: Thazha P. Prakash, Carlsbad, CA (US); Eric E. Swayze, Encinitas, CA (US); Walter F. Lima, San Diego, CA (US); Garth A. Kinberger, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 588 days.

(21) Appl. No.: 14/342,196

(22) PCT Filed: Aug. 29, 2012

(86) PCT No.: PCT/US2012/052884
§ 371 (c)(1),
(2), (4) Date: Sep. 17, 2014

(87) PCT Pub. No.: WO2013/033230
PCT Pub. Date: Mar. 7, 2013

(65) Prior Publication Data
US 2015/0018540 A1    Jan. 15, 2015

Related U.S. Application Data

(60) Provisional application No. 61/528,740, filed on Aug. 29, 2011, provisional application No. 61/532,529, filed on Sep. 8, 2011, provisional application No. 61/535,323, filed on Sep. 15, 2011, provisional application No. 61/583,963, filed on Jan. 6, 2012.

(51) Int. Cl.
| | |
|---|---|
| *C07H 21/04* | (2006.01) |
| *C12N 15/113* | (2010.01) |
| *C12N 15/11* | (2006.01) |
| *C07H 21/00* | (2006.01) |

(52) U.S. Cl.
CPC ........... *C12N 15/113* (2013.01); *C07H 21/00* (2013.01); *C12N 15/111* (2013.01); *C12N 2310/11* (2013.01); *C12N 2310/315* (2013.01); *C12N 2310/322* (2013.01); *C12N 2310/341* (2013.01); *C12N 2310/351* (2013.01); *C12N 2310/3515* (2013.01); *C12N 2320/51* (2013.01)

(58) Field of Classification Search
CPC ..... C07H 21/00; C12N 15/111; C12N 15/113; C12N 2310/11; C12N 2310/315; C12N 2310/322; C12N 2310/351; C12N 2310/3515; C12N 2310/3525; C12N 2310/341; C12N 2320/51
See application file for complete search history.

(56) References Cited

U.S. PATENT DOCUMENTS

| | | | |
|---|---|---|---|
| 3,687,808 A | 8/1972 | Merigan et al. | |
| 4,469,863 A | 9/1984 | Ts'o et al. | |
| 4,751,219 A | 6/1988 | Kempen et al. | |
| 4,845,205 A | 7/1989 | Huynh Dinh et al. | |
| 5,023,243 A | 6/1991 | Tullis | |
| 5,130,302 A | 7/1992 | Spielvogel et al. | |
| 5,134,066 A | 7/1992 | Rogers et al. | |
| 5,175,273 A | 12/1992 | Bischofberger et al. | |
| 5,177,198 A | 1/1993 | Spielvogel et al. | |
| 5,223,618 A | 6/1993 | Cook et al. | |
| 5,256,775 A | 10/1993 | Froehler | |
| 5,264,562 A | 11/1993 | Matteucci | |
| 5,264,564 A | 11/1993 | Matteucci | |
| 5,366,878 A | 11/1994 | Pederson et al. | |
| 5,367,066 A | 11/1994 | Urdea et al. | |
| 5,378,825 A | 1/1995 | Cook et al. | |
| 5,386,023 A | 1/1995 | Sanghvi et al. | |
| 5,432,272 A | 7/1995 | Benner | |
| 5,434,257 A | 7/1995 | Matteucci et al. | |
| 5,457,187 A | 10/1995 | Gmelner et al. | |
| 5,459,255 A | 10/1995 | Cook et al. | |
| 5,476,925 A | 12/1995 | Letsinger et al. | |
| 5,484,908 A | 1/1996 | Froehler et al. | |
| 5,489,677 A | 2/1996 | Sanghvi et al. | |
| 5,502,177 A | 3/1996 | Matteucci et al. | |
| 5,508,270 A | 4/1996 | Baxter et al. | |
| 5,525,711 A | 6/1996 | Hawkins et al. | |
| 5,552,540 A | 9/1996 | Haralambidis | |
| 5,587,469 A | 12/1996 | Cook et al. | |

(Continued)

FOREIGN PATENT DOCUMENTS

| | | |
|---|---|---|
| WO | WO 1994/002499 | 2/1994 |
| WO | WO 1994/017093 | 8/1994 |

(Continued)

OTHER PUBLICATIONS

Bock et al., "Glycosylation Reactions With Di-O-Acetyl-2,6-Dibromo-2,6-Dideoxy-Alpha-D-Mannopyranosyl Bromide: A Simple Synthesis of Methyl 2,6-Dideoxy-Barabino-Hexopyranoside" Acta Chemica Scandinavica (1998) B42: 640-645.

Chen et al., "Strand-specific 5'-O-methylation of siRNA duplexes controls guide strand selection and targeting specificity" RNA. (2008) 14:263-74.

Jervis et al., "New CD1d agonists: synthesis and biological activity of 6"-triazole-substituted α-galactosyl ceramides" Bioorg Med Chem Lett. (2012) 22(13):4348-52.

Lima et al., "Single-stranded siRNAs activate RNAi in animals" Cell (2012) 150:883-94.

Prakash et al., "Identification of metabolically stable 5'-phosphate analogs that support single-stranded siRNA activity" Nucleic Acids Res. (2015) 43:2993-3011.

(Continued)

*Primary Examiner* — Lawrence E Crane
(74) *Attorney, Agent, or Firm* — McNeill Baur PLLC

(57) ABSTRACT

Oligonucleotides, chemically-modified oligonucleotides, and oligonucleotide-conjugate complexes for use in research, diagnostics, and/or therapeutics are described herein. In some embodiments, oligonucleotides comprising a stabilized phosphate moiety covalently attached to the 5'-terminal nucleoside are provided.

21 Claims, 2 Drawing Sheets

(56) References Cited

U.S. PATENT DOCUMENTS

| | | | |
|---|---|---|---|
| 5,594,121 A | 1/1997 | Froehler et al. |
| 5,596,091 A | 1/1997 | Switzer |
| 5,602,240 A | 2/1997 | De Mesmaeker et al. |
| 5,610,289 A | 3/1997 | Cook et al. |
| 5,614,617 A | 3/1997 | Cook et al. |
| 5,625,050 A | 4/1997 | Beaton et al. |
| 5,645,985 A | 7/1997 | Froehler et al. |
| 5,681,941 A | 10/1997 | Cook et al. |
| 5,750,692 A | 5/1998 | Cook et al. |
| 5,763,588 A | 6/1998 | Matteucci et al. |
| 5,830,653 A | 11/1998 | Froehler et al. |
| 5,994,517 A | 11/1999 | Ts'o et al. |
| 5,998,203 A | 12/1999 | Matulic-Adamic |
| 6,005,096 A | 12/1999 | Matteucci et al. |
| 6,268,490 B1 | 7/2001 | Imanishi et al. |
| 6,300,319 B1 | 10/2001 | Manoharan |
| 6,383,812 B1 | 5/2002 | Chen et al. |
| 6,525,031 B2 | 2/2003 | Manoharan |
| 6,525,191 B1 | 2/2003 | Ramasamy |
| 6,660,720 B2 | 12/2003 | Manoharan et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 7,034,133 B2 | 4/2006 | Wengel et al. |
| 7,053,207 B2 | 5/2006 | Wengel |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,439,043 B2 | 10/2008 | DeFrees et al. |
| 7,491,805 B2 | 2/2009 | Vargeese et al. |
| 7,582,744 B2 | 9/2009 | Manoharan et al. |
| 7,696,344 B2 | 4/2010 | Khvorova et al. |
| 7,723,509 B2 | 5/2010 | Manoharan et al. |
| 7,741,457 B2 | 6/2010 | Swayze et al. |
| 8,106,022 B2 | 1/2012 | Manoharan et al. |
| 8,137,695 B2 | 3/2012 | Rozema et al. |
| 8,158,601 B2 | 4/2012 | Chen et al. |
| 8,344,125 B2 | 1/2013 | Manoharan et al. |
| 8,349,308 B2 | 1/2013 | Yurkovetskiy et al. |
| 8,450,467 B2 | 5/2013 | Manoharan et al. |
| 8,501,805 B2 | 8/2013 | Seth et al. |
| 8,530,640 B2 | 9/2013 | Seth et al. |
| 8,541,548 B2 | 9/2013 | Rozema |
| 8,546,556 B2 | 10/2013 | Seth et al. |
| 8,552,163 B2 | 10/2013 | Lee et al. |
| 9,127,276 B2 * | 9/2015 | Prakash | C12N 15/113 |
| 9,181,549 B2 * | 11/2015 | Prakash | C12N 15/113 |
| 2002/0082227 A1 | 6/2002 | Henry et al. |
| 2003/0077829 A1 | 4/2003 | MacLachlan |
| 2003/0170249 A1 | 9/2003 | Hakomori et al. |
| 2004/0171570 A1 | 9/2004 | Allerson et al. |
| 2005/0112118 A1 | 5/2005 | Cimbora et al. |
| 2005/0130923 A1 | 6/2005 | Bhat et al. |
| 2005/0164235 A1 | 7/2005 | Manoharan et al. |
| 2006/0148740 A1 | 7/2006 | Platenburg |
| 2006/0183886 A1 | 8/2006 | Tso et al. |
| 2007/0287831 A1 | 12/2007 | Seth et al. |
| 2008/0039618 A1 | 2/2008 | Allerson et al. |
| 2008/0108801 A1 | 5/2008 | Manoharan et al. |
| 2008/0206869 A1 | 8/2008 | Smith et al. |
| 2008/0281041 A1 | 11/2008 | Rozema et al. |
| 2008/0281044 A1 | 11/2008 | Manoharan et al. |
| 2009/0012281 A1 | 1/2009 | Swayze et al. |
| 2009/0203132 A1 | 8/2009 | Swayze et al. |
| 2009/0203135 A1 | 8/2009 | Forst et al. |
| 2009/0286973 A1 | 11/2009 | Manoharan et al. |
| 2010/0093085 A1 | 4/2010 | Yamada et al. |
| 2010/0240730 A1 | 9/2010 | Beigelman et al. |
| 2011/0077386 A1 | 3/2011 | Lee et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0207799 A1 | 8/2011 | Rozema et al. |
| 2011/0269814 A1 | 11/2011 | Manoharan et al. |
| 2012/0035115 A1 | 2/2012 | Manoharan et al. |
| 2012/0071641 A1 | 3/2012 | Manoharan et al. |
| 2012/0095075 A1 | 4/2012 | Manoharan et al. |
| 2012/0101148 A1 | 4/2012 | Aking et al. |
| 2012/0128760 A1 | 5/2012 | Manoharan et al. |
| 2012/0157509 A1 | 6/2012 | Hadwiger et al. |
| 2012/0165393 A1 | 6/2012 | Rozema et al. |
| 2012/0183602 A1 | 7/2012 | Chen et al. |
| 2013/0004427 A1 | 1/2013 | El-Sayed et al. |
| 2013/0023579 A1 | 1/2013 | Crooke et al. |
| 2013/0053431 A1 | 2/2013 | Tachas et al. |
| 2013/0109817 A1 | 5/2013 | Yurkovetskiy et al. |
| 2013/0121954 A1 | 5/2013 | Wakefield et al. |
| 2013/0178512 A1 | 7/2013 | Manoharan et al. |
| 2013/0236968 A1 | 9/2013 | Manoharan et al. |
| 2014/0343123 A1 | 11/2014 | Prakash et al. |
| 2016/0046939 A1 * | 2/2016 | Prakash | C07H 19/067 514/44 A |

FOREIGN PATENT DOCUMENTS

| | | |
|---|---|---|
| WO | WO 1997/020563 | 6/1997 |
| WO | WO 1997/046098 | 12/1997 |
| WO | WO 1999/014226 | 3/1999 |
| WO | WO 2000/014048 | 3/2000 |
| WO | WO 2000/076554 | 12/2000 |
| WO | WO 2002/043771 | 6/2002 |
| WO | WO 2004/024757 | 3/2004 |
| WO | WO 2004/101619 | 11/2004 |
| WO | WO 2004/106356 | 12/2004 |
| WO | WO 2005/021570 | 3/2005 |
| WO | WO 2005/097155 | 10/2005 |
| WO | WO 2006/031461 | 3/2006 |
| WO | WO 2007/134181 | 11/2007 |
| WO | WO 2008/098788 | 8/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/082607 | 7/2009 |
| WO | WO 2009/126933 | 10/2009 |
| WO | WO 2009/134487 | 11/2009 |
| WO | WO 2010/048549 | 4/2010 |
| WO | WO 2010/048585 | 4/2010 |
| WO | WO 2010/054406 | 5/2010 |
| WO | WO 2010/088537 | 8/2010 |
| WO | WO 2010/103204 | 9/2010 |
| WO | WO 2010/129709 | 11/2010 |
| WO | WO 2010/144740 | 12/2010 |
| WO | WO 2010/148013 | 12/2010 |
| WO | WO 2011/005860 | 1/2011 |
| WO | WO 2011/005861 | 1/2011 |
| WO | WO 2011/038356 | 3/2011 |
| WO | WO 2011/100131 | 8/2011 |
| WO | WO 2011/120053 | 9/2011 |
| WO | WO 2011/133871 | 10/2011 |
| WO | WO 2011/139702 | 10/2011 |
| WO | WO 2012/037254 | 3/2012 |
| WO | WO 2012/068187 | 5/2012 |
| WO | WO 2012/083046 | 6/2012 |
| WO | WO 2012/083185 | 6/2012 |
| WO | WO 2012/089352 | 7/2012 |
| WO | WO 2012/089602 | 7/2012 |
| WO | WO 2012/177784 | 12/2012 |
| WO | WO 2012/177947 | 12/2012 |
| WO | WO 2013/033230 | 3/2013 |
| WO | WO 2013/075035 | 5/2013 |
| WO | WO 2013/165816 | 11/2013 |
| WO | WO 2013/166121 | 11/2013 |
| WO | WO 2014/025805 | 2/2014 |

OTHER PUBLICATIONS

Trappeniers et al., "6'-derivatised alpha-GalCer analogues capable of inducing strong CD1d-mediated Th1-biased NKT cell responses in mice" J Am Chem Soc. (2008) 130(49):16468-9.

(56) References Cited

OTHER PUBLICATIONS

Winkler et al., "Oligonucleotide conjugates for therapeutic applications" Ther. Deliv. (2013) 4(7):791-809.
Asseline et al., "Modification of the 5' Terminus of Oligodeoxyribonucleotides for Conjugation with Ligands" in Current Protocols in Nucleic Acid Chemistry, 2001, Supplement 5, Chapter 4: Unit 4.9 (4.9.1-4.9.28); John Wiley & Sons.
Beaucage et al., "The functionalization of oligonucleotides via phosphoramidate derivatives" Tetrahedron (1993) 49(10): 1925-1963.
Zhao et al., "Synthesis and preliminary biochemical studies with 5'-deoxy-5'-methylidyne phosphonate linked thymidine oligonucleotides" Tetrahedron Letters (1996) 37(35): 6239-6242.
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Andre et al., "Determination of modulation of ligand properties of synthetic complex-type biantennary N-glycans by introduction of bisecting GlcNAc in silico, in vitro and in vivo" Eur. J. Biochem. (2004) 271: 118-134.
Biessen et al., "Novel hepatotrophic prodrugs of the antiviral nucleoside 9-(2-phosphonylmethoxyethyl)adenine with improved pharmacokinetics and antiviral activity" FASEB J. (2000) 14: 1784-1792.
Biessen et al., "Synthesis of Cluster Galactosides with High Affinity for the Hepatic Asialoglycoprotein Receptor" J. Med. Chem. (1995) 38:1538-1546.
Biessen et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852.
Braasch et al., "Locked nucleic acid (LNA): fine-tuning the recognition of DNA and RNA" Chem. Biol. (2001) 8:1-7.
Chiang et al., "Antisense Oligonucleotides Inhibit Intercellular Adhesion Molecule 1 Expression by Two Distinct Mechanisms" J. Biol. Chem. (1991) 266:18162-18171.
Coltart et al., "Principles of Mucin Architecture: Structural Studies on Synthetic Glycopeptides Bearing Clustered Mono-, Di-, Tri-, and Hexasaccharide Glycodomains" J. Am. Chem. Soc. (2002) 124: 9833-9844.
Crooke et al., "Pharmacokinetic Properties of Several Novel Oligonucleotide Analogs in mice" J. Pharmacol. Exp. Ther. (1996) 277(2):923-937.
Dellinger et al., "Solid-Phase Chemical Synthesis of Phosphonoacetate and Thiophosphonoacetate Oligodeoxynucleotides" J. Am .Chem. Soc. (2003) 125: 940-950.
Duff et al., "Intrabody Tissue-Specific Delivery of Antisense Conjugates in Animals: Ligand-Linker-Antisense Oligomer Conjugates" Methods in Enzymology (1999) 313: 297-321.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Agnew Chem. Int. Ed. Engl. (1991) 30:613-629.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Geary et al., "Pharmacokinetic Properties of 2'-O-(2-Methoxyethyl)-Modified Oligonucleotide Analogs in Rats" The Journal of Pharmacology and Experimental Therapeutics (2001) 296:890-897.
Hoffman et al., "'Brain-type' N-glycosylation of asialo-transferrin from human cerebrospinal fluid" FEBS Letters (1995) 359: 164-168.

Jayaprakash et al., "Non-Nucleoside Building Blocks for Copper-Assisted and Copper-Free Click Chemistry for the Efficient Synthesis of RNA Conjugates" Organic Letters (2010) 12(23): 5410-5413.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Khorev et al., "Trivalent, Gal/GalNAc-containing ligands designed for the asialoglycoprotein receptor" Bioorganic & Medicinal Chemistry (2008) 16: 5216-5231.
Kim et al., "Oligomeric Glycopeptidomimetics Bearing the Cancer Related TN-Antigen" Tetrahedron Letters (1997) 38(20): 3487-3490.
Kornilova et al., "Development of a fluorescence polarization binding assay for asialoglycoprotein receptor" Analytical Biochemistry (2012) 425: 43-46.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Lee et al., "Facile Synthesis of a High-Affinity Ligand for Mammalian Hepatic Lectin Containing Three Terminal N-Acetylgalactosamine Residues" Bioconjugate Chem. (1997) 8: 762-765.
Lee et al., "New and more efficient multivalent glyco-ligands for asialoglycoprotein receptor of mammalian hepatocytes" Bioorganic & Medicinal Chemistry (2011) 19:2494-2500.
Lee et al., "Preparation of Cluster Glycosides of Nacetylgalactosamine That Have Subnanomolar Binding Constants Towards the Mammalian Hepatic Gal/GalNAc-specific Receptor" Glycoconjugate J. (1987) 4: 317-328.
Lee et al., "Synthesis of Peptide-Based Trivalent Scaffold for Preparation of Cluster Glycosides" Methods in Enzymology (2003) 362: 38-43.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Maier et al., "Synthesis of Antisense Oligonucleotides Conjugated to a Multivalent Carbohydrate Cluster for Cellular Targeting" Bioconjugate Chem. (2003) 14: 18-29.
Maierhofer et al., "Probing multivalent carbohydrate—lectin interactions by an enzyme-linked lectin assay employing covalently immobilized carbohydrates" Bioorganic & Medicinal Chemistry (2007) 15: 7661-7676.
Manoharan et al., "Chemical Modifications to Improve Uptake and Bioavailability of Antisense Oligonucleotides" Ann. N. Y. Acad. Sci. (1992) 660: 306-309.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "Oligonucleotide Conjugates: Alteration of the Pharmacokinetic Properties of Antisense Agents" Nucleosides & Nucleotides (1995) 14(3-5):969-973.
Manoharan, "Oligonucleotide Conjugates as Potential Antisense Drugs with Improved Uptake, Biodistribution, Targeted Delivery, and Mechanism of Action" Antisense & Nucleic Acid Drug Development (2002) 12: 103-128.

(56) References Cited

OTHER PUBLICATIONS

Manoharan et al., "N-(2-Cyanoethoxycarbonyloxy)succinimide: A New Reagent for Protection of Amino Groups in Oligonucleotides" J. Org. Chem. (1999) 64: 6468-6472.

Marcaurelle et al., "Synthesis of Oxime-Linked Mucin Mimics Containing the Tumor-Related TN and Sialyl TN Antigens" Organic Letters (2001) 3(23): 3691-3694.

Mishra et al., "Improved leishmanicidal effect of phosphorotioate antisense oligonucleotides by LDL-mediated delivery" Biochim. Biophys. Acta (1995) 1264:229-237.

Miura et al., "Fluorometric determination of total mRNA with oligo(dT) immobilized on microtiter plates" Clin. Chem. (1996) 42:1758-1764.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Orum et al., "Locked nucleic acids: A promising molecular family for gene-function analysis and antisense drug development" Curr. Opinion Mol. Ther. (2001) 3:239-243.

Pujol et al., "A Sulfur Tripod Glycoconjugate that Releases a High-Affinity Copper Chelator in Hepatocytes" Angew. Chem. Int. Ed. (2012) 51: 7445-7448.

Rajur et al., "Covalent Protein-Oligonucleotide Conjugates for Efficient Delivery of Antisense Molecules" Bioconjugate Chem. (1997) 8: 935-940.

Raouane et al., "Synthesis, Characterization, and in Vivo Delivery of siRNA-Squalene Nanoparticles Targeting Fusion Oncogene in Papillary Thyroid Carcinoma" J. Med. Chem. (2011) 54: 4067-4076.

Rensen et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808.

Rensen et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

Sanghvi, Chapter 15, Antisense Research and Applications, Crooke and Lebleu ed., CRC Press (1993).

Sato et al., "Glycoinsulins: Dendritic Sialyloligosaccharide-Displaying Insulins Showing a Prolonged Blood-Sugar-Lowering Activity" J. Am. Chem. Soc. (2004) 126: 14013-14022.

Shea et al., "Synthesis, hybridization properties and antiviral activity of lipid-oligodeoxynucleotide conjugates" Nucl. Acids Res. (1990) 18(13):3777-3783.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Sliedregt et al., "Design and Synthesis of Novel Amphiphilic Dendritic Galactosides for Selective Targeting of Liposomes to the Hepatic Asialoglycoprotein Receptor" J. Med. Chem. (1999) 42:609-618.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75:49-54.

Tomiya et al., "Liver-targeting of primaquine-(poly-c-glutamic acid) and its degradation in rat hepatocytes" Bioorganic & Medicinal Chemistry (2013) 21: 5275-5281.

Valentijn et al., "Solid-phase Synthesis of Lysine-based Cluster Galactosides with High Affinity for the Asialoglycoprotein Receptor" Tetrahedron (1997) 53(2): 759-770.

Wahlestedt et al., "Potent and nontoxic antisense oligonucleotide containing locked nucleic acids" Proc. Natl. Acad. Sci. USA (2000) 97: 5633-5638.

Westerlind et al., "Ligands of the asialoglycoprotein receptor for targeted gene delivery, part 1: Synthesis of and binding studies with biotinylated cluster glycosides containing N-acetylgalactosamine" Glycoconjugate Journal (2004) 21: 227-241.

Wu et al., "A New N-Acetylgalactosamine Containing Peptide as a Targeting Vehicle for Mammalian Hepatocytes Via Asialoglycoprotein Receptor Endocytosis" Current Drug Delivery (2004) 1: 119-127.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

International Search Report for Application PCT/US12/52884 dated Nov. 20, 2012.

European Search Report for Application No. 14792010.2, dated Jan. 18, 2017, 5 pages.

Kallanthottathil, R., "Conjugation Strategies for In Vivo siRNA Delivery," 8th Annual Meeting of the Oligonucleotide Therapeutics Society, Oct. 29, 2012, 30 pages.

\* cited by examiner

OLIGOMER-CONJUGATE COMPLEXES AND THEIR USE

CROSS REFERENCED TO RELATED APPLICATIONS

This application is a U.S. National Phase filing under 35 U.S.C. § 371 claiming priority to International Serial No. PCT/US2012/052884 filed Aug. 29, 2012, which claims priority to U.S. Provisional Application 61/528,740, filed Aug. 29, 2011, U.S. Provisional Application 61/532,529, filed Sep. 8, 2011, U.S. Provisional Application 61/535,323, filed Sep. 15, 2011, and U.S. Provisional Application 61/583,963, filed Jan. 6, 2012, each of which is incorporated herein by reference in its entirety.

SEQUENCE LISTING

The present application is being filed along with a Sequence Listing in electronic format. The Sequence Listing is provided as a file entitled CORE0098USASEQ_ST25.txt, created on Feb. 24, 2014, which is 16 Kb in size. The information in the electronic format of the sequence listing is incorporated herein by reference in its entirety.

BACKGROUND OF THE INVENTION

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. An additional example of modulation of RNA target function by an occupancy-based mechanism is modulation of microRNA function. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

SUMMARY OF THE INVENTION

Provided herein are modified nucleosides, analogs thereof and oligomeric compounds prepared therefrom. In certain embodiments, a single 5'-modified nucleoside or analog thereof is linked to the terminus of an oligomeric compound, preferably at the 5'-terminus. In certain embodiments, oligomeric compounds with conjugate groups are described. In certain embodiments, the oligomeric compounds provided herein are expected to have enhanced nuclease stability. In certain embodiments, the oligomeric compounds and compositions provided herein are expected to hybridize to a portion of a target RNA resulting in loss of normal function of the target RNA. In certain embodiments, the oligomeric compounds provided herein are expected to be useful as primers and probes in diagnostic applications.

The variables are defined individually in further detail herein. It is to be understood that the 5'-modified nucleosides, analogs thereof and oligomeric compounds prepared therefrom as provided herein include all combinations of the embodiments disclosed and variables defined herein.

The present disclosure provides the following non-limiting numbered embodiments:

EMBODIMENT 1

A compound comprising an oligonucleotide consisting of 10-30 linked nucleosides and at least one conjugate group.

EMBODIMENT 2

The compound of embodiment 1, wherein the oligomeric compound comprises a stabilized phosphate moiety covalently attached to the 5'-terminal nucleoside.

EMBODIMENT 3

The compound of embodiment 2, wherein the stabilized phosphate moiety comprises a phosphorus-carbon bond.

EMBODIMENT 4

The compound of embodiment 3, wherein the stabilized phosphate moiety is attached to the 5'-terminal nucleoside via a phosphorus-carbon bond.

EMBODIMENT 5

The compound of any of embodiments 1-4, wherein the stabilized phosphate moiety comprises the following formula:

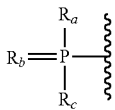

wherein:
R$_a$ and R$_c$ are each, independently, OH, SH, C$_1$-C$_6$ alkyl, substituted C$_1$-C$_6$ alkyl, C$_1$-C$_6$ alkoxy, substituted C$_1$-C$_6$ alkoxy, amino or substituted amino; and
R$_b$ is O or S.

EMBODIMENT 6

The compound of any of embodiments 1-5, wherein the stabilized phosphate moiety comprises the following formula:

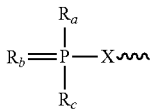

wherein:
R$_a$ and R$_c$ are each, independently, OH, SH, C$_1$-C$_6$ alkyl, substituted C$_1$-C$_6$ alkyl, C$_1$-C$_6$ alkoxy, substituted C$_1$-C$_6$ alkoxy, amino or substituted amino;
R$_b$ is O or S; and
X is C(R$_1$)(R$_2$) wherein R$_1$ and R$_2$ are independently selected from among: H, halogen, OH, SH, C$_1$-C$_6$ alkyl, substituted C$_1$-C$_6$ alkyl, C$_1$-C$_6$ alkoxy, substituted C$_1$-C$_6$ alkoxy, amino or substituted amino.

EMBODIMENT 7

The compound of any of embodiments 1-6, wherein the stabilized phosphate moiety comprises the following formula:

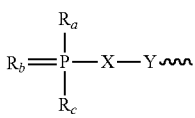

wherein:
R$_a$ and R$_c$ are each, independently, OH, SH, C$_1$-C$_6$ alkyl, substituted C$_1$-C$_6$ alkyl, C$_1$-C$_6$ alkoxy, substituted C$_1$-C$_6$ alkoxy, amino or substituted amino;
R$_b$ is O or S;
X is C(R$_1$)(R$_2$) and;
Y is selected from C(R$_3$)(R$_4$), S, and N; wherein
R$_1$ and R$_3$ are independently selected from among: H, halogen, OH, SH, C$_1$-C$_6$ alkyl, substituted C$_1$-C$_6$ alkyl, C$_1$-C$_6$ alkoxy, substituted C$_1$-C$_6$ alkoxy, amino or substituted amino or R$_1$ and R$_3$ together form a bond; and
R$_2$ and R$_4$ are independently selected from among: H, halogen, OH, SH, C$_1$-C$_6$ alkyl, substituted C$_1$-C$_6$ alkyl, C$_1$-C$_6$ alkoxy, substituted C$_1$-C$_6$ alkoxy, amino or substituted amino or R$_2$ and R$_4$ together form a bond.

EMBODIMENT 8

The compound of any of embodiments 1 to 7, wherein the 5'-terminal nucleoside has a structure represented by Formula I below:

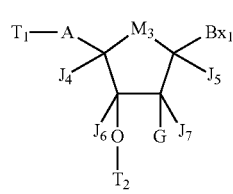

wherein:
T$_1$ is a phosphorus moiety;
T$_2$ is an internucleoside linking group linking the compound of Formula I to the remainder of the oligomeric compound;
M$_1$ is H, OH or OR$_1$;
M$_2$ is OH, OR$_1$ or N(R$_1$)(R$_2$);
each R$_1$ and R$_2$ is, independently, C$_1$-C$_6$ alkyl, substituted C$_1$-C$_6$ alkyl;
r is 0 or 1;
A is has one of the formulas:

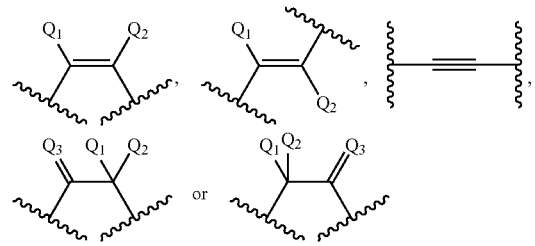

Q$_1$ and Q$_2$ are each, independently, H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_1$-C$_6$ alkoxy, substituted C$_1$-C$_6$ alkoxy or N(R$_3$)(R$_4$);
Q$_3$ is O, S, N(R$_5$) or C(R$_6$)(R$_7$);
each R$_3$, R$_4$, R$_5$, R$_6$ and R$_7$ is, independently, H, C$_1$-C$_6$ alkyl, substituted C$_1$-C$_6$ alkyl or C$_1$-C$_6$ alkoxy;
M$_3$ is O, S, NR$_{14}$, C(R$_{15}$)(R$_{16}$), C(R$_{15}$)(R$_{16}$)C(R$_{17}$)(R$_{18}$), C(R$_{15}$)=C(R$_{17}$), OC(R$_{15}$)(R$_{16}$) or OC(R$_{15}$)(Bx$_2$);
R$_{14}$ is H, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
R$_{15}$, R$_{16}$, R$_{17}$ and R$_{18}$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
one of Bx$_1$ and Bx$_2$ is a heterocyclic base moiety and the other of Bx$_1$ and Bx$_2$, if present, is H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
J$_4$, J$_5$, J$_6$ and J$_7$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
or J$_4$ forms a bridge with either J$_5$ or J$_7$ wherein said bridge comprises from 1 to 3 linked biradical groups selected from O, S, NR$_{19}$, C(R$_{20}$)(R$_{21}$), C(R$_{20}$)=C(R$_{21}$), C[=C(R$_{20}$)(R$_{21}$)] and C(=O) and the other two of J$_5$, J$_6$ and J$_7$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen, a conjugate group, or O—[C($R_8$)($R_9$)]$_n$—[(C=O)$_m$—$X_1$]$_j$—Z;

each $R_8$ and $R_9$ is, independently, H, halogen, $C_1$-$C_6$ alkyl or substituted $C_1$-$C_6$ alkyl;

$X_1$ is O, S or N($E_1$);

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl; and when j is 1 then Z is other than halogen or N($E_2$)($E_3$).

EMBODIMENT 9

The compound of embodiment 8 wherein $M_3$ is O, $CH_2CH_2$, CH=CH, $OCH_2$ or OC(H)($Bx_2$) wherein $Bx_2$ is a heterocyclic base moiety.

EMBODIMENT 10

The compound of any one of embodiments 8 or 9 wherein $J_4$, $J_5$, $J_6$ and $J_7$ are each H.

EMBODIMENT 11

The compound of any of embodiments 1-10 wherein the 5'-terminal nucleoside has Formula II:

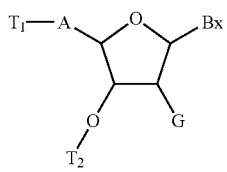

wherein:

Bx is a heterocyclic base moiety;

$T_1$ is an optionally protected phosphorus moiety;

$T_2$ is an internucleoside linking group linking the compound of Formula II to the remainder of the oligomeric compound;

A has one of the formulas:

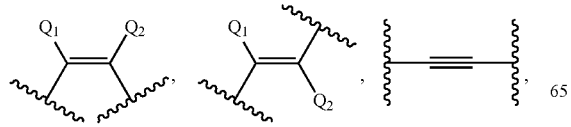

-continued

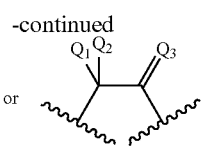

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen, a conjugate group, or O—[C($R_8$)($R_9$)]$_n$—[(C=O)$_m$—X]$_j$—Z;

each $R_8$ and $R_9$ is, independently, H, halogen, $C_1$-$C_6$ alkyl or substituted $C_1$-$C_6$ alkyl;

X is O, S or N($E_1$);

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or N($E_2$)($E_3$).

EMBODIMENT 12

The compound of any one of embodiments 1 to 11 wherein the 5'-terminal nucleoside has Formula III:

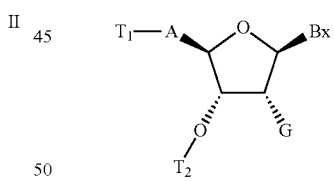

wherein:

Bx is a heterocyclic base moiety;

$T_1$ is an optionally protected phosphorus moiety;

$T_2$ is an internucleoside linking group linking the compound of Formula II to the remainder of the oligomeric compound;

A has one of the formulas:

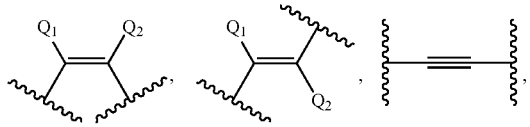

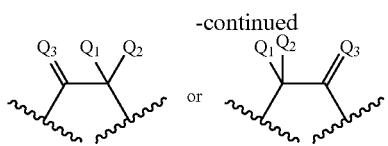 or 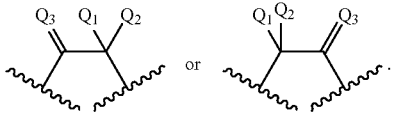

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen, a conjugate group, or O—$[C(R_8)(R_9)]_n$—$[(C=O)_m$—$X]_j$—Z;

each $R_8$ and $R_9$ is, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

EMBODIMENT 13

The compound of any one of embodiments 8-12 wherein A has one of the formulas:

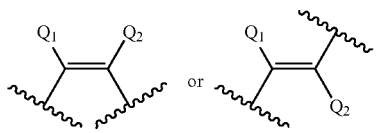

EMBODIMENT 14

The compound of any one of embodiments 8-12 wherein A has the formula:

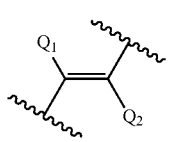

EMBODIMENT 15

The compound of any one of embodiments 8-12 wherein A has one of the formulas:

EMBODIMENT 16

The compound of any one of embodiments 8-13 wherein $Q_1$ and $Q_2$ are each H.

EMBODIMENT 17

The compound of any one of embodiments 8-18 wherein one of $Q_1$ and $Q_2$ is H and the other of $Q_1$ and $Q_2$ is halogen, $C_1$-$C_6$ alkyl, substituted $C_1$-$C_6$ alkyl, $C_1$-$C_6$ alkoxy or substituted $C_1$-$C_6$ alkoxy.

EMBODIMENT 18

The compound of any one of embodiments 8-15 wherein one of $Q_1$ and $Q_2$ is H and the other of $Q_1$ and $Q_2$ is F or $CH_3$.

EMBODIMENT 19

The compound of any one of embodiments 8-15 wherein $Q_1$ and $Q_2$ are each, independently, F or $CH_3$.

EMBODIMENT 20

The compound of any one of embodiments 8-15 wherein $Q_3$ is O.

EMBODIMENT 21

The compound of any one of embodiments 8-15 wherein $Q_3$ is S.

EMBODIMENT 22

The compound of any one of embodiments 8-15 wherein $Q_3$ is $N(R_5)$.

EMBODIMENT 23

The compound of embodiment 22 wherein $R_5$ is H.

EMBODIMENT 24

The compound of embodiment 23 wherein $R_5$ is $C_1$-$C_6$ alkyl or substituted $C_1$-$C_6$ alkyl.

EMBODIMENT 25

The compound of embodiment 22 wherein $R_5$ is $CH_3$.

EMBODIMENT 26

The compound of any one of embodiments 8-15 to wherein $Q_3$ is $C(R_6)(R_7)$.

EMBODIMENT 27

The compound of embodiment 26 wherein $R_6$ and $R_7$ are each H.

EMBODIMENT 28

The compound of embodiment 26 wherein one of $R_6$ and $R_7$ is H and the other of $R_6$ and $R_7$ is $C_1$-$C_6$ alkyl or substituted $C_1$-$C_6$ alkyl.

EMBODIMENT 29

The compound of embodiment 26 wherein one of $R_6$ and $R_7$ is H and the other of $R_6$ and $R_7$ is $CH_3$.

EMBODIMENT 30

The compound of embodiment 26 wherein $R_6$ and $R_7$ are each, independently, $C_1$-$C_6$ alkyl, substituted $C_1$-$C_6$ alkyl or $C_1$-$C_6$ alkoxy.

EMBODIMENT 31

The compound of any one of embodiments 8-12 wherein A has the formula:

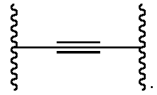

EMBODIMENT 32

The compound of any of embodiments 1-31 wherein said 5'-terminal nucleoside has Formula IV:

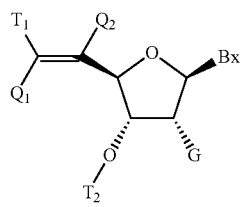

IV

EMBODIMENT 33

The compound of embodiment 32 wherein $Q_1$ and $Q_2$ are each H.

EMBODIMENT 34

The compound of any of embodiments 1 to 42, wherein the 5'-terminal nucleoside has a structure represented by Formula V below:

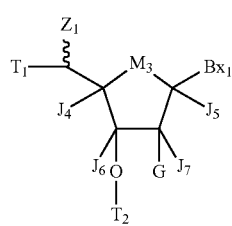

V wherein:
$T_1$ is an optionally protected phosphorus moiety;
$T_2$ is an internucleoside linking group linking the compound of Formula I to the remainder of the oligomeric compound;
$Z_1$ $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;
$M_1$ is H, OH or $OR_1$;
$M_2$ is OH, $OR_1$ or $N(R_1)(R_2)$;
each $R_1$ and $R_2$ is, independently, $C_1$-$C_6$ alkyl, substituted $C_1$-$C_6$ alkyl;
r is 0 or 1;
each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;
$M_3$ is O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$ or $OC(R_{15})(Bx_2)$;
$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
one of $Bx_1$ and $Bx_2$ is a heterocyclic base moiety and the other of $Bx_1$ and $Bx_2$, if present, is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
or $J_4$ forms a bridge with either $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
G is H, OH, halogen, a conjugate group, or O—$[C(R_8)(R_9)]_n$—$[(C=O)_m$—$X_1]_j$—Z;
each $R_8$ and $R_9$ is, independently, H, halogen, $C_1$-$C_6$ alkyl or substituted $C_1$-$C_6$ alkyl;
$X_1$ is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;
$X_2$ is O, S or $NJ_3$;
each $J_1$, $J_2$ and $J_3$ is, independently, H or $C_1$-$C_6$ alkyl; and
when j is 1 then Z is other than halogen or $N(E_2)(E_3)$.

EMBODIMENT 35

The compound of embodiment 34 wherein $M_3$ is O, $CH_2CH_2$, CH=CH, $OCH_2$ or $OC(H)(Bx_2)$ wherein $Bx_2$ is a heterocyclic base moiety.

EMBODIMENT 36

The compound of any one of embodiments 34 or 35 wherein $J_4$, $J_5$, $J_6$ and $J_7$ are each H.

EMBODIMENT 37

The compound of any one of embodiments 8 to 36 wherein $T_1$ has the formula:

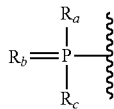

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and
$R_b$ is O or S.

EMBODIMENT 38

The compound of any one of embodiments 8-36, wherein $T_1$ has the formula:

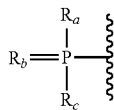

wherein:

$R_a$ and $R_c$ are each a protected hydroxyl; and
$R_b$ is O or S.

EMBODIMENT 39

The compound of any one of embodiments 8-36 wherein $T_1$ has the formula:

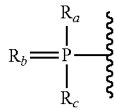

wherein:

$R_a$ and $R_c$ are each, independently, $OCH_3$, $OCH_2CH_3$ or $CH(CH_3)_2$; and
$R_b$ is O.

EMBODIMENT 40

The compound of any of embodiments 8-39 wherein Bx is a pyrimidine, substituted pyrimidine, purine or substituted purine.

EMBODIMENT 41

The compound of embodiment 40 wherein Bx is uracil, 5-thiazolo-uracil, thymine, cytosine, 5-methylcytosine, 5-thiazolo-cytosine, adenine, guanine or 2,6-diaminopurine.

EMBODIMENT 42

The compound of any one of embodiments 8-41 wherein G is a conjugate group, halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—$N(R_{12})$—$(CH_2)_2$—$N(R_{10})(R_{11})$ or $O(CH_2)_2$—$N(R_{12})$—$C(=NR_{13})[N(R_{10})(R_{11})]$ wherein $R_{10}$, $R_{11}$, $R_{12}$ and $R_{13}$ are each, independently, H or $C_1$-$C_6$ alkyl.

EMBODIMENT 43

The compound of any one of embodiments 8-42 wherein G is a conjugate group, halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—$N(H)$—$C(=NH)NH_2$.

EMBODIMENT 44

The compound of any one of embodiments 8-43 wherein G is a conjugate group, F, $OCH_3$, $O(CH_2)_2$—$OCH_3$, a linker group, $OCH_2(=O)$—$N(H)CH_3$ or $OCH_2C(=O)$—$N(H)$—$(CH_2)_2$—$N(CH_3)_2$.

EMBODIMENT 45

The compound of any one of embodiments 8-44 wherein G is $O(CH_2)_2$—$OCH_3$.

EMBODIMENT 46

The compound of any one of embodiments 8-44 wherein G is F.

EMBODIMENT 47

The compound of any of embodiments 8-44, wherein G is a conjugate group.

EMBODIMENT 48

The compound of any of embodiments 1-47, wherein at least a conjugate group is attached to the oligonucleotide at a nucleoside at position 1, 2, 3, 4, 6, 7, 8, 9, 18, 19, 20, or 21 from the 5'-end of the oligonucleotide or at position 1, 2, 3, 12, 13, 4, 15, 17, 18, 19, 20, or 21 from the 3'-end of the oligonucleotide.

EMBODIMENT 49

The compound of any of embodiments 1-48, comprising a conjugate group attached to any of the 1 to 4 5'-most nucleosides of the oligonucleotide.

EMBODIMENT 50

The compound of any of embodiments 1-49, comprising a conjugate group attached to the 5'-terminal nucleoside of the oligonucleotide.

EMBODIMENT 51

The compound of any of embodiments 1-50, comprising a conjugate group attached to the $2^{nd}$ nucleoside from the 5'-terminal end of the oligonucleotide.

EMBODIMENT 52

The compound of any of embodiments 1-51, comprising a conjugate group attached to the $3^{rd}$ nucleoside from the 5'-terminal end of the oligonucleotide.

EMBODIMENT 53

The compound of any of embodiments 1-52, comprising a conjugate group attached to the $4^{th}$ nucleoside from the 5'-terminal end of the oligonucleotide.

EMBODIMENT 54

The compound of any of embodiments 1-53, comprising a conjugate group attached to any of the 6 to 9 5'-most nucleosides.

EMBODIMENT 55

The compound of any of embodiments 1-54, comprising a conjugate group attached to the $5^{th}$ nucleoside from the 5'-terminal end of the oligonucleotide.

EMBODIMENT 56

The compound of any of embodiments 1-55, comprising a conjugate group attached to the $6^{th}$ nucleoside from the 5'-terminal end of the oligonucleotide.

EMBODIMENT 57

The compound of any of embodiments 1-56, comprising a conjugate group attached to the $7^{th}$ nucleoside from the 5'-terminal end of the oligonucleotide.

EMBODIMENT 58

The compound of any of embodiments 1-57, comprising a conjugate group attached to the $8^{th}$ nucleoside from the 5'-terminal end of the oligonucleotide.

EMBODIMENT 59

The compound of any of embodiments 1-58, comprising a conjugate group attached to the $9^{th}$ nucleoside from the 5'-terminal end of the oligonucleotide.

EMBODIMENT 60

The compound of any of embodiments 1-59, comprising a conjugate group attached to the $10^{th}$ nucleoside from the 5'-terminal end of the oligonucleotide.

EMBODIMENT 61

The compound of any of embodiments 1-60, comprising a conjugate group attached to the $11^{th}$ nucleoside from the 5'-terminal end of the oligonucleotide.

EMBODIMENT 62

The compound of any of embodiments 1-61, comprising a conjugate group attached to the $12^{th}$ nucleoside from the 5'-terminal end of the oligonucleotide.

EMBODIMENT 63

The compound of any of embodiments 1-62, comprising a conjugate group attached to the $13^{th}$ nucleoside from the 5'-terminal end of the oligonucleotide.

EMBODIMENT 64

The compound of any of embodiments 1-63, comprising a conjugate group attached to the $14^{th}$ nucleoside from the 5'-terminal end of the oligonucleotide.

EMBODIMENT 65

The compound of any of embodiments 1-64, comprising a conjugate group attached to the $15^{th}$ nucleoside from the 5'-terminal end of the oligonucleotide.

EMBODIMENT 66

The compound of any of embodiments 1-65, comprising a conjugate group attached to the $16^{th}$ nucleoside from the 5'-terminal end of the oligonucleotide.

EMBODIMENT 67

The compound of any of embodiments 1-66, comprising a conjugate group attached to the $17^{th}$ nucleoside from the 5'-terminal end of the oligonucleotide.

EMBODIMENT 68

The compound of any of embodiments 1-67, comprising a conjugate group attached to any of the 18 to 21 5'-most phosphate stabilized nucleosides.

EMBODIMENT 69

The compound of any of embodiments 1-68, comprising a conjugate group attached to the $18^{th}$ nucleoside from the 5'-terminal end of the oligonucleotide.

EMBODIMENT 70

The compound of any of embodiments 1-69, comprising a conjugate group attached to the $19^{th}$ nucleoside from the 5'-terminal end of the oligonucleotide.

EMBODIMENT 71

The compound of any of embodiments 1-70, comprising a conjugate group attached to the 20$^{th}$ nucleoside from the 5'-terminal end of the oligonucleotide.

EMBODIMENT 72

The compound of any of embodiments 1-71, comprising a conjugate group attached to the 21$^{st}$ nucleoside from the 5'-terminal end of the oligonucleotide.

EMBODIMENT 73

The compound of any of embodiments 1-72, comprising a conjugate group attached to the 2$^{nd}$ nucleoside from the 3'-terminal end of the oligonucleotide.

EMBODIMENT 74

The compound of any of embodiments 1-73, comprising a conjugate group attached to the 3$^{rd}$ nucleoside from the 3'-terminal end of the oligonucleotide.

EMBODIMENT 75

The compound of any of embodiments 1-74, comprising a conjugate group attached to any of the 12$^{th}$ to 21$^{st}$ nucleoside from the 3'-terminal end of the oligonucleotide.

EMBODIMENT 76

The compound of any of embodiments 1-75, comprising a conjugate group attached to the 12$^{th}$ nucleoside from the 3'-terminal end of the oligonucleotide.

EMBODIMENT 77

The compound of any of embodiments 1-76, comprising a conjugate group attached to the 13$^{th}$ nucleoside from the 3'-terminal end of the oligonucleotide.

EMBODIMENT 78

The compound of any of embodiments 1-77, comprising a conjugate group attached to the 14$^{th}$ nucleoside from the 3'-terminal end of the oligonucleotide.

EMBODIMENT 79

The compound of any of embodiments 1-78, comprising a conjugate group attached to the 15$^{th}$ nucleoside from the 3'-terminal end of the oligonucleotide.

EMBODIMENT 80

The compound of any of embodiments 1-79, comprising a conjugate group attached to the 16$^{th}$ nucleoside from the 3'-terminal end of the oligonucleotide.

EMBODIMENT 81

The compound of any of embodiments 1-80, comprising a conjugate group attached to the 17$^{th}$ nucleoside from the 3'-terminal end of the oligonucleotide.

EMBODIMENT 82

The compound of any of embodiments 1-81, comprising a conjugate group attached to the 18$^{th}$ nucleoside from the 3'-terminal end of the oligonucleotide.

EMBODIMENT 83

The compound of any of embodiments 1-82, comprising a conjugate group attached to the 19$^{th}$ nucleoside from the 3'-terminal end of the oligonucleotide.

EMBODIMENT 84

The compound of any of embodiments 1-83, comprising a conjugate group attached to the 20$^{th}$ nucleoside from the 3'-terminal end of the oligonucleotide.

EMBODIMENT 85

The compound of any of embodiments 1-84, comprising a conjugate group attached to the 21$^{st}$ nucleoside from the 3'-terminal end of the oligonucleotide.

EMBODIMENT 86

The compound of any of embodiments 1-85, wherein the 3'-terminal nucleoside does not comprise a conjugate group.

EMBODIMENT 87

The compound of any of embodiments 1-86, wherein the conjugate group is attached at the 2'-position of the nucleoside.

EMBODIMENT 88

The compound of any of embodiments 1-87, wherein the conjugate group is attached at the nucleobase of the nucleoside.

EMBODIMENT 89

The compound of any of embodiments 1-88, wherein the conjugate group is attached at phosphate linkage of the nucleoside

EMBODIMENT 90

The compound of any of embodiments 1-89, wherein the oligonucleotide comprises at least two conjugate groups, wherein at least two conjugate groups are attached to different nucleosides.

EMBODIMENT 91

The compound of any of embodiments 1-90, wherein the oligonucleotide consists of 17 linked nucleosides.

EMBODIMENT 92

The compound of any of embodiments 1-90, wherein the oligonucleotide consists of 18 linked nucleosides.

EMBODIMENT 93

The compound of any of embodiments 1-90, wherein the oligonucleotide consists of 19 linked nucleosides.

EMBODIMENT 94

The compound of any of embodiments 1-90, wherein the oligonucleotide consists of 20 linked nucleosides.

EMBODIMENT 95

The compound of any of embodiments 1-90, wherein the oligonucleotide consists of 21 linked nucleosides.

EMBODIMENT 96

The compound of any of embodiments 1-90, wherein the oligonucleotide consists of 22 linked nucleosides.

EMBODIMENT 97

The compound of any of embodiments 1-90, wherein the oligonucleotide consists of 23 linked nucleosides.

EMBODIMENT 98

The compound of any of embodiments 1-90, wherein the oligonucleotide consists of 24 linked nucleosides groups.

EMBODIMENT 99

The compound of any of embodiments 1-98, wherein each nucleoside is a modified nucleoside.

EMBODIMENT 100

The compound of any of embodiments 1-99, comprising at least one 2'-modified nucleosides.

EMBODIMENT 101

The compound of any of embodiments 1-100, wherein each nucleoside comprises 2'-substituent independently selected from among: 2'-F, 2'-OMe, 2'-MOE, and a conjugate group.

EMBODIMENT 102

The compound of any of embodiments 1-101, wherein each of the 1 to 5 3'-most nucleosides are stabilizing nucleosides.

EMBODIMENT 103

The compound of embodiment 102 wherein the stabilizing nucleosides are 2'-modified nucleosides.

EMBODIMENT 104

The compound of embodiment 103 wherein the stabilizing nucleosides are 2'-MOE modified nucleosides.

EMBODIMENT 105

The compound of any of embodiments 102-104, wherein each of the 2 to 4 3'-most nucleosides are stabilizing nucleosides.

EMBODIMENT 106

The compound of any of embodiments 102-104, wherein each of the 2 3'-most nucleosides are stabilizing nucleosides.

EMBODIMENT 107

The compound of any of embodiments 1 to 106, wherein the 2 3'-most nucleosides are 2'-MOE modified nucleosides and the remaining nucleosides comprise 2-substituents selected from among: 2'-F, 2'-OMe, and a conjugate group.

EMBODIMENT 108

The compound of any of embodiments 1 to 107, wherein the nucleobase of each of the 1 to 5 3'-most terminal nucleosides is a purine.

EMBODIMENT 109

The compound of embodiment 108, wherein the nucleobase of each of the 1 to 5 3'-most terminal nucleoside is an adenine.

EMBODIMENT 110

The compound of any of embodiments 1 to 108, wherein the nucleobase of each of the 2 3'-most terminal nucleosides is a purine.

EMBODIMENT 111

The compound of embodiment 110, wherein the nucleobase of each of the 2 3'-most terminal nucleoside is an adenine.

EMBODIMENT 112

The compound of any of embodiments 1 to 111 wherein each internucleoside linking group is, independently, a phosphodiester internucleoside linking group or a phosphorothioate internucleoside linking group.

EMBODIMENT 113

The compound of any of embodiments 1 to 112 wherein each of the 6 to 9 3'-most internucleoside linkages is a phosphorothioate linkage.

EMBODIMENT 114

The compound of any of embodiments 1 to 113 wherein each of the 6 to 9 3'-most internucleoside linkages is a phosphorothioate linkage and each of the other internucleoside linkages is a phosphodiester linkage.

EMBODIMENT 115

The compound of any of embodiments 1 to 113 wherein each of the 6 to 9 3'-most internucleoside linkages is a phosphorothioate linkage and each of the other internucleoside linkages is a phosphodiester or a phosphorothioate linkage.

EMBODIMENT 116

The compound of any of embodiments 112-115 comprising a linkage alternating region wherein the linkages within the linkage alternating region alternate between phosphodiester linkages and phosphorothioate linkages.

EMBODIMENT 117

The compound of embodiment 116, wherein the linkage alternating region comprises at least 5 linkages.

EMBODIMENT 118

The compound of any of embodiments 1 to 117 wherein each of the 7 3'-most internucleoside linkages is a phosphorothioate linkage.

EMBODIMENT 119

The compound of any of embodiments 1 to 118 wherein each of the 7 3'-most internucleoside linkages is a phosphorothioate linkage, wherein the internucleoside linkage between the 5'-terminal nucleoside and the $2^{nd}$ nucleoside from the 5'-end is a phosphorothioate linkage, and wherein each of the remaining internucleoside linkages are alternate between phosphorothioate linkages and phosphodiester linkages.

EMBODIMENT 120

The compound of any of embodiments 1-119 having the motif:

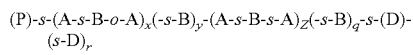

wherein,
P is a 5'-terminal nucleoside comprising a stabilized phosphate;
each A is independently, either a nucleoside of a first type or a nucleoside that comprises a conjugate group;
each B is independently, either a nucleoside of a second type or a nucleoside that comprises a conjugate group;
each D is independently, either a nucleoside of a third type or a nucleoside that comprises a conjugate group;
wherein the oligonucleotide comprises at least one conjugate group;
s is a phosphorothioate linkage;
o is a phosphodiester linkage;
X is 1-8; and
Y is 1 or 0;
Z is 1-5;
q is 1 or 0; and
r is 0-3.

EMBODIMENT 121

The compound of embodiment 120, wherein each A that does not comprise a conjugate is a 2'-F nucleoside.

EMBODIMENT 122

The compound of any of embodiments 120 to 121, wherein each B that does not comprise a conjugate is a 2'-OMe nucleoside.

EMBODIMENT 123

The compound of any of embodiments 120 to 122, wherein each D that does not comprise a conjugate is a 2'-MOE nucleoside.

EMBODIMENT 124

The compound of any of embodiments 120 to 123, wherein P comprises a conjugate group.

EMBODIMENT 125

The compound of any of embodiments 120 to 123, wherein P comprises a 2'-conjugate group.

EMBODIMENT 126

The compound of any of embodiments 120 to 123, wherein P comprises a 2'-MOE.

EMBODIMENT 127

The compound of any of embodiments 120 to 126, wherein one A comprises a conjugate group.

EMBODIMENT 128

The compound of any of embodiments 120 to 126, wherein one B comprises a conjugate group.

EMBODIMENT 129

The compound of any of embodiments 120 to 128, wherein one D comprises a conjugate group.

EMBODIMENT 130

The compound of any of embodiments 1 to 129, wherein the conjugate group comprises a dye.

EMBODIMENT 131

The compound of embodiment 130, wherein the dye is selected from among an acridine dye, a coumarine dye, a rhodamine dye, a xanthene dye, a cyanine dye and a pyrene dye, Texas Red, Alexa Fluor® dye, BODLPY® dye, Fluorescein, Oregon Green® dye, and Rhodamine Green™ dye.

EMBODIMENT 132

The compound of embodiment 130, wherein the dye is selected from an acridine dye, a coumarine dye, a rhodamine dye, a xanthene dye, a cyanine dye, and a pyrene dye.

EMBODIMENT 133

The compound of any of embodiments 1 to 129, wherein the conjugate group comprises a targeting moiety.

EMBODIMENT 134

The compound of embodiment 133, wherein the targeting moiety is selected from arginine-glycine-aspartate (RGD) peptide, fibronectin, folate, galactose, an apolipoprotein, insulin, transferrin, a fibroblast growth factor (FOF), an epidermal growth factor (EGF) and an antibody.

EMBODIMENT 135

The compound of any of embodiments 1 to 129, wherein the conjugate group comprises a magnetic resonance imaging moiety comprising a paramagnetic compound.

EMBODIMENT 136

The compound of any of embodiments 1 to 129, wherein the conjugate group comprises a vitamin.

EMBODIMENT 137

The compound of embodiment 136, wherein the vitamin is a B vitamin.

EMBODIMENT 138

The compound of embodiment 137, wherein the B vitamin is selected from the group consisting of vitamin $B_1$, vitamin $B_2$, vitamin $B_3$, vitamin $B_5$, vitamin $B_6$, vitamin $B_7$, vitamin $B_9$, vitamin $B_{12}$.

EMBODIMENT 139

The compound of embodiment 136, wherein the vitamin is a C vitamin.

EMBODIMENT 140

The compound of embodiment 136, wherein the vitamin is a D vitamin.

EMBODIMENT 141

The compound of any of embodiments 1 to 129, wherein the conjugate group comprises an intercalator.

EMBODIMENT 142

The compound of any of embodiments 1 to 129, wherein the conjugate group comprises a reporter molecule.

EMBODIMENT 143

The compound of any of embodiments 1 to 129, wherein the conjugate group comprises a polyamine.

EMBODIMENT 144

The compound of any of embodiments 1 to 129, wherein the conjugate group comprises a polyamide.

EMBODIMENT 145

The compound of any of embodiments 1 to 129, wherein the conjugate group comprises polyethylene glycol.

EMBODIMENT 146

The compound of any of embodiments 1 to 129, wherein the conjugate group comprises a thioether.

EMBODIMENT 147

The compound of any of embodiments 1 to 129, wherein the conjugate group comprises a polyether.

EMBODIMENT 148

The compound of any of embodiments 1 to 129, wherein the conjugate group comprises cholesterol.

EMBODIMENT 149

The compound of any of embodiments 1 to 129, wherein the conjugate group comprises a thiocholesterol.

EMBODIMENT 150

The compound of any of embodiments 1 to 129, wherein the conjugate group comprises a cholic acid moiety.

EMBODIMENT 151

The compound of any of embodiments 1 to 129, wherein the conjugate group comprises a folate.

EMBODIMENT 152

The compound of any of embodiments 1 to 129, wherein the conjugate group comprises a folic acid or folic acid derivative.

EMBODIMENT 153

The compound of any of embodiments 1 to 129, wherein the conjugate group comprises gallic acid or a gallic acid derivative.

EMBODIMENT 154

The compound of any of embodiments 1 to 129, wherein the conjugate group comprises a lipid.

EMBODIMENT 155

The compound of any of embodiments 1 to 129, wherein the conjugate group comprises a phospholipid.

EMBODIMENT 156

The compound of any of embodiments 1 to 129, wherein the conjugate group comprises a fatty acid or fatty acid derivative.

EMBODIMENT 157

The compound of any of embodiments 1 to 129, wherein the conjugate group comprises a carbohydrate.

EMBODIMENT 158

The compound of any of embodiments 1 to 129, wherein the conjugate group comprises a modified carbohydrate.

EMBODIMENT 159

The compound of any of embodiments 1 to 129, wherein the conjugate group comprises a carbohydrate derivative.

EMBODIMENT 160

The compound of any of embodiments 1 to 129, wherein the conjugate group comprises a polysaccharide.

EMBODIMENT 161

The compound of any of embodiments 1 to 129, wherein the conjugate group comprises modified polysaccharide.

EMBODIMENT 162

The compound of any of embodiments 1 to 129, wherein the conjugate group comprises mannose.

EMBODIMENT 163

The compound of any of embodiments 1 to 129, wherein the conjugate group comprises galactose.

EMBODIMENT 164

The compound of any of embodiments 1 to 129, wherein the conjugate group comprises mannose derivative.

EMBODIMENT 165

The compound of any of embodiments 1 to 129, wherein the conjugate group comprises galactose derivative.

EMBODIMENT 166

The compound of any of embodiments 1 to 129, wherein the conjugate group comprises a modified mannose.

EMBODIMENT 167

The compound of any of embodiments 1 to 129, wherein the conjugate group comprises a modified galactose.

EMBODIMENT 168

The compound of any of embodiments 1 to 129, wherein the conjugate group comprises a D-mannopyranose.

EMBODIMENT 169

The compound of any of embodiments 1 to 129, wherein the conjugate group comprises a L-Mannopyranose.

EMBODIMENT 170

The compound of any of embodiments 1 to 129, wherein the conjugate group comprises a D-Arabinose.

EMBODIMENT 171

The compound of any of embodiments 1 to 129, wherein the conjugate group comprises a L-Galactose.

EMBODIMENT 172

The compound of any of embodiments 1 to 129, wherein the conjugate group comprises a D-xylofuranose.

EMBODIMENT 173

The compound of any of embodiments 1 to 129, wherein the conjugate group comprises a L-xylofuranose.

EMBODIMENT 174

The compound of any of embodiments 1 to 129, wherein the conjugate group comprises a D-glucose.

EMBODIMENT 175

The compound of any of embodiments 1 to 129, wherein the conjugate group comprises a L-glucose.

EMBODIMENT 176

The compound of any of embodiments 1 to 129, wherein the conjugate group comprises a D-Galactose.

EMBODIMENT 177

The compound of any of embodiments 1 to 129, wherein the conjugate group comprises a L-Galactose.

EMBODIMENT 178

The compound of any of embodiments 1 to 129, wherein the conjugate group comprises $\alpha$-D-Mannofuranose.

EMBODIMENT 179

The compound of any of embodiments 1 to 129, wherein the conjugate group comprises $\beta$-D-Mannofuranose.

EMBODIMENT 180

The compound of any of embodiments 1 to 129, wherein the conjugate group comprises $\alpha$-D-Mannopyranose

EMBODIMENT 181

The compound of any of embodiments 1 to 129, wherein the conjugate group comprises $\beta$-D-Mannopyranose.

EMBODIMENT 182

The compound of any of embodiments 1 to 129, wherein the conjugate group comprises $\alpha$-D-Glucopyranose.

EMBODIMENT 183

The compound of any of embodiments 1 to 129, wherein the conjugate group comprises $\beta$-D-Glucopyranose.

EMBODIMENT 184

The compound of any of embodiments 1 to 129, wherein the conjugate group comprises $\alpha$-D-Glucofuranose.

EMBODIMENT 185

The compound of any of embodiments 1 to 129, wherein the conjugate group comprises $\beta$-D-Glucofuranose.

EMBODIMENT 186

The compound of any of embodiments 1 to 129, wherein the conjugate group comprises $\alpha$-D-fructofuranose.

EMBODIMENT 187

The compound of any of embodiments 1 to 129, wherein the conjugate group comprises $\alpha$-D-fructopyranose.

EMBODIMENT 188

The compound of any of embodiments 1 to 129, wherein the conjugate group comprises α-D-Galactopyranose.

EMBODIMENT 189

The compound of any of embodiments 1 to 129, wherein the conjugate group comprises β-D-Galactopyranose.

EMBODIMENT 190

The compound of any of embodiments 1 to 129, wherein the conjugate group comprises α-D-Galactofuranose.

EMBODIMENT 191

The compound of any of embodiments 1 to 129, wherein the conjugate group comprises β-D-Galactofuranose.

EMBODIMENT 192

The compound of any of embodiments 1 to 129, wherein the conjugate group comprises glucosamine.

EMBODIMENT 193

The compound of any of embodiments 1 to 129, wherein the conjugate group comprises sialic acid.

EMBODIMENT 194

The compound of any of embodiments 1 to 129, wherein the conjugate group comprises α-D-galactosamine.

EMBODIMENT 195

The compound of any of embodiments 1 to 129, wherein the conjugate group comprises N-Acetylgalactosamine.

EMBODIMENT 196

The compound of any of embodiments 1 to 129, wherein the conjugate group comprises 2-Amino-3-O—[(R)-1-carboxyethyl]-2-deoxy-β-D-glucopyranose.

EMBODIMENT 197

The compound of any of embodiments 1 to 129, wherein the conjugate group comprises 2-Deoxy-2-methylamino-L-glucopyranose.

EMBODIMENT 198

The compound of any of embodiments 1 to 129, wherein the conjugate group comprises 4,6-Dideoxy-4-formamido-2,3-di-O-methyl-D-mannopyranose.

EMBODIMENT 199

The compound of any of embodiments 1 to 129, wherein the conjugate group comprises 2-Deoxy-2-sulfoamino-D-glucopyranose

EMBODIMENT 200

The compound of any of embodiments 1 to 129, wherein the conjugate group comprises N-Glycoloyl-α-neuraminic acid.

EMBODIMENT 201

The compound of any of embodiments 1 to 129, wherein the conjugate group comprises 5-thio-β-D-glucopyranose.

EMBODIMENT 202

The compound of any of embodiments 1 to 129, wherein the conjugate group comprises methyl 2,3,4-tri-O-acetyl-1-thio-6-O-trityl-α-D-glucopyranoside.

EMBODIMENT 203

The compound of any of embodiments 1 to 129, wherein the conjugate group comprises 4-Thio-β-D-galactopyranose.

EMBODIMENT 204

The compound of any of embodiments 1 to 129, wherein the conjugate group comprises ethyl 3,4,6,7-tetra-O-acetyl-2-deoxy-1,5-dithio-α-D-gluco-heptopyranoside.

EMBODIMENT 205

The compound of any of embodiments 1 to 129, wherein the conjugate group comprises 2,5-Anhydro-D-allononitrile.

EMBODIMENT 206

The compound of any of embodiments 1 to 129, wherein the conjugate group comprises ribose.

EMBODIMENT 207

The compound of any of embodiments 1 to 129, wherein the conjugate group comprises D-ribose.

EMBODIMENT 208

The compound of any of embodiments 1 to 129, wherein the conjugate group comprises D-4-thioribose.

EMBODIMENT 209

The compound of any of embodiments 1 to 129, wherein the conjugate group comprises L-ribose.

EMBODIMENT 210

The compound of any of embodiments 1 to 129, wherein the conjugate group comprises L-4-thioribose.

EMBODIMENT 211

The compound of any of embodiments 1 to 129, wherein the conjugate group comprises modified ribose.

EMBODIMENT 212

The compound of any of embodiments 1 to 129, wherein the conjugate group comprises a ribose derivative.

EMBODIMENT 213

The compound of any of embodiments 1 to 129, wherein the conjugate group comprises biotin.

EMBODIMENT 214

The compound of any of embodiments 1 to 129, wherein the conjugate group comprises phenazine.

EMBODIMENT 215

The compound of any of embodiments 1 to 129, wherein the conjugate group comprises phenanthridine.

EMBODIMENT 216

The compound of any of embodiments 1 to 129, wherein the conjugate group comprises an aromatic compound or an aromatic compound derivative.

EMBODIMENT 217

The compound of any of embodiments 1 to 129, wherein the conjugate group comprises anthraquinone.

EMBODIMENT 218

The compound of any of embodiments 1 to 129, wherein the conjugate group comprises adamantane.

EMBODIMENT 219

The compound of any of embodiments 1 to 129, wherein the conjugate group comprises acridine.

EMBODIMENT 220

The compound of any of embodiments 1 to 129, wherein the conjugate group comprises fluorescein.

EMBODIMENT 221

The compound of any of embodiments 1 to 129, wherein the conjugate group comprises a rhodamine.

EMBODIMENT 222

The compound of any of embodiments 1 to 129, wherein the conjugate group comprises coumarin.

EMBODIMENT 223

The compound of any of embodiments 1 to 129, wherein the conjugate group comprises an optical imaging moiety.

EMBODIMENT 224

The compound of any of embodiments 1 to 129, wherein the conjugate group comprises a magnetic resonance moiety.

EMBODIMENT 225

The compound of embodiment 162, wherein the magnetic resonance moiety is a paramagnetic compound.

EMBODIMENT 226

The compound of any of embodiments 1 to 129, wherein the conjugate group comprises a hydrophobic compound.

EMBODIMENT 227

The compound of any of embodiments 1 to 129, wherein the conjugate group comprises a hydrophilic compound.

EMBODIMENT 228

The compound of any of embodiments 1 to 129, wherein the conjugate group comprises a peptide.

EMBODIMENT 229

The compound of any of embodiments 1 to 129, wherein the conjugate group comprises an amino acid.

EMBODIMENT 230

The compound of any of embodiments 1 to 129, wherein the conjugate group comprises an amino acid derivative.

EMBODIMENT 231

The compound of any of embodiments 1 to 129, wherein the conjugate group comprises a nucleic acid.

EMBODIMENT 232

The compound of embodiments 1 to 129, wherein the conjugate group comprises a nucleic acid derivative.

EMBODIMENT 233

The compound of any of embodiments 1 to 129, wherein the conjugate group comprises a heterocycle.

EMBODIMENT 234

The compound of any of embodiments 1 to 129, wherein the conjugate group comprises a steroid.

EMBODIMENT 235

The compound of any of embodiments 1 to 129, wherein the conjugate group comprises an ionic complex.

EMBODIMENT 236

The compound of any of embodiments 1 to 129, wherein the conjugate group comprises a polyionic complex.

EMBODIMENT 237

The compound of any of embodiments 1 to 129, wherein the conjugate group comprises a cationic complex.

EMBODIMENT 238

The compound of any of embodiments 1 to 129, wherein the conjugate group comprises an anionic complex.

EMBODIMENT 239

The compound of any of embodiments 1 to 129, wherein the conjugate group comprises a taxane.

EMBODIMENT 240

The compound of any of embodiments 1 to 129, wherein the conjugate group comprises a camptotheca.

EMBODIMENT 241

The compound of any of embodiments 1 to 129, wherein the conjugate group comprises an anthracycline.

EMBODIMENT 242

The compound of any of embodiments 1 to 129, wherein the conjugate group comprises cholesterol.

EMBODIMENT 243

The compound of any of embodiments 1 to 129, wherein the conjugate group comprises palmityl.

EMBODIMENT 244

The compound of any of embodiments 1 to 129, wherein the conjugate group comprises stearoyl.

EMBODIMENT 245

The compound of any of embodiments 1 to 129, wherein the conjugate group comprises lithocholic-oleyl.

EMBODIMENT 246

The compound of any of embodiments 1 to 129, wherein the conjugate group comprises $C_{22}$ alkyl.

EMBODIMENT 247

The compound of any of embodiments 1 to 129, wherein the conjugate group comprises $C_{20}$ alkyl.

EMBODIMENT 248

The compound of any of embodiments 1 to 129, wherein the conjugate group comprises $C_{16}$ alkyl.

EMBODIMENT 249

The compound of any of embodiments 1 to 129, wherein the conjugate group comprises $C_{10}$ alkyl.

EMBODIMENT 250

The compound of any of embodiments 1 to 129, wherein the conjugate group comprises $C_{21}$ alkyl.

EMBODIMENT 251

The compound of any of embodiments 1 to 129, wherein the conjugate group comprises $C_{19}$ alkyl.

EMBODIMENT 252

The compound of any of embodiments 1 to 129, wherein the conjugate group comprises $C_{18}$ alkyl.

EMBODIMENT 253

The compound of any of embodiments 1 to 129, wherein the conjugate group comprises $C_{15}$ alkyl.

EMBODIMENT 254

The compound of any of embodiments 1 to 129, wherein the conjugate group comprises $C_{14}$ alkyl.

EMBODIMENT 255

The compound of any of embodiments 1 to 129, wherein the conjugate group comprises $C_{13}$ alkyl.

EMBODIMENT 256

The compound of any of embodiments 1 to 129, wherein the conjugate group comprises $C_{12}$ alkyl.

EMBODIMENT 257

The compound of any of embodiments 1 to 129, wherein the conjugate group comprises $C_{11}$ alkyl.

EMBODIMENT 258

The compound of any of embodiments 1 to 129, wherein the conjugate group comprises $C_9$ alkyl.

EMBODIMENT 259

The compound of any of embodiments 1 to 129, wherein the conjugate group comprises $C_8$ alkyl.

EMBODIMENT 260

The compound of any of embodiments 1 to 129, wherein the conjugate group comprises $C_7$ alkyl.

EMBODIMENT 261

The compound of any of embodiments 1 to 129, wherein the conjugate group comprises $C_6$ alkyl.

EMBODIMENT 262

The compound of any of embodiments 1 to 129, wherein the conjugate group comprises $C_5$ alkyl.

EMBODIMENT 263

The compound of any of embodiments 1 to 129, wherein the conjugate group comprises $C_{22}$ alkenyl.

EMBODIMENT 264

The compound of any of embodiments 1 to 129, wherein the conjugate group comprises $C_{20}$ alkenyl.

EMBODIMENT 265

The compound of any of embodiments 1 to 129, wherein the conjugate group comprises $C_{16}$ alkenyl.

EMBODIMENT 266

The compound of any of embodiments 1 to 129, wherein the conjugate group comprises $C_{10}$ alkenyl.

EMBODIMENT 267

The compound of any of embodiments 1 to 129, wherein the conjugate group comprises $C_{21}$ alkenyl.

EMBODIMENT 268

The compound of any of embodiments 1 to 129, wherein the conjugate group comprises $C_{19}$ alkenyl.

EMBODIMENT 269

The compound of any of embodiments 1 to 129, wherein the conjugate group comprises $C_{18}$ alkenyl.

EMBODIMENT 270

The compound of any of embodiments 1 to 129, wherein the conjugate group comprises $C_{15}$ alkenyl.

EMBODIMENT 271

The compound of any of embodiments 1 to 129, wherein the conjugate group comprises $C_{14}$ alkenyl.

EMBODIMENT 272

The compound of any of embodiments 1 to 129, wherein the conjugate group comprises $C_{13}$ alkenyl.

EMBODIMENT 273

The compound of any of embodiments 1 to 129, wherein the conjugate group comprises $C_{12}$ alkenyl.

EMBODIMENT 274

The compound of any of embodiments 1 to 129, wherein the conjugate group comprises $C_{11}$ alkenyl.

EMBODIMENT 275

The compound of any of embodiments 1 to 129, wherein the conjugate group comprises $C_9$ alkenyl.

EMBODIMENT 276

The compound of any of embodiments 1 to 129, wherein the conjugate group comprises $C_8$ alkenyl.

EMBODIMENT 277

The compound of any of embodiments 1 to 129, wherein the conjugate group comprises $C_7$ alkenyl.

EMBODIMENT 278

The compound of any of embodiments 1 to 129, wherein the conjugate group comprises $C_6$ alkenyl.

EMBODIMENT 279

The compound of any of embodiments 1 to 129, wherein the conjugate group comprises $C_5$ alkenyl.

EMBODIMENT 280

The compound of any of embodiments 1 to 129, wherein the conjugate group comprises $C_{22}$ alkynyl.

EMBODIMENT 281

The compound of any of embodiments 1 to 129, wherein the conjugate group comprises $C_{20}$ alkynyl.

EMBODIMENT 282

The compound of any of embodiments 1 to 129, wherein the conjugate group comprises $C_{16}$ alkynyl.

EMBODIMENT 283

The compound of any of embodiments 1 to 129, wherein the conjugate group comprises $C_{10}$ alkynyl.

EMBODIMENT 284

The compound of any of embodiments 1 to 129, wherein the conjugate group comprises $C_{21}$ alkynyl.

EMBODIMENT 285

The compound of any of embodiments 1 to 129, wherein the conjugate group comprises $C_{19}$ alkynyl.

EMBODIMENT 286

The compound of any of embodiments 1 to 129, wherein the conjugate group comprises $C_{18}$ alkynyl.

EMBODIMENT 287

The compound of any of embodiments 1 to 129, wherein the conjugate group comprises $C_{15}$ alkynyl.

EMBODIMENT 288

The compound of any of embodiments 1 to 129, wherein the conjugate group comprises $C_{14}$ alkynyl.

EMBODIMENT 289

The compound of any of embodiments 1 to 129, wherein the conjugate group comprises $C_{13}$ alkynyl.

EMBODIMENT 290

The compound of any of embodiments 1 to 129, wherein the conjugate group comprises $C_{12}$ alkynyl.

EMBODIMENT 291

The compound of any of embodiments 1 to 129, wherein the conjugate group comprises $C_{11}$ alkynyl.

EMBODIMENT 292

The compound of any of embodiments 1 to 129, wherein the conjugate group comprises $C_9$ alkynyl.

EMBODIMENT 293

The compound of any of embodiments 1 to 129, wherein the conjugate group comprises $C_8$ alkynyl.

EMBODIMENT 294

The compound of any of, embodiments 1 to 129, wherein the conjugate group comprises $C_7$ alkynyl.

EMBODIMENT 295

The compound of any of embodiments 1 to 129, wherein the conjugate group comprises $C_6$ alkynyl.

EMBODIMENT 296

The compound of any of embodiments 1 to 129, wherein the conjugate group comprises $C_5$ alkynyl.

EMBODIMENT 297

The compound of any of embodiments 1 to 129, wherein the conjugate group comprises squalene.

EMBODIMENT 298

The compound of any of embodiments 1 to 129, wherein the conjugate group comprises:

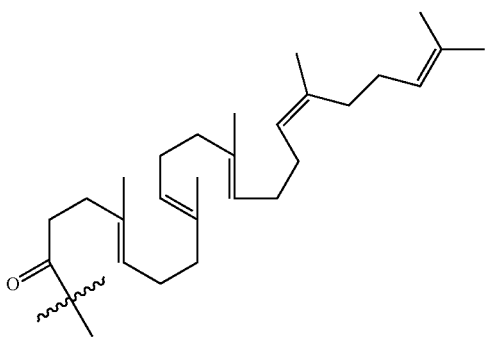 [SMILES: *C(=O)CC/C(C)=C/CC/C(C)=C/CC/C(C)=C/CC/C=C(/C)CCC=C(C)C]

EMBODIMENT 299

The compound of any of embodiments 1 to 299, wherein the conjugate group has a pH value of greater than 7.

EMBODIMENT 300

The compound of any of embodiments 1 to 299, wherein the conjugate group has a pH value of less than 7.

EMBODIMENT 301

The compound of any of embodiments 1 to 299, wherein the conjugate group increases the binding affinity to lipoproteins.

EMBODIMENT 302

The compound of any of embodiments 1 to 299, wherein the conjugate group increases the lipophilicity of the oligonucleotide-conjugate complex.

EMBODIMENT 303

The compound of any of embodiments 1 to 299, wherein the conjugate group decreases the lipophilicity of the oligonucleotide-conjugate complex.

EMBODIMENT 304

The compound of any of embodiments 1 to 299, wherein the conjugate group increases the lipophobicity of the oligonucleotide-conjugate complex.

EMBODIMENT 305

The compound of any of embodiments 1 to 299, wherein the conjugate group decreases the lipophobicity of the oligonucleotide-conjugate complex.

EMBODIMENT 306

The compound of any of embodiments 1 to 299, wherein the conjugate group comprises a group that increases lipoprotein binding affinity.

EMBODIMENT 307

The compound of any of embodiments 1 to 299, wherein the conjugate group increases the binding affinity of the oligonucleotide-conjugate complex to albumin.

EMBODIMENT 308

The compound of any of embodiments 1 to 299, wherein the conjugate group decreases the binding affinity of the oligonucleotide-conjugate complex to albumin.

EMBODIMENT 309

The compound of any of embodiments 1 to 299, wherein the conjugate group increases the binding affinity of the oligonucleotide-conjugate complex to glycoproteins.

EMBODIMENT 310

The compound of any of embodiments 1 to 299, wherein the conjugate group decreases the binding affinity of the oligonucleotide-conjugate complex to glycoproteins.

EMBODIMENT 311

The compound of any of embodiments 1 to 299, wherein the conjugate group increases the binding affinity of the oligonucleotide-conjugate complex to α-globulins, β-globulins, and γ-globulins.

EMBODIMENT 312

The compound of any of embodiments 1 to 299, wherein the conjugate group decreases the binding affinity of the oligonucleotide-conjugate complex to α-globulins, β-globulins, and γ-globulins.

EMBODIMENT 313

The compound of any of embodiments 1 to 312, wherein the conjugate group comprises a linker group.

EMBODIMENT 314

The compound of any of embodiments 1 to 313, comprising a linker group selected from the group consisting of a carbamate, N,N-hexyl carbamate, hexanamide, 8-amino-3,6-dioxaoctanoic acid (ADO), succinimidyl 4-(N-maleimidomethyl)cyclohexane-1-carboxylate (SMCC), 6-aminohexanoic acid (AHEX or AHA), substituted $C_1$-$C_{10}$ alkyl, substituted or unsubstituted $C_2$-$C_{10}$ alkenyl, and substituted or unsubstituted $C_2$-$C_{10}$ allynyl.

EMBODIMENT 315

The compound of any of embodiments 313 to 314, wherein the linker group is hexanamide.

EMBODIMENT 316

The compound of any of embodiments 313 to 314, wherein the linker group is a carbamate.

EMBODIMENT 317

The compound of any of embodiments 313 to 314, wherein the linker group is N,N-hexyl carbamate.

EMBODIMENT 318

The compound of embodiment 313, wherein the linker is an alkyl.

EMBODIMENT 319

The compound of embodiment 313, wherein the linker is an ester.

EMBODIMENT 320

The compound of embodiment 313, wherein the linker is an anhydride.

EMBODIMENT 321

The compound of embodiment 313, wherein the linker is an ether.

EMBODIMENT 322

The compound of embodiment 313, wherein the linker is an amide.

EMBODIMENT 323

The compound of any of embodiments 1 to 322, wherein two or more conjugate groups are attached to the oligomer.

EMBODIMENT 324

The compound of embodiment 323, wherein each conjugate group comprises a linker group.

EMBODIMENT 325

The compound of any of embodiments 323 or 324, wherein at least one conjugate group is selected from the group consisting of cholesterol, palmityl, $C_{22}$ alkyl, $C_{20}$ alkyl, $C_{16}$ alkyl, and $C_{10}$ alkyl.

EMBODIMENT 326

The compound of any of embodiments 323 or 324, wherein at least one conjugate group comprises cholesterol.

EMBODIMENT 327

The compound of any of embodiments 323 or 324, wherein at least one conjugate group comprises palmityl.

EMBODIMENT 328

The compound of any of embodiments 323 or 324, wherein at least one conjugate group comprises stearoyl.

EMBODIMENT 329

The compound of any of embodiments 323 or 324, wherein at least one conjugate group comprises lithocholic-oleyl.

EMBODIMENT 330

The compound of any of embodiments 323 or 324, wherein at least one conjugate group comprises $C_{22}$ alkyl.

EMBODIMENT 331

The compound of any of embodiments 323 or 324, wherein at least one conjugate group comprises $C_{20}$ alkyl.

EMBODIMENT 332

The compound of any of embodiments 323 or 324, wherein at least one conjugate group comprises $C_{16}$ alkyl.

EMBODIMENT 333

The compound of any of embodiments 323 or 324, wherein at least one conjugate group comprises $C_{10}$ alkyl.

EMBODIMENT 334

The compound of any of embodiments 1 to 129 or 300 to 333, wherein the conjugate group comprises a structure represented by Formula VIII below:

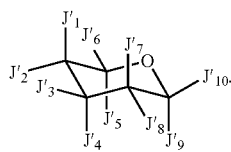

VIII wherein:

each $J'_1$, $J'_2$, $J'_3$, $J'_4$, $J'_5$, $J'_6$, $J'_7$, $J'_8$, $J'_9$, and $J'_{10}$ is, independently, H, halogen, hydroxyl, alcohol, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl, $N(A'_1)(A'_2)$, $C(=L')A'_1$, or $C(=L')N(A'_1)(A'_2)$, $C(A'_3)(A'_4)$, a linker group, or a point of attachment to a linker group, oligomer, or nucleoside;

wherein L' is O or S;

wherein each $A'_1$ and $A'_2$ is, independently, H, halogen, hydroxyl, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, or substituted $C_2$-$C_6$ alkynyl; and wherein each $A'_3$ and $A'_4$ is, independently, H, OH, hydroxyl, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl.

EMBODIMENT 335

The compound of embodiment 334, wherein one of $J'_1$, $J'_2$, $J'_3$, $J'_4$, $J'_5$, $J'_6$, $J'_7$, $J'_8$, $J'_9$, and $J'_{10}$ is H.

EMBODIMENT 336

The compound of embodiment 334, wherein one of $J'_1$, $J'_2$, $J'_3$, $J'_4$, $J'_5$, $J'_6$, $J'_7$, $J'_8$, $J'_9$, and $J'_{10}$ is $C(A'_3)(A'_4)$.

EMBODIMENT 337

The compound of embodiment 334, wherein $J'_6$ is a hydroxyl.

EMBODIMENT 338

The compound of embodiment 334, wherein the conjugate group comprises:

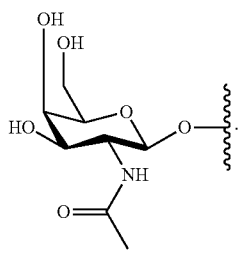

EMBODIMENT 339

The compound of any of embodiments 1 to 129 or 300 to 333, wherein at least one conjugate group comprises mannose.

EMBODIMENT 340

The compound of any of embodiments 1 to 129 or 300 to 333, wherein at least conjugate group comprises a carbohydrate cluster.

EMBODIMENT 341

The compound of any of embodiments 1 to 129 or 300 to 333, wherein at least conjugate group comprises a multivalent carbohydrate cluster.

EMBODIMENT 342

The compound of embodiment 340 or 341, wherein at least one of the carbohydrates in the carbohydrate cluster is 2-acetamido-2-deoxy-D-galactopyranose.

EMBODIMENT 343

The compound of embodiment 340 or 341, wherein each of the carbohydrates in the carbohydrate cluster is 2-acetamido-2-deoxy-D-galactopyranose.

EMBODIMENT 344

The compound of embodiment 340 or 341, wherein at least one of the carbohydrates in the carbohydrate cluster comprises galactose.

EMBODIMENT 345

The compound of embodiment 340 or 341, wherein each of the carbohydrates in the carbohydrate cluster comprises galactose.

EMBODIMENT 346

The compound of embodiment 340 or 341, wherein at least one of the carbohydrates in the carbohydrate cluster comprises mannose.

EMBODIMENT 347

The compound of embodiment 340 or 341, wherein each of the carbohydrates in the carbohydrate cluster comprises mannose.

EMBODIMENT 348

The compound of embodiment 340 or 341, wherein at least one of the carbohydrates in the carbohydrate cluster comprises galactosamine.

EMBODIMENT 349

The compound of embodiment 340 or 341, wherein each of the carbohydrates in the carbohydrate cluster comprises galactosamine.

EMBODIMENT 350

The compound of embodiment 340 or 341, wherein at least one of the carbohydrates in the carbohydrate cluster comprises a polysaccharide.

EMBODIMENT 351

The compound of embodiment 340 or 341, wherein each of the carbohydrates in the carbohydrate cluster comprises a polysaccharide.

EMBODIMENT 352

The compound of any of embodiments 1 to 129 or 300 to 333, wherein the conjugate group comprises an amino sugar.

EMBODIMENT 353

The compound of any of embodiments 1 to 129 or 300 to 333, wherein the conjugate group comprises a thio sugar.

EMBODIMENT 354

The compound of any of embodiments 1 to 129 or 300 to 333, wherein the conjugate group comprises:

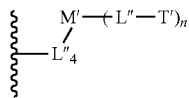

wherein $L''_4$ comprises a linker group;
M' is a scaffold;
L" is a linker group;
n is 0 or an integer between 1 and 10;
T' is selected from the group consisting of a carbohydrate, a modified carbohydrate, and a carbohydrate derivative.

EMBODIMENT 355

The compound of embodiment 354, wherein M' comprises an ether.

EMBODIMENT 356

The compound of embodiment 354, wherein M' comprises an anhydride.

EMBODIMENT 357

The compound of embodiment 354, wherein M' comprises an amide.

EMBODIMENT 358

The compound of embodiment 354, wherein M' comprises an amine.

EMBODIMENT 359

The compound of embodiment 354, wherein n is 0.

EMBODIMENT 360

The compound of embodiment 354, wherein n is 1.

EMBODIMENT 361

The compound of embodiment 354, wherein n is 2.

EMBODIMENT 362

The compound of embodiment 354, wherein n is 3.

EMBODIMENT 363

The compound of embodiment 354, wherein n is 4.

EMBODIMENT 364

The compound of embodiment 354, wherein n is 5.

EMBODIMENT 365

The compound of embodiment 354, wherein n is 6.

EMBODIMENT 366

The compound of embodiment 354, wherein n is 7.

EMBODIMENT 367

The compound of embodiment 354, wherein n is 8.

EMBODIMENT 368

The compound of embodiment 354, wherein n is 9.

EMBODIMENT 369

The compound of embodiment 354, wherein n is 10.

EMBODIMENT 370

The compound of any of embodiments 1 to 129 or 300 to 333, wherein the conjugate group comprises:

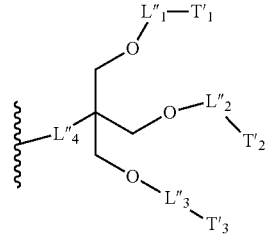

wherein each $L''_1$, $L''_2$, $L''_3$, and $L''_4$ comprises a linker group; and
wherein each of $T'_1$, $T'_2$, and $T'_3$ is independently selected from the group consisting of a targeting agent, a carbohydrate, a modified carbohydrate, and a carbohydrate derivative.

EMBODIMENT 371

The compound of any of embodiments 1 to 129 or 300 to 333, wherein the conjugate group comprises:

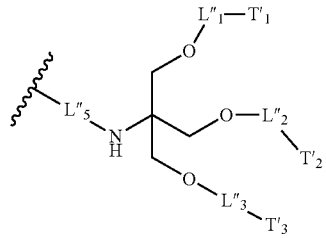

wherein each $L''_1$, $L''_2$, $L''_3$, and $L''_5$ comprises a linker group; and wherein each T'₁, T'₂, and T'₃ is independently selected from the group consisting of a targeting agent, a carbohydrate, a modified carbohydrate, and a carbohydrate derivative.

EMBODIMENT 372

The compound of any of embodiments 1 to 129 or 300 to 333, wherein the conjugate group comprises:

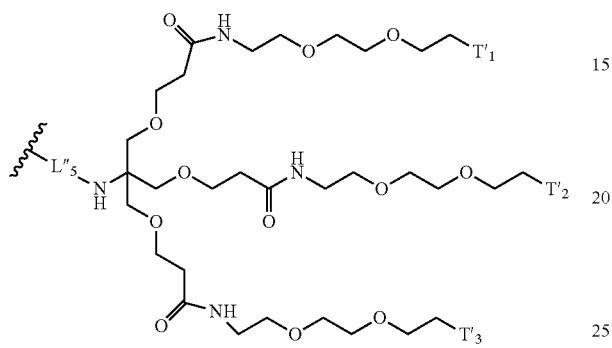

wherein L"₅ comprises a linker group; and
wherein each T'₁, T'₂, and T'₃ is independently selected from the group consisting of a targeting agent, a carbohydrate, a modified carbohydrate, and a carbohydrate derivative.

EMBODIMENT 373

The compound of any of embodiments 1 to 129 or 300 to 333, wherein the conjugate group comprises:

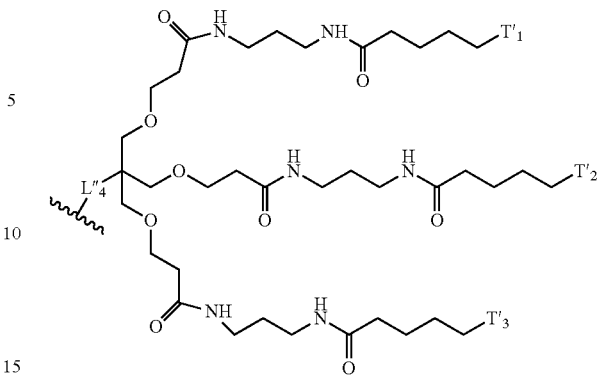

wherein L"₄ comprises a linker group; and
wherein each T'₁, T'₂, and T'₃ is independently selected from the group consisting of a targeting agent, a carbohydrate, a modified carbohydrate, and a carbohydrate derivative.

EMBODIMENT 374

The compound of any of embodiments 1 to 129 or 300 to 333, wherein the conjugate group comprises:

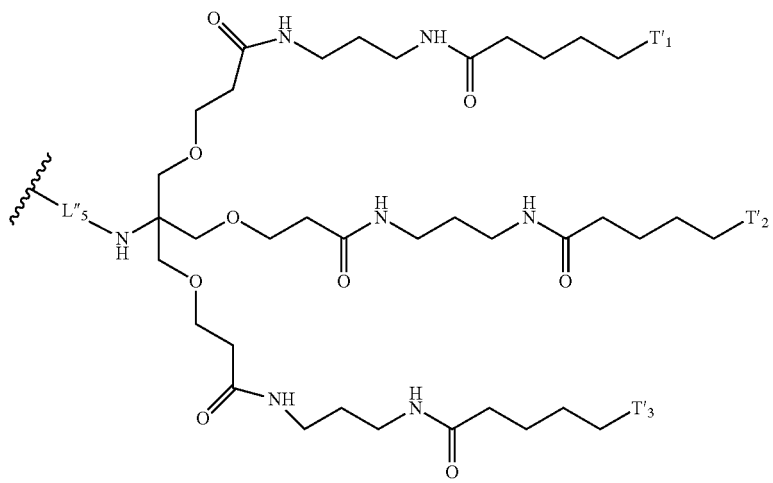

wherein L"₅ comprises a linker group; and
wherein each T'₁, T'₂, and T'₃ is independently selected from the group consisting of a targeting agent, a carbohydrate, a modified carbohydrate, and a carbohydrate derivative.

EMBODIMENT 375

The compound of any of embodiments 1 to 129 or 300 to 333, wherein the conjugate group comprises:

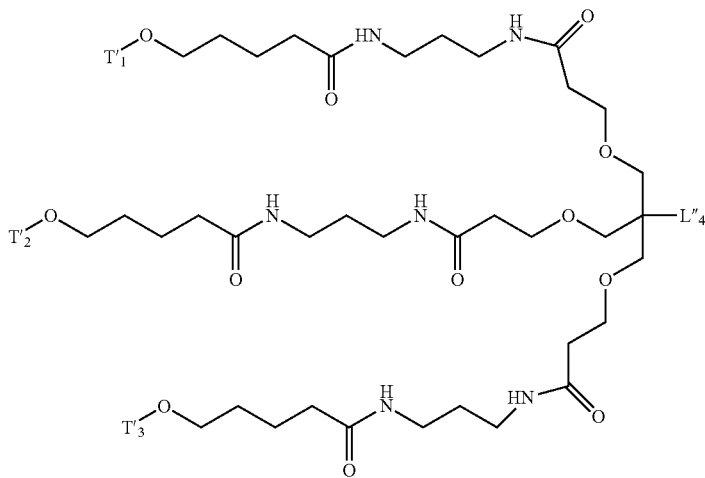

wherein L"$_4$ comprises a linker group; and
wherein each T'$_1$, T'$_2$, and T'$_3$ is independently selected from the group consisting of a targeting agent, a carbohydrate, a modified carbohydrate, and a carbohydrate derivative.

EMBODIMENT 376

The compound of any of embodiments 1 to 129 or 300 to 333, wherein the conjugate group comprises:

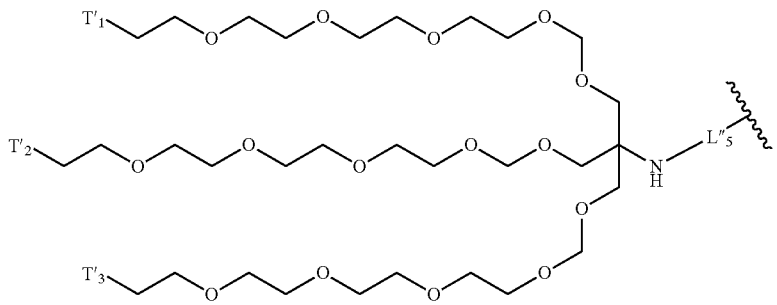

wherein L"$_5$ comprises a linker group; and
wherein each T'$_1$, T'$_2$, and T'$_3$ is independently selected from the group consisting of a targeting agent, a carbohydrate, a modified carbohydrate, and a carbohydrate derivative.

EMBODIMENT 377

The compound of any of embodiments 1 to 129 or 300 to 333, wherein the conjugate group comprises:

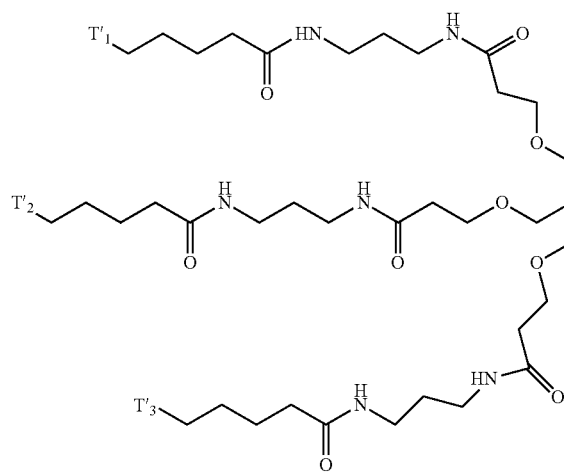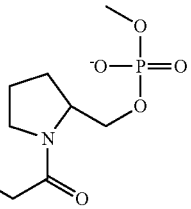

wherein each T'₁, T'₂, and T'₃ is independently selected from the group consisting of a targeting agent, a carbohydrate, a modified carbohydrate, and a carbohydrate derivative.

EMBODIMENT 378

The compound of any of embodiments 354 to 378, wherein one of T'₁, T'₂, or T'₃ comprises a thio sugar.

EMBODIMENT 379

The compound of any of embodiments 354 to 378, wherein one of T'₁, T'₂, or T'₃ comprises an amino sugar.

EMBODIMENT 380

The compound of any of embodiments 354 to 378, wherein one of T'₁, T'₂, or T'₃ is mannose.

EMBODIMENT 381

The compound of any of embodiments 354 to 378, wherein one of T'₁, T'₂, or T'₃ is galactose.

EMBODIMENT 382

The compound of any of embodiments 354 to 378, wherein one of T'₁, T'₂, or T'₃ is D-mannopyranose.

EMBODIMENT 383

The compound of any of embodiments 354 to 378, wherein one of T'₁, T'₂, or T'₃ is L-Mannopyranose.

EMBODIMENT 384

The compound of any of embodiments 354 to 378, wherein one of T'₁, T'₂, or T'₃ is D-Arabinose.

EMBODIMENT 385

The compound of any of embodiments 354 to 378, wherein one of T'₁, T'₂, or T'₃ is L-Galactose.

EMBODIMENT 386

The compound of any of embodiments 354 to 378, wherein one of T'₁, T'₂, or T'₃ is D-xylofuranose.

EMBODIMENT 387

The compound of any of embodiments 354 to 378, wherein one of T'₁, T'₂, or T'₃ is L-xylofuranose.

EMBODIMENT 388

The compound of any of embodiments 354 to 378, wherein one of T'₁, T'₂, or T'₃ is D-glucose.

EMBODIMENT 389

The compound of any of embodiments 354 to 378, wherein one of T'₁, T'₂, or T'₃ is L-glucose.

EMBODIMENT 390

The compound of any of embodiments 354 to 378, wherein one of T'₁, T'₂, or T'₃ is D-Galactose.

EMBODIMENT 391

The compound of any of embodiments 354 to 378, wherein one of T'₁, T'₂, or T'₃ is L-Galactose.

EMBODIMENT 392

The compound of any of embodiments 354 to 378, wherein one of T'₁, T'₂, or T'₃ is α-D-Mannofuranose.

EMBODIMENT 393

The compound of any of embodiments 354 to 378, wherein one of T'₁, T'₂, or T'₃ is β-D-Mannofuranose.

EMBODIMENT 394

The compound of any of embodiments 354 to 378, wherein one of T'₁, T'₂, or T'₃ is α-D-Mannopyranose

EMBODIMENT 395

The compound of any of embodiments 354 to 378, wherein one of $T'_1$, $T'_2$, or $T'_3$ is β-D-Mannopyranose.

EMBODIMENT 396

The compound of any of embodiments 354 to 378, wherein one of $T'_1$, $T'_2$, or $T'_3$ is α-D-Glucopyranose.

EMBODIMENT 397

The compound of any of embodiments 354 to 378, wherein one of $T'_1$, $T'_2$, or $T'_3$ is β-D-Glucopyranose.

EMBODIMENT 398

The compound of any of embodiments 354 to 378, wherein one of $T'_1$, $T'_2$, or $T'_3$ is α-D-Glucofuranose.

EMBODIMENT 399

The compound of any of embodiments 354 to 378, wherein one of $T'_1$, $T'_2$, or $T'_3$ is β-D-Glucofuranose.

EMBODIMENT 400

The compound of any of embodiments 354 to 378, wherein one of $T'_1$, $T'_2$, or $T'_3$ is α-D-fructofuranose.

EMBODIMENT 401

The compound of any of embodiments 354 to 378, wherein one of $T'_1$, $T'_2$, or $T'_3$ is α-D-fructopyranose.

EMBODIMENT 402

The compound of any of embodiments 354 to 378, wherein one of $T'_1$, $T'_2$, or $T'_3$ is α-D-Galactopyranose.

EMBODIMENT 403

The compound of any of embodiments 354 to 378, wherein one of $T'_1$, $T'_2$, or $T'_3$ is β-D-Galactopyranose.

EMBODIMENT 404

The compound of any of embodiments 354 to 378, wherein one of $T'_1$, $T'_2$, or $T'_3$ is α-D-Galactofuranose.

EMBODIMENT 405

The compound of any of embodiments 354 to 378, wherein one of $T'_1$, $T'_2$, or $T'_3$ is β-D-Galactofuranose.

EMBODIMENT 406

The compound of any of embodiments 354 to 378, wherein one of $T'_1$, $T'_2$, or $T'_3$ is glucosamine.

EMBODIMENT 407

The compound of any of embodiments 354 to 378, wherein one of $T'_1$, $T'_2$, or $T'_3$ is sialic acid.

EMBODIMENT 408

The compound of any of embodiments 354 to 378, wherein one of $T'_1$, $T'_2$, or $T'_3$ is α-D-galactosamine.

EMBODIMENT 409

The compound of any of embodiments 354 to 378, wherein one of $T'_1$, $T'_2$, or $T'_3$ is N-Acetylgalactosamine.

EMBODIMENT 410

The compound of any of embodiments 354 to 378, wherein one of $T'_1$, $T'_2$, or $T'_3$ is 2-Amino-3-O—[(R)-1-carboxyethyl]-2-deoxy-β-D-glucopyranose.

EMBODIMENT 411

The compound of any of embodiments 354 to 378, wherein one of $T'_1$, $T'_2$, or $T'_3$ is 2-Deoxy-2-methylamino-L-glucopyranose.

EMBODIMENT 412

The compound of any of embodiments 354 to 378, wherein one of $T'_1$, $T'_2$, or $T'_3$ is 4,6-Dideoxy-4-formamido-2,3-di-O-methyl-D-mannopyranose.

EMBODIMENT 413

The compound of any of embodiments 354 to 378, wherein one of $T'_1$, $T'_2$, or $T'_3$ is 2-Deoxy-2-sulfoamino-D-glucopyranose.

EMBODIMENT 414

The compound of any of embodiments 354 to 378, wherein one of $T'_1$, $T'_2$, or $T'_3$ is N-Glycoloyl-α-neuraminic acid.

EMBODIMENT 415

The compound of any of embodiments 354 to 378, wherein one of $T'_1$, $T'_2$, or $T'_3$ is 5-thio-β-D-glucopyranose.

EMBODIMENT 416

The compound of any of embodiments 354 to 378, wherein one of $T'_1$, $T'_2$, or $T'_3$ is methyl-2,3,4-tri-O-acetyl-1-thio-6-O-trityl-α-D-glucopyranoside.

EMBODIMENT 417

The compound of any of embodiments 354 to 378, wherein one of $T'_1$, $T'_2$, or $T'_3$ is 4-Thio-β-D-galactopyranose.

EMBODIMENT 418

The compound of any of embodiments 354 to 378, wherein one of $T'_1$, $T'_2$, or $T'_3$ is ethyl 3,4,6,7-tetra-O-acetyl-2-deoxy-1,5-dithio-α-D-gluco-heptopyranoside.

EMBODIMENT 419

The compound of any of embodiments 354 to 378, wherein one of $T'_1$, $T'_2$, or $T'_3$ is 2,5-Anhydro-D-allononitrile.

EMBODIMENT 420

The compound of any of embodiments 354 to 378, wherein one of $T'_1$, $T'_2$, or $T'_3$ is pyranose or a pyranose derivative.

EMBODIMENT 421

The compound of any of embodiments 354 to 378, wherein one of $T'_1$, $T'_2$, or $T'_3$ is furanose or a furanose derivative.

EMBODIMENT 422

The compound of any of embodiments 354 to 378, wherein one of $T'_1$, $T'_2$, and $T'_3$ is ribose.

EMBODIMENT 423

The compound of any of embodiments 354 to 378, wherein one of $T'_1$, $T'_2$, and $T'_3$ is D-ribose.

EMBODIMENT 424

The compound of any of embodiments 354 to 378, wherein one of $T'_1$, $T'_2$, and $T'_3$ is D-4-thioribose.

EMBODIMENT 425

The compound of any of embodiments 354 to 378, wherein one of $T'_1$, $T'_2$, and $T'_3$ is L-ribose.

EMBODIMENT 426

The compound of any of embodiments 354 to 378, wherein one of $T'_1$, $T'_2$, and $T'_3$ is L-4-thioribose.

EMBODIMENT 427

The compound of any of embodiments 354 to 378, wherein each of $T'_1$, $T'_2$, and $T'_3$ comprises a thio sugar.

EMBODIMENT 428

The compound of any of embodiments 354 to 378, wherein each of $T'_1$, $T'_2$, and $T'_3$ comprises an amino sugar.

EMBODIMENT 429

The compound of any of embodiments 354 to 378, wherein each of $T'_1$, $T'_2$, and $T'_3$ is mannose.

EMBODIMENT 430

The compound of any of embodiments 354 to 378, wherein each of $T'_1$, $T'_2$, and $T'_3$ is galactose.

EMBODIMENT 431

The compound of any of embodiments 354 to 378, wherein each of $T'_1$, $T'_2$, and $T'_3$ is D-mannopyranose.

EMBODIMENT 432

The compound of any of embodiments 354 to 378, wherein each of $T'_1$, $T'_2$, and $T'_3$ is L-Mannopyranose.

EMBODIMENT 433

The compound of any of embodiments 354 to 378, wherein each of $T'_1$, $T'_2$, and $T'_3$ is D-Arabinose.

EMBODIMENT 434

The compound of any of embodiments 354 to 378, wherein each of $T'_1$, $T'_2$, and $T'_3$ is L-Galactose.

EMBODIMENT 435

The compound of any of embodiments 354 to 378, wherein each of $T'_1$, $T'_2$, and $T'_3$ is D-xylofuranose.

EMBODIMENT 436

The compound of any of embodiments 354 to 378, wherein each of $T'_1$, $T'_2$, and $T'_3$ is L-xylofuranose.

EMBODIMENT 437

The compound of any of embodiments 354 to 378, wherein each of $T'_1$, $T'_2$, and $T'_3$ is D-glucose.

EMBODIMENT 438

The compound of any of embodiments 354 to 378, wherein each of $T'_1$, $T'_2$, and $T'_3$ is L-glucose.

EMBODIMENT 439

The compound of any of embodiments 354 to 378, wherein each of $T'_1$, $T'_2$, and $T'_3$ is D-Galactose.

EMBODIMENT 440

The compound of any of embodiments 354 to 378, wherein each of $T'_1$, $T'_2$, and $T'_3$ is L-Galactose.

EMBODIMENT 441

The compound of any of embodiments 354 to 378, wherein each of $T'_1$, $T'_2$, and $T'_3$ is α-D-Mannofuranose.

EMBODIMENT 442

The compound of any of embodiments 354 to 378, wherein each of $T'_1$, $T'_2$, and $T'_3$ is β-D-Mannofuranose.

EMBODIMENT 443

The compound of any of embodiments 354 to 378, wherein each of $T'_1$, $T'_2$, and $T'_3$ is α-D-Mannopyranose

EMBODIMENT 444

The compound of any of embodiments 354 to 378, wherein each of $T'_1$, $T'_2$, and $T'_3$ is β-D-Mannopyranose.

EMBODIMENT 445

The compound of any of embodiments 354 to 378, wherein each of $T'_1$, $T'_2$, and $T'_3$ is α-D-Glucopyranose.

EMBODIMENT 446

The compound of any of embodiments 354 to 378, wherein each of $T'_1$, $T'_2$, and $T'_3$ is β-D-Glucopyranose.

EMBODIMENT 447

The compound of any of embodiments 354 to 378, wherein each of $T'_1$, $T'_2$, and $T'_3$ is α-D-Glucofuranose.

EMBODIMENT 448

The compound of any of embodiments 354 to 378, wherein each of $T'_1$, $T'_2$, and $T'_3$ is β-D-Glucofuranose.

EMBODIMENT 449

The compound of any of embodiments 354 to 378, wherein each of $T'_1$, $T'_2$, and $T'_3$ is α-D-fructofuranose.

EMBODIMENT 450

The compound of any of embodiments 354 to 378, wherein each of $T'_1$, $T'_2$, and $T'_3$ is α-D-fructopyranose.

EMBODIMENT 451

The compound of any of embodiments 354 to 378, wherein each of $T'_1$, $T'_2$, and $T'_3$ is α-D-Galactopyranose.

EMBODIMENT 452

The compound of any of embodiments 354 to 378, wherein each of $T'_1$, $T'_2$, and $T'_3$ is β-D-Galactopyranose.

EMBODIMENT 453

The compound of any of embodiments 354 to 378, wherein each of $T'_1$, $T'_2$, and $T'_3$ is α-D-Galactofuranose.

EMBODIMENT 454

The compound of any of embodiments 354 to 378, wherein each of $T'_1$, $T'_2$, and $T'_3$ is β-D-Galactofuranose.

EMBODIMENT 455

The compound of any of embodiments 354 to 378, wherein each of $T'_1$, $T'_2$, and $T'_3$ is glucosamine.

EMBODIMENT 456

The compound of any of embodiments 354 to 378, wherein each of $T'_1$, $T'_2$, and $T'_3$ is sialic acid.

EMBODIMENT 457

The compound of any of embodiments 354 to 378, wherein each of $T'_1$, $T'_2$, and $T'_3$ is α-D-galactosamine.

EMBODIMENT 458

The compound of any of embodiments 354 to 378, wherein each of $T'_1$, $T'_2$, and $T'_3$ is N-Acetylgalactosamine.

EMBODIMENT 459

The compound of any of embodiments 354 to 378, wherein each of $T'_1$, $T'_2$, and $T'_3$ is 2-Amino-3-O—[(R)-1-carboxyethyl]-2-deoxy-β-D-glucopyranose.

EMBODIMENT 460

The compound of any of embodiments 354 to 378, wherein each of $T'_1$, $T'_2$, and $T'_3$ is 2-Deoxy-2-methylamino-L-glucopyranose.

EMBODIMENT 461

The compound of any of embodiments 354 to 378, wherein each of $T'_1$, $T'_2$, and $T'_3$ is 4,6-Dideoxy-4-formamido-2,3-di-O-methyl-D-mannopyranose.

EMBODIMENT 462

The compound of any of embodiments 354 to 378, wherein each of $T'_1$, $T'_2$, and $T'_3$ is 2-Deoxy-2-sulfoamino-D-glucopyranose.

EMBODIMENT 463

The compound of any of embodiments 354 to 378, wherein each of $T'_1$, $T'_2$, and $T'_3$ is N-Glycoloyl-α-neuraminic acid.

EMBODIMENT 464

The compound of any of embodiments 354 to 378, wherein each of $T'_1$, $T'_2$, and $T'_3$ is 5-thio-β-D-glucopyranose.

EMBODIMENT 465

The compound of any of embodiments 354 to 378, wherein each of $T'_1$, $T'_2$, and $T'_3$ is methyl 2,3,4-tri-O-acetyl-1-thio-6-O-trityl-α-D-glucopyranoside.

EMBODIMENT 466

The compound of any of embodiments 354 to 378, wherein each of $T'_1$, $T'_2$, and $T'_3$ is 4-Thio-β-D-galactopyranose.

EMBODIMENT 467

The compound of any of embodiments 354 to 378, wherein each of $T'_1$, $T'_2$, and $T'_3$ is ethyl 3,4,6,7-tetra-O-acetyl-2-deoxy-1,5-dithio-α-D-gluco-heptopyranoside.

EMBODIMENT 468

The compound of any of embodiments 354 to 378, wherein each of $T'_1$, $T'_2$, and $T'_3$ is 2,5-Anhydro-D-allono-nitrile.

EMBODIMENT 469

The compound of any of embodiments 354 to 378, wherein each of $T'_1$, $T'_2$, and $T'_3$ is pyranose or a pyranose derivative.

EMBODIMENT 470

The compound of any of embodiments 354 to 378, wherein each of $T'_1$, $T'_2$, and $T'_3$ is furanose or a furanose derivative.

EMBODIMENT 471

The compound of any of embodiments 354 to 378, wherein each of $T'_1$, $T'_2$, and $T'_3$ is ribose.

EMBODIMENT 472

The compound of any of embodiments 354 to 378, wherein each of $T'_1$, $T'_2$, and $T'_3$ is D-ribose.

EMBODIMENT 473

The compound of any of embodiments 354 to 378, wherein each of $T'_1$, $T'_2$, and $T'_3$ is D-4-thioribose.

EMBODIMENT 474

The compound of any of embodiments 354 to 378, wherein each of $T'_1$, $T'_2$, and $T'_3$ is L-ribose.

EMBODIMENT 475

The compound of any of embodiments 354 to 378, wherein each of $T'_1$, $T'_2$, and $T'_3$ is L-4-thioribose.

EMBODIMENT 476

The compound of any of embodiments 1 to 129 or 300 to 333, wherein the conjugate group comprises:

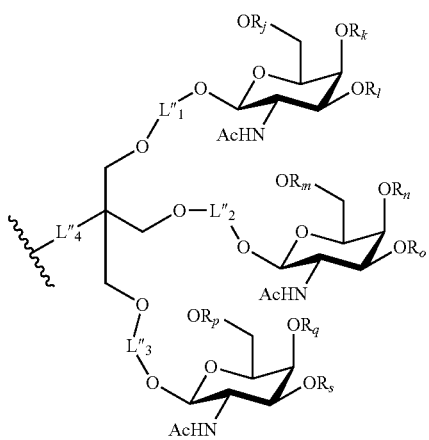

wherein each $L''_1$, $L''_2$, $L''_3$, and $L''_4$ is a linker group; and
wherein each $R_j$, $R_k$, $R_l$, $R_m$, $R_n$, $R_o$, $R_p$, $R_q$, and $R_s$ is independently selected from the group consisting of H, a protecting group, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, amino, and amido.

EMBODIMENT 477

The compound of any of embodiments 1 to 129 or 300 to 333, wherein the conjugate group comprises:

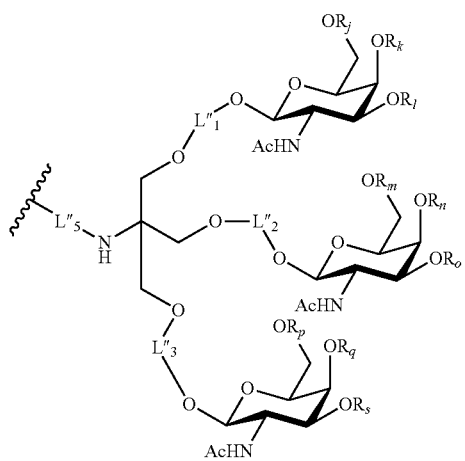

wherein each $L''_1$, $L''_2$, $L''_3$, and $L''_4$ is a linker group$_5$; and
wherein each $R_j$, $R_k$, $R_l$, $R_m$, $R_n$, $R_o$, $R_p$, $R_q$, and $R_s$ is independently selected from the group consisting of H, a protecting group, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, amino, and amido.

EMBODIMENT 478

The compound of any of embodiments 1 to 129 or 300 to 333, wherein the conjugate group comprises:

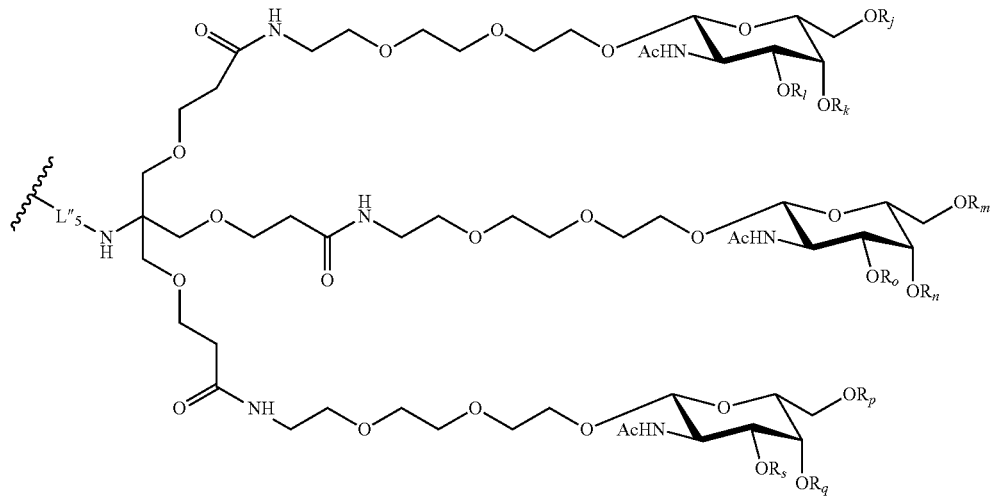

wherein L″$_5$ is a linker group; and
wherein each R$_j$, R$_k$, R$_l$, R$_m$, R$_n$, R$_o$, R$_p$, R$_q$, and R$_s$ is independently selected from the group consisting of H, a protecting group, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_1$-C$_6$ alkoxy, substituted C$_1$-C$_6$ alkoxy, amino, and amido.

EMBODIMENT 479

The compound of any of embodiments 1 to 129 or 300 to 333, wherein the conjugate group comprises:

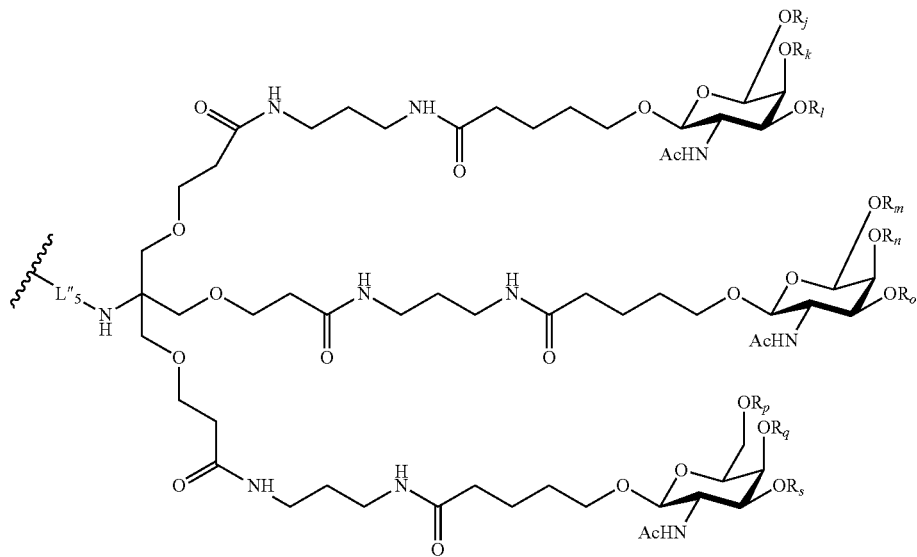

wherein L″$_5$ is a linker group; and
wherein each R$_j$, R$_k$, R$_l$, R$_m$, R$_n$, R$_o$, R$_p$, R$_q$, and R$_s$ is independently selected from the group consisting of H, a protecting group, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_1$-C$_6$ alkoxy, substituted C$_1$-C$_6$ alkoxy, amino, and amido.

EMBODIMENT 480

The compound of any of embodiments 1 to 129 or 300 to 333, wherein the conjugate group comprises:

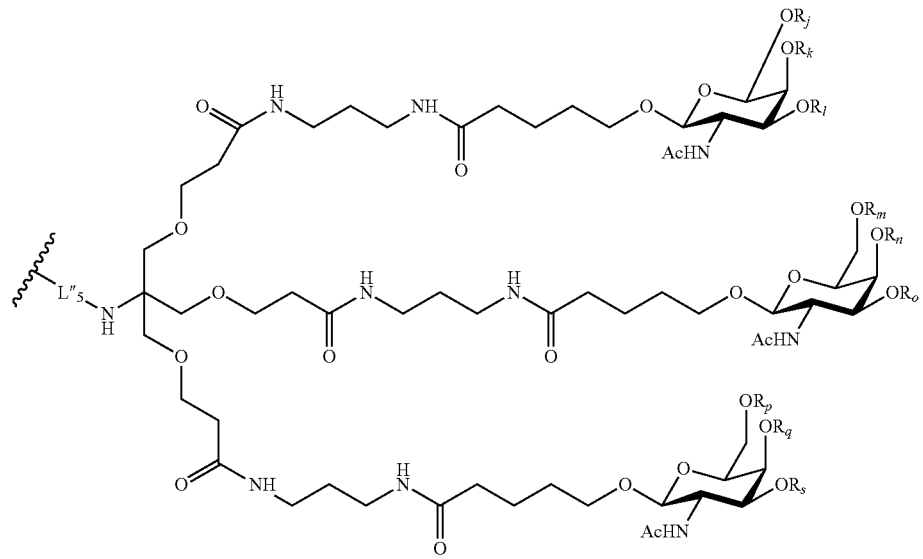

wherein L″₅ is a linker group; and wherein each $R_j$, $R_k$, $R_l$, $R_m$, $R_n$, $R_o$, $R_p$, $R_q$, and $R_s$ is independently selected from the group consisting of H, a protecting group, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, amino, and amido.

EMBODIMENT 481

The compound of any of embodiments 476 to 480, wherein each one of $R_j$, $R_k$, $R_l$, $R_m$, $R_n$, $R_o$, $R_p$, $R_q$, and $R_s$ is H.

EMBODIMENT 482

The compound of any of embodiments 476 to 480, wherein each one of $R_j$, $R_k$, $R_l$, $R_m$, $R_n$, $R_o$, $R_p$, $R_q$, and $R_s$ comprises a protecting group.

EMBODIMENT 483

The compound of embodiment 482, wherein the protecting group comprises an acetate.

EMBODIMENT 484

The compound of any of embodiments 476 to 480, wherein at least one of $R_j$, $R_k$, $R_l$, $R_m$, $R_n$, $R_o$, $R_p$, $R_q$, and $R_s$ is H.

EMBODIMENT 485

The compound of any of embodiments 476 to 480, wherein at least one of $R_j$, $R_k$, $R_l$, $R_m$, $R_n$, $R_o$, $R_p$, $R_q$, and $R_s$ comprises a protecting group.

EMBODIMENT 486

The compound of embodiment 485, wherein the protecting group comprises an acetate.

EMBODIMENT 487

The compound of any of embodiments 1 to 129 or 300 to 333, wherein the conjugate group comprises:

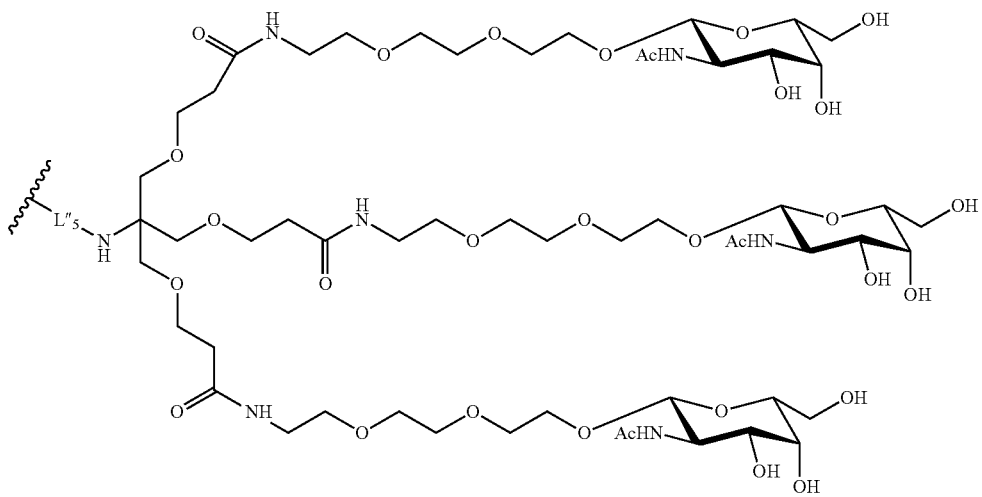

wherein L″₅ is a linker group.

EMBODIMENT 488

The compound of any of embodiments 1 to 129 or 300 to 333, wherein the conjugate group comprises:

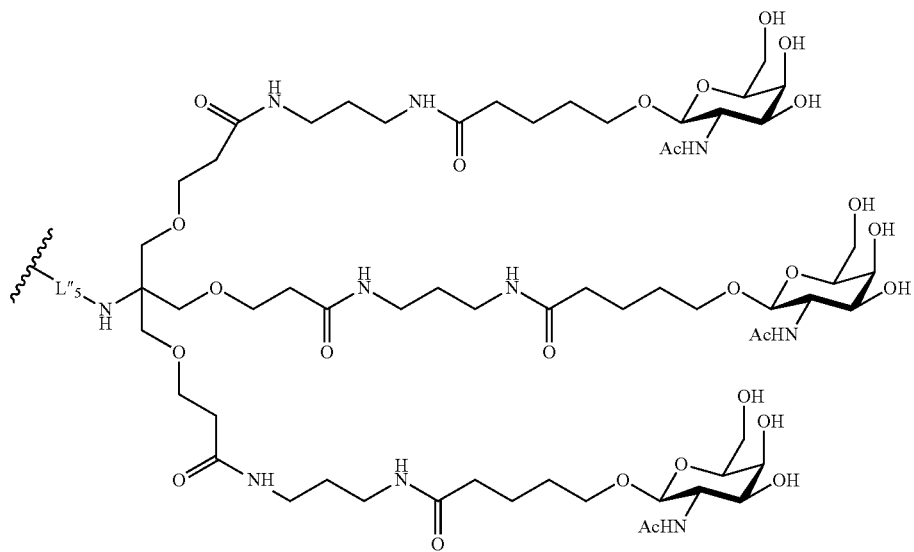
wherein L"₅ is a linker group.
EMBODIMENT 489
The compound of any of embodiments 1 to 129 or 300 to 333, wherein the conjugate group comprises:
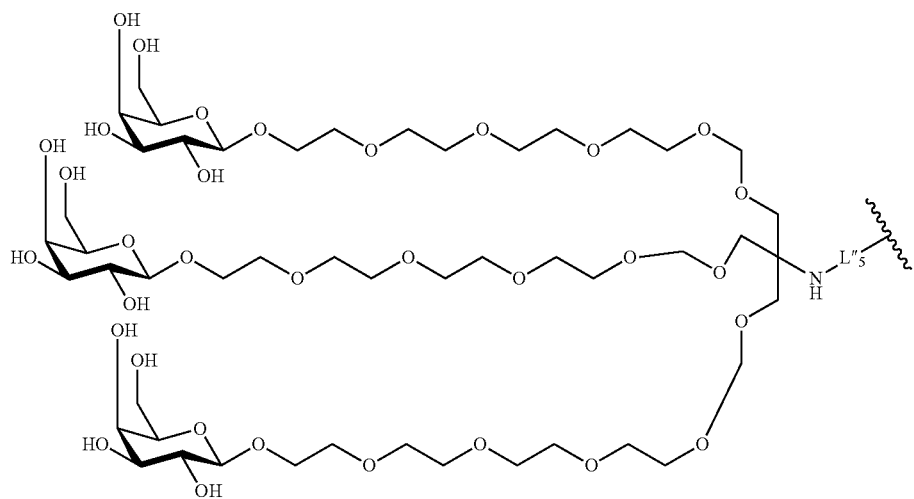
wherein L"₅ is a linker group.
EMBODIMENT 490
The compound of any of embodiments 1 to 129 or 300 to 333, wherein the conjugate group comprises:

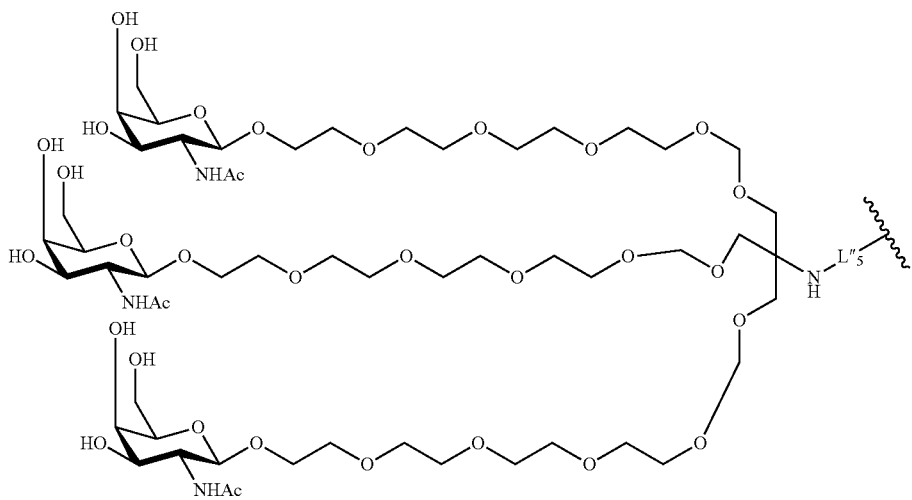

wherein L″₅ is a linker group.

EMBODIMENT 491

The compound of any of embodiments 354 to 490, wherein each linker group is independently selected from the group consisting of a peptide, an ether, polyethylene glycol, alkyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_1$-$C_{20}$ alkoxy, substituted $C_1$-$C_{20}$ alkoxy, amino, amido, pyrrolidine, 8-amino-3,6-dioxaoctanoic acid (ADO), succinimidyl 4-(N-maleimidomethyl)cyclohexane-1-carboxylate, and 6-aminohexanoic acid.

EMBODIMENT 492

The compound of any of embodiments 354 to 490, wherein each one of L″₁, L″₂, L″₃, L″₄, and L″₅, is independently selected from the group consisting of a peptide, an ether, polyethylene glycol, alkyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_1$-$C_{20}$ alkoxy, substituted $C_1$-$C_{20}$ alkoxy, amino, amido, pyrrolidine, 8-amino-3,6-dioxaoctanoic acid (ADO), succinimidyl 4-(N-maleimidomethyl)cyclohexane-1-carboxylate, and 6-aminohexanoic acid.

EMBODIMENT 493

The compound of any of embodiments 1 to 129 or 300 to 333, wherein the conjugate group comprises:

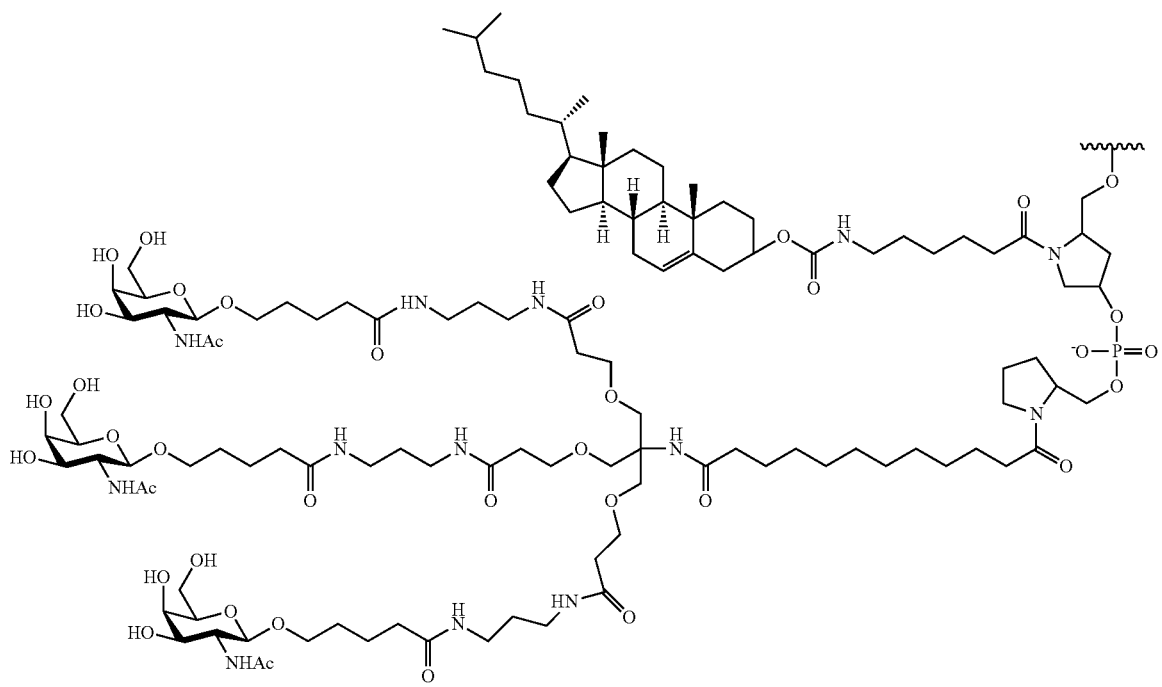

EMBODIMENT 494
The compound of any of embodiments 1 to 129 or 300 to 333, wherein the conjugate group comprises:
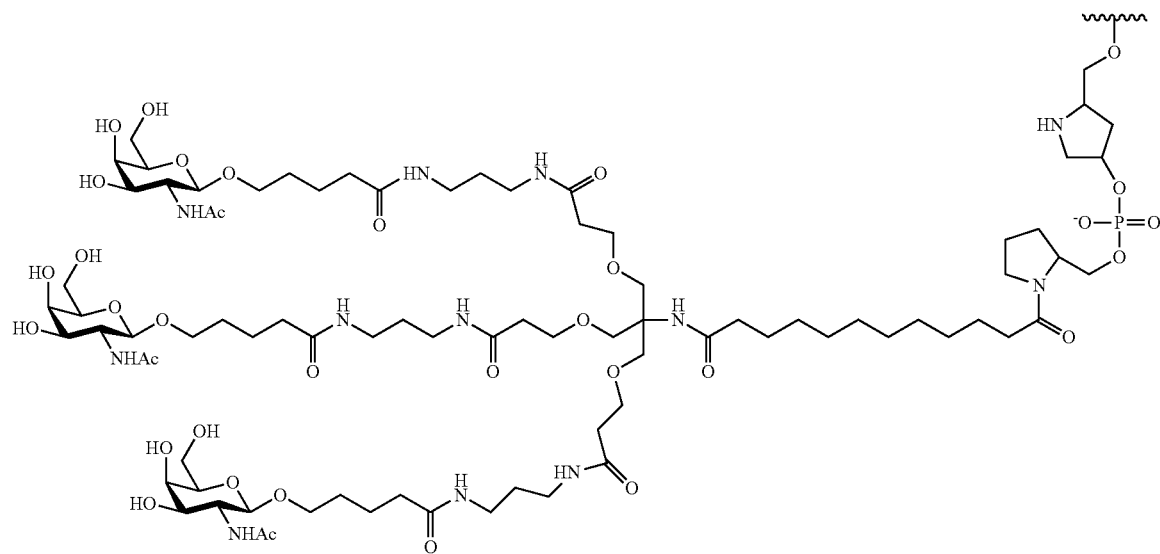
EMBODIMENT 495
The compound of any of embodiments 1 to 129 or 300 to 333, wherein the conjugate group comprises:
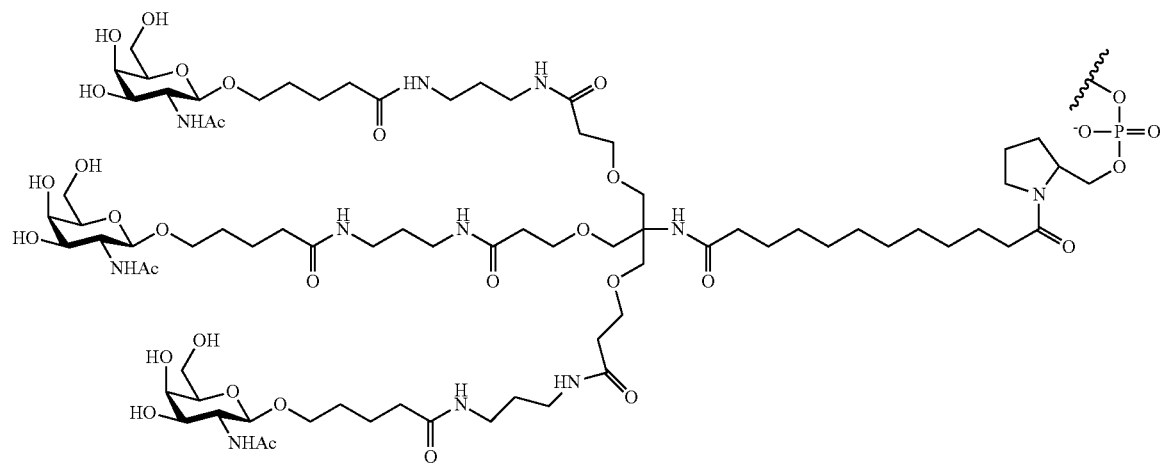

EMBODIMENT 496
The compound of any of embodiments 1 to 129 or 300 to 333, wherein the conjugate group comprises:
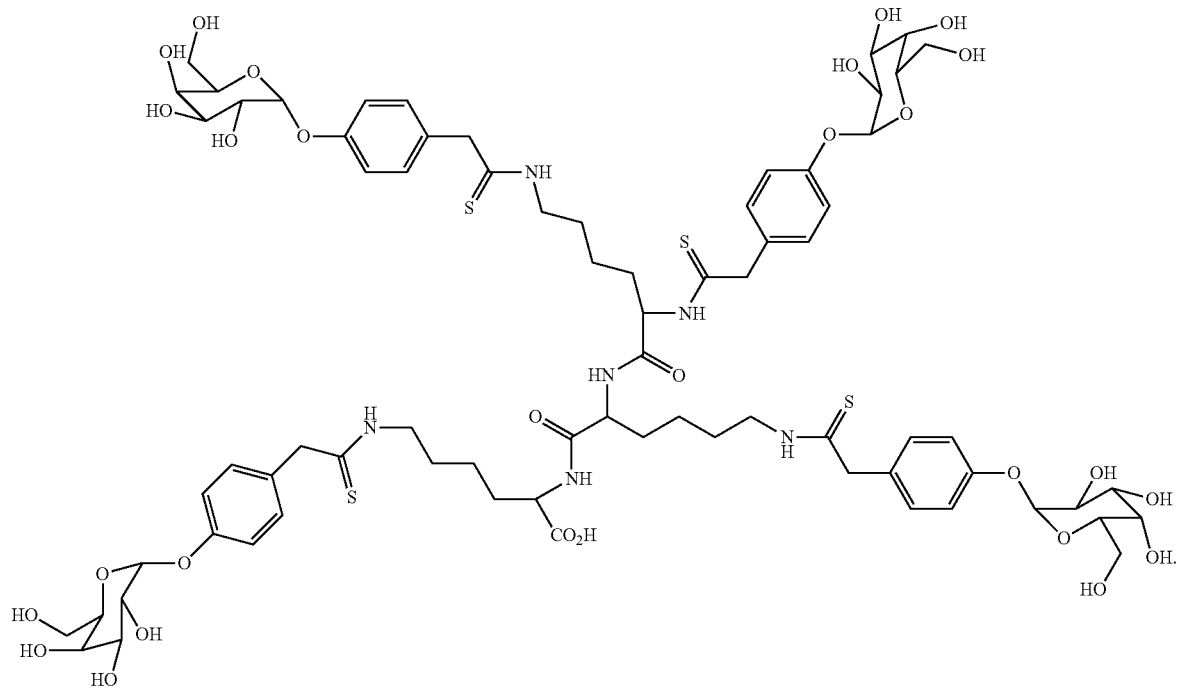 [SMILES: O=C(O)C(CCCCNC(=S)Cc1ccc(OC2OC(CO)C(O)C(O)C2O)cc1)NC(=O)C(CCCCNC(=S)Cc1ccc(OC2OC(CO)C(O)C(O)C2O)cc1)NC(=O)C(CCCCNC(=S)Cc1ccc(OC2OC(CO)C(O)C(O)C2O)cc1)NC(=S)Cc1ccc(OC2OC(CO)C(O)C(O)C2O)cc1]
EMBODIMENT 497
The compound of any of embodiments 1 to 129 or 300 to 333, wherein the conjugate group comprises:
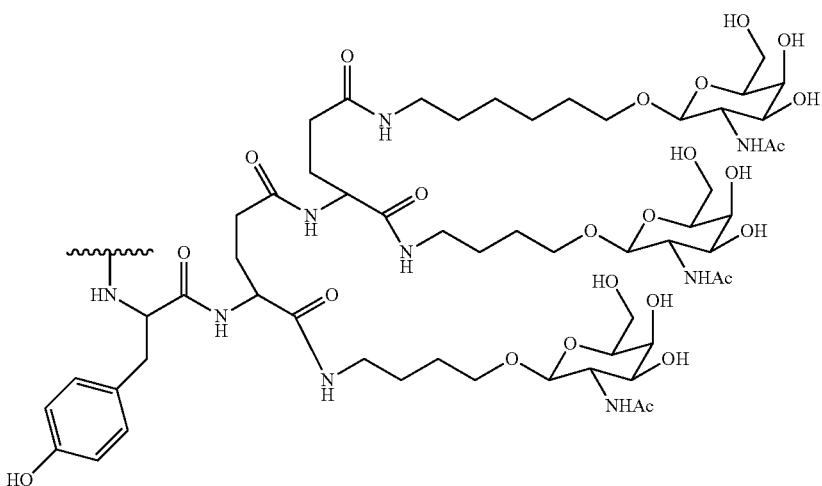 [SMILES: *NC(Cc1ccc(O)cc1)C(=O)NC(CCC(=O)NC(CCC(=O)NCCCCCCOC1OC(CO)C(O)C(O)C1NC(C)=O)C(=O)NCCCCOC1OC(CO)C(O)C(O)C1NC(C)=O)C(=O)NCCCCOC1OC(CO)C(O)C(O)C1NC(C)=O]

EMBODIMENT 498

The compound of any of embodiments 1 to 129 or 300 to 333, wherein the conjugate group comprises arachidonoyl.

EMBODIMENT 499

The compound of any of embodiments 1 to 323, wherein the conjugate group increases the binding affinity towards higher molecular weight proteins.

EMBODIMENT 500

The compound of any of embodiments 1 to 323, wherein the conjugate group increases the binding affinity towards higher molecular weight plasma proteins.

EMBODIMENT 501

The compound of any of embodiments, 1 to 500 wherein the conjugate group decreases the binding affinity towards higher molecular weight plasma proteins.

EMBODIMENT 502

The compound of any of embodiments, 1 to 500 wherein the conjugate group increases the stability of the compound.

EMBODIMENT 503

The compound of any of embodiments, 1 to 500 wherein the conjugate group increases the concentration of the compound in the liver.

EMBODIMENT 504

The compound of any of embodiments, 1 to 500 wherein the conjugate group increases the affinity of the compound in the liver.

EMBODIMENT 505

The compound of any of embodiments, 1 to 500 wherein the conjugate group modulates the amount or activity of a target nucleic acid in the liver.

EMBODIMENT 506

The compound of any of embodiments, 1 to 500 wherein the conjugate group decreases the amount or activity of a target nucleic acid in the liver.

EMBODIMENT 507

The compound of any of embodiments, 1 to 500 wherein the conjugate group increases the concentration of the compound in adipose tissue.

EMBODIMENT 508

The compound of any of embodiments, 1 to 500 wherein the conjugate group increases the affinity of the compound in adipose tissue.

EMBODIMENT 509

The compound of any of embodiments, 1 to 500 wherein the conjugate group modulates the amount or activity of a target nucleic acid in adipose tissue.

EMBODIMENT 510

The compound of any of embodiments, 1 to 500 wherein the conjugate group decreases the amount or activity of a target nucleic acid in adipose tissue.

EMBODIMENT 511

The compound of any of embodiments 499 to 510, wherein the conjugate comprises a group selected from $C_{16}$, cholesterol, and $C_8$.

EMBODIMENT 512

The compound of any of embodiments 499 to 510, wherein the conjugate comprises $C_{16}$.

EMBODIMENT 513

The compound of any of embodiments 499 to 510, wherein the conjugate comprises cholesterol.

EMBODIMENT 514

The compound of any of embodiments 499 to 510, wherein the conjugate comprises $C_8$.

EMBODIMENT 515

The compound of any of embodiments 1 to 514, wherein the conjugate group comprises a linker group.

EMBODIMENT 516

The compound of any of embodiments 1 to 514, wherein the conjugate group consists of a conjugate.

EMBODIMENT 517

The compound of any of embodiments 1 to 129 or 300 to 333, wherein the conjugate group comprises a cell penetrating peptide.

EMBODIMENT 518

The compound of any of embodiments 1 to 517, wherein the compound is single-stranded.

EMBODIMENT 519

A double-stranded composition comprising:
a first oligomeric compound and a second oligomeric compound; wherein the first oligomeric compound is partially complementary to the second oligomeric compound and the second oligomeric compound is complementary to a nucleic acid target; and wherein at least one of the first compound comprises an oligomeric compound according to any one of embodiments 1 to 496.

EMBODIMENT 520

The double-stranded compound of embodiment 519, wherein the second oligomeric compound comprises a compound according to any one of embodiments 1 to 517.

EMBODIMENT 521

The double-stranded compound of embodiment 499, wherein the first oligomeric compound comprises a compound according to any one of embodiments 1 to 517.

EMBODIMENT 522

A pharmaceutical composition comprising the compound of any one of embodiments 1 to 517 and a pharmaceutically acceptable carrier or diluent.

EMBODIMENT 523

A pharmaceutical composition comprising a therapeutically effective amount of the compound of any one of embodiments 1 to 517 and a pharmaceutically acceptable carrier or diluent.

EMBODIMENT 524

A method of inhibiting protein expression in a cell by contacting the cell with the oligomeric compound according to any one of embodiments 1 to 517 or the pharmaceutical composition of embodiment 522 or 523.

EMBODIMENT 525

A method of treating or ameliorating a disease or condition comprising administering an effective amount of the oligomer compound of any one of embodiments 1 to 516 or the pharmaceutical composition of embodiment 522 or 523.

EMBODIMENT 526

The method of embodiment 525, wherein the disease or condition is selected from the group consisting of cardiovascular disease, metabolic disease, cancer, inflammatory disease, and neurodegenerative disease.

EMBODIMENT 527

Use of the compound of any of embodiments 1 to 517 or the pharmaceutical composition of embodiment 522 or 523, for the preparation of a medicament for treating a disease or condition.

EMBODIMENT 528

Use of the compound of any of embodiments 1 to 517 or the pharmaceutical composition of embodiment 522 or 523, to activate the RISC pathway.

EMBODIMENT 529

Use of the compound of any of embodiments 1 to 517 or the pharmaceutical composition of embodiment 522 or 523, to activate RNAi in a cell.

DETAILED DESCRIPTION

Figure 1:
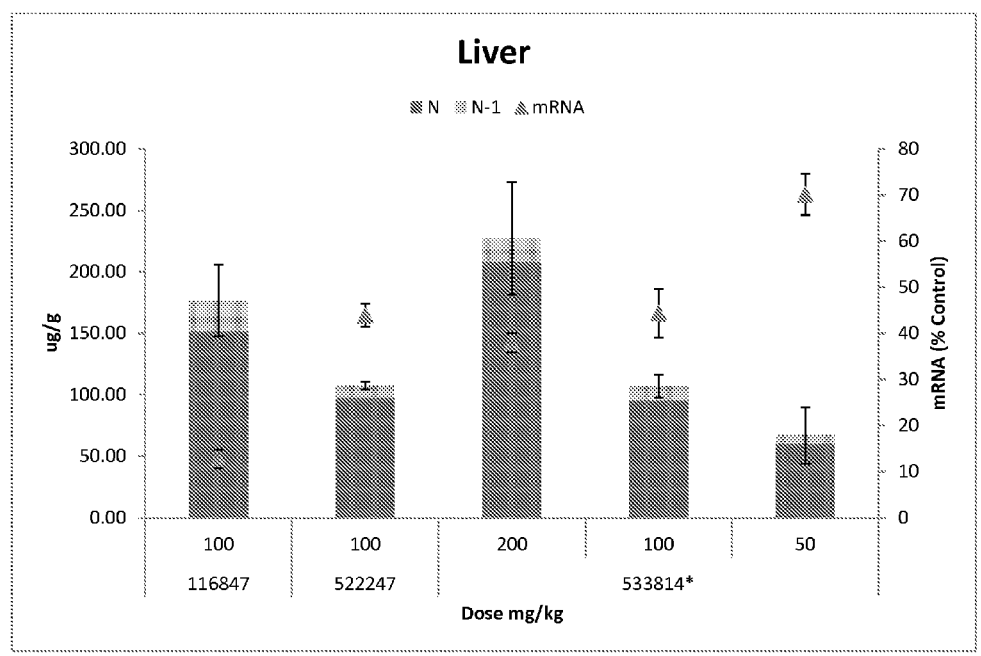
FIG. 1 illustrates the accumulation of C10 conjugated ASOs and ASOs without conjugates in the liver.

It is to be understood that both the foregoing general description and the following detailed description are exemplary and explanatory only and are not restrictive of the disclosure. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. DEFINITIONS

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications)

and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein, "2'-F ANA" refers to a 2'-F substituted nucleoside, wherein the fluoro group is in the arabino position.

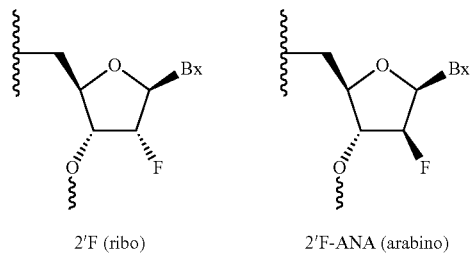

2'F (ribo)　　　　　　2'F-ANA (arabino)

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2' bridge.

As used herein, "locked nucleic acid nucleoside" or "LNA" means a nucleoside comprising a bicyclic sugar moiety comprising a 4'-CH$_2$—O-2' bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 2'-endo furanosyl nucleosides and RNA surrogates.

As used herein, "2'-endo-furanosyl nucleoside" means an RNA-like nucleoside that comprises a substituted sugar moiety that has a 2'-endo conformation. 2'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "phosphorous moiety" refers to a to monovalent $P^V$ phosphorus radical group. In certain embodiments, a phosphorus moiety is selected from: a phosphate, phosphonate, alkylphosphonate, aminoalkyl phosphonate, phosphorothioate, phosphoramidite, alkylphosphonothioate, phosphorodithioate, thiophosphoramidate, phosphotriester and the like.

In certain embodiments, modified phosphorous moieties have the following structural formula:

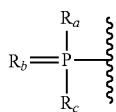

wherein:
$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and
$R_b$ is O or S.

The term "phosphate moiety" as used herein, refers to a terminal phosphate group that includes unmodified phosphates (—O—P(=O)(OH)OH) as well as modified phosphates. Modified phosphates include but are not limited to phosphates in which one or more of the O and OH groups is replaced with H, O, S, N(R) or alkyl where R is H, an amino protecting group or unsubstituted or substituted alkyl.

As used herein, "phosphate stabilizing modification" refers to a modification that results in stabilization of a 5'-phosphate moiety of the 5'-terminal nucleoside of an oligonucleotide, relative to the stability of an unmodified 5'-phosphate of an unmodified nucleoside under biologic conditions. Such stabilization of a 5'-phosphate group includes but is not limited to resistance to removal by phosphatases. Phosphate stabilizing modifications include, but are not limited to, modification of one or more of the atoms that binds directly to the phosphorus atom, modification of one or more atoms that link the phosphorus to the 5'-carbon of the nucleoside, and modifications at one or more other positions of the nucleoside that result in stabilization of the phosphate. Phosphate moieties that are stabilized by one or more phosphate stabilizing modification are referred to herein as "stabilized phosphate moieties."

In certain embodiments, compounds of the present invention comprise oligonucleotides comprising a stabilized phosphate moiety at the 5'-terminus. In certain such embodiments, the phosphorus atom of the stabilized phosphate moiety is attached to the 5'-terminal nucleoside through a phosphorus-carbon bond. In certain embodiments, the carbon of that phosphorus-carbon bond is in turn bound to the 5'-position of the nucleoside.

In certain embodiments, the oligonucleotide optionally comprises a conjugate group and optionally comprises a 5'-stabilized phosphate moiety having the following formula:

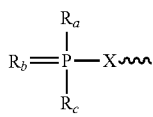

wherein:
$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino;
$R_b$ is O or S;
X is substituted or unsubstituted C; and wherein X is attached to the 5'-terminal nucleoside. In certain embodiments, X is bound to an atom at the 5'-position of the 5'-terminal nucleoside. In certain such embodiments, the 5'-atom is a carbon and the bond between X and the 5'-carbon of the 5'-terminal nucleoside is a carbon-carbon single bond. In certain embodiments, it is a carbon-carbon double bond. In certain embodiments, it is a carbon-carbon triple bond. In certain embodiments, the 5'-carbon is substituted. In certain embodiments, X is substituted. In certain embodiments, X is unsubstituted.

In certain embodiments, the oligonucleotide optionally comprises a conjugate group and comprises a 5'-stabilized phosphate moiety having the following formula:

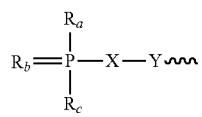

wherein:
$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino;
$R_b$ is O or S;
X is substituted or unsubstituted C;
Y is selected from C, S, and N. In certain embodiments, Y is substituted or unsubstituted C. The bond between X and Y may be a single-, double-, or triple-bond.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" or "conjugate group" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "linking group" means any atom or group of atoms used to attach a conjugate to an oligonucleotide or oligomeric compound, or any atom or group of atoms used to attach or connect two different moieties, substrates, linkers, or scaffolds together.

As used herein, "multivalent carbohydrate cluster" means any compound having one or more carbohydrate residues attached to a scaffold or linker group. (see, e.g., Maier et al., "Synthesis of Antisense Oligonucleotides Conjugated to a Multivalent Carbohydrate Cluster for Cellular Targeting," *Bioconjugate Chemistry,* 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications.

As used herein, "carbohydrate derivative" means any compound which may be synthesized using a carbohydrate as a starting material or intermediate.

As used herein "protecting group" means any compound or protecting group known to those having skill in the art. Non-limiting examples of protecting groups may be found in "Protective Groups in Organic Chemistry", T. W. Greene, P. G. M. Wuts, ISBN 0-471-62301-6, John Wiley & Sons, Inc, New York, which is incorporated herein by reference in its entirety.

As used herein, "single-stranded" means an oligomeric compound that is not hybridized to its complement and which lacks sufficient self-complementarity to form a stable self-duplex.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenylation, addition of 5'-cap), and translation.

As used herein, "target nucleic acid" means a nucleic acid molecule to which an antisense compound hybridizes.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substitutent is any atom or group at the 2'-position of a nucleoside other than H or OH). Substituent groups can be protected or unprotected. In certain embodiments, compounds of the present disclosure have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino (=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)$OR_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2$ $R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "oligonucleotide-conjugate complex" means an oligonucleotide comprising one or more conjugate groups attached to one or more nucleosides on the oligonucleotide.

As used herein, unless otherwise indicated or modified, the term "double-stranded" refers to two separate oligomeric compounds that are hybridized to one another. Such double stranded compounds may have one or more or non-hybridizing nucleosides at one or both ends of one or both strands (overhangs) and/or one or more internal non-hybridizing nucleosides (mismatches) provided there is sufficient complementarity to maintain hybridization under physiologically relevant conditions.

B. CERTAIN COMPOUNDS

In certain embodiments, oligomeric compounds comprising one or more conjugates are described. In certain embodiments, oligomeric compounds comprising an oligonucleotide and a conjugate group and/or terminal group are described. In certain embodiments, oligomeric compounds comprising an oligonucleotide and a conjugate group selectively placed at a nucleoside are described.

a. Certain 5'-Terminal Nucleosides

In certain embodiments, compounds of the present disclosure comprise oligonucleotides comprising a stabilized phosphate moiety at the 5'-terminus. In certain embodiments, such oligonucleotides comprise a 5' terminal nucleoside having Formula I:

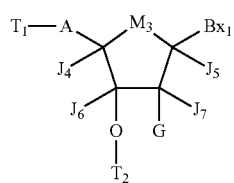

I wherein:

$T_1$ is a phosphorus moiety;

$T_2$ is an internucleoside linking group linking the nucleoside of Formula I to the remainder of the oligonucleotide;

A has one of the formulas:

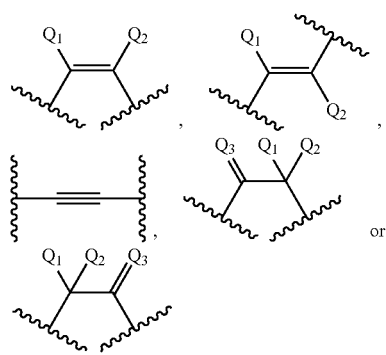

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})$=$C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

one of $Bx_1$ and $Bx_2$ is a nucleobase and the other of $Bx_1$ and $Bx_2$, if present, is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with either $J_5$ or $J_7$ wherein said bridge comprises from 1 to 3 linked biradical groups selected from O, S, $NR_{19}$, $C(R_{20})(R_{21})$, $C(R_{20})$=$C(R_{21})$, $C[$=$C(R_{20})(R_{21})]$ and $C($=$O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C$=$O)_m$—$X_1]_j$—Z, or a conjugate group;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, =$NJ_1$, $SJ_1$, $N_3$, CN, $OC($=$X_2)J_1$, $OC($=$X_2)N(J_1)(J_2)$ and $C($=$X_2)N(J_1)(J_2)$;

$X_2$ is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, oligonucleotides comprise a 5'-terminal nucleoside having Formula II:

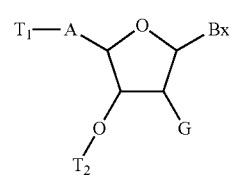

II wherein:

Bx is a nucleobase;

$T_1$ is an phosphorus moiety;

$T_2$ is an internucleoside linking group linking the compound of Formula II to the remainder of the oligonucleotide;

A has one of the formulas:

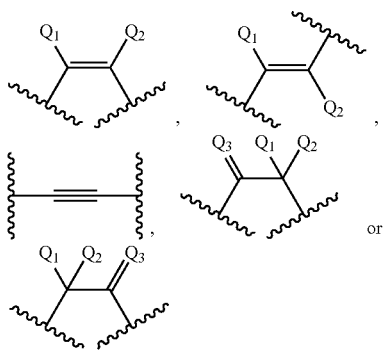

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen, O—$[C(R_8)(R_9)]_n$—$[(C=O)_m$—$X]_j$—Z, or a conjugate group;

each $R_8$ and $R_9$ is, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, =$NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, oligonucleotides comprise a 5'-terminal nucleoside having Formula III:

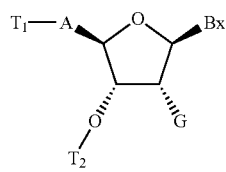

III wherein:

Bx is a nucleobase;

$T_1$ is a phosphorus moiety;

$T_2$ is an internucleoside linking group linking the compound of Formula III to the remainder of the oligonucleotide;

A has one of the formulas:

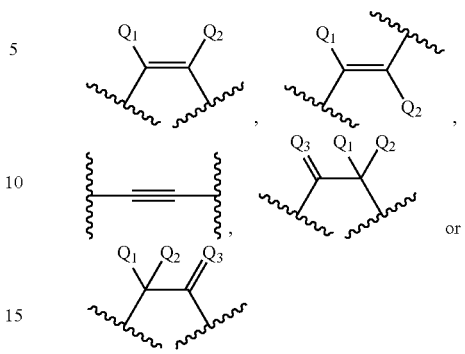

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen, O—$[C(R_8)(R_9)]_n$—$[(C=O)_m$—$X]_j$—Z, or a conjugate group;

each $R_8$ and $R_9$ is, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, =$NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, oligonucleotides comprise a 5'-terminal nucleoside having Formula IV:

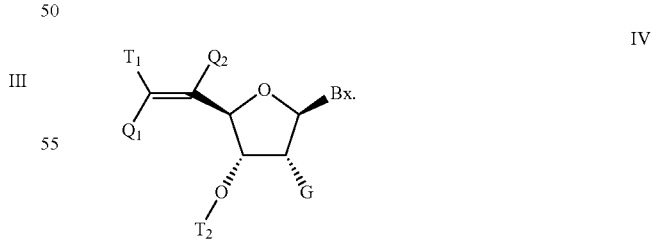

IV

In certain embodiments, oligonucleotides are provided comprising a compound having Formula IV wherein $Q_1$ and $Q_2$ are each H. In certain embodiments, oligonucleotide are provided comprising a compound having Formula IV wherein G is $O(CH_2)_2OCH_3$.

In certain embodiments, oligonucleotides comprise a 5'-terminal nucleoside having Formula IV:

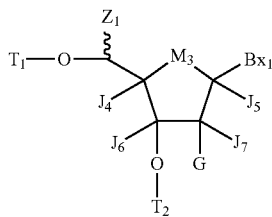

V wherein:
T$_1$ is an optionally protected phosphorus moiety;
T$_2$ is an internucleoside linking group linking the compound of Formula I to the remainder of the oligomeric compound;
Z$_1$C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl or substituted C$_2$-C$_6$ alkynyl;
M$_1$ is H, OH or OR$_1$;
M$_2$ is OH, OR$_1$ or N(R$_1$)(R$_2$);
each R$_1$ and R$_2$ is, independently, C$_1$-C$_6$ alkyl, substituted C$_1$-C$_6$ alkyl;
r is 0 or 1;
each R$_3$, R$_4$, R$_5$, R$_6$ and R$_7$ is, independently, H, C$_1$-C$_6$ alkyl, substituted C$_1$-C$_6$ alkyl or C$_1$-C$_6$ alkoxy;
M$_3$ is O, S, NR$_{14}$, C(R$_{15}$)(R$_{16}$), C(R$_{15}$)(R$_{16}$)C(R$_{17}$)(R$_{18}$), C(R$_{15}$)=C(R$_{17}$), OC(R$_{15}$)(R$_{16}$) or OC(R$_{15}$)(Bx$_2$);
R$_{14}$ is H, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
R$_{15}$, R$_{16}$, R$_{17}$ and R$_{18}$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
one of Bx$_1$ and Bx$_2$ is a heterocyclic base moiety and the other of Bx$_1$ and Bx$_2$, if present, is H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
J$_4$, J$_5$, J$_6$ and J$_7$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
or J$_4$ forms a bridge with either J$_5$ or J$_7$ wherein said bridge comprises from 1 to 3 linked biradical groups selected from O, S, NR$_{19}$, C(R$_{20}$)(R$_{21}$), C(R$_{20}$)=C(R$_{21}$), C[=C(R$_{20}$)(R$_{21}$)] and C(=O) and the other two of J$_5$, J$_6$ and J$_7$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
each R$_{19}$, R$_{20}$ and R$_{21}$ is, independently, H, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
G is H, OH, halogen, a conjugate group, or O—[C(R$_8$)(R$_9$)]$_n$—[(C=O)$_m$—X$_1$]$_j$—Z;
each R$_8$ and R$_9$ is, independently, H, halogen, C$_1$-C$_6$ alkyl or substituted C$_1$-C$_6$ alkyl;
X$_1$ is O, S or N(E$_1$);
Z is H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl or N(E$_2$)(E$_3$);
E$_1$, E$_2$ and E$_3$ are each, independently, H, C$_1$-C$_6$ alkyl or substituted C$_1$-C$_6$ alkyl;
n is from 1 to about 6;
m is 0 or 1;
j is 0 or 1;
each substituted group comprises one or more optionally protected substituent groups independently selected from halogen, OJ$_1$, N(J$_1$)(J$_2$), =NJ$_1$, SJ$_1$, N$_3$, CN, OC(=X$_2$)J$_1$, OC(=X$_2$)N(J$_1$)(J$_2$) and C(=X$_2$)N(J$_1$)(J$_2$);
X$_2$ is O, S or NJ$_3$;
each J$_1$, J$_2$ and J$_3$ is, independently, H or C$_1$-C$_6$ alkyl; and
when j is 1 then Z is other than halogen or N(E$_2$)(E$_3$).

In certain embodiments, oligonucleotides comprise a 5'-terminal nucleoside having Formula VI:

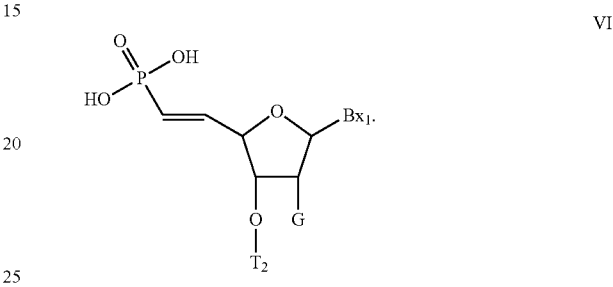

VI

In certain embodiments, oligonucleotides comprise a nucleoside of Formula I, II, III, IV, V, or VI. In certain such embodiments, the nucleoside of Formula I, II, III, IV, V, or VI is at the 5'-terminus. In certain such embodiments, the remainder of the oligonucleotide comprises one or more modifications. Such modifications may include modified sugar moieties, modified nucleobases and/or modified internucleoside linkages. Certain such modifications which may be incorporated in an oligonucleotide comprising a nucleoside of Formula I, II, III, IV, V, or VI at the 5'-terminus are known in the art.

b. Certain Sugar Moieties

In certain embodiments, compounds of the disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, $CF_3$, $OCF_3$, O, S, or $N(R_m)$-alkyl; O, S, or $N(R_m)$-alkenyl; O, S or $N(R_m)$-alkynyl; O-alkylenyl-O-alkyl, alkynyl, alkaryl, aralkyl, O-alkaryl, O-aralkyl, $O(CH_2)_2SCH_3$, $O-(CH_2)_2-O-N(R_m)(R_n)$ or $O-CH_2-C(=O)-N(R_m)(R_n)$, where each $R_m$ and $R_n$ is, independently, H, an amino protecting group or substituted or unsubstituted $C_1-C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, $O-CH_3$, $O(CH_2)_3NH_2$, $CH_2-CH=CH_2$, $O-CH_2-CH=CH_2$, $OCH_2CH_2OCH_3$, $O(CH_2)_2SCH_3$, $O-(CH_2)_2-O-N(R_m)(R_n)$, $O(CH_2)_2O(CH_2)_2N(CH_3)_2$, and N-substituted acetamide ($O-CH_2-C(=O)-N(R_m)(R_n)$) where each $R_m$ and $R_n$ is, independently, H, an amino protecting group or substituted or unsubstituted $C_1-C_{10}$ alkyl.

In certain embodiments, a 2'-substituted nucleoside comprises a sugar moiety comprising a 2'-substituent group selected from F, $OCF_3$, $O-CH_3$, $OCH_2CH_2OCH_3$, $O(CH_2)_2SCH_3$, $O-(CH_2)_2-O-N(CH_3)_2$, $-O(CH_2)_2O(CH_2)_2N(CH_3)_2$, and $O-CH_2-C(=O)-N(H)CH_3$.

In certain embodiments, a 2'-substituted nucleoside comprises a sugar moiety comprising a 2'-substituent group selected from F, $O-CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: $-[C(R_a)(R_b)]_n-$, $-[C(R_a)(R_b)]_n-O-$, $-C(R_aR_b)-N(R)-O-$ or, $-C(R_aR_b)-O-N(R)-$; 4'- $CH_2$-2', 4'-$(CH_2)_2$-2', 4'-$(CH_2)_3$-2', 4'-$(CH_2)-O$-2' (LNA); 4'-$(CH_2)-S$-2; 4'-$(CH_2)_2-O$-2' (ENA); 4'-$CH(CH_3)-O$-2' (cEt) and 4'-CH($CH_2OCH_3$)-O-2', and analogs thereof (see, e.g., U.S. Pat. No. 7,399,845, issued on Jul. 15, 2008); 4'-$C(CH_3)(CH_3)-O$-2' and analogs thereof, (see, e.g., WO2009/006478, published Jan. 8, 2009); 4'-$CH_2-N(OCH_3)$-2' and analogs thereof (see, e.g., WO2008/150729, published Dec. 11, 2008); 4'-$CH_2-O-N(CH_3)$-2' (see, e.g., US2004/0171570, published Sep. 2, 2004); 4'-$CH_2-O-N(R)$-2', and 4'-$CH_2-N(R)-O$-2'-, wherein each R is, independently, H, a protecting group, or $C_1-C_{12}$ alkyl; 4'-$CH_2-N(R)-O$-2', wherein R is H, $C_1-C_{12}$ alkyl, or a protecting group (see, U.S. Pat. No. 7,427,672, issued on Sep. 23, 2008); 4'-$CH_2-C(H)(CH_3)$-2' (see, e.g., Chattopadhyaya, et al., *J. Org. Chem.*, 2009, 74, 118-134); and 4'-$CH_2-C(=CH_2)$-2' and analogs thereof (see, published PCT International Application WO 2008/154401, published on Dec. 8, 2008).

In certain embodiments, such 4' to 2' bridges independently comprise from 1 to 4 linked groups independently selected from $-[C(R_a)(R_b)]_n-$, $-C(R_a)=C(R_b)-$, $-C(R_a)=N-$, $-C(=NR_a)-$, $-C(=O)-$, $-C(=S)-$, $-O-$, $-Si(R_a)_2-$, $-S(=O)_x-$, and $-N(R_a)-$;

wherein:

x is 0, 1, or 2;

n is 1, 2, 3, or 4;

each $R_a$ and $R_b$ is, independently, H, a protecting group, hydroxyl, $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl, $C_5-C_{20}$ aryl, substituted $C_5-C_{20}$ aryl, heterocycle radical, substituted heterocycle radical, heteroaryl, substituted heteroaryl, $C_5-C_7$ alicyclic radical, substituted $C_5-C_7$ alicyclic radical, halogen, $OJ_1$, $NJ_1J_2$, $SJ_1$, $N_3$, $COOJ_1$, acyl (C(=O)-H), substituted acyl, CN, sulfonyl ($S(=O)_2-J_1$), or sulfoxy ($S(=O)-J_1$); and each $J_1$ and $J_2$ is, independently, H, $C_1-C_{12}$ alkyl, substituted $C_1-C_{12}$ alkyl, $C_2-C_{12}$ alkenyl, substituted $C_2-C_{12}$ alkenyl, $C_2-C_{12}$ alkynyl, substituted $C_2-C_{12}$ alkynyl, $C_5-C_{20}$ aryl, substituted $C_5-C_{20}$ aryl, acyl (C(=O)-H), substituted acyl, a heterocycle radical, a substituted heterocycle radical, $C_1-C_{12}$ aminoalkyl, substituted $C_1-C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2-O$-2') BNA, (B) β-D-Methyleneoxy (4'-$CH_2-O$-2') BNA (also referred to as locked nucleic acid or LNA), (C) Ethyleneoxy (4'-$(CH_2)_2-O$-2') BNA, (D) Aminooxy (4'-$CH_2-O-N(R)$-2') BNA, (E) Oxyamino (4'-$CH_2-N(R)-O$-2') BNA, (F) Methyl(methyleneoxy) (4'-$CH(CH_3)-O$-2') BNA (also referred to as constrained ethyl or cEt), (G) methylene-thio (4'-$CH_2-S$-2') BNA, (H) methylene-amino (4'-CH2-N(R)-2') BNA, (I) methyl carbocyclic (4'-$CH_2-CH(CH_3)$-2') BNA, and (J) propylene carbocyclic (4'-$(CH_2)_3$-2') BNA as depicted below.

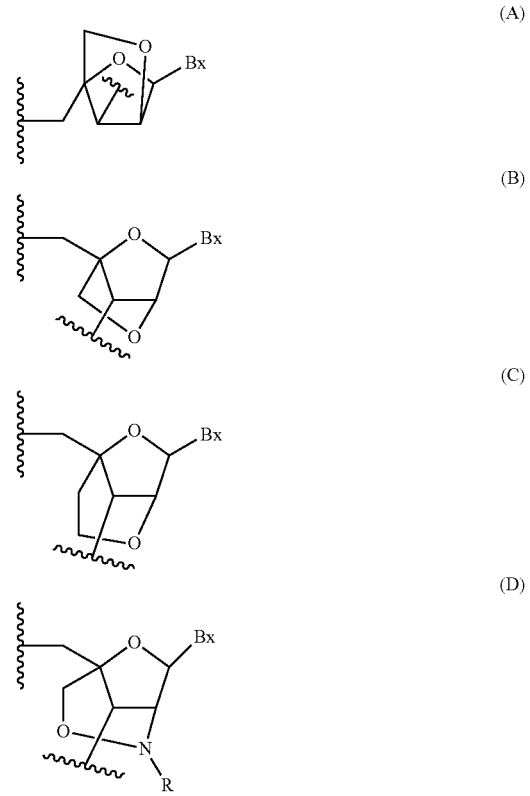

(E)
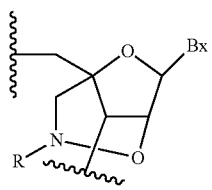

(F)
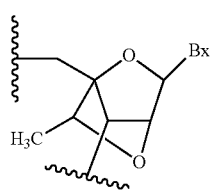

(G)
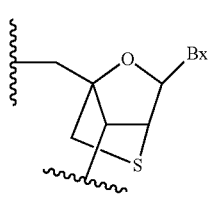

(H)
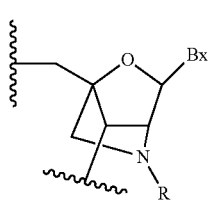

(I)
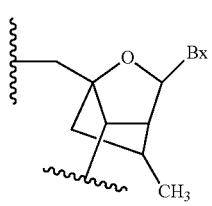

(J)
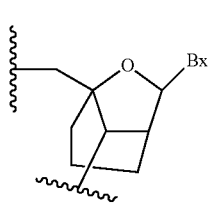

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), mannitol nucleic acid (MNA) (see Leumann, C J. *Bioorg. & Med. Chem.* (2002) 10:841-854), fluoro HNA (F-HNA), and those compounds having Formula VI:

VII
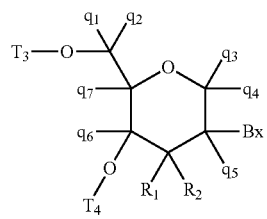

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VI are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VI are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present disclosure provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

c. Certain Nucleobases

In certain embodiments, nucleosides of the present disclosure comprise one or more unmodified nucleobases. In certain embodiments, nucleosides of the present disclosure comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

d. Certain Internucleoside Linkages

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), □ or □ such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-52 amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (Y—S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

e. Certain Motifs
  i. Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides of the present disclosure comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides of the present disclosure may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a 5' terminal nucleoside of formula I, II, III, IV, V, or VI.

In certain embodiments, oligonucleotides of the present disclosure comprise a region having a 2-2-3 motif. Such regions comprises the following motif:

$-(A)_2-(B)_x-(A)_2-(C)_y-(A)_3$ wherein: A is a first type of modified nucleoside;
B and C, are nucleosides that are differently modified than A, however, B and C may have the same or different modifications as one another;
x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

It is to be understood, that certain of the above described motifs and modifications may be combined. Since a motif may comprises only a few nucleosides, a particular oligonucleotide may comprise two or more motifs. By way of non-limiting example, in certain embodiments, oligonucleotides may have nucleoside motifs as described in the table below. In the table below, the term "None" indicates that a particular feature is not present in the oligonucleotide. For example, "None" in the column labeled "5' motif/modification" indicates that the 5' end of the oligonucleotide comprises the first nucleoside of the central motif

| 5' motif/modification | Central Motif | 3'-motif |
|---|---|---|
| Compound of Formula I, II, III, IV, V, or VI | Alternating | 2 MOE nucleosides |
| Compound of Formula I, II, III, IV, V, or VI | 2-2-3 motif | 2 MOE nucleosides |
| Compound of Formula I, II, III, IV, V, or VI | Uniform | 2 MOE nucleosides |
| Compound of Formula I, II, III, IV, V, or VI | Alternating | 2 MOE nucleosides |
| Compound of Formula I, II, III, IV, V, or VI | Alternating | 2 MOE A's |
| Compound of Formula I, II, III, IV, V, or VI | 2-2-3 motif | 2 MOE A's |
| Compound of Formula I, II, III, IV, V, or VI | Uniform | 2 MOE A's |
| Compound of Formula I, II, III, IV, V, or VI | Alternating | 2 MOE U's |
| Compound of Formula I, II, III, IV, V, or VI | 2-2-3 motif | 2 MOE U's |
| Compound of Formula I, II, III, IV, V, or VI | Uniform | 2 MOE U's |
| Compound of Formula I, II, III, IV, V, or VI | Alternating | 2 MOE nucleosides |
| Compound of Formula I, II, III, IV, V, or VI | 2-2-3 motif | 2 MOE nucleosides |
| Compound of Formula I, II, III, IV, V, or VI | Uniform | 2 MOE nucleosides |

In certain embodiments, oligonucleosides have the following sugar motif:

$5'-(Q)-(E)_w-(A)_2-(B)_x-(A)_2-(C)_y-(A)_3-(D)_z$ wherein:
Q is a nucleoside comprising a stabilized phosphate moiety. In certain embodiments, Q is a nucleoside having Formula I, II, III, IV, V, or VI;
A is a first type of modified nucleoside;
B, C, D, and E are nucleosides that are differently modified than A, however, B, C, D, and E may have the same or different modifications as one another;
w and z are from 0 to 15;
x and y are from 1 to 15.
In certain embodiments, the sum of w, x, and y is 5-25.
In certain embodiments, oligonucleosides have the following sugar motif:

$5'-(Q)-(AB)_x A_y-(D)_z$ wherein:
Q is a nucleoside comprising a stabilized phosphate moiety. In certain embodiments, Q is a nucleoside having Formula I, II, III, IV, V, or VI;
A is a first type of modified nucleoside;
B is a second type of modified nucleoside;
D is a modified nucleoside comprising a modification different from the nucleoside adjacent to it. Thus, if y is 0, then D must be differently modified than B and if y is 1, then D must be differently modified than A. In certain embodiments, D differs from both A and B.
X is 5-15;
Y is 0 or 1;
Z is 0-4.
In certain embodiments, oligonucleosides have the following sugar motif:

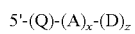

$5'-(Q)-(A)_x-(D)_z$ wherein:
Q is a nucleoside comprising a stabilized phosphate moiety. In certain embodiments, Q is a nucleoside having Formula I, II, III, IV, V, or VI;
A is a first type of modified nucleoside;
D is a modified nucleoside comprising a modification different from A.
X is 11-30;
Z is 0-4.
In certain embodiments A, B, C, and D in the above motifs are selected from: 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

ii. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides of the present disclosure comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS | iii. Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

In certain embodiments, chemical modifications to nucleobases comprise attachment of certain conjugate groups to nucleobases. In certain embodiments, each purine or each pyrimidine in an oligonucleotide may be optionally modified to comprise a conjugate group.

C. CERTAIN OVERALL LENGTHS

In certain embodiments, the present disclosure provides oligonucleotides of any of a variety of ranges of lengths. In certain embodiments, oligonucleotides consist of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the oligonucleotide may consist of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligonucleotide of a compound is limited, whether to a range or to a specific number, the compound may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugate groups, terminal groups, or other substituents.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

D. CERTAIN OLIGONUCLEOTIDES

In certain embodiments, oligonucleotides of the present disclosure are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides, such as those provided in the non-limiting table below. As is apparent from the above, non-limiting tables, the lengths of the regions defined by a nucleoside motif and that of a linkage motif need not be the same. To further illustrate, and not to limit in any way, nucleoside motifs and sequence motifs are combined to show five non-limiting examples in the table below. The first column of the table lists nucleosides and linkages by position from N1 (the first nucleoside at the 5'-end) to N20 (the $20^{th}$ position from the 5'-end). In certain embodiments, oligonucleotides of the present disclosure are longer than 20 nucleosides (the table is merely exemplary). Certain positions in the table recite the nucleoside or linkage "none" indicating that the oligonucleotide has no nucleoside at that position.

| Pos | A | B | C | D | E |
|-----|---|---|---|---|---|
| N1 | Formula I, II, III, IV, V, or VI | Formula I, II, III, IV, V, or VI | Formula I, II, III, IV, V, or VI | Formula I, II, III, IV, V, or VI | Formula I, II, III, IV, V, or VI |
| L1 | PS | PS | PS | PS | PO |
| N2 | 2'-F | 2'-F | 2'-F | 2'-OMe | MOE |
| L2 | PS | PS | PS | PO | PS |

-continued

| Pos | A | B | C | D | E |
|---|---|---|---|---|---|
| N3 | 2'-OMe | 2'-F | 2'-F | 2'-F | 2'-F |
| L3 | PO | PS | PS | PS | PS |
| N4 | 2'-F | 2'-F | 2'-F | 2'-OMe | 2'-F |
| L4 | PS | PS | PS | PO | PS |
| N5 | 2'-OMe | 2'-F | 2'-F | 2'-F | 2'-OMe |
| L5 | PO | PS | PS | PS | PO |
| N6 | 2'-F | 2'-OMe | 2'-F | 2'-OMe | 2'-OMe |
| L6 | PS | PO | PS | PO | PO |
| N7 | 2'-OMe | 2'-OMe | 2'-F | 2'-F | 2'-OMe |
| L7 | PO | PO | PS | PS | PO |
| N8 | 2'-F | 2'-F | 2'-F | 2'-OMe | 2'-F |
| L8 | PS | PS | PS | PO | PS |
| N9 | 2'-OMe | 2'-F | 2'-F | 2'-F | 2'-F |
| L9 | PO | PS | PS | PS | PS |
| N10 | 2'-F | 2'-OMe | 2'-F | 2'-OMe | 2'-OMe |
| L10 | PS | PO | PS | PO | PO |
| N11 | 2'-OMe | 2'-OMe | 2'-F | 2'-F | 2'OMe |
| L11 | PO | PO | PS | PS | PO |
| N12 | 2'-F | 2'-F | 2'-F | 2'-F | 2'-F |
| L12 | PS | PS | PS | PO | PS |
| N13 | 2'-OMe | 2'-F | 2'-F | 2'-F | 2'-F |
| L13 | PO | PS | PS | PS | PS |
| N14 | 2'-F | 2'-OMe | 2'-F | 2'-F | 2'-F |
| L14 | PS | PS | PS | PS | PS |
| N15 | 2'-OMe | 2'OMe | 2'-F | 2'-F | 2'-MOE |
| L15 | PS | PS | PS | PS | PS |
| N16 | 2'-F | 2'OMe | 2'-F | 2'-F | 2'-MOE |
| L16 | PS | PS | PS | PS | PS |
| N17 | 2'-OMe | 2'-MOE U | 2'-F | 2'-F | 2'-MOE |
| L17 | PS | PS | PS | PS | None |
| N18 | 2'-F | 2'-MOE U | 2'-F | 2'-OMe | None |
| L18 | PS | None | PS | PS | None |
| N19 | 2'-MOE U | None | 2'-MOE U | 2'-MOE A | None |
| L19 | PS | None | PS | PS | None |
| N20 | 2'-MOE U | None | 2'-MOE U | 2'-MOE A | None |

In the above, non-limiting examples:

Column A represent an oligonucleotide consisting of 20 linked nucleosides, wherein the oligonucleotide comprises: a modified 5'-terminal nucleoside of Formula I, II, III, IV, V, or VI; a region of alternating nucleosides; a region of alternating linkages; two 3'-terminal MOE nucleosides, each of which comprises a uracil base; and a region of six phosphorothioate linkages at the 3'-end.

Column B represents an oligonucleotide consisting of 18 linked nucleosides, wherein the oligonucleotide comprises: a modified 5'-terminal nucleoside of Formula I, II, III, IV, V, or VI; a 2-2-3 motif wherein the modified nucleoside of the 2-2-3 motif are 2'O-Me and the remaining nucleosides are all 2'-F; two 3'-terminal MOE nucleosides, each of which comprises a uracil base; and a region of six phosphorothioate linkages at the 3'-end.

Column C represents an oligonucleotide consisting of 20 linked nucleosides, wherein the oligonucleotide comprises: a modified 5'-terminal nucleoside of Formula I, II, III, IV, V, or VI; a region of uniformly modified 2'-F nucleosides; two 3'-terminal MOE nucleosides, each of which comprises a uracil base; and wherein each internucleoside linkage is a phosphorothioate linkage.

Column D represents an oligonucleotide consisting of 20 linked nucleosides, wherein the oligonucleotide comprises: a modified 5'-terminal nucleoside of Formula I, II, III, IV, V, or VI; a region of alternating 2'-OMe/2'-F nucleosides; a region of uniform 2'F nucleosides; a region of alternating phosphorothioate/phosphodiester linkages; two 3'-terminal MOE nucleosides, each of which comprises an adenine base; and a region of six phosphorothioate linkages at the 3'-end.

Column E represents an oligonucleotide consisting of 17 linked nucleosides, wherein the oligonucleotide comprises: a modified 5'-terminal nucleoside of Formula I, II, III, IV, V, or VI; a 2-2-3 motif wherein the modified nucleoside of the 2-2-3 motif are 2'F and the remaining nucleosides are all 2'-OMe; three 3'-terminal MOE nucleosides.

The above examples are provided solely to illustrate how the described motifs may be used in combination and are not intended to limit the disclosure to the particular combinations or the particular modifications used in illustrating the combinations. Further, specific examples herein, including, but not limited to those in the above table are intended to encompass more generic embodiments. For example, column A in the above table exemplifies a region of alternating 2'-OMe and 2'-F nucleosides. Thus, that same disclosure also exemplifies a region of alternating different 2'-modifications. It also exemplifies a region of alternating 2'-O-alkyl and 2'-halogen nucleosides. It also exemplifies a region of alternating differently modified nucleosides. All of the examples throughout this specification contemplate such generic interpretation.

It is also noted that the lengths of the oligonucleotides, such as those exemplified in the above tables, can be easily manipulated by lengthening or shortening one or more of the described regions, without disrupting the motif.

In certain embodiments, the disclosure provides oligonucleotides wherein the 5'-terminal nucleoside (position 1) is a compound of Formula I, II, III, IV, V, or VI and the position 2 nucleoside comprises a 2'-modification. In certain such embodiments, the 2'-modification of the position 2 nucleoside is selected from halogen, alkyl, and substituted alkyl. In certain embodiments, the 2'-modification of the position 2 nucleoside is selected from 2'-F and 2'-alkyl. In certain embodiments, the 2'-modification of the position 2 nucleoside is 2'-F. In certain embodiments, the 2'-substituted of the position 2 nucleoside is an unmodified OH (as in naturally occurring RNA).

In certain embodiments, the position 3 nucleoside is a modified nucleoside. In certain embodiments, the position 3 nucleoside is a bicyclic nucleoside. In certain embodiments, the position 3 nucleoside comprises a sugar surrogate. In certain such embodiments, the sugar surrogate is a tetrahydropyran. In certain embodiments, the sugar of the position 3 nucleoside is a F-HNA.

In certain embodiments, an antisense compound comprises an oligonucleotide comprising 10 to 30 linked nucleosides wherein the oligonucleotide comprises: a position 1 modified nucleoside of Formula I, II, III, IV, V, or VI; a position 2 nucleoside comprising a sugar moiety which is differently modified compared to the sugar moiety of the position 1 modified nucleoside; and from 1 to 4 3'-terminal group nucleosides each comprising a 2'-modification; and wherein at least the seven 3'-most internucleoside linkages are phosphorothioate linkages.

E. CERTAIN CONJUGATE GROUPS

In certain embodiments, oligonucleotides are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

In certain embodiments at least one conjugate group is selected from the group consisting of, folic acid, gallic acid, vitamins, fatty acids, carbohydrates, optical imaging moieties, targeting moieties, magnetic resonance imaging moieties, hydrophobic moieties, hydrophilic moieties, magnetic resonance imaging moieties, peptides, amino acids, amino acid derivatives, nucleic acids, nucleic acid derivatives, heterocycles, steroids, ionic complexes, and polyionic complexes.

In certain embodiments the dye is selected from an acridine dye, a coumarine dye, a rhodamine dye, a xanthene dye, a cyanine dye, and a pyrene dye, Texas Red, Alexa Fluor® dye, BODIPY® dye, Fluorescein, Oregon Green® dye, and Rhodamine Green™ dye or any other suitable dye known to those having skill in the art.

In certain embodiments the conjugate group is a magnetic resonance imaging moiety, for example a paramagnetic compound. In certain embodiments the conjugate group increases the binding affinity to lipoproteins. In certain embodiments the conjugate group is a hydrophobic compound. In certain embodiments the conjugate group is a hydrophilic compound. In certain embodiments the conjugate group is a peptide, an amino acid, an amino acid derivative, a nucleic acid, a nucleic acid derivative, a heterocycle, a steroid, an ionic complex, a polyionic complex, a cationic complex, an anion complex, or a zwitterion.

In certain embodiments, the conjugate group is a carbohydrate, carbohydrate derivative, modified carbohydrate, multivalent carbohydrate cluster, polysaccharide, modified polysaccharide, or polysaccharide derivative. In certain embodiments, the conjugate group is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-glucoheptopyranoside.

In certain embodiments, the multivalent carbohydrate cluster comprises any compound having one or more carbohydrate residues attached to a scaffold or linker group. The scaffold or linker group may comprise any suitable compound known to those in the art. For example, a scaffold or linker group may comprise glycerol or a glycerol derivative, an amine or amine derivative, an ester or ester derivative, an anhydride or anhydride derivative, an amino acid, amino acid derivative, peptide, peptide derivative, or any other suitable compound known to those having skill in the art. For example, in certain embodiments, the scaffold may have the following structure:

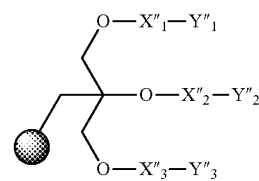

wherein each $X''_1$, $X''_2$, and $X''_3$, comprises a linker group and each $Y''_1$, $Y''_2$, and $Y''_3$, comprises a carbohydrate, modified carbohydrate, or carbohydrate derivative. In certain embodiments, each Y"$_1$, Y"$_2$, and Y"$_3$ is independently selected from the group consisting of mannose, glucose, fructose, galactose, amino sugars, and thio sugars.

In some embodiments the multivalent carbohydrate cluster has one carbohydrate attached to the scaffold. In some embodiments the multivalent carbohydrate cluster has two carbohydrates attached to the scaffold. In some embodiments the multivalent carbohydrate cluster has three carbohydrate attached to the scaffold. In some embodiments the multivalent carbohydrate cluster has four carbohydrate attached to the scaffold. In some embodiments the multivalent carbohydrate cluster has one or more carbohydrates attached to the scaffold.

In certain embodiments, the conjugate group comprises:

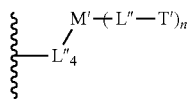

wherein L"$_4$ is a linker group, M' is a scaffold, L" is a linker group, n is 0 or an integer between 1 and 10, T' is selected from the group consisting of a carbohydrate, a modified carbohydrate, and a carbohydrate derivative. For example, when n is >0, the scaffold, M', comprises more than one linker group L" and more than one carbohydrate, modified carbohydrate, and carbohydrate derivative, T". For example, when n=2, the scaffold, M' comprises two separate linker groups, L"$_1$ and L"$_2$, wherein each L"$_1$ and each L"$_2$ each independently link to two carbohydrates, modified carbohydrates, and carbohydrate derivatives, T'$_1$ and T'$_2$.

In certain embodiments, T', T'$_1$, T'$_2$, and T'$_3$ comprise carbohydrates, modified carbohydrates, and carbohydrate derivatives. In certain embodiments, one or more of T', T'$_1$, T'$_2$, and T'$_3$ is independently mannose, galactose, D-mannopyranose, L-Mannopyranose, D-Arabinose, L-Galactose, D-xylofuranose, L-xylofuranose, D-glucose, L-glucose, D-Galactose, L-Galactose, 2-acetamido-2-deoxy-D-galactopyranose (GalNAc), α-D-Mannofuranose, β-D-Mannofuranose, α-D-Mannopyranose, β-D-Mannopyranose, α-D-Glucopyranose, β-D-Glucopyranose, α-D-Glucofuranose, β-D-Glucofuranose, α-D-fructofuranose, α-D-fructopyranose, α-D-Galactopyranose, β-D-Galactopyranose, α-D-Galactofuranose, β-D-Galactofuranose, glucosamine, sialic acid, α-D-galactosamine, N-Acetylgalactosamine, 2-Amino-3-O—[(R)-1-carboxyethyl]-2-deoxy-β-D-glucopyranose, 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose, N-Glycoloyl-α-neuraminic acid, 5-thio-β-D-glucopyranose, methyl 2,3,4-tri-O-acetyl-1-thio-6-O-trityl-α-D-glucopyranoside, 4-Thio-β-D-galactopyranose, ethyl 3,4,6,7-tetra-O-acetyl-2-deoxy-1,5-dithio-α-D-gluco-heptopyranoside, 2,5-Anhydro-D-allononitrile.

In certain embodiments, L"$_1$, L"$_2$, L"$_3$, L"$_4$, and L"$_5$ each independently comprise a linker group. In certain embodiments, one or more of L"$_1$, L"$_2$, L"$_3$, L"$_4$, and L"$_5$ is independently a peptide, an ether, polyethylene glycol, alkyl, C$_1$-C$_{20}$ alkyl, substituted C$_1$-C$_{20}$ alkyl, C$_2$-C$_{20}$ alkenyl, substituted C$_2$-C$_{20}$ alkenyl, C$_2$-C$_{20}$ alkynyl, substituted C$_2$-C$_{20}$ alkynyl, C$_1$-C$_{20}$ alkoxy, substituted C$_1$-C$_{20}$ alkoxy, amino, amido, pyrrolidine, 8-amino-3,6-dioxaoctanoic acid (ADO), succinimidyl 4-(N-maleimidomethyl)cyclohexane-1-carboxylate, and 6-aminohexanoic acid.

In certain embodiments, the linker group comprises an amine. In certain embodiments the linker group comprises polyethylene glycol. In certain embodiments the linker group comprises an ether. In certain embodiments, the linker group comprises a carbamoyl. In certain embodiments, the linker group comprises a carbamate. In certain embodiments, the linker group comprises a structure as shown below:

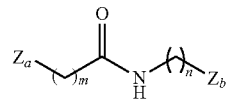

wherein m and n are 0 or integers between 1 and 20, and wherein Z$_a$ and Z$_b$ are each independently a conjugate group, a carbohydrate, a modified carbohydrate, a carbohydrate derivative, H, a peptide, ether, polyethylene glycol, alkyl, C$_1$-C$_{20}$ alkyl, substituted C$_1$-C$_{20}$ alkyl, C$_2$-C$_{20}$ alkenyl, substituted C$_2$-C$_{20}$ alkenyl, C$_2$-C$_{20}$ alkynyl, substituted C$_2$-C$_{20}$ alkynyl, C$_1$-C$_{20}$ alkoxy, substituted C$_1$-C$_{20}$ alkoxy, amino, amido, pyrrolidine, 8-amino-3,6-dioxaoctanoic acid (ADO), succinimidyl 4-(N-maleimidomethyl)cyclohexane-1-carboxylate, and 6-aminohexanoic acid.

In certain embodiments, the linker group comprises a structure as shown below:

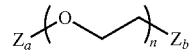

wherein n is 0 or an integer between 1 and 20, and wherein Z$_a$ and Z$_b$ are each independently a conjugate group, a carbohydrate, a modified carbohydrate, a carbohydrate derivative, H, a peptide, ether, polyethylene glycol, alkyl, C$_1$-C$_{20}$ alkyl, substituted C$_1$-C$_{20}$ alkyl, C$_2$-C$_{20}$ alkenyl, substituted C$_2$-C$_{20}$ alkenyl, C$_2$-C$_{20}$ alkynyl, substituted C$_2$-C$_{20}$ alkynyl, C$_1$-C$_{20}$ alkoxy, substituted C$_1$-C$_{20}$ alkoxy, amino, amido, pyrrolidine, 8-amino-3,6-dioxaoctanoic acid (ADO), succinimidyl 4-(N-maleimidomethyl)cyclohexane-1-carboxylate, and 6-aminohexanoic acid.

In certain embodiments, one or more of the hydroxyl groups of the carbohydrates, modified carbohydrates, and carbohydrate derivatives may be protected by a protecting group. Non-limiting examples of protecting groups may be found in "Protective Groups in Organic Chemistry", T. W. Greene, P. G. M. Wuts, ISBN 0-471-62301-6, John Wiley & Sons, Inc, New York, which is incorporated herein by reference in its entirety. Examples of protecting groups include any protecting group known to those having skill in the art, including acetates, anhydrides, esters, benzyl, substituted benzyl, and allyl. Non-limiting examples of ester protecting groups include acetate, benzoate, chloroacetate, pivalate, levulinate, and silyl ethers. Non-limiting examples of acetals include benzylidene, isopropylidene, and butane diacetal. Non-limiting examples of silyl ether protecting groups include trimethylsilyl (TMS), t-butyldimethylsilyl (TBDMS), and t-butyldiphenylsilyl TBDPS.

In certain embodiments, the multivalent carbohydrate cluster has the following structure:

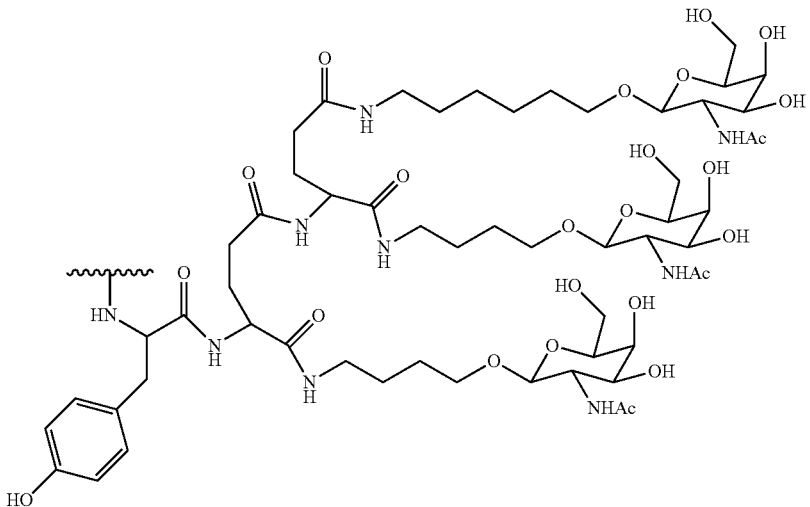 [SMILES: *NC(Cc1ccc(O)cc1)C(=O)NC(CCC(=O)NC(CCC(=O)NCCCCCCOC1OC(CO)C(O)C(O)C1NC(C)=O)C(=O)NCCCCOC1OC(CO)C(O)C(O)C1NC(C)=O)C(=O)NCCCCOC1OC(CO)C(O)C(O)C1NC(C)=O]

In certain embodiments, the multivalent carbohydrate cluster has the following structure:

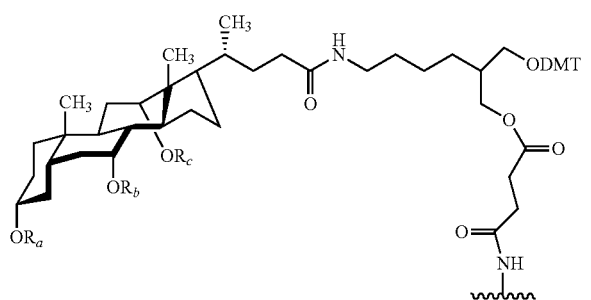

wherein $R_a$, $R_b$, and $R_c$ are each independently a protecting group, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, amino, amido, and:

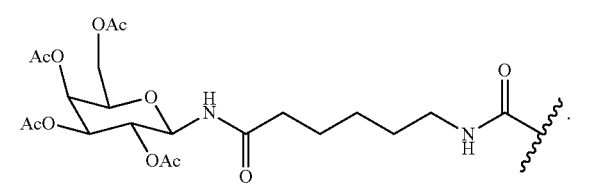 [SMILES: *C(=O)NCCCCCC(=O)NC1OC(COC(C)=O)C(OC(C)=O)C(OC(C)=O)C1OC(C)=O]

In certain embodiments, the multivalent carbohydrate cluster has the following structure:

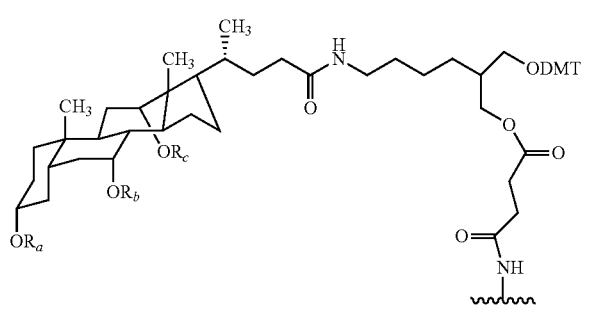

wherein $R_a$, $R_b$, and $R_c$ are each independently a protecting group, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, amino, amido, and:

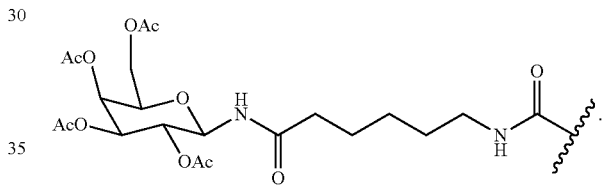

In certain embodiments, the multivalent carbohydrate cluster has the following structure:

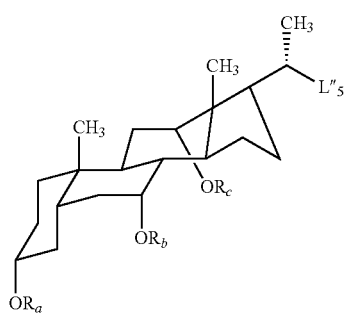

wherein $R_a$, $R_b$, and $R_c$ are each independently a protecting group, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy, amino, and amido, and wherein $L''_5$ is a linker group, wherein the linker group comprises a peptide, an ether, polyethylene glycol, alkyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_1$-$C_{20}$ alkoxy, substituted $C_1$-$C_{20}$ alkoxy, amino, amido, pyrrolidine, 8-amino-3,6-dioxaoctanoic acid (ADO), succinimidyl 4-(N-maleimidomethyl)cyclohexane-1-carboxylate, and 6-aminohexanoic acid, or any other suitable linker group known to those having skill in the art.

In certain embodiments the conjugate group is a targeting moiety. In certain embodiments, the targeting moiety is selected from the group consisting of an arginine-glycine-aspartate (RGD) peptide, fibronectin, folate, galactose, an apolipoprotein, insulin, transferrin, a fibroblast growth factor (FOF), an epidermal growth factor (EGF) and an antibody.

In certain embodiments the conjugate group is a group that increases lipoprotein binding affinity. In certain embodiments, the conjugate group is a group that decreases lipoprotein binding affinity. In certain embodiments, the conjugate group has a pH value of greater than or equal to 7, and in certain embodiments the conjugate group has a pH value of less than or equal to 7.

In certain embodiments the conjugate group increases the lipophilicity of the oligonucleotide-conjugate complex. In certain embodiments the conjugate group decreases the lipophilicity of the oligonucleotide-conjugate complex. In certain embodiments the conjugate group increases the lipophobicity of the oligonucleotide-conjugate complex. In certain embodiments the conjugate group decreases the lipophobicity of the oligonucleotide-conjugate complex.

In certain embodiments, the conjugate group may modify the plasma protein binding properties of the oligonucleotide-conjugate complex. In certain embodiments, the conjugate group may increase and alter the binding affinity of the oligonucleotide for albumin. In certain embodiments, the conjugate group may increase and alter the binding affinity of the oligonucleotide for glycoprotein. In certain embodiments the conjugate group may increase and alter the binding affinity of the oligonucleotide for globulins. In certain embodiments the conjugate group may increase and alter the binding affinity of the oligonucleotide for $\alpha$-1 globulins, $\alpha$-2 globulins, $\beta$-globulins, and $\gamma$-globulins.

In certain embodiments, conjugate groups increase, decrease, or alter the amount of an oligonucleotide that binds to proteins. In certain embodiments, conjugate groups increase, decrease, or alter the amount of an oligonucleotide that binds to plasma proteins. In certain embodiments, conjugate groups increase the amount of an oligonucleotide that binds to plasma proteins. For example, in certain embodiments, the attachment or association of a conjugate group with an oligonucleotide is expected to result in an oligonucleotide-conjugate complex having increased protein binding affinity. In certain embodiments, conjugate groups decrease the amount of an oligonucleotide that binds to plasma proteins. For example, in certain embodiments, the attachment or association of a conjugate group with an oligonucleotide result in an oligonucleotide-conjugate complex having decreased protein binding affinity.

In certain embodiments, conjugate groups increase, decrease, or alter the amount of an oligonucleotide that binds to high molecular weight proteins. In certain embodiments, conjugate groups increase the proportion of an oligonucleotide that binds to high molecular weight proteins. In certain embodiments, the selective placement of conjugate groups along the oligonucleoside increases the proportion of an oligonucleotide that binds to high molecular weight proteins. For example, in certain embodiments, the attachment or association of a conjugate group with an oligonucleotide results in an oligonucleotide-conjugate complex having increased binding affinity for high molecular weight proteins.

In certain embodiments, conjugate groups increase, decrease, or alters the amount of an oligonucleotide that accumulates in one or more tissues. In certain embodiments, conjugate groups increase, decrease, or alters amount of an oligonucleotide that accumulates in adipose tissue. In certain embodiments, conjugate groups increase, decrease, or alters amount of an oligonucleotide that accumulates in the liver. In certain embodiments, conjugate groups increase, decrease, or alters amount of an oligonucleotide that accumulates in the kidney.

In certain embodiments, conjugate groups increase the amount of an oligonucleotide that accumulates in adipose tissue. In certain embodiments, conjugate groups increase the amount of an oligonucleotide that accumulates in the liver. In certain embodiments, conjugate groups increase the amount of an oligonucleotide that accumulates in the kidney.

In certain embodiments, conjugate groups decrease the amount of an oligonucleotide that accumulates in adipose tissue. In certain embodiments, conjugate groups decrease the amount of an oligonucleotide that accumulates in the liver. In certain embodiments, conjugate groups decrease the amount of an oligonucleotide that accumulates in the kidney.

In certain embodiments, conjugate groups may be covalently attached to an oligonucleotide by any one of a number of linkers known to those having skill in the art. In certain embodiments, a linker may be selected to prevent cleavage by any number of enzymes. In certain embodiments, a linker may be selected that is resistant to hydrolytic cleavage. In certain embodiments, a linker may be selected that is resistant to enzymatic cleavage. In certain embodiments, the cleavage resistant linker is selected from a carbamate or carbamoyl moiety.

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. In certain embodiments, a conjugate group comprises an active drug substance, for example, a taxane, a comptotheca, or an anthracycline.

In certain embodiments, conjugate groups are directly attached to oligonucleotides. In certain embodiments, conjugate groups are attached to oligonucleotides by a conjugate linking group. In certain such embodiments, conjugate linking groups, include, but are not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligonucleotide. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker group comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include polyethylene glycol (PEG), pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the linking group is represented by a compound of formula VIII:

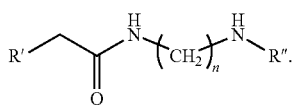
VIII wherein, n is any integer between 1 and 10, R' comprises a nucleoside, and R" comprises a conjugate group, or has the formula R"($R_{1a}$)($R_{1b}$)($R_{1c}$), wherein $R_{1a}$, $R_{2a}$, and $R_{3a}$ are each, independently, a conjugate group, H, halogen, $C_1$-$C_{24}$ alkyl, substituted $C_1$-$C_{24}$ alkyl, $C_1$-$C_{24}$ alkoxy, substituted $C_1$-$C_{24}$ alkoxy, $C_2$-$C_{24}$ alkenyl, substituted $C_2$-$C_{24}$ alkenyl, $C_2$-$C_{24}$ alkynyl, substituted $C_2$-$C_{24}$ alkynyl, or where $R_{1a}$ and one of $R_{2a}$ or $R_{3a}$ together form Q', where Q' is O.

For example, in certain embodiments, the linking group is attached to a nucleoside as shown below:

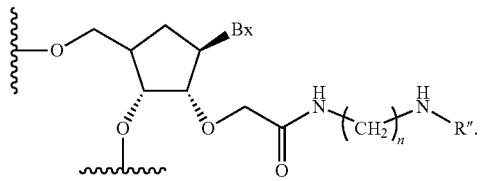

In certain embodiments, the linking group comprises a thiodiester, thionocarbamate, siloxane, carbamate, sulfamate, morpholino sulfamide, sulfonamide, sulfide, sulfonate, N,N'-dimethylhydrazine, thioformacetal, formacetal, thioketal, ketal, amine, hydroxylamine, hydroxylamine, or a hydrazinyl group.

In certain embodiments, the linker group comprises an amine. In certain embodiments the linker group comprises polyethylene glycol. In certain embodiments the linker group comprises an ether. In certain embodiments, the linker group comprises a structure as shown below:

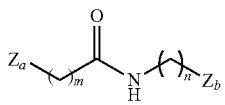

wherein m and n are 0 or integers between 1 and 20, and wherein $Z_a$ and $Z_b$ are each independently a conjugate group, a carbohydrate, a modified carbohydrate, a carbohydrate derivative, H, a peptide, ether, polyethylene glycol, alkyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_1$-$C_{20}$ alkoxy, substituted $C_1$-$C_{20}$ alkoxy, amino, amido, pyrrolidine, 8-amino-3,6-dioxaoctanoic acid (ADO), succinimidyl 4-(N-maleimidomethyl)cyclohexane-1-carboxylate, and 6-aminohexanoic acid.

In certain embodiments, the linker group comprises a structure as shown below:

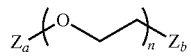

wherein n is 0 or an integer between 1 and 20, and wherein $Z_a$ and $Z_b$ are each independently a conjugate group, a carbohydrate, a modified carbohydrate, a carbohydrate derivative, H, a peptide, ether, polyethylene glycol, alkyl, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_1$-$C_{20}$ alkoxy, substituted $C_1$-$C_{20}$ alkoxy, amino, amido, pyrrolidine, 8-amino-3,6-dioxaoctanoic acid (ADO), succinimidyl 4-(N-maleimidomethyl)cyclohexane-1-carboxylate, and 6-aminohexanoic acid.

In certain embodiments the linker group attaches the conjugate group to the 2'-position of any nucleoside in the oligonucleotide. In certain embodiments the linker group attaches the conjugate group to the phosphate backbone of any nucleoside in the oligonucleotide. In certain embodiments the linker group attaches the conjugate group to the nucleobase of any nucleoside in the oligonucleotide.

In certain embodiments, conjugate groups may be attached to either or both ends of an oligonucleotide (terminal conjugate groups) and/or at any internal position.

In certain embodiments, conjugate groups are at the 3'-end of an oligonucleotide. In certain embodiments, conjugate groups are near the 3'-end. In certain embodiments, conjugate groups are attached at the 3' end of an oligonucleotide, but before one or more terminal group nucleosides. In certain embodiments, conjugate groups are placed within a terminal group. In certain embodiments, a conjugate group is attached to the 3'-terminal nucleoside. In certain such embodiment, the conjugate group is attached at the 3'-position of the 3'-terminal nucleoside. In certain embodiments, the conjugate group is attached at the 2'-position of the 3'-terminal nucleoside.

In certain embodiments, compounds comprise an oligonucleotide. In certain embodiments, compounds comprises an oligonucleotide and one or more conjugate group and/or terminal groups. Such conjugate group and/or terminal groups may be added to oligonucleotides having any of the chemical motifs discussed above. Thus, for example, a compound comprising an oligonucleotide having region of alternating nucleosides may comprise a terminal group.

In certain embodiments, a conjugate group is attached at the 2'-position of a nucleoside. In certain embodiments, a conjugate group is attached at the 3'-position of the 5'-terminal or 3'-terminal nucleoside. In certain embodiments, the conjugate group is attached at any point along the oligomer's phosphate backbone. In certain embodiments, the conjugate group is attached to the nucleobase.

F. SELECTIVE PLACEMENT OF CERTAIN CONJUGATE GROUPS

In certain embodiments, oligonucleotides are modified by attachment of one or more conjugate groups. In general, conjugate groups modify one or more properties of the attached oligonucleotide, including but not limited to pharmacodynamics, pharmacokinetics, stability, binding, protein binding, absorption, cellular distribution, cellular uptake, charge, accumulation in specific tissues or organs, and clearance.

In certain embodiments, the selective placement of one or more conjugate groups at various positions along the oligonucleotide serve to enhance one or more properties of the oligonucleotide-conjugate complex. In certain embodiments, the selective placement of one or more conjugate groups at various nucleobases along the oligonucleotide serve to enhance one or more properties of the oligonucleotide-conjugate complex. In general, the selective placement of a conjugate group may enhance the pharmacodynamics, pharmacokinetics, stability, binding, absorption, cellular distribution, cellular uptake, charge, clearance, and other desired properties of the oligonucleotide-conjugate complex.

In certain embodiments, the selective placement of one or more conjugate groups onto an oligonucleotide enhances the nuclease resistance of the oligonucleotide-conjugate complex. In certain embodiments, the selective placement of one or more conjugate groups onto an oligonucleotide enhances the distribution of the oligonucleotide-conjugate complex in one or more organs or tissues. In certain embodiments, the selective placement of one or more conjugate groups onto an oligonucleotide enhances the accumulation of the oligonucleotide-conjugate complex in the liver. In certain embodiments, the selective placement of one or more conjugate groups onto an oligonucleotide enhances the accumulation of the oligonucleotide-conjugate complex in the kidney. In certain embodiments, the selective placement of one or more conjugate groups onto an oligonucleotide enhances the accumulation of the oligonucleotide-conjugate complex in the spleen. In certain embodiments, the selective placement of one or more conjugate groups onto an oligonucleotide enhances the accumulation of the oligonucleotide-conjugate complex in the pancreas. In certain embodiments, the selective placement of one or more conjugate groups onto an oligonucleotide enhances the accumulation of the oligonucleotide-conjugate complex in the adipose tissue.

In certain embodiments, the selective placement of one or more conjugate groups onto an oligonucleotide enhances the accumulation of the oligonucleotide-conjugate complex in a cell. In certain embodiments, the selective placement of one or more conjugate groups onto an oligonucleotide enhances the accumulation of the oligonucleotide-conjugate complex in the nucleus. In certain embodiments, the selective placement of one or more conjugate groups onto an oligonucleotide enhances the accumulation of the oligonucleotide-conjugate complex in the cytoplasm.

In certain embodiments, one or more conjugate groups may be attached at any position on any nucleoside in an oligonucleotide. For example, in certain embodiments, the disclosure provides oligonucleotides consisting of 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, or 14 to 30 linked nucleosides.

In certain embodiments, the oligonucleotide consists of 14 nucleosides and a conjugate group attached to the 1, 2, 3, 4, 5, 6, 7, 8, 9, 10, 11, 12, 13 or 14 nucleoside from the 5' end or the 14, 13, 12, 11, 10, 9, 8, 7, 6, 5, 4, 3, 2, or 1 nucleoside from the 3' end. In certain embodiments, the oligonucleotide consists of 15 nucleosides and a conjugate group attached to the 1, 2, 3, 4, 5, 6, 7, 8, 9, 10, 11, 12, 13, 14, or 15 nucleoside from the 5' end or the 15, 14, 13, 12, 11, 10, 9, 8, 7, 6, 5, 4, 3, 2, or 1 nucleoside from the 3' end. In certain embodiments, the oligonucleotide consists of 16 nucleosides and a conjugate group attached to the 1, 2, 3, 4, 5, 6, 7, 8, 9, 10, 11, 12, 13, 14, 15, or 16 nucleoside from the 5' end or the 16, 15, 14, 13, 12, 11, 10, 9, 8, 7, 6, 5, 4, 3, 2, or 1 nucleoside from the 3' end. In certain embodiments, the oligonucleotide consists of 17 nucleosides and a conjugate group attached to the 1, 2, 3, 4, 5, 6, 7, 8, 9, 10, 11, 12, 13, 14, 15, 16, or 17 nucleoside from the 5' end or the 17, 16, 15, 14, 13, 12, 11, 10, 9, 8, 7, 6, 5, 4, 3, 2, or 1 nucleoside from the 3' end. In certain embodiments, the oligonucleotide consists of 18 nucleosides and a conjugate group attached to the 1, 2, 3, 4, 5, 6, 7, 8, 9, 10, 11, 12, 13, 14, 15, 16, 17, or 18 nucleoside from the 5' end or the 18, 17, 16, 15, 14, 13, 12, 11, 10, 9, 8, 7, 6, 5, 4, 3, 2, or 1 nucleoside from the 3' end. In certain embodiments, the oligonucleotide consists of 19 nucleosides and a conjugate group attached to the 1, 2, 3, 4, 5, 6, 7, 8, 9, 10, 11, 12, 13, 14, 15, 16, 17, 18, or 19 nucleoside from the 5' end or the 19, 18, 17, 16, 15, 14, 13, 12, 11, 10, 9, 8, 7, 6, 5, 4, 3, 2, or 1 nucleoside from the 3' end.

In certain embodiments, the oligonucleotide consists of 20 nucleosides and a conjugate group attached to the 1, 2, 3, 4, 5, 6, 7, 8, 9, 10, 11, 12, 13, 14, 15, 16, 17, 18, 19, or 20 nucleoside from the 5' end or the 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 21 nucleosides and a conjugate group attached to the 1, 2, 3, 4, 5, 6, 7, 8, 9, 10, 11, 12, 13, 14, 15, 16, 17, 18, 19, 20 or 21 nucleoside from the 5' end or the 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 22 nucleosides and a conjugate group attached to the 1, 2, 3, 4, 5, 6, 7, 8, 9, 10, 11, 12, 13, 14, 15, 16, 17, 18, 19, 20, 21 or 22 nucleoside from the 5' end or the 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 23 nucleosides and a conjugate group attached to the 1, 2, 3, 4, 5, 6, 7, 8, 9, 10, 11, 12, 13, 14, 15, 16, 17, 18, 19, 20, 21, 22, or 23 nucleoside from the 5' end or the 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 24 nucleosides and a conjugate group attached to the 1, 2, 3, 4, 5, 6, 7, 8, 9, 10, 11, 12, 13, 14, 15, 16, 17, 18, 19, 20, 21, 22, 23, or 24 nucleoside from the 5' end or the 24, 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 25 nucleosides and a conjugate group attached to the 1, 2, 3, 4, 5, 6, 7, 8, 9, 10, 11, 12, 13, 14, 15, 16, 17, 18, 19, 20, 21, 22, 23, 24, or 25 nucleoside from the 5' end or the 25, 24, 23, 22, 21, 20, 19, 18, 17, 16, 15, 14, 13, 12, 11, 10, 9, 8, 7, 6, 5, 4, 3, 2, or 1 nucleoside from the 3' end.

In certain embodiments, the oligonucleotide consists of 26 nucleosides and a conjugate group attached to the 1, 2, 3, 4, 5, 6, 7, 8, 9, 10, 11, 12, 13, 14, 15, 16, 17, 18, 19, 20, 21, 22, 23, 24, 25, or 26 nucleoside from the 5' end or the 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 27 nucleosides and a conjugate group attached to the 1, 2, 3, 4, 5, 6, 7, 8, 9, 10, 11, 12, 13, 14, 15, 16, 17, 18, 19, 20, 21, 22, 23, 24, 25, 26, or 27 nucleoside from the 5' end or the 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 28 nucleosides and a conjugate group attached to the 1, 2, 3, 4, 5, 6, 7, 8, 9, 10, 11, 12, 13, 14, 15, 16, 17, 18, 19, 20, 21, 22, 23, 24, 25, 26, 27, or 28 nucleoside from the 5' end or the 28, 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 29 nucleosides and a conjugate group attached to the 1, 2, 3, 4, 5, 6, 7, 8, 9, 10, 11, 12, 13, 14, 15, 16, 17, 18, 19, 20, 21, 22, 23, 24, 25, 26, 27, 28, or 29 nucleoside from the 5' end or the 29, 28, 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 30 nucleosides and a conjugate group attached to the 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleoside from the 5' end or the 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end.

In certain embodiments, a conjugate group is attached to a nucleoside at one or more of position 1, 6 or 8 of the oligonucleotide, counting from the 5'-end. In certain embodiments a conjugate group is attached to a nucleoside at one or more of: position 13, 15, or 20 of the oligonucleotide, counting from the 3'-end.

In certain embodiments, conjugate groups interrupt motifs. For example, in certain embodiments, oligonucleotides of the present disclosure have an alternating motif that spans positions 1-19 and a conjugate group at position 8 (from the 5'-end) as follows:

Po-ABABABAXABABABABABA-

Wherein A represents nucleosides of a first-type;

B represents nucleosides of a second type; and

X represents a nucleoside to which a conjugate group is attached.

In certain embodiments, A and B are 2'-modifications and X is a conjugate group attached at the 2'-position. Thus, the motif of alternating 2'-modifications is interrupted by the conjugate group. Such an oligonucleotide may, nevertheless be described as having an alternating motif.

G. SELECTIVE PLACEMENT OF TWO OR MORE CONJUGATE GROUPS

In certain embodiments, oligonucleotides are modified by attachment of two or more conjugate groups. In general, each of the two or more conjugate groups may modify one or more properties of the attached oligonucleotide, including, but not limited to, the pharmacodynamics, pharmacokinetics, stability, binding, absorption, cellular distribution, cellular uptake, charge and clearance. In certain embodiments, one conjugate group may be selected to enhance the pharmacodynamic, pharmacokinetic, stability, binding, absorption, cellular distribution, cellular uptake, or charge and clearance properties of the attached oligonucleoside, and a second conjugate group may also be selected further to modify the pharmacodynamic, pharmacokinetic, stability, binding, absorption, cellular distribution, cellular uptake, or charge and clearance properties of the attached oligonucleoside. For example, in certain embodiments, a first conjugate group may modify the pharmacokinetic properties of the attached oligonucleotide and a second conjugate group may modify the stability of the attached oligonucleotide, resulting in an oligonucleotide-conjugate complex having both modified pharmacokinetic properties and modified stability.

In certain embodiments, the selective placement of two or more conjugate groups at various positions along the oligonucleotide serve to enhance one or more properties of the oligonucleotide-conjugate complex. In general, the selective placement of two or more conjugate groups may enhance the pharmacodynamics, pharmacokinetics, stability, binding, absorption, cellular distribution, cellular uptake, charge, clearance, and other desired properties of the oligonucleotide-conjugate complex.

In certain embodiments, the selective placement of two or more conjugate groups onto an oligonucleotide enhances the nuclease resistance of the oligonucleotide-conjugate complex. In certain embodiments, the selective placement of two or more conjugate groups onto an oligonucleotide enhances the distribution of the oligonucleotide-conjugate complex in one or more organs or tissues. In certain embodiments, the selective placement of two or more conjugate groups onto an oligonucleotide enhances the accumulation of the oligonucleotide-conjugate complex in the liver. In certain embodiments, the selective placement of two or more conjugate groups onto an oligonucleotide enhances the accumulation of the oligonucleotide-conjugate complex in the kidney. In certain embodiments, the selective placement of two or more conjugate groups onto an oligonucleotide enhances the accumulation of the oligonucleotide-conjugate complex in the spleen. In certain embodiments, the selective placement of two or more conjugate groups onto an oligonucleotide enhances the accumulation of the oligonucleotide-conjugate complex in the pancreas.

In certain embodiments, the selective placement of two or more conjugate groups onto an oligonucleotide enhances the accumulation of the oligonucleotide-conjugate complex in a cell. In certain embodiments, the selective placement of two or more conjugate groups onto an oligonucleotide enhances the accumulation of the oligonucleotide-conjugate complex in the nucleus. In certain embodiments, the selective placement of two or more conjugate groups onto an oligonucleotide enhances the accumulation of the oligonucleotide-conjugate complex in the cytoplasm.

In certain embodiments, two or more conjugate groups may be attached at any position on any nucleoside in an oligonucleotide. For example, in certain embodiments, the disclosure provides oligonucleotides consisting of 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, or 14 to 30 linked nucleosides.

In certain embodiments, the oligonucleotide consists of 14 nucleosides and a conjugate group is attached to the 1, 2, 3, 4, 5, 6, 7, 8, 9, 10, 11, 12, 13 or 14 nucleoside from the 5' end or the 14, 13, 12, 11, 10, 9, 8, 7, 6, 5, 4, 3, 2, or 1 nucleoside from the 3' end and a second conjugate group is attached to the 1, 2, 3, 4, 5, 6, 7, 8, 9, 10, 11, 12, 13 or 14 nucleoside from the 5' end or the 14, 13, 12, 11, 10, 9, 8, 7, 6, 5, 4, 3, 2, or 1 nucleoside from the 3' end. In certain embodiments, the oligonucleotide consists of 15 nucleosides and a conjugate group attached to the 1, 2, 3, 4, 5, 6, 7, 8, 9, 10, 11, 12, 13, 14, or 15 nucleoside from the 5' end or the 15, 14, 13, 12, 11, 10, 9, 8, 7, 6, 5, 4, 3, 2, or 1 nucleoside from the 3' end and a second conjugate group is attached to the 1, 2, 3, 4, 5, 6, 7, 8, 9, 10, 11, 12, 13, 14, or 15 nucleoside from the 5' end or the 15, 14, 13, 12, 11, 10, 9, 8, 7, 6, 5, 4, 3, 2, or 1 nucleoside from the 3' end. In certain embodiments, the oligonucleotide consists of 16 nucleosides and a conjugate group is attached to the 1, 2, 3, 4, 5, 6, 7, 8, 9, 10, 11, 12, 13, 14, 15, or 16 nucleoside from the 5' end or the 16, 15, 14, 13, 12, 11, 10, 9, 8, 7, 6, 5, 4, 3, 2, or 1 nucleoside from the 3' end and a second conjugate group is attached to the 1, 2, 3, 4, 5, 6, 7, 8, 9, 10, 11, 12, 13, 14, 15, or 16 nucleoside from the 5' end or the 16, 15, 14, 13, 12, 11, 10, 9, 8, 7, 6, 5, 4, 3, 2, or 1 nucleoside from the 3' end. In certain embodiments, the oligonucleotide consists of 17 nucleosides and a conjugate group attached to the 1, 2, 3, 4, 5, 6, 7, 8, 9, 10, 11, 12, 13, 14, 15, 16, or 17 nucleoside from the 5' end or the 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, or 17 nucleoside from the 5' end or the 17, 16, 15, 14, 13, 12, 11, 10, 9, 8, 7, 6, 5, 4, 3, 2, or 1 nucleoside from the 3' end. In certain embodiments, the oligonucleotide consists of 18 nucleosides and a conjugate group attached to the 1, 2, 3, 4, 5, 6, 7, 8, 9, 10, 11, 12, 13, 14, 15, 16, 17, or 18 nucleoside from the 5' end or the 18, 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, 17, or 18 nucleoside from the 5' end or the 18, 17, 16, 15, 14, 13, 12, 11, 10, 9, 8, 7, 6, 5, 4, 3, 2, or 1 nucleoside from the 3' end. In certain embodiments, the oligonucleotide consists of 19 nucleosides and a conjugate group attached to the 1, 2, 3, 4, 5, 6, 7, 8, 9, 10, 11, 12, 13, 14, 15, 16, 17, 18, or 19 nucleoside from the 5' end or the 19, 18, 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, 17, 18, or 19 nucleoside from the 5' end or the 19, 18, 17, 16, 15, 14, 13, 12, 11, 10, 9, 8, 7, 6, 5, 4, 3, 2, or 1 nucleoside from the 3' end.

In certain embodiments, the oligonucleotide consists of 20 nucleosides and a conjugate group attached to the 1, 2, 3, 4, 5, 6, 7, 8, 9, 10, 11, 12, 13, 14, 15, 16, 17, 18, 19, or 20 nucleoside from the 5' end or the 20, 19, 18, 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, 17, 18, 19, or 20 nucleoside from the 5' end or the 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 21 nucleosides and a conjugate group attached to the 1, 2, 3, 4, 5, 6, 7, 8, 9, 10, 11, 12, 13, 14, 15, 16, 17, 18, 19, 20 or 21 nucleoside from the 5' end or the 21, 20, 19, 18, 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, 17, 18, 19, 20 or 21 nucleoside from the 5' end or the 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 22 nucleosides and a conjugate group attached to the 1, 2, 3, 4, 5, 6, 7, 8, 9, 10, 11, 12, 13, 14, 15, 16, 17, 18, 19, 20, 21 or 22 nucleoside from the 5' end or the 22, 21, 20, 19, 18, 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, 17, 18, 19, 20, 21 or 22 nucleoside from the 5' end or the 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 23 nucleosides and a conjugate group attached to the 1, 2, 3, 4, 5, 6, 7, 8, 9, 10, 11, 12, 13, 14, 15, 16, 17, 18, 19, 20, 21, 22, or 23 nucleoside from the 5' end or the 23, 22, 21, 20, 19, 18, 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, 17, 18, 19, 20, 21, 22, or 23 nucleoside from the 5' end or the 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 24 nucleosides and a conjugate group attached to the 1, 2, 3, 4, 5, 6, 7, 8, 9, 10, 11, 12, 13, 14, 15, 16, 17, 18, 19, 20, 21, 22, 23, or 24 nucleoside from the 5' end or the 24, 23, 22, 21, 20, 19, 18, 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, 17, 18, 19, 20, 21, 22, 23, or 24 nucleoside from the 5' end or the 24, 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 25 nucleosides and a conjugate group attached to the 1, 2, 3, 4, 5, 6, 7, 8, 9, 10, 11, 12, 13, 14, 15, 16, 17, 18, 19, 20, 21, 22, 23, 24, or 25 nucleoside from the 5' end or the 25, 24, 23, 22, 21, 20, 19, 18, 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, 17, 18, 19, 20, 21, 22, 23, 24, or 25 nucleoside from the 5' end or the 25, 24, 23, 22, 21, 20, 19, 18, 17, 16, 15, 14, 13, 12, 11, 10, 9, 8, 7, 6, 5, 4, 3, 2, or 1 nucleoside from the 3' end.

In certain embodiments, the oligonucleotide consists of 26 nucleosides and a conjugate group attached to the 1, 2, 3, 4, 5, 6, 7, 8, 9, 10, 11, 12, 13, 14, 15, 16, 17, 18, 19, 20, 21, 22, 23, 24, 25, or 26 nucleoside from the 5' end or the 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end and a second conjugate group is attached to the 1, 2, 3, 4, 5, 6, 7, 8, 9, 10, 11, 12, 13, 14, 15, 16, 17, 18, 19, 20, 21, 22, 23, 24, 25, or 26 nucleoside from the 5' end or the 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 27 nucleosides and a conjugate group attached to the 1, 2, 3, 4, 5, 6, 7, 8, 9, 10, 11, 12, 13, 14, 15, 16, 17, 18, 19, 20, 21, 22, 23, 24, 25, 26, or 27 nucleoside from the 5' end or the 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end and a second conjugate group is attached to the 1, 2, 3, 4, 5, 6, 7, 8, 9, 10, 11, 12, 13, 14, 15, 16, 17, 18, 19, 20, 21, 22, 23, 24, 25, 26, or 27 nucleoside from the 5' end or the 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 28 nucleosides and a conjugate group attached to the 1, 2, 3, 4, 5, 6, 7, 8, 9, 10, 11, 12, 13, 14, 15, 16, 17, 18, 19, 20, 21, 22, 23, 24, 25, 26, 27, or 28 nucleoside from the 5' end or the 28, 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, 17, 18, 19, 20, 21, 22, 23, 24, 25, 26, 27, or 28 nucleoside from the 5' end or the 28, 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 29 nucleosides and a conjugate group attached to the 1, 2, 3, 4, 5, 6, 7, 8, 9, 10, 11, 12, 13, 14, 15, 16, 17, 18, 19, 20, 21, 22, 23, 24, 25, 26, 27, 28, or 29 nucleoside from the 5' end or the 29, 28, 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, 17, 18, 19, 20, 21, 22, 23, 24, 25, 26, 27, 28, or 29 nucleoside from the 5' end or the 29, 28, 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end. In certain embodiments, the oligonucleotide consists of 30 nucleosides and a conjugate group attached to the 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleoside from the 5' end or the 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end and a second conjugate group attached to the 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleoside from the 5' end or the 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 nucleoside from the 3' end.

In certain embodiments, a conjugate group is attached to a nucleoside at position 8 from the 5' end and a second conjugate group is attached to the nucleoside at position 6 from the 5' end. In certain embodiments, a conjugate group is attached to a nucleoside at position 1 from the 5' end and a second conjugate group is attached to the nucleoside at position 6 from the 5' end. In certain embodiments, a conjugate group is attached to a nucleoside at position 1 from the 5' end and a second conjugate group is attached to the nucleoside at position 8 from the 5' end. In certain embodiments, a conjugate group is attached to a nucleoside at position 21 from the 5' end and a second conjugate group is attached to the nucleoside at position 6 from the 5' end. In certain embodiments, a conjugate group is attached to a nucleoside at position 21 from the 5' end and a second conjugate group is attached to the nucleoside at position 8 from the 5' end. In certain embodiments, a conjugate group is attached to a nucleoside at position 1 from the 5' end and a second conjugate group is attached to the nucleoside at position 21 from the 5' end.

H. ANTISENSE COMPOUNDS

In certain embodiments, compounds of the present disclosure are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid or reduce non-specific hybridization to non-target nucleic acid sequences under conditions in which specific hybridization is desired (e.g., under physiological conditions for in vivo or therapeutic uses, and under conditions in which assays are performed in the case of in vitro assays). In certain embodiments, oligonucleotides are selective between a target and non-target, even though both target and non-target comprise the target sequence. In such embodiments, selectivity may result from relative accessability of the target region of one nucleic acid molecule compared to the other.

In certain embodiments, the present disclosure provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments, oligonucleotides comprise a hybridizing region and a terminal region. In certain such embodiments, the hybridizing region consists of 12-30 linked nucleosides and is fully complementary to the target nucleic acid. In certain embodiments, the hybridizing region includes one mismatch relative to the target nucleic acid. In certain embodiments, the hybridizing region includes two mismatches relative to the target nucleic acid. In certain embodiments, the hybridizing region includes three mismatches relative to the target nucleic acid. In certain embodiments, the hybridizing region includes four mismatches relative to the target nucleic acid. In certain embodiments, the terminal region consists of 1-4 terminal nucleosides. In certain embodiments, the terminal nucleosides are at the 3' end. In certain embodiments, one or more of the terminal nucleosides are not complementary to the target nucleic acid.

Antisense mechanisms include any mechanism involving the hybridization of an oligonucleotide with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms.

In certain embodiments, antisense compounds of the present disclosure are RNAi compounds. In certain embodiments, antisense compounds of the present disclosure are ssRNA compounds. In certain embodiments, antisense compounds of the present disclosure are paired with a second oligonucleotide to form an siRNA. In certain such embodiments, the second oligonucleotide is also a compound of the present disclosure. In certain embodiments, the second oligonucleotide is any modified or oligonucleotide. In certain embodiments, the oligonucleotide of the present disclosure is the antisense strand in an siRNA compound. In certain embodiments, the oligonucleotide of the present disclosure is the sense strand in an siRNA compound.

i. Single-Stranded RNAi Compounds

In certain embodiments, oligonucleotides of the present disclosure are particularly suited for use as single-stranded antisense compounds. In certain such embodiments, such oligonucleotides are single-stranded RNAi compounds. In certain embodiments, such oligonucleotides are ssRNA compounds or microRNA mimics. Certain 5'-terminal nucleosides described herein are suited for use in such single-stranded oligonucleotides. In certain embodiments, such 5'-terminal nucleosides stabilize the 5'-phosphorous moiety. In certain embodiments, 5'-terminal nucleosides of the present disclosure are resistant to nucleases. In certain embodiments, the motifs of the present disclosure are particularly suited for use in single-stranded oligonucleotides.

For further description of single-stranded RNAi compounds, see, e.g., WO 2010/048585, WO 2010/048549, and PCT/US2011/033968.

Use of single-stranded RNAi compounds has been limited. In certain instances, single stranded RNAi compounds are quickly degraded and/or do not load efficiently into RISC. Design of single-stranded RNAi compounds for use in cells and/or for use in vivo presents several challenges. For example, the compound must be chemically stable, resistant to nuclease degradation, capable of entering cells, capable of loading into RISC (e.g., binding Ago1 or Ago2), capable of hybridizing with a target nucleic acid, and not toxic to cells or animals. In certain instances, a modification or motif that improves one such feature may worsen another feature, rendering a compound having such modification or motif unsuitable for use as an RNAi compound. For example, certain modifications, particularly if placed at or near the 5'-end of an oligonucleotide, may make the compound more stable and more resistant to nuclease degradation, but may also inhibit or prevent loading into RISC by blocking the interaction with RISC components, such as Ago1 or Ago2. Despite its improved stability properties, such a compound would be unsuitable for use in RNAi.

In certain instances, a single-stranded oligonucleotide comprising a 5'-phosphorous moiety is desired. For example, in certain embodiments, such 5'-phosphorous moiety is necessary or useful for RNAi compounds, particularly, single-stranded RNAi compounds. In such instances, it is further desirable to stabilize the phosphorous moiety against degradation or de-phosphorylation, which may inactivate the compound. Further, it is desirable to stabilize the entire 5'-nucleoside from degradation, which could also inactivate the compound. Thus, in certain embodiments, oligonucleotides in which both the 5'-phosphorous moiety and the 5'-nucleoside have been stabilized are desired. In certain embodiments, provided are modified nucleosides that may be placed at the 5'-end of an oligonucleotide, resulting in a stabilized phosphorous and stabilized nucleoside. In certain such embodiments, the phosphorous moiety is resistant to removal in biological systems, relative to unmodified nucleosides and/or the 5'-nucleoside is resistant to cleavage by nucleases. In certain embodiments, such nucleosides are modified at one, at two or at all three of: the 2'-position, the 5'-position, and at the phosphorous moiety. Such modified nucleosides may be incorporated at the 5'-end of an oligonucleotide.

Although certain oligonucleotides described herein have particular use as single-stranded compounds, such compounds may also be paired with a second strand to create a double-stranded compound. In such embodiments, the second strand of the double-stranded duplex may or may not also be an oligonucleotide as described herein.

In some embodiments, oligonucleotides described herein comprise a double stranded composition comprising a first oligomeric compound and a second oligomeric compound, wherein the first oligomeric compound is partially complementary to the second oligomeric compound and the second oligomeric compound is complementary to a nucleic acid target, and wherein at least one of the first and second oligomeric compounds is an oligomeric compound according to any one of the oligonucleotides described herein.

In certain embodiments, such oligonucleotides may be paired with a second strand to form a double-stranded compound. In such embodiments, the second strand of such double-stranded compounds may comprise a motif of the present invention, may comprise another motif of modifications, may be of any suitable length, or may be unmodified. In certain embodiments, such oligonucleotides may be paired with a second strand to form a double-stranded RNAi compound. In such embodiments, the second strand of such double-stranded RNAi compounds may comprise a motif of the present invention, may comprise another motif of modifications, may be of any suitable length, or may be unmodified.

In certain embodiments, oligonucleotides as described herein interact with an argonaute protein (Ago). In certain embodiments, such oligonucleotides first enter the RISC pathway by interacting with another member of the pathway (e.g., dicer). In certain embodiments, oligonucleotides first enter the RISC pathway by interacting with Ago. In certain embodiments, such interaction ultimately results in antisense activity. In certain embodiments, provided are methods of activating Ago comprising contacting Ago with an oligonucleotide. In certain embodiments, such oligonucleotides comprise a modified 5'-phosphate group. In certain embodiments, provided are methods of modulating the expression or amount of a target nucleic acid in a cell comprising contacting the cell with an oligonucleotide capable of activating Ago, ultimately resulting in cleavage of the target nucleic acid. In certain embodiments, the cell is in an animal. In certain embodiments, the cell is in vitro. In certain embodiments, the methods are performed in the presence of manganese. In certain embodiments, the manganese is endogenous. In certain embodiment the methods are performed in the absence of magnesium. In certain embodiments, the Ago is endogenous to the cell. In certain such embodiments, the cell is in an animal. In certain embodiments, the Ago is human Ago. In certain embodiments, the Ago is Ago2. In certain embodiments, the Ago is human Ago2.

In certain embodiments, provided are oligonucleotides having motifs (nucleoside motifs and/or linkage motifs) that result in improved properties. Certain such motifs result in single-stranded oligonucleotides with improved stability and/or cellular uptake properties while retaining antisense activity. For example, oligonucleotides having an alternating nucleoside motif and seven phosphorothioate linkages at to 3'-terminal end have improved stability and activity. Similar compounds that comprise phosphorothioate linkages at each linkage have further improved stability, but are not active as RNAi compounds, presumably because the additional phosphorothioate linkages interfere with the interaction of the oligonucleotide with the RISC pathway components (e.g., with Ago). In certain embodiments, the oligonucleotides having motifs herein result in single-stranded RNAi compounds having desirable properties. In certain embodiments, such oligonucleotides may be paired with a second strand to form a double-stranded RNAi compound. In such embodiments, the second strand of such double-stranded RNAi compounds may comprise a motif as described herein, may comprise another motif of modifications or may be unmodified.

It has been shown that in certain circumstances for single-stranded RNA comprising a 5'-phosphate group has RNAi activity but has much less RNAi activity if it lacks such 5'-phosphate group. The present inventors have recognized that in certain circumstances unmodified 5'-phosphate groups may be unstable (either chemically or enzymatically). Accordingly, in certain circumstances, it is desirable to modify the oligonucleotide to stabilize the 5'-phosphate. In certain embodiments, this is achieved by modifying the phosphate group. In certain embodiments, this is achieved by modifying the sugar of the 5'-terminal nucleoside. In certain embodiments, this is achieved by modifying the phosphate group and the sugar. In certain embodiments, the sugar is modified at the 5'-position, the 2'-position, or both the 5'-position and the 2'-position. As with motifs, above, in embodiments in which RNAi activity is desired, a phosphate stabilizing modification must not interfere with the ability of the oligonucleotide to interact with RISC pathway components (e.g., with Ago).

In certain embodiments, provided are oligonucleotides comprising a phosphate-stabilizing modification and a motif described herein. In certain embodiments, such oligonucleotides are useful as single-stranded RNAi compounds having desirable properties. In certain embodiments, such oligonucleotides may be paired with a second strand to form a double-stranded RNAi compound. In such embodiments, the second strand may comprise a motif as described herein, may comprise another motif of modifications or may be unmodified RNA.

In certain embodiments, provided are compounds and methods for antisense activity in a cell. In certain embodiments, the cell is in an animal. In certain embodiments, the animal is a human. In certain embodiments, provided are methods of administering a compound as described herein to an animal to modulate the amount or activity or function of one or more target nucleic acid.

In certain embodiments oligonucleotides comprise one or more motifs as described herein, but do not comprise a phosphate stabilizing modification. In certain embodiments, such oligonucleotides are useful for in vitro applications.

I. CERTAIN PHARMACEUTICAL COMPOSITIONS

In certain embodiments, the present disclosure provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligonucleotide which are cleaved by endogenous nucleases within the body, to form the active antisense oligonucleotide.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present disclosure to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present disclosure provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present disclosure provides methods of administering a pharmaceutical composition comprising an oligonucleotide of the present disclosure to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

J. CERTAIN USES AND ROUTES OF ADMINISTRATION

In certain embodiments, provided herein are methods of contacting a cell with an oligonucleotide described herein. In certain embodiments, the cell is in vitro. In certain embodiments, the cell is in an animal (e.g., rodent, primate, monkey or human). In certain embodiments, antisense activity is detected.

In certain embodiments, the disease is any of atrophin 1 (DRPLA), Huntington's Disease, Huntington disease-like 2 (HDL2), spinal and bulbar muscular atrophy, Kennedy disease, spinocerebellar ataxia 1, spinocerebellar ataxia 12, spinocerebellar ataxia 17, Huntington disease-like 4 (HDL4), spinocerebellar ataxia 2, spinocerebellar ataxia 3, Machado-Joseph disease, spinocerebellar ataxia 6, spinocerebellar ataxia 7 (OPCA3), ataxin 8 opposite strand (ATXN8OS), myotonic dystrophy (DM1), DM2, and spinocerebellar ataxia 8.

In certain embodiments, compounds as described herein are administered to an animal (e.g., a human) to provide a therapeutic effect. In certain embodiments, the disease is selected from among: ataxin 8, atrophin 1, fragile X syndrome, Friedrich's ataxia, Huntington's disease, Huntington's disease-like 2, myotonic dystrophy, spinal and bulbar muscular atrophy, and spinocerebellar ataxia. In certain embodiments, the disease is Huntington's disease. In certain embodiments, the disease is myotonic dystrophy. In certain embodiments, the myotonic dystrophy is myotonic dystrophy type 1. In certain embodiments, the myotonic dystrophy is myotonic dystrophy type 2. In certain embodiments, the disease is spinocerebellar ataxia. In certain embodiments, the spinocerebellar ataxia is spinocerebellar ataxia 10.

In certain embodiments, pharmaceutical compositions as described herein are administered to a subject. In certain embodiments, such pharmaceutical compositions are administered by injection. In certain embodiments, such pharmaceutical compositions are administered by infusion.

In certain embodiments, pharmaceutical compositions are administered by injection or infusion into the CSF. In certain such embodiments, pharmaceutical compositions are administered by direct injection or infusion into the spine. In certain embodiments, pharmaceutical compositions are administered by injection or infusion into the brain. In certain embodiments, pharmaceutical compositions are administered by intrathecal injection or infusion rather than into the spinal cord tissue itself. Without being limited as to theory, in certain embodiments, the antisense compound released into the surrounding CSF and may penetrate into the spinal cord parenchyma. An additional advantage of intrathecal delivery is that the intrathecal route mimics lumbar puncture administration (i.e., spinal tap) already in routine use in humans.

In certain embodiments, pharmaceutical compositions are administered by intracerebroventricular (ICV) injection or infusion. Intracerebroventricular or intraventricular delivery of a pharmaceutical composition comprising one or more oligonucleotide may be performed in any one or more of the brain's ventricles, which are filled with cerebrospinal fluid (CSF). CSF is a clear fluid that fills the ventricles, is present in the subarachnoid space, and surrounds the brain and spinal cord. CSF is produced by the choroid plexuses and via the weeping or transmission of tissue fluid by the brain into the ventricles. The choroid plexus is a structure lining the floor of the lateral ventricle and the roof of the third and fourth ventricles. Certain studies have indicated that these structures are capable of producing 400-600 ccs of fluid per day consistent with an amount to fill the central nervous system spaces four times in a day. In adult humans, the volume of this fluid has been calculated to be from 125 to 150 ml (4-5 oz). The CSF is in continuous formation, circulation and absorption. Certain studies have indicated that approximately 430 to 450 ml (nearly 2 cups) of CSF may be produced every day. Certain calculations estimate that production equals approximately 0.35 ml per minute in adults and 0.15 per minute in infant humans. The choroid plexuses of the lateral ventricles produce the majority of CSF. It flows through the foramina of Monro into the third ventricle where it is added to by production from the third ventricle and continues down through the aqueduct of Sylvius to the fourth ventricle. The fourth ventricle adds more CSF; the fluid then travels into the subarachnoid space through the foramina of Magendie and Luschka. It then circulates throughout the base of the brain, down around the spinal cord and upward over the cerebral hemispheres. The CSF empties into the blood via the arachnoid villi and intracranial vascular sinuses.

In certain embodiments, such pharmaceutical compositions are administered systemically. In certain embodiments, pharmaceutical compositions are administered subcutaneously. In certain embodiments, pharmaceutical compositions are administered intravenously. In certain embodiments, pharmaceutical compositions are administered by intramuscular injection.

In certain embodiments, pharmaceutical compositions are administered both directly to the CSF (e.g., IT and/or ICV injection and/or infusion) and systemically. In certain such embodiments, compounds as described herein have one or more desirable properties making them suitable for such administration. Drug design typically requires a balance of several variables, including, but not limited to: potency, toxicity, stability, tissue distribution, convenience, and cost of a candidate compound. Such balancing is influenced by a number of factors, including the severity and typical duration of the disease treated. For example, greater drug-related toxicity is tolerated for use in treating acute lethal diseases than chronic sub-lethal diseases. In certain embodiments, compounds as described herein will have one or more improved properties compared to similar compounds that lack certain features as described herein. For example, compared to other compounds, the compounds as described herein, may, in certain embodiments, have improved potency or may have similar potency but reduced toxicity and consequently improved therapeutic index. In certain embodiments, compounds as described herein may have improved pharmacokinetics or distribution to a particular desired target tissue.

In certain embodiments, oligonucleotides as described herein are used in cells in vitro. In certain such embodiments, such uses are to identify and/or study repeat-containing nucleic acids and mechanisms surrounding them and associated diseases.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "AT$^{me}$CGAUCG," wherein $^{me}$C indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Examples

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

Synthesis of Oligomeric Compounds

The oligomeric compounds used in accordance with this disclosure may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P═O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P═S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P═O or P═S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 2

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32 +/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 3

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated NH$_4$OH at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 4

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 5

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

Lipofectin™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 6

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 7

Analysis of Oligonucleotide Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 8

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 9

RNA Isolation

Poly(A)+ mRNA Isolation

Poly(A)+ mRNA is isolated according to Miura et al., (Clin. Chem., 1996, 42, 1758-1764). Other methods for poly(A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 10

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
                                          (SEQ ID NO: 2)
     Forward primer:    AATGGCTAAGTGAAGATGACAATCAT (SEQ ID NO: 3)
     Reverse primer:    TGCACATATCATTACACCAGTTCGT
```

And the PCR probe:

```
                                          (SEQ ID NO: 4)
     FAM-TTGCAGCAATTCACTGTAAAGCTGGAAAGG-TAMRA,
``` where FAM is the fluorescent dye and TAMRA is the quencher dye.

Example 11

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 12

General Method for the Preparation of Oligomeric Compounds Containing Modified Nucleosides as Provided Herein at the 5'-Terminus Via Solid Phase Techniques (Preparation of 505739)

Unless otherwise stated, all reagents and solutions used for the synthesis of oligomeric compounds were purchased from commercial sources. Standard phosphoramidites and solid support were used for incorporation of A, U, G, $^{me}C$ and C residues. A 0.1 M solution of 2'-F and 2'-O-Me phosphoramidites in anhydrous acetonitrile ($CH_3CN$) along with 2'-O-MOE-5'-deoxy-5'-methylenediethylphosphonate and 2'-O-MOE-deoxy-5'-vinyldimethylphosphonate 3'-phosphoramidites in 30% dichloromethane ($CH_2Cl_2$) in anhydrous $CH_3CN$ were used for the synthesis. The oligomeric compounds were synthesized on VIMAD UnyLinker™ solid support and the appropriate amounts of solid support were packed in the column for synthesis. Dichloroacetic acid (6%) in toluene was used as detritylating reagent. 4,5-Dicyanoimidazole in the presence of N-methylimidazole or 1H-tetrazole in $CH_3CN$ was used as activator during the coupling step. The synthesis of oligomeric compounds was performed either on an ÄKTAOligopilot synthesizer (GE Healthcare Bioscience) or an ABI394 synthesizer (Applied Biosystems) on a 2-200 µmol scale using the procedures set forth below.

A solid support preloaded with the Unylinker™ was loaded into a synthesis column after closing the column bottom outlet and $CH_3CN$ was added to form a slurry. The swelled support-bound Unylinker™ was treated with a detritylating reagent containing 6% dichloroacetic acid in toluene to provide the free hydroxyl groups. During the coupling step, four to fourteen equivalents of phosphoramidite solutions were delivered with coupling for 10 minutes. All of the other steps followed standard protocols. Phosphorothioate linkages were introduced by sulfurization with a 0.05 M solution of DDTT (3-((dimethylamino-methylidene)amino)-3H-1,2,4-dithiazole-3-thione) in 1:1 pyridine/$CH_3CN$ for a contact time of 3 minutes. Phosphite triester internucleoside linkages were oxidized to phosphate diester internucleoside linkages using a solution of tert-butyl hydroperoxide/$CH_3CN$/water (10:87:3) over 12 minutes.

After the desired sequence was assembled, the solid support bound oligomeric compound was washed with $CH_2Cl_2$ and dried under high vacuum. After 4 hrs, the dried solid support was suspended in a solution of iodotrimethylsilane (TMSI) and pyridine in $CH_2Cl_2$ to remove the 5'-phosphonate protecting group (ethyl ether or methyl ether). The deprotection solution was prepared by dissolving 0.75 mL TMSI and 0.53 mL pyridine in 28.2 mL $CH_2Cl_2$ (used 0.5 mL/µmol of solid support). After 30 min at room temperature, the reaction was quenched with 1M 2-mercaptoethanol in 1:1 TEA/$CH_3CN$ (used 0.5 mL/µmol of solid support). The supernatant was decanted and the solid-support was washed with additional 2-mercaptoethanol solution. After 45 minutes at room temperature the wash step with additional 2-mercaptoethanol solution was repeated. The supernatant was decanted and the solid-support bound oligomeric compound was suspended in ammonia (28-30 wt %) in 1 M 2-mercaptoethanol (used 0.75 mL/µmol of solid support) and heated at 55° C. for 2 hrs to cleave the oligomeric compound from the solid support.

The cleaved solution was allowed to cool to ambient temperature (20° C.) for 24 hrs. The unbound oligomeric compound was then filtered and the support was rinsed and filtered with water:ethanol (1:1) followed by water. The filtrate was combined and concentrated to dryness. The residue obtained was purified by HPCL on a reverse phase column (Waters X-Bridge C-18 5 µm, 19×250 mm, A=5 mM tributylammonium acetate in 5% aqueous $CH_3CN$, B=$CH_3CN$, 0 to 90% B in 80 min, flow 7 mL min$^{-1}$, $\lambda$=260 nm). Fractions containing full-length oligomeric compound were pooled together (assessed by LC/MS analysis >95%) and the tributylammonium counter ion was exchanged to sodium by HPLC on a strong anion exchange column (GE Healthcare Bioscience, Source 30Q, 30 µm, 2.54×8 cm, A=100 mM ammonium acetate in 30% aqueous $CH_3CN$, B=1.5 M NaBr in A, 0-40% of B in 60 min, flow 14 mL min$^{-1}$). The residue was desalted by HPLC on a reverse phase column to yield the oligomeric compound in an isolated yield of 15-20% based on solid-support loading. The unbound oligomeric compound was characterized by ion-pair-HPLC-MS analysis with Agilent 1100 MSD system.

The modified oligonucleotides comprising a 5'-(E)-vinylphosphonate group is described in Table 1. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH)-$. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside.

TABLE 1

Modified oligomeric compound comprising a 5'-(E)-vinyphosphonate

| ISIS NO. | Composition (5' to 3') | 5'-Chemistry | SEQ ID NO. |
|---|---|---|---|
| 505739 | Pv-T$_{es}$U$_{fs}$G$_m$U$_{fs}$C$_m$U$_{fs}$C$_m$U$_{fs}$G$_m$G$_{fs}$U$_m$C$_{fs}$C$_m$U$_{fs}$U$_{ms}$A$_{fs}$C$_{ms}$U$_{fs}$U$_{ms}$A$_{es}$A$_e$ | (E)-(PO(OH)$_2$(CH=CH)- | 5 |

Example 13

Preparation of Modified Oligomeric Compounds Comprising a Modified 5'-Nucleoside (5'-Deoxy-5'-Methylenediethylphosphonate and 5'-Deoxy-5'-Vinyldimethylphosphonate)

Oligomeric compounds were prepared on either a 2 or 200 µmol scale following procedures illustrated in Example 12. Both ÄKTAOligopilot synthesizer (GE Healthcare Bioscience) and ABI394 synthesizer (Applied Biosystems) were used for particular runs. The unbound oligomeric compounds were cleaved from the solid support and analyzed by ion-pair-HPLC-MS.

The modified oligonucleotides comprising a 5'-(E)-vinylphosphonate group, $(PO(OH)_2(CH=CH-)$, and a 5'-methylenediethylphosphonate group, $(PO(OCH_2CH_3)_2(CH_2CH_2-)$ are described in Table 2. A subscript "s" between two nucleosides indicates a phosphorothioate internucleoside linkage (going 5' to 3'). The absence of a subscript "s" between two nucleosides indicates a phosphodiester internucleoside linkage. A "Py" at the 5'-end indicates a 5'-methylenediethylphosphonate group, $(PO(OCH_2CH_3)_2(CH_2CH_2-)$. A "Pv" at the 5'-end indicates a 5'-(E)-vinylphosphonate group, $(PO(OH)_2(CH=CH-)$. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside.

TABLE 2

Modified oligonucleotides comprising a modified 5'-terminus group

| ISIS NO. | Composition (5' to 3') | 5'-Chemistry | SEQ ID NO. |
|---|---|---|---|
| 508027 | Py-$T_{es}U_{fs}G_mU_{fs}C_mU_{fs}C_mU_{fs}G_mG_{fs}$ $U_mC_{fs}C_mU_{fs}U_{ms}A_{fs}C_{ms}U_{fs}U_{ms}A_{es}A_e$ | (PO(OCH$_2$CH$_3$)$_2$(CH$_2$CH$_2$-) | 5 |
| 505739 | Pv-$T_{es}U_{fs}G_mU_{fs}C_mU_{fs}C_mU_{fs}G_mG_{fs}$ $U_mC_{fs}C_mU_{fs}U_{ms}A_{fs}C_{ms}U_{fs}U_{ms}A_{es}A_e$ | (E)-(PO(OH)$_2$(CH=CH-) | 5 |
| 508016 | Py-$T_{es}U_{fs}A_mU_{fs}C_mU_{fs}A_mU_{fs}A_mA_{fs}$ $U_mG_{fs}A_mU_{fs}C_{ms}A_{fs}G_{ms}G_{fs}U_{ms}A_{es}A_e$ | (PO(OCH$_2$CH$_3$)$_2$(CH$_2$CH$_2$-) | 6 |
| 522247 | Pv-$T_{es}U_{fs}A_mU_{fs}C_mU_{fs}A_mU_{fs}A_mA_{fs}U_m$ $G_{fs}A_mU_{fs}C_{ms}A_{fs}G_{ms}G_{fs}U_{ms}A_{es}A_e$ | (E)-(PO(OH)$_2$(CH=CH-) | 6 |
| 508015 | Py-$T_{es}G_{fs}A_mA_{fs}C_mA_{fs}U_mU_{fs}G_mG_{fs}$ $A_mA_{fs}U_mA_{fs}G_{ms}U_{fs}U_{ms}U_{fs}C_{ms}A_{es}A_e$ | (PO(OCH$_2$CH$_3$)$_2$(CH$_2$CH$_2$-) | 7 |
| 522246 | Pv-$T_{es}G_{fs}A_mA_{fs}C_mA_{fs}U_mU_{fs}G_mG_{fs}$ $A_mA_{fs}U_mA_{fs}G_{ms}U_{fs}U_{ms}U_{fs}C_{ms}A_{es}A_e$ | (E)-(PO(OH)$_2$(CH=CH-) | 7 |

Example 14

General Method for the Preparation of C16- and Cholesterol-Conjugated Oligomeric Compounds 2 and 3

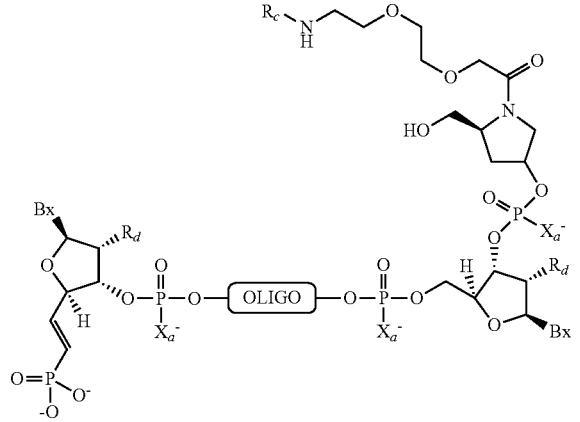

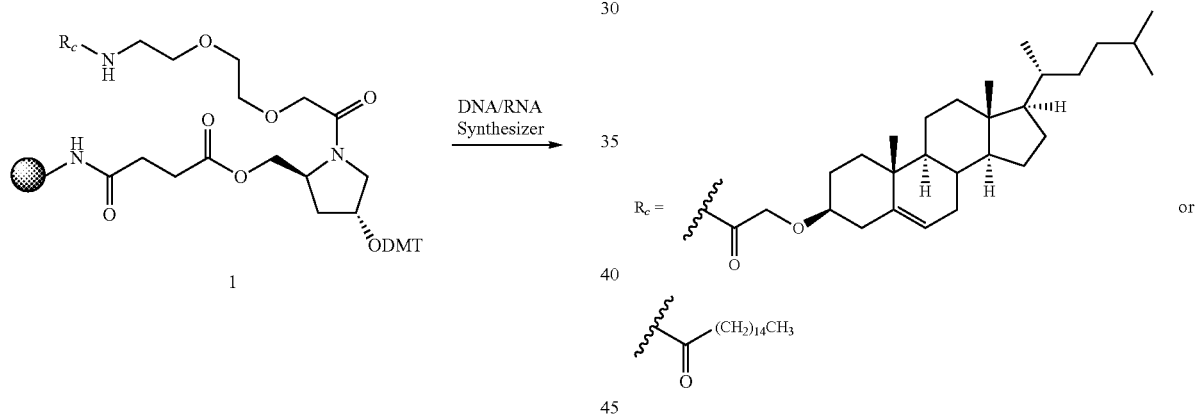

$B_x$ = heterocyclic base moiety
$R_d$ = sugar substituent group
$X_a$ = O or S

= solid support $R_c$ = or

-(CH$_2$)$_{14}$CH$_3$

Compound 1 and conjugated oligomeric Compounds 2 and 3 are prepared according to published procedures (see Swayze et al., WO 2006/031461) and procedures illustrated in Example 12.

Example 15

Preparation of C16- and Cholesterol-Conjugated Oligomeric Compounds

The C16 and cholesterol conjugated oligomeric compounds shown in Table 3 were prepared as per the procedures illustrated in Examples 12 and 14.

The conjugated oligomeric compounds were cleaved from the solid support, analyzed by ion-pair-HPLC-MS and are described in Table 3. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group (PO(OH)$_2$(CH=CH—). Nucleosides followed by a subscript f, m or e are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. The C16 alkyl chain and cholesterol conjugated through a pyrrolidine linker group are shown below. Underlined nucleosides indicate the conjugate position.

Table 4. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group $(PO(OH)_2(CH=CH-))$. Nucleosides followed by a subscript "1", "m" or "e" are sugar modified nucleosides. A subscript "f" indicates a 2'-fluoro modified nucleoside, a

TABLE 3

Modified oligonucleotides comprising conjugates

| ISIS NO. | Composition (5' to 3') | Mass (Da) Calculated | Observed | SEQ ID NO. |
|---|---|---|---|---|
| 526608 | Pv-$T_{es}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}A_{es}\underline{A_e}$-C16 | 7879.2 | 7877.6 | 6 |
| 527155 | Pv-$T_{es}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}A_{es}\underline{A_e}$-Cholesterol | 8067.5 | 8066.5 | 6 |

C16

Cholesterol

Example 16

Preparation of C16- and Cholesterol-Conjugated Oligomeric Compounds

Additional C16- and cholesterol-conjugated oligonucleotides comprising a 5'-(E)-vinylphosphonate group were designed based on the parent oligonucleotide, ISIS 522247 and were tested for their ability to reduce PTEN mRNA levels in hepatocytes. The modified oligonucleotides were created with C16 or cholesterol conjugate group at the 3'-terminus. The potency of the 3'-C16 or 3'-cholesterol-conjugated oligonucleotides were evaluated and compared to the parent oligonucleotide lacking a conjugate group, ISIS 522247 or 5-10-5 MOE gapmer, ISIS 116847.

The conjugated oligonucleotides were prepared as per the procedures illustrated in Example 14 and are described in subscript "m" indicates a 2'-O-methyl modified nucleoside and a subscript "e" indicates a 2'-O-methoxyethyl (MOE) modified nucleoside. Nucleosides not followed by a subscript is β-D-2'-deoxyribonucleoside. $^{me}C$ indicates a 5-methyl cytosine nucleoside. The C16 alkyl chain and cholesterol conjugated through a pyrrolidine linker group are shown below. Underlined nucleosides indicate the conjugate position.

The 3'-C16 or 3'-cholesterol-conjugated oligonucleotides were tested in vitro. Hepatocytes were treated with the modified oligonucleotides shown in Table 4 using LIPOFECTAMINE™ 2000 (Lipo) as transfection method as described herein. The $IC_{50}$'s were calculated using the linear regression equation generated by plotting the normalized mRNA levels to the log of the concentrations used and the results are presented in Table 4.

The parent oligomeric compound, ISIS 522247, from which the newly designed oligonucleotides were derived from is marked with an asterisk (*) in the table. The 5-10-5 MOE gapmer, ISIS 116847 was also included in the study as a benchmark oligonucleotide against which the potency of the 3'-C16 or 3'-cholesterol-conjugated oligonucleotides could be compared.

As illustrated in Table 4, modified oligonucleotide comprising a C16 conjugate at the 3' terminus exhibited comparable potency while the 3'-cholesterol conjugate showed no improvement in potency comparing to the parent oligonucleotide, ISIS 522247 and 5-10-5 MOE gapmer.

TABLE 4

Comparison of inhibition of PTEN mRNA levels of 3'-C16 or 3'-cholesterol-conjugated oligonucleotides with ISIS 116847 and ISIS 522247

| ISIS NO. | Composition (5' to 3') | Chemistry | $IC_{50}$ (nM) | SEQ ID NO. |
|---|---|---|---|---|
| 116847 | $^{me}C_{es}T_{es}G_{es}{}^{me}C_{es}T_{es}A_sG_s{}^{me}C_s{}^{me}C_sT_s{}^{me}C_sT_sG_sG_sA_sT_{es}T_{es}T_{es}G_eA_e$ | 5-10-5 MOE gapmer | 1 | 8 |
| 522247 | $Pv-T_{es}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}A_{es}A_e$ | 5'-(E)-(PO(OH)$_2$(CH=CH)- | 0.9 | 6 |
| 526608 | $Pv-T_{es}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}A_{es}\underline{A_e}$-C16 | 3'-C16 | 2 | 6 |
| 529106 | $Pv-T_{es}U_{fs}A_mU_{fs}C_mU_{fs}A_mU_{fs}A_mA_{fs}U_mG_{fs}A_mU_{fs}C_{ms}A_{fs}G_{ms}G_{fs}U_mA_{es}\underline{A_e}$-Cholesterol | 3'-Cholesterol | 10 | 6 |

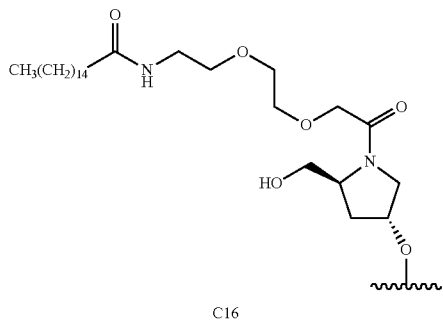

C16

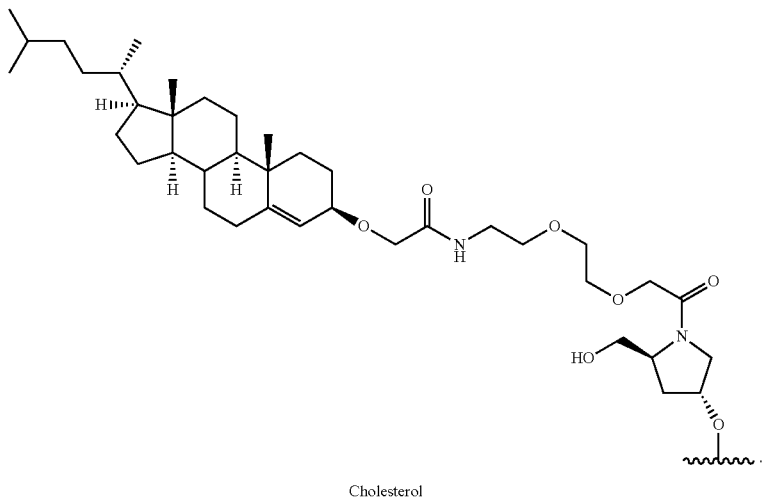

Cholesterol

Example 17

General Method for the Preparation of C10-Conjugated Oligomeric Compound 6

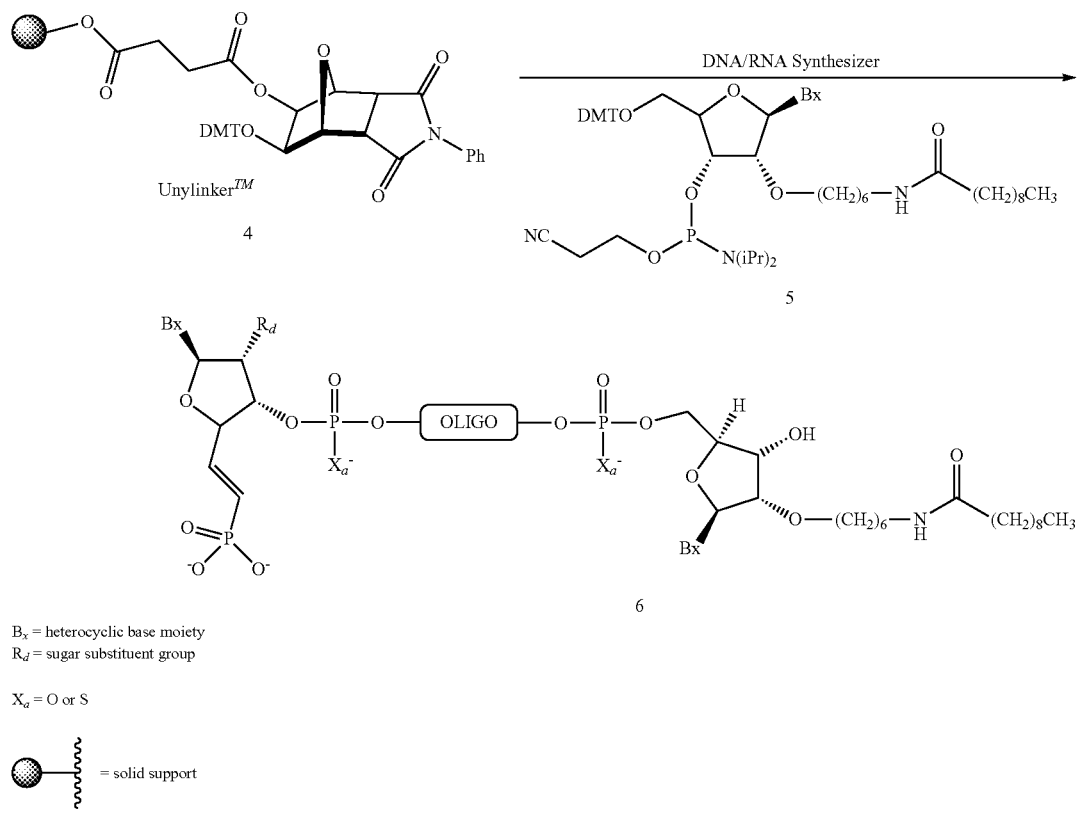

$B_x$ = heterocyclic base moiety
$R_d$ = sugar substituent group $X_a$ = O or S

⬤⌇ = solid support

The Unylinker™ 4 is commercially available. Conjugated oligomeric Compound 6 is prepared similar to published procedures (see Swayze et al., WO 2006/031461) and procedures illustrated in Examples 12-14.

Example 18

Preparation of C10-Conjugated Oligonucleotides

The conjugated oligonucleotides in Table 5 were prepared as per the procedures illustrated in Example 17 comprising a C10 conjugate attached to either at the 5', 3' or at any internal positions of the oligomeric compound.

The modified oligonucleotides comprising a 5'-(E)-vinyl-phosphonate group and a C10 conjugate are described in Table 5. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH-)$. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. Nucleosides with a subscript "C10" are shown below. Underlined nucleosides indicate the conjugate position.

Table 5

| | Modified oligonucleotides comprising C10 conjugate | | | |
|---|---|---|---|---|
| | | Conjugate position counted from | | SEQ ID |
| ISIS NO. | Composition (5' to 3') | 5' | 3' | NO. |
| 530340 or341 | Pv-$T_{es}U_{fs}G_{m}U_{fs}C_{m}U_{fs}C_{m}U_{fs}G_{m}G_{fs}U_{m}C_{fs}C_{m}U_{fs}U_{ms}A_{fs}C_{ms}U_{fs}\underline{T_{C10s}}A_{es}A_{e}$ | 19 | 3 | 9 |
| 530334 | Pv-$T_{es}U_{fs}G_{m}U_{fs}C_{m}U_{fs}C_{m}U_{fs}G_{m}G_{fs}U_{m}C_{fs}C_{m}U_{fs}\underline{T_{C10s}}A_{fs}C_{ms}U_{fs}U_{ms}A_{es}A_{e}$ | 15 | 7 | 10 |
| 530335 | Pv-$T_{es}U_{fs}G_{m}U_{fs}C_{m}U_{fs}C_{m}U_{fs}G_{m}G_{fs}\underline{T_{C10}}C_{fs}C_{m}U_{fs}U_{ms}A_{fs}C_{ms}U_{fs}U_{ms}A_{es}A_{e}$ | 11 | 11 | 11 |
| 530336 | Pv-$T_{es}U_{fs}G_{m}U_{fs}C_{m}\underline{T_{C10s}}C_{m}U_{fs}G_{m}G_{fs}U_{m}C_{fs}C_{m}U_{fs}U_{ms}A_{fs}C_{ms}U_{fs}U_{ms}A_{es}A_{e}$ | 6 | 16 | 12 |

| | Modified oligonucleotides comprising C10 conjugate | | | |
|---|---|---|---|---|
| | | Conjugate position counted from | | SEQ ID |
| ISIS NO. | Composition (5' to 3') | 5' | 3' | NO. |
| 530337 | Pv-$T_{es}U_{fs}G_mU_{fs}C_mU_{fs}C_mU_{fs}G_mG_{fs}U_mC_{fs}C_mU_{fs}U_{ms}A_{fs}C_{ms}U_{fs}U_{ms}A_{es}\underline{T_{C10}}$ | 21 | 1 | 13 |
| 549621 | Pv-$\underline{T_{C10s}}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}\underline{A_{es}}A_e$ | 1 | 21 | 14 |

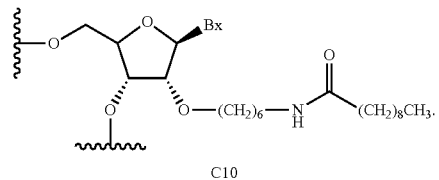

C10

Example 19

Preparation of C10-Conjugated Oligonucleotides

Additional C10-conjugated oligonucleotides comprising a 5'-(E)-vinylphosphonate group were designed based on the parent oligonucleotide, ISIS 522247 from Table 2 in an effort to evaluate the effects of conjugate groups on cellular uptake and potency. The modified oligonucleotides were designed by introducing a C10 conjugate, wherein the C10 conjugate will be shifted slightly upstream or downstream throughout the antisense oligonucleotides (i.e. "microwalk").

The C10-conjugated oligonucleotides were prepared as per the procedures illustrated in Example 17 and are described in Table 6. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, (PO(OH)$_2$(CH=CH—). A "Po" at the 5'-end indicates a 5'-phosphate group, (PO(OH)$_2$)—. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. Nucleosides with a subscript "C10" are shown below. Underlined nucleosides indicate the conjugate position.

The C10-conjugated oligonucleotides were tested in vitro. HeLa cells and hepatocytes were treated with modified oligonucleotides shown in Table 6 using transfection methods such as LIPOFECTAMINE' 2000 (Lipo), electroporation (Electro) or free up-take as described herein. The IC$_{50}$'s were calculated using the linear regression equation generated by plotting the normalized mRNA levels to the log of the concentrations used and the results are presented in Table 7.

The parent oligomeric compound, ISIS 522247, from which the newly designed oligonucleotides were derived from is marked with an asterisk (*) in the table and was included in the study as a benchmark oligonucleotide against which the cellular uptake and potency of the C10-conjugated oligonucleotides could be compared. Oligonucleotides without data are denoted as "ND".

As illustrated in Table 7, modified oligonucleotides comprising a C10 conjugate group at positions 1, 6 or 8, as counted from the 5'-terminus, or positions 21, 16, or 14, as counted from the 3'-terminus showed comparable potency and were well tolerated for cellular uptake in a similar manner as the parent oligonucleotide lacking a conjugate group, ISIS 522247. The remaining oligonucleotides (ISIS 534711 and ISIS 534713) showed little to no improvement in cellular uptake.

TABLE 6

| | Modified oligonucleotides comprising C10 conjugate | | | |
|---|---|---|---|---|
| | | Conjugate position counted from | | |
| ISIS NO. | Composition (5' to 3') | 5' | 3' | SEQ ID NO. |
| 522247* | PV-$T_{es}U_{fs}A_mU_{fs}C_mU_{fs}A_mU_{fs}A_mA_{fs}$ $U_mG_{fs}A_mU_{fs}C_{ms}A_{fs}G_{ms}G_{fs}U_{ms}A_{es}A_e$ | N/A | N/A | 6 |
| 534714 | Pv-$T_{es}U_{fs}A_mU_{fs}C_mU_{fs}A_mU_{fs}A_mA_{fs}$ $U_mG_{fs}A_mU_{fs}C_{ms}A_{fs}G_{ms}G_{fs}U_{ms}A_{es}\underline{T_{C10}}$ | 21 | 1 | 15 |
| 534711 | Pv-$T_{es}U_{fs}A_mU_{fs}C_mU_{fs}A_mU_{fs}A_mA_{fs}$ $U_mG_{fs}A_mU_{fs}C_{ms}A_{fs}G_{ms}G_{fs}\underline{T_{C10s}}A_{es}A_e$ | 19 | 3 | 16 |
| 534713 | Pv-$T_{es}U_{fs}A_mU_{fs}C_mU_{fs}A_mU_{fs}A_mA_{fs}$ $\underline{T_{C10}}G_{fs}A_mU_{fs}C_{ms}A_{fs}G_{ms}G_{fs}U_{ms}A_{es}A_e$ | 11 | 11 | 17 |
| 533814 | Pv-$T_{es}U_{fs}A_mU_{fs}C_mU_{fs}A_mU_{fs}\underline{T_{C10s}}A_mA_{fs}$ $U_mG_{fs}A_mU_{fs}C_{ms}A_{fs}G_{ms}G_{fs}U_{ms}A_{es}A_e$ | 8 | 14 | 18 |

TABLE 6-continued

Modified oligonucleotides comprising C10 conjugate

| | | Conjugate position counted from | | |
|---|---|---|---|---|
| ISIS NO. | Composition (5' to 3') | 5' | 3' | SEQ ID NO. |
| 533815 | Pv-T$_{es}$U$_{fs}$A$_m$U$_{fs}$C$_m$T$_{C10s}$A$_m$U$_{fs}$A$_m$A$_{fs}$U$_m$G$_{fs}$A$_m$U$_{fs}$C$_{ms}$A$_{fs}$G$_{ms}$G$_{fs}$U$_{ms}$A$_{es}$A$_e$ | 6 | 16 | 19 |
| 533813 | Pv-T$_{es}$U$_{fs}$A$_m$T$_{C10s}$C$_m$U$_{fs}$A$_m$U$_{fs}$A$_m$A$_{fs}$U$_m$G$_{fs}$A$_m$U$_{fs}$C$_{ms}$A$_{fs}$G$_{ms}$G$_{fs}$U$_{ms}$A$_{es}$A$_e$ | 4 | 18 | 20 |
| 533816 | Po-T$_{es}$U$_{fs}$A$_m$T$_{C10s}$C$_m$U$_{fs}$A$_m$U$_{fs}$A$_m$A$_{fs}$U$_m$G$_{fs}$A$_m$U$_{fs}$C$_{ms}$A$_{fs}$G$_{ms}$G$_{fs}$U$_{ms}$A$_{es}$A$_e$ | 1 | 21 | 6 |

TABLE 7

Comparison of inhibition of PTEN mRNA levels of C10-conjugated oligonucleotides designed by microwalk with ISIS 522247

| | Conjugate position counted from | | IC$_{50}$ (nM) | | IC$_{50}$ (µm) | |
|---|---|---|---|---|---|---|
| ISIS NO. | 5' | 3' | HeLa/ Lipo | Hepato/ Lipo | Hepato/ Free up-take | Hepato/ Electro |
| 522247* | N/A | N/A | 1.5 | 1.5 | 0.07 | 2 |
| 534714 | 21 | 1 | 1.5 | 2.5 | 2 | 5 |
| 534711 | 19 | 3 | 1.5 | 3 | 2 | 7 |
| 534713 | 11 | 11 | >50 | >10 | ND | 20 |
| 533814 | 8 | 14 | 0.8 | 1.5 | 0.1 | 1.5 |
| 533815 | 6 | 16 | 1 | 3 | 0.8 | 1.5 |
| 533813 | 4 | 18 | 1.8 | 5 | >20 | 8 |
| 533816 | 1 | 21 | 1 | 2 | >20 | 2 |

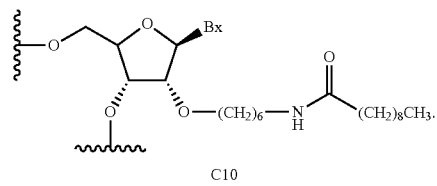

C10

Example 20

Protein Binding in Mouse Plasma for C10-Conjugated Oligonucleotides

Several modified oligonucleotides from Table 6 were selected and evaluated for protein binding in mouse plasma. The protein binding of the oligonucleotides was measured by ultracentrifugation using the procedures as described herein.

The C10-conjugated oligomeric compounds were prepared as per the procedures illustrated in Example 17 and are described in Table 8. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, (PO(OH)$_2$(CH=CH—). A "Po" at the 5'-end indicates a 5'-phosphate group, (PO(OH)$_2$)—. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. $^{me}$C indicates a 5-methyl cytosine nucleoside. Nucleosides with a subscript "C10" are shown below. Underlined nucleosides indicate the conjugate position. "NA" indicates not applicable.

Recovery Testing

Samples of oligonucleotides were prepared at 1 µM in PBS. Ultrafree-MC (Millipore) 30,000 NMWL filter units were placed in clean microcentrifuge tubes and pre-treated with 20 µL 0.5% Tween 80 in PBS and centrifuged for 10 minutes at 2,000 g. Pre-treated filters were transferred to the original collection tubes provided by Millipore. 300 µL of 1 µM of oligonucleotide was loaded onto the filters and immediately centrifuged for 20 min at 2,000 g. The concentrations in unfiltered solution and filtered solution were measured by Hybridization-Dependent ELISA using a complementary DNA probes conjugated with biotin and digoxigenin. The percent recovery was calculated using the formula provided: % Recovery=([pre-filtered]−[filtered])/ [pre-filtered].

Capacity Study

Oligonucleotides were prepared at 1 μM in fresh CD-1 mouse plasma preserved with EDTA (K3) (BioChemed Services), mixed well, and kept on ice. Ultrafree-MC 30,000 NMWL spin filters (Millipore) were placed in clean microcentrifuge tubes and pre-treated with 20 μL 0.5% Tween 80 in PBS as described in recovery testing. Pre-treated spin filters were placed in collection tubes they were supplied with and 300 μL aliquots of 1 μM were then loaded onto spin filters in triplicate and incubated at 37° C. for 30 minutes. After incubation, samples were immediately centrifuged at 2,000 g for 20 minutes at room temperature (~45 μL filtrate was collected). The concentration of oligonucleotide in unfiltered plasma and filtered plasma samples were determined by Hybridization-Dependent ELISA using complementary DNA probes conjugated with biotin and digoxigenin. The proportion of unbound oligonucleotide, adjusted for recovery was determined using the formulae provided:

% Unbound=[filtered]/[unfiltered])  Formula 1.

Adjust % Unbound=% Unbound/% Recovery  Formula 2.

Protein Binding Analysis

The protein binding in mouse plasma for modified oligonucleotides was analyzed using the procedures as described above. Results in Table 8 are presented as Adjusted % Unbound and is denoted as "Unbound (%)".

The parent oligonucleotide lacking a conjugate group, ISIS 522247, from which the newly designed oligonucleotides were derived from is marked with an asterisk (*) in the table. The 5-10-5 MOE gapmer, 104838 was also included in the study as a benchmark oligonucleotide against which the protein binding of the conjugated oligonucleotides could be compared.

As illustrated in Table 8, C10-conjugated oligonucleotides showed comparable protein binding in mouse plasma as compared to 5-10-5 MOE gapmer, ISIS 104838 while exhibiting a significant improvement in protein binding as compared to the non-conjugated parent oligonucleotide, ISIS 522247.

Example 21

Modified Oligonucleotides Comprising Various Conjugates at Various Positions

A series of conjugated oligonucleotides comprising a 5'-(E)-vinylphosphonate or a 5'-phosphate group were designed based on the parent oligomeric compound, ISIS 522247 from Table 2 and is marked with an asterisk (*) in the table. The modified oligonucleotides were designed by introducing C16, C22 or cholesterol conjugate group at various positions of the oligonucleotides in an effort to determine the effects of conjugate groups on potency in reducing PTEN mRNA levels.

The conjugated oligonucleotides were prepared as per the procedures illustrated in Example 17 and are described in Table 9. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH-)$. A "Po" at the 5'-end indicates a 5'-phosphate group, $(PO(OH)_2-)$. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. Nucleosides with a subscript "C16", "C22" or "Cholesterol" are shown below. Underlined nucleosides indicate the conjugate position. "NA" indicates not applicable.

TABLE 8

Comparison of protein binding in mouse plasma of C10-conjugated oligonucleotides with ISIS 522247 and ISIS 104838

| | | Conjugate position counted from | | Unbound | SEQ ID |
|---|---|---|---|---|---|
| ISIS NO. | Composition (5' to 3') | 5' | 3' | (%) | NO. |
| 104838 (5-10-5) MOE gapmer | $G_{es}{}^{me}C_{es}T_{es}G_{es}A_{es}T_sT_sA_sG_sA_sG_sA_sG_sA_sG_sG_{es}T_{es}{}^{me}C_{es}{}^{me}C_{es}{}^{me}C_e$ | N/A | N/A | 1.76 | 21 |
| 522247* | Pv-$T_{es}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}A_{es}A_e$ | N/A | N/A | 7.06 | 6 |
| 533814 | Pv-$T_{es}U_{fs}A_mU_{fs}C_mU_{fs}A_mT_{C10s}A_mA_{fs}U_mG_{fs}A_mU_{fs}C_{ms}A_{fs}G_{ms}G_{fs}U_{ms}A_{es}A_e$ | 8 | 14 | 3.32 | 22 |
| 533815 | Pv-$T_{es}U_{fs}A_mU_{fs}C_mT_{C10s}A_mU_{fs}A_mA_{fs}U_mG_{fs}A_mU_{fs}C_{ms}A_{fs}G_{ms}G_{fs}U_{ms}A_{es}A_e$ | 6 | 16 | 1.68 | 23 |
| 533816 | Po-$T_{C10s}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}A_{es}A_e$ | 1 | 21 | 1.38 | 6 |

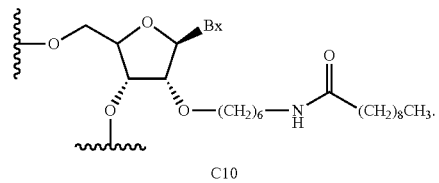

C10

TABLE 9

Modified oligonucleotides comprising C16, C22 or cholesterol conjugate

| ISIS NO. | Composition (5' to 3') | Conjugate | Conjugate position counted from 5' | Conjugate position counted from 3' | SEQ ID NO. |
|---|---|---|---|---|---|
| 522247* | Pv-T$_{es}$U$_{fs}$A$_{m}$U$_{fs}$C$_{m}$U$_{fs}$A$_{m}$U$_{fs}$A$_{m}$A$_{fs}$U$_{m}$G$_{fs}$A$_{m}$U$_{fs}$C$_{ms}$A$_{fs}$G$_{ms}$G$_{fs}$U$_{ms}$A$_{es}$A$_{e}$ | No conjugate | N/A | N/A | 6 |
| 543911 | Pv-T$_{es}$U$_{fs}$A$_{m}$U$_{fs}$C$_{m}$U$_{fs}$A$_{m}$T$_{\underline{C16s}}$A$_{m}$A$_{fs}$U$_{m}$G$_{fs}$A$_{m}$U$_{fs}$C$_{ms}$A$_{fs}$G$_{ms}$G$_{fs}$U$_{ms}$A$_{es}$A$_{e}$ | C16 | 8 | 14 | 18 |
| 543912 | Pv-T$_{es}$U$_{fs}$A$_{m}$U$_{fs}$C$_{m}$T$_{\underline{C16s}}$A$_{m}$$\overline{U_{fs}}$A$_{m}$A$_{fs}$U$_{m}$G$_{fs}$A$_{m}$U$_{fs}$C$_{ms}$A$_{fs}$G$_{ms}$G$_{fs}$U$_{ms}$A$_{es}$A$_{e}$ | C16 | 6 | 16 | 19 |
| 549166 | Po-T$_{\underline{C16s}}$U$_{fs}$A$_{m}$U$_{fs}$C$_{m}$$\overline{U_{fs}}$A$_{m}$U$_{fs}$A$_{m}$A$_{fs}$U$_{m}$G$_{fs}$A$_{m}$U$_{fs}$C$_{ms}$A$_{fs}$G$_{ms}$G$_{fs}$U$_{ms}$A$_{es}$A$_{e}$ | C16 | 1 | 21 | 14 |
| 551906 | Pv-T$_{es}$$\overline{U_{fs}}$A$_{m}$U$_{fs}$C$_{m}$U$_{fs}$A$_{m}$T$_{\underline{C22s}}$A$_{m}$A$_{fs}$U$_{m}$G$_{fs}$A$_{m}$U$_{fs}$C$_{ms}$A$_{fs}$G$_{ms}$G$_{fs}$U$_{ms}$A$_{es}$A$_{e}$ | C22 | 8 | 14 | 18 |
| 551907 | Pv-T$_{es}$U$_{fs}$A$_{m}$U$_{fs}$C$_{m}$T$_{\underline{C22s}}$A$_{m}$$\overline{U_{fs}}$A$_{m}$A$_{fs}$U$_{m}$G$_{fs}$A$_{m}$U$_{fs}$C$_{ms}$A$_{fs}$G$_{ms}$G$_{fs}$U$_{ms}$A$_{es}$A$_{e}$ | C22 | 6 | 16 | 19 |
| 551908 | Po-T$_{\underline{C22s}}$U$_{fs}$A$_{m}$U$_{fs}$C$_{m}$U$_{fs}$A$_{m}$U$_{fs}$A$_{m}$A$_{fs}$U$_{m}$G$_{fs}$A$_{m}$U$_{fs}$C$_{ms}$A$_{fs}$G$_{ms}$G$_{fs}$U$_{ms}$A$_{es}$A$_{e}$ | C22 | 1 | 21 | 14 |
| 543913 | Pv-T$_{es}$$\overline{U_{fs}A_{m}}$U$_{fs}$C$_{m}$U$_{fs}$A$_{m}$T$_{\underline{Cholesterols}}$A$_{m}$A$_{fs}$U$_{m}$G$_{fs}$A$_{m}$U$_{fs}$C$_{ms}$A$_{fs}$G$_{ms}$G$_{fs}$U$_{ms}$A$_{es}$A$_{e}$ | Cholesterol | 8 | 14 | 22 |
| 543914 | Pv-T$_{es}$U$_{fs}$A$_{m}$U$_{fs}$C$_{m}$T$_{\underline{Cholesterols}}$A$_{m}$U$_{fs}$A$_{m}$A$_{fs}$U$_{m}$G$_{fs}$A$_{m}$U$_{fs}$C$_{ms}$A$_{fs}$G$_{ms}$G$_{fs}$U$_{ms}$A$_{es}$A$_{e}$ | Cholesterol | 6 | 16 | 23 |
| 550959 | Po-T$_{\underline{Cholesterols}}$U$_{fs}$A$_{m}$U$_{fs}$C$_{m}$U$_{fs}$A$_{m}$U$_{fs}$A$_{m}$A$_{fs}$U$_{m}$G$_{fs}$A$_{m}$U$_{fs}$C$_{m}$A$_{fs}$G$_{ms}$G$_{fs}$U$_{ms}$A$_{es}$A$_{e}$ | Cholesterol | 1 | 21 | 6 |

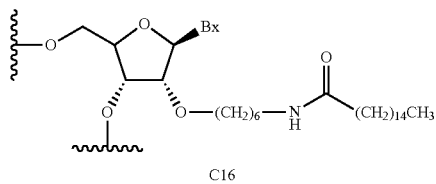

C16

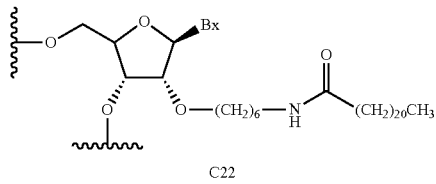

C22

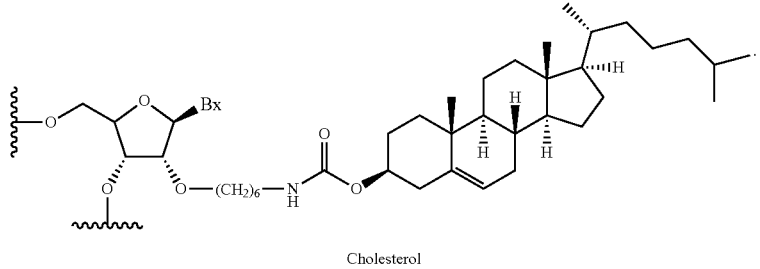

Cholesterol

Example 22

Modified Oligonucleotides Comprising Cholesterol Conjugate Targeting PTEN

In Vitro Study

The conjugated oligonucleotide, ISIS 543913 from Table 8 comprising a 5'-(E)-vinylphosphonate and cholesterol conjugate at position 8, as counted from the 5'-terminus or position 14, as counted from the 3'-terminus was selected and evaluated for inhibition of PTEN mRNA levels.

The cholesterol-conjugated oligonucleotide was tested in vitro. Hepatocytes were treated with modified oligonucleotides using LIPOFECTAMINE™ 2000 (Lipo) as transfection method as described herein. The IC$_{50}$'s were calculated using the linear regression equation generated by plotting the normalized mRNA levels to the log of the concentrations used and the results are presented in Table 10.

The parent oligomeric compound, ISIS 522247, from which the newly designed oligonucleotide was derived from is marked with an asterisk (*) in the table and was included in the study as a benchmark oligonucleotide against which potency of the cholesterol-conjugated oligonucleotides could be compared. "NA" indicates not applicable.

As illustrated in Table 10, the modified oligonucleotide comprising a cholesterol conjugate at position 8, as counted from the 5'-terminus or position 14, as counted from the 3'-terminus exhibited comparable potency as compared to the parent oligonucleotide, ISIS 522247.

TABLE 10

Comparison of inhibition of PTEN mRNA levels of cholesterol-conjugated oligonucleotides in hepatocytes with ISIS 522247

| ISIS NO. | Composition (5' to 3') | $IC_{50}$ (µM) | Conjugate | Conjugate position counted from 5' | Conjugate position counted from 3' | SEQ ID NO. |
|---|---|---|---|---|---|---|
| 522247* | Pv-$T_{es}U_{fs}A_mU_{fs}C_mU_{fs}A_mU_{fs}A_mA_{fs}$ $U_mG_{fs}A_mU_{fs}C_{ms}A_{fs}G_{ms}G_{fs}U_{ms}A_{es}A_e$ | 1 | No conjugate | N/A | N/A | 6 |
| 543913 | Pv-$T_{es}U_{fs}A_mU_{fs}C_mU_{fs}A_mT_{Cholesterols}$ $A_mA_{fs}U_mG_{fs}A_mU_{fs}C_{ms}A_{fs}G_{ms}G_{fs}U_{ms}A_{es}A_e$ | 3 | Cholesterol | 8 | 14 | 22 |

Example 23

Modified Oligonucleotides Comprising Various Conjugates Targeting PTEN

In Vivo Single Dose Response Study

The modified oligonucleotides from Table 8 comprising a 5'-(E)-vinylphosphonate and various conjugates at position 8, as counted from the 5'-terminus or position 14, as counted from the 3'-terminus, were selected and evaluated for inhibition of PTEN mRNA levels in vivo.

Six week old BALB/C mice (Jackson Laboratory, Bar Harbor, Me.) were injected intravenously with modified oligonucleotides once a day at dosage 10, 50 or 100 mg/kg for one day. The mice were sacrificed 48 hrs following last administration. Liver tissues were homogenized and mRNA levels were quantitated using real-time PCR and normalized to Cyclophilin as described herein for comparison to untreated control levels (% UTC). The results are listed as the average % of PTEN mRNA expression for each treatment group relative to saline-injected control.

The parent oligonucleotide, ISIS 522247, from which the newly designed oligonucleotides was derived from is marked with an asterisk (*) in the table and was included in the study as a benchmark oligonucleotide against which potency of the conjugated oligonucleotides could be compared.

As illustrated in Table 11, treatment with modified oligonucleotides comprising a C16- or C22-conjugate at position 8, as counted from the 5'-terminus, or position 14, as counted from the 3'-terminus exhibited a significant increase in potency at 50 mg/kg or 100 mg/kg (ISIS 543911 and ISIS 551906) while the cholesterol-conjugate (ISIS 543913) showed comparable potency comparing to the parent oligonucleotide (ISIS 522247). The data presented in Table 11 demonstrated that inhibition of PTEN mRNA levels can be achieved with conjugated oligonucleotides.

TABLE 11

Comparison of PTEN mRNA levels of conjugated oligonucleotides with ISIS 522247 in vivo

| ISIS NO | Dosage (mg/kg) | UTC (%) | Conjugate | Conjugate position counted from 5' | Conjugate position counted from 3' | SEQ ID NO |
|---|---|---|---|---|---|---|
| 522247* | 10 | 99 | No conjugate | N/A | N/A | 6 |
| | 50 | 87.9 | | | | |
| | 100 | 61.2 | | | | |
| 543911 | 10 | 88.3 | C16 | 8 | 14 | 18 |
| | 50 | 35.6 | | | | |
| | 100 | 28.1 | | | | |
| 551906 | 10 | 93.7 | C22 | 8 | 14 | 18 |
| | 50 | 40.9 | | | | |
| 543913 | 10 | 99.4 | Cholesterol | 8 | 14 | 22 |
| | 100 | 67.2 | | | | |

Example 24

Modified Oligonucleotides Comprising Various Conjugates Targeting PTEN

In Vivo Multiple Dose Study

Several modified oligonucleotides from Table 8 comprising a 5'-(E)-vinylphosphonate and various conjugates at position 8, as counted from the 5'-terminus or position 14, as counted from the 3'-terminus, were selected and evaluated for inhibition of PTEN mRNA levels in vivo.

Six week old BALB/C mice (Jackson Laboratory, Bar Harbor, Me.) were injected subcutaneously with the modified oligonucleotides twice a day at dosage 25 mg/kg (100 mg/kg total) for two days. The mice were sacrificed 48 hrs following last administration. Liver tissues were homogenized and mRNA levels were quantitated using real-time PCR and normalized to Cyclophilin as described herein for comparison to untreated control levels (% UTC). The results are listed as the average % of PTEN mRNA expression for each treatment group relative to saline-injected control.

The parent oligonucleotide, ISIS 522247, from which the newly designed oligonucleotides were derived from is marked with an asterisk (*) in the table and was included in the study as a benchmark oligonucleotide against which potency of the conjugated oligonucleotides could be compared.

As illustrated in Table 12, modified oligonucleotides comprising a C16- or C22-conjugate at position 8 as counted from the 5' terminus or position 14, as counted from the 3'-terminus showed a significant increase in potency at 50 mg/kg or 100 mg/kg (ISIS 543911 and ISIS 551906) while the cholesterol-conjugate (ISIS 543913) showed no improvement in potency comparing to the parent oligonucleotide (ISIS 522247).

TABLE 12

Comparison of PTEN mRNA levels of conjugated oligonucleotides with ISIS 522247 in vivo

| ISIS NO | Dosage (mg/kg total) | % UTC | Conjugate | Conjugate position counted from 5' | 3' | SEQ ID NO |
|---|---|---|---|---|---|---|
| 522247* | 100 | 45.5 | No conjugate | N/A | N/A | 6 |
| 543911 | 100 | 17.9 | C16 | 8 | 14 | 18 |
| 551906 | 100 | 21.5 | C22 | 8 | 14 | 18 |
| 543913 | 100 | 98.9 | Cholesterol | 8 | 14 | 22 |

Example 25

Evaluation of the Stability of Modified Oligonucleotides

In Vivo Study

The stability of modified oligonucleotides can be evaluated in vivo using the procedures as described herein. Liver tissues were harvested and collected on ice from BALB/C mice treated with modified oligonucleotides. 100-200 mg samples were minced and homogenized in 400 µL homogenization buffer (20 mM Tris, pH 8, 20 mM EDTA, 0.1 M NaCl, 0.5% NP-40). A standard curve ranging from 1 µg-75 µg was prepared for each ssRNA in 500 µL aliquots of control liver homogenate (400 µg/mL) with 10 µg internal standard (SEQ ID NO: 24, Isis NO: 355868, a 27-mer, 2'-O-methoxyethyl-modified phosphorothioate oligonucleotide). Tissue homogenates were then extracted using phenol/chloroform and solid support phase extraction techniques as described below with 300 µL NH$_4$OH and 800 µL phenol/chloroform/isoamyl alcohol used in the phenol/chloroform extraction.

Phenol/Chloroform Extraction

Stability of modified oligonucleotides was evaluated at time points 0, 5, 10, 20, 30, 40 and 60 minutes, except for SEQ ID NO: 25, Isis NO: 408877 which was evaluated at time points 0, 15, 30, 60, 120 and 240 mins; and SEQ ID NO: 26, Isis NO: 409044, at time points 0, 0.5, 1, 2, 4, 8, and 18 hours. An internal standard (SEQ ID NO: 24, Isis NO: 355868, a 27-mer, 2'-O-methoxyethyl-modified phosphorothioate oligonucleotide) with final concentration of 2.5 µM was added to each sample prior to extraction. Samples were extracted with 70 µL of NH$_4$OH and 240 µL of phenol/chloroform/isoamyl alcohol (25:24:1). The supernatant was removed after centrifugation at 14000 rpm for 2 min. The remaining extractant was vortexed with an additional 500 µL of water and the aqueous layer was removed and combined with the supernatant after centrifugation at 14000 rpm for 2 minutes.

Solid Phase Extraction

Triethylammonium acetate solution at 1M (500 µL) was added to the supernatant. The aqueous layer of the mixture was loaded onto the pre-conditioned Biotage™ Phenyl Solid Phase Extraction Plate (SPE plate) after centrifugation at 9000 rpm for 20 minutes. The SPE plate was washed several times with water. The sample was then eluted with 1.5 mL of 1% TEA in 90% MeOH and filtered through the Protein Precipitation Plate (Phenomenex™). The eluent was evaporated to dryness and diluted to 200 µL with 50% quenching buffer (8 M urea, 50 mM EDTA) and water before sample injection.

LC-MS

An Agilent 1100 Series LC/MSD system was connected in-line to a mass spectrometer. Mass spectrometer was operated in the electrospray negative ionization mode. The nebulizer nitrogen gas was set at 325 psi and the drying nitrogen gas was set at 12 L/min. The drying temperature was 325° C. Samples (25 µL/well) were introduced via an auto sampler and reversed-phase chromatography was carried out with an) (Bridge OST C18 2.5 µm 2.1 mm×50 mm HPLC column using a flow rate of 300 µL/min at 55° C. The ion pair buffers consisted of A: 5 mM tributylammonium acetate (TBAA) in 20% acetonitrile and B: 5 mM TBAA in 90% acetonitrile and the loading buffer was 25 mM TBAA in 25% Acetonitrile. Separation was performed on a 30% to 70% B in 9 min and then 80% B in 11 min gradient.

Quantitative analysis of oligonucleotide and internal standard by extracted ion chromatograms of the most abundant ions was performed using MSD ChemStation software.

The internal standard oligonucleotides are described in Table 12a. A subscript "s" between two nucleosides indicates a phosphorothioate internucleoside linkage (from the 5' to the 3' end). The absence of a subscript "s" between two nucleosides indicates a phosphodiester internucleoside linkage. A "Po" at the 5'-end indicates a 5'-phosphate group, (PO(OH)$_2$—). Nucleosides without a subscript are β-D-2'-deoxyribonucleosides. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. $^{me}C$ indicates a 5-methyl cytosine nucleoside.

TABLE 12a

Internal standard oligonucleotides

| ISIS NO | Sequence (5' to 3') | 5'-Chemistry | SEQ ID NO |
|---|---|---|---|
| 355868 | G$_{es}$$^{me}$C$_{es}$G$_s$T$_s$T$_s$G$_s$C$_s$T$_s$C$_s$T$_s$<br>C$_s$T$_s$T$_s$$^{me}$C$_{es}$T$_{es}$T$_{es}$G$_{es}$$^{me}$C$_{es}$G$_{es}$T$_s$<br>T$_s$T$_s$T$_s$T$_e$ | OH | 24 |
| 408877 | Po-U$_m$U$_f$G$_f$U$_f$C$_f$U$_m$C$_m$U$_f$G$_f$G$_{ms}$U$_{ms}$<br>C$_{fs}$C$_{fs}$U$_{fs}$U$_{fs}$A$_{fs}$C$_{ms}$U$_{ms}$U$_{ms}$T$_{es}$T$_e$ | Phosphate | 25 |
| 409044 | Po-U$_{ms}$U$_f$G$_m$U$_f$C$_m$U$_f$C$_m$U$_f$G$_m$G$_f$U$_m$C$_f$<br>C$_m$U$_{fs}$U$_{ms}$A$_{fs}$C$_{ms}$U$_{fs}$U$_{ms}$A$_{es}$A$_e$ | Phosphate | 26 |

Example 26

Modified Oligonucleotides Comprising C10-Conjugate Targeting PTEN

In Vivo Multiple Dose Response and Stability Studies

The modified antisense oligonucleotide, ISIS 533814 from Table 6 comprising a 5'-(E)-vinylphosphonate and a C-10 conjugate group at position 8, as counted from the 5'-terminus or position 14, as counted from the 3'-terminus, was selected and evaluated for inhibition of PTEN mRNA levels in vivo.

Six week old BALB/C mice (Jackson Laboratory, Bar Harbor, Me.) were injected subcutaneously twice a day at dosage 25 mg/kg (50, 100, or 200 mg/kg total) for one, two or four days with C10-conjugated oligonucleotide, ISIS 533814 or twice a day at dosage 25 mg/kg (100 mg/kg total) for two days with the parent oligonucleotide, ISIS 522247 or the 5-10-5 MOE gapmer, ISIS 116847. The mice were sacrificed 48 hrs following last administration. Liver tissues were homogenized and mRNA levels were quantitated using real-time PCR and normalized to Cyclophilin as described herein for comparison to untreated control levels (% UTC). The results in Table 13 are listed as the average % of PTEN mRNA expression for each treatment group relative to saline-injected control.

The parent oligonucleotide lacking a conjugate group, ISIS 522247, from which the newly designed oligonucleotides were derived from is marked with an asterisk (*) in the table. The 5-10-5 MOE gapmer is described in Table 4 and was also included in the study as a benchmark oligonucleotide against which potency of the conjugated oligonucleotides could be compared. "NA" indicates not applicable.

As illustrated in Table 13, modified oligonucleotides comprising a C10-conjugate at position 8, as counted from the 5'-terminus, or position 14, as counted from the 3'-terminus showed reduction in PTEN mRNA levels in a similar manner as the parent oligonucleotide, ISIS 522247.

The modified oligonucleotides were also evaluated for in vivo stability at dosage 100 mg/kg total and the tissue samples were collected and prepared using the same technique described in Example 25. Quantitative analysis of the oligonucleotides standard were performed by extracted ion chromatograms in the most abundant charge state (−4) using Chemstation software. The liver concentration (μg/g) of full length oligonucleotides comprising a 5'-terminal phosphonate group was measured by LC/MS and the results are presented below.

As illustrated in Table 14 and in FIG. 1, similar concentration of full-length oligonucleotide was observed for C10-conjugate (ISIS 533814) in liver accumulation as compared to the parent oligonucleotide, ISIS 522247. The full-length oligonucleotide for ISIS 533814 lacks a C10 conjugate due to hydrolysis at the amide bond between the alkyl linker group and the conjugate.

TABLE 13

Comparison of PTEN mRNA levels of C10-conjugated oligonucleotides with ISIS 116847 and ISIS 522247 in multiple dose response study in vivo

| ISIS NO. | Day(s) | Dosage (mg/kg total) | UTC (%) | Conjugate | Conjugate position counted from 5' | Conjugate position counted from 3' | SEQ ID NO. |
|---|---|---|---|---|---|---|---|
| 116847 (5-10-5) MOE gapmer | 2 | 100 | 12.7 | No conjugate | N/A | N/A | 8 |
| 522247* | 2 | 100 | 43.9 | No conjugate | N/A | N/A | 6 |
| 533814 | 1 | 50 | 70.1 | C10 | 8 | 14 | 18 |
|  | 2 | 100 | 44.4 |  |  |  |  |
|  | 4 | 200 | 38.0 |  |  |  |  |

TABLE 14

Comparison of full-length C10-conjugated oligonucleotides in liver accumulation with ISIS 522247 in vivo

| ISIS NO. | Day(s) | Dosage (mg/kg total) | Liver conc. of full length ssRNA (μg/g) | Conjugate/position counted from 5' |
|---|---|---|---|---|
| 116847 (5-10-5) MOE gapmer | 2 | 100 | 151.62 ± 29.2 |  |
| 522247* | 2 | 100 | 98.22 ± 3 | No conjugate |
| 533814 | 1 | 50 | 208.61 ± 45.8 | C10, pos 8 |
|  | 2 | 100 | 95.4 ± 9.4 | C10 conjugate |
|  | 4 | 200 | 60.88 ± 22.9 | hydrolyzed |

Example 27

Modified Oligonucleotides Comprising C16 Conjugate at the 3'-Terminus Targeting PTEN—In Vivo Multiple Dose Response Study The modified oligonucleotides from Table 4 comprising a 5'-(E)-vinylphosphonate and C16 conjugate at the 3'-terminus were selected and evaluated for inhibition of PTEN mRNA levels in vivo.

Six week old BALB/C mice (Jackson Laboratory, Bar Harbor, Me.) were injected subcutaneously with modified oligonucleotides twice a day at dosage 25 mg/kg (50 or 100 mg/kg total) for one or two days. The mice were sacrificed 48 hrs following last administration. Liver tissues were homogenized and mRNA levels were quantitated using real-time PCR and normalized to Cyclophilin as described herein for comparison to untreated control levels (% UTC). The results in Table 15 are listed as the average % of PTEN mRNA expression for each treatment group relative to saline-injected control.

The parent oligonucleotide lacking a conjugate group, ISIS 522247, from which the newly designed oligonucleotides were derived from is marked with an asterisk (*) in the table. The 5-10-5 MOE gapmer, ISIS 116847 was also included in the study as a benchmark oligonucleotide against which potency of the conjugated oligonucleotides could be compared. "NA" indicates not applicable.

As illustrated in Table 15, the modified oligonucleotide comprising a C16-conjugate at the 3'-terminus showed reduction in PTEN mRNA levels in a similar manner as the parent oligonucleotide, ISIS 522247.

TABLE 15

Comparison of PTEN mRNA levels of conjugated oligonucleotides with ISIS 116847 and ISIS 522247 in multiple dose response study in vivo

| ISIS NO | Day(s) | Dosage (mg/kg total) | UTC (%) | Conjugate | Conjugate position counted from 5' | Conjugate position counted from 3' | SEQ ID NO |
|---|---|---|---|---|---|---|---|
| 116847 (5-10-5) MOE gapmer | 1 | 50 | 42.9 | No conjugate | N/A | N/A | 8 |
| 522247* | 1 | 50 | 74.9 | No conjugate | N/A | N/A | 6 |
|  | 2 | 100 | 47.1 |  |  |  |  |
| 526608 | 1 | 50 | 95.0 | C16 | 21 | 1 | 6 |
|  | 2 | 100 | 69.7 |  |  |  |  |

Example 28

Relative Distribution of 5'-(E)-Vinyl Phosphonate ssRNA Lipid Conjugates in Mouse Plasma Oligonucleotides, Isis Nos. 116847, 52247, 533814, and 543911, were prepared in 50% mouse plasma (K3, EDTA) at the following concentrations (uM): 0.1, 0.5, 1, 5, 10, and 25. A PBS control was prepared at 1 uM. The oligonucleotides in plasma or PBS were then incubated at 37° C. on an HPLC autosampler for at least 30 minutes. 100 uL samples were then separated by HPLC on a Zenix SEC300 (4.5×300 mm) size exclusion column using 0.35 mL/min PBS mobile phase. The column was kept at 10° C. during separation. Four 1.5 minute fractions were collected from 5-11 minutes. Fractions correspond with elution times of proteins with the approximate masses: 5-6.5 min=>300 kDa; 6.5-8 min=100-300 kDa; 8-9.5 min=30-100 kDa, and 9.5-11 min=<30 kDa, or unbound oligonucleotide. The concentration of the oligonucleotides in each fraction was determined by hybridization-dependent ELISA and the distribution of oligonucleotides across fractions was reported relative to total. The results of the assay are illustrated in Table 16. The results illustrate that oligonucleotides with C16 conjugates at position 8 from the 5'-end or position 14 from the 3' end increase and alter binding to high molecular weight plasma proteins.

TABLE 16

Relative Distribution of 5'-(E)-Vinyl Phosphonate ssRNA Lipid Conjugates In Mouse Plasma

| Isis No | Fractional Concentration (μM) | 5 μM | % Bound | 10 μM | % Bound | 25 μM | % Bound | Conjugate Position Counted From 5' | Conjugate Position Counted From 3' | SEQ ID NO. |
|---|---|---|---|---|---|---|---|---|---|---|
| 116847 | >300 kDa | 0.1 | 2 | 0.1 | 1 | 0.2 | 0.8 | N/A | N/A | 8 |
|  | 100-300 kDa | 0.2 | 4 | 0.2 | 2 | 0.2 | 0.8 | N/A | N/A |  |
|  | 30-100 kDa | 1.3 | 26 | 1.4 | 14 | 1.5 | 6 | N/A | N/A |  |
|  | >30 kDa | 3.4 | 68 | 8.3 | 83 | 23.1 | 92.4 | N/A | N/A |  |
| 52247 | >300 kDa | 0 | 0 | 0.1 | 1 | 0 | 0 | N/A | N/A | 6 |
|  | 100-300 kDa | 0.1 | 2 | 0.2 | 2 | 0.3 | 1.2 | N/A | N/A |  |
|  | 30-100 kDa | 1.9 | 38 | 2.3 | 23 | 2.6 | 10.4 | N/A | N/A |  |
|  | >30 kDa | 3 | 60 | 7.4 | 74 | 22.1 | 88.4 | N/A | N/A |  |
| 533814 ($C_{10}$) | >300 kDa | 0.3 | 6 | 0.4 | 4 | 0.6 | 2.4 | 8 | 14 | 18 |
|  | 100-300 kDa | 0.7 | 14 | 0.8 | 8 | 1.3 | 5.2 | 8 | 14 |  |
|  | 30-100 kDa | 1.9 | 38 | 2.5 | 25 | 2.2 | 8.8 | 8 | 14 |  |
|  | >30 kDa | 2 | 40 | 6.2 | 62 | 20.9 | 83.6 | 8 | 14 |  |
| 543911 ($C_{16}$) | >300 kDa | 0.2 | 4 | 0.5 | 5 | 1.1 | 4.4 | 8 | 14 | 18 |
|  | 100-300 kDa | 1.2 | 24 | 1.2 | 12 | 2.9 | 11.6 | 8 | 14 |  |
|  | 30-100 kDa | 2.5 | 50 | 4.3 | 43 | 9.4 | 37.6 | 8 | 14 |  |
|  | >30 kDa | 1 | 20 | 4 | 40 | 11.5 | 46 | 8 | 14 |  |

Example 29

Preparation of Compound 10, 2-Acetamido-2-deoxy-D-galactopyranose conjugate

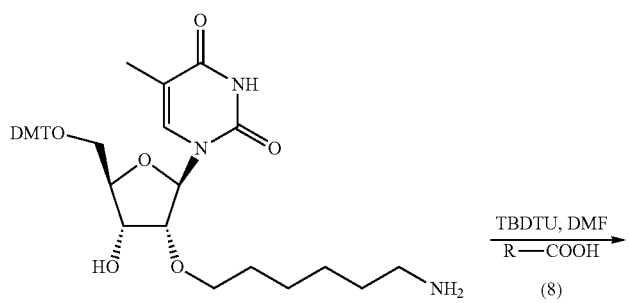

-continued
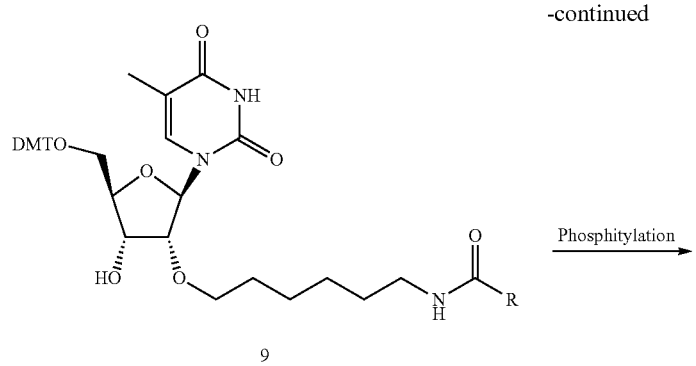
9
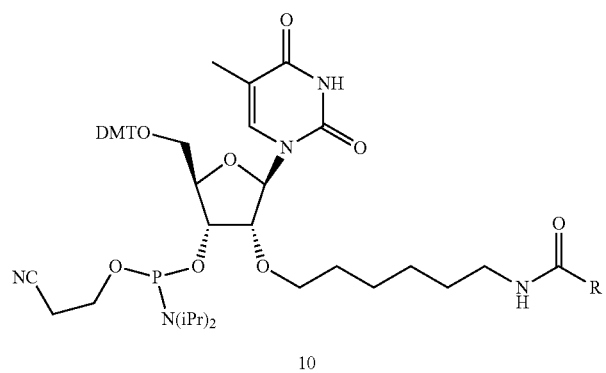
10
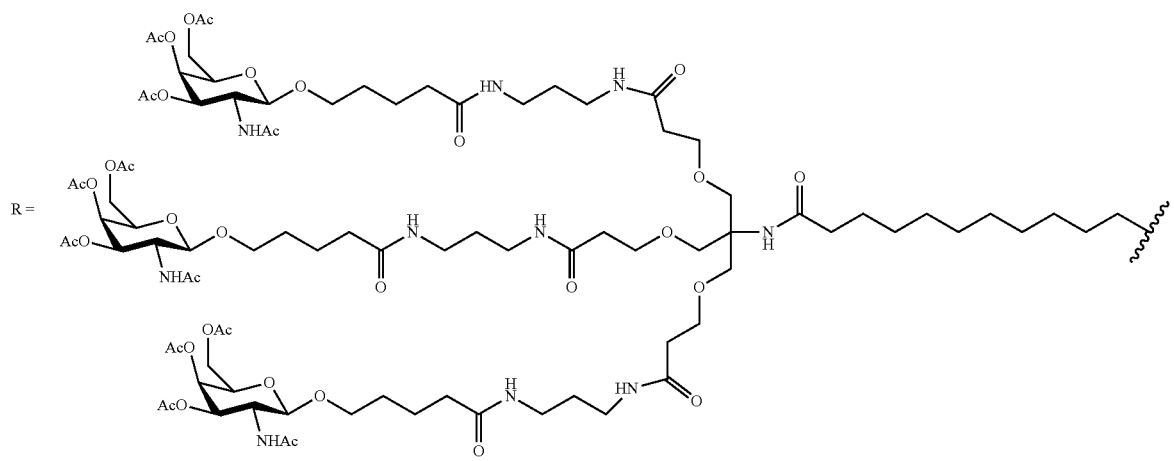
8
Compound 7 is prepared according to the procedures published in WO 2000/14048 or by Manoharan et al., *J. Org. Chem.*, 1999, 64, 6468-6472. Compound 8 is prepared according to the procedures published by Rensen et al., *J. Med. Chem.*, 2004, 47, 5798-5808.

Example 30
Preparation of Compound 14, Squalene Conjugate
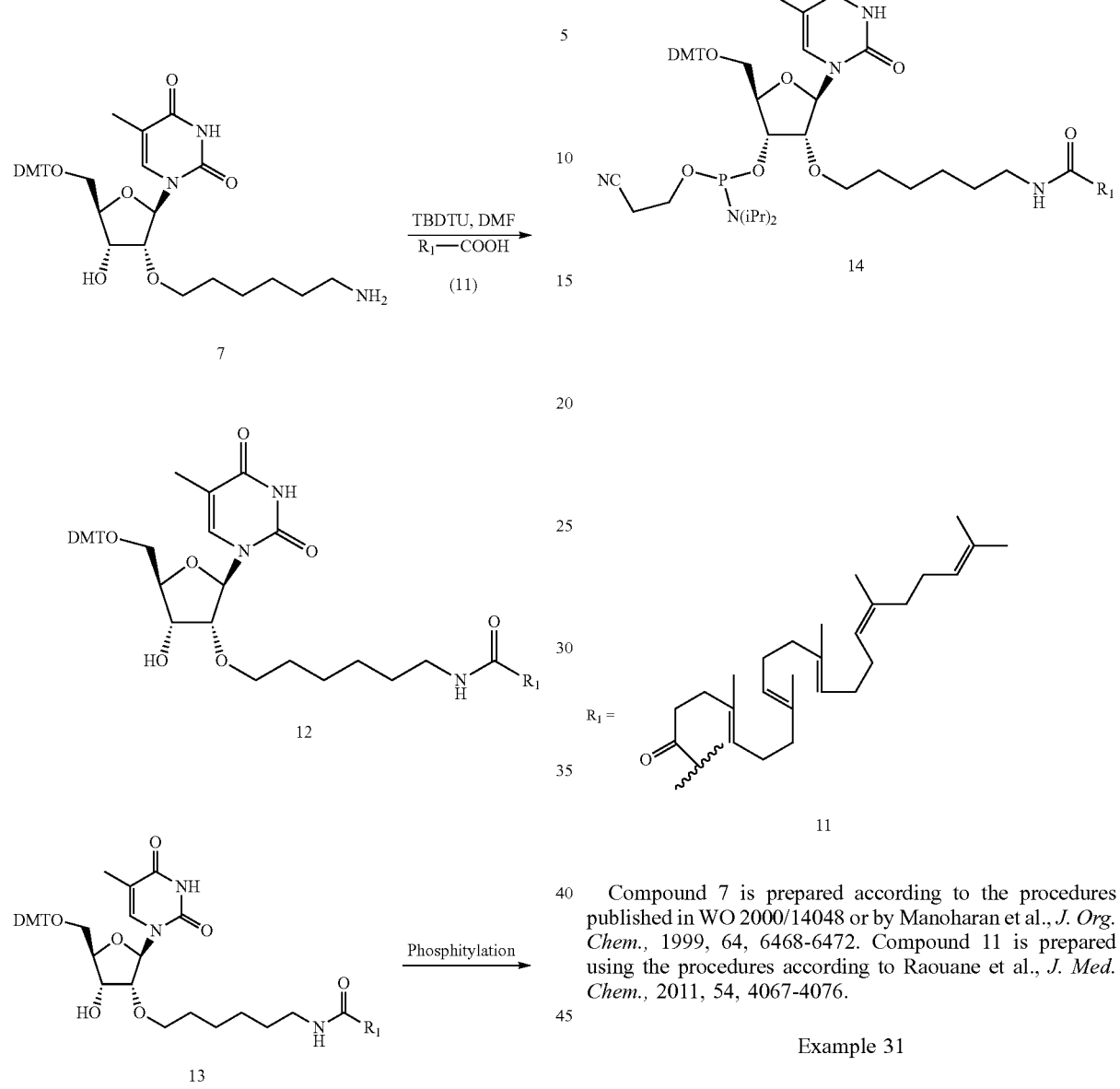
Compound 7 is prepared according to the procedures published in WO 2000/14048 or by Manoharan et al., *J. Org. Chem.*, 1999, 64, 6468-6472. Compound 11 is prepared using the procedures according to Raouane et al., *J. Med. Chem.*, 2011, 54, 4067-4076.
Example 31
Preparation of Compounds 27-32
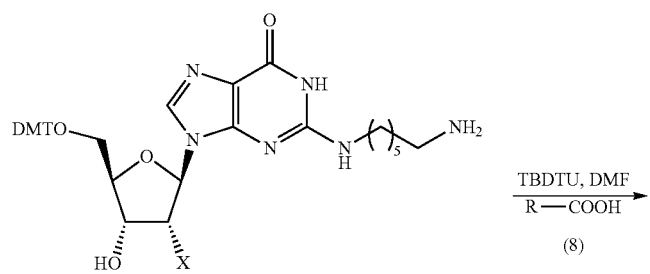
15 X = F
16 X = OMe
17 X = MOE
18 X = NMA
19 X = DMAEOE
20 X = FEt

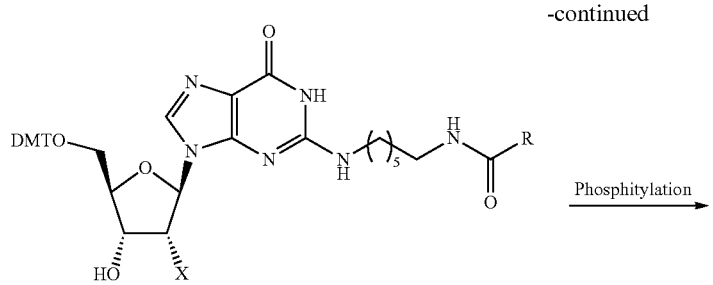
21 X = F
22 X = OMe
23 X = MOE
24 X = NMA
25 X = DMAEOE
26 X = FEt
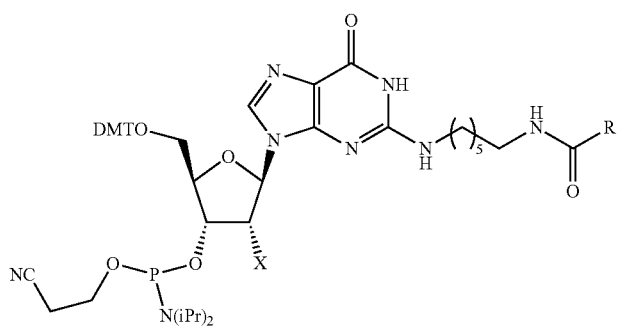
27 X = F
28 X = OMe
29 X = MOE
30 X = NMA
31 X = DMAEOE
32 X = FEt
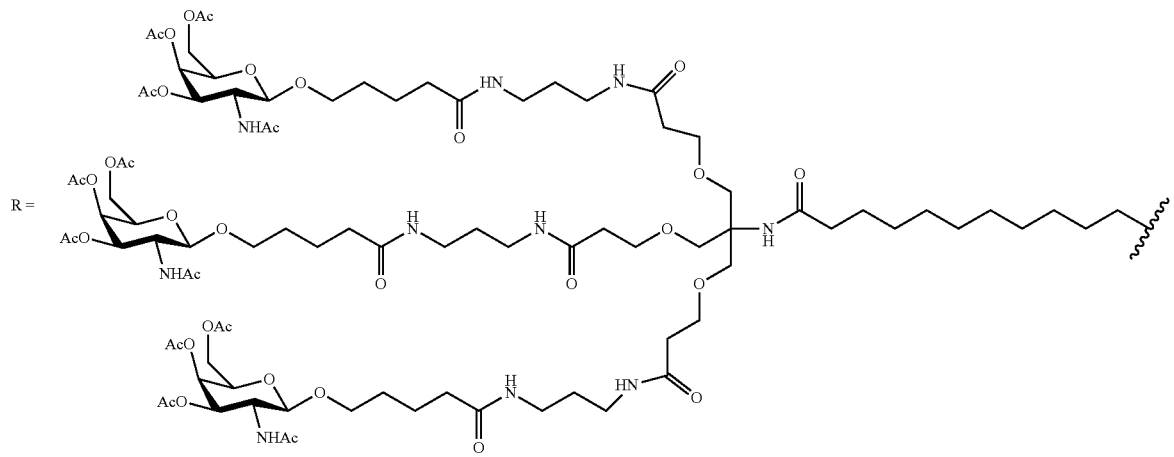
8
Compounds 15-20 are prepared as per the procedures illustrated in Examples 40 and 41. Compound 8 is prepared according to the procedures published by Rensen et al., *J. Med. Chem.*, 2004, 47, 5798-5808.

Example 32
Preparation of Compounds 45-50
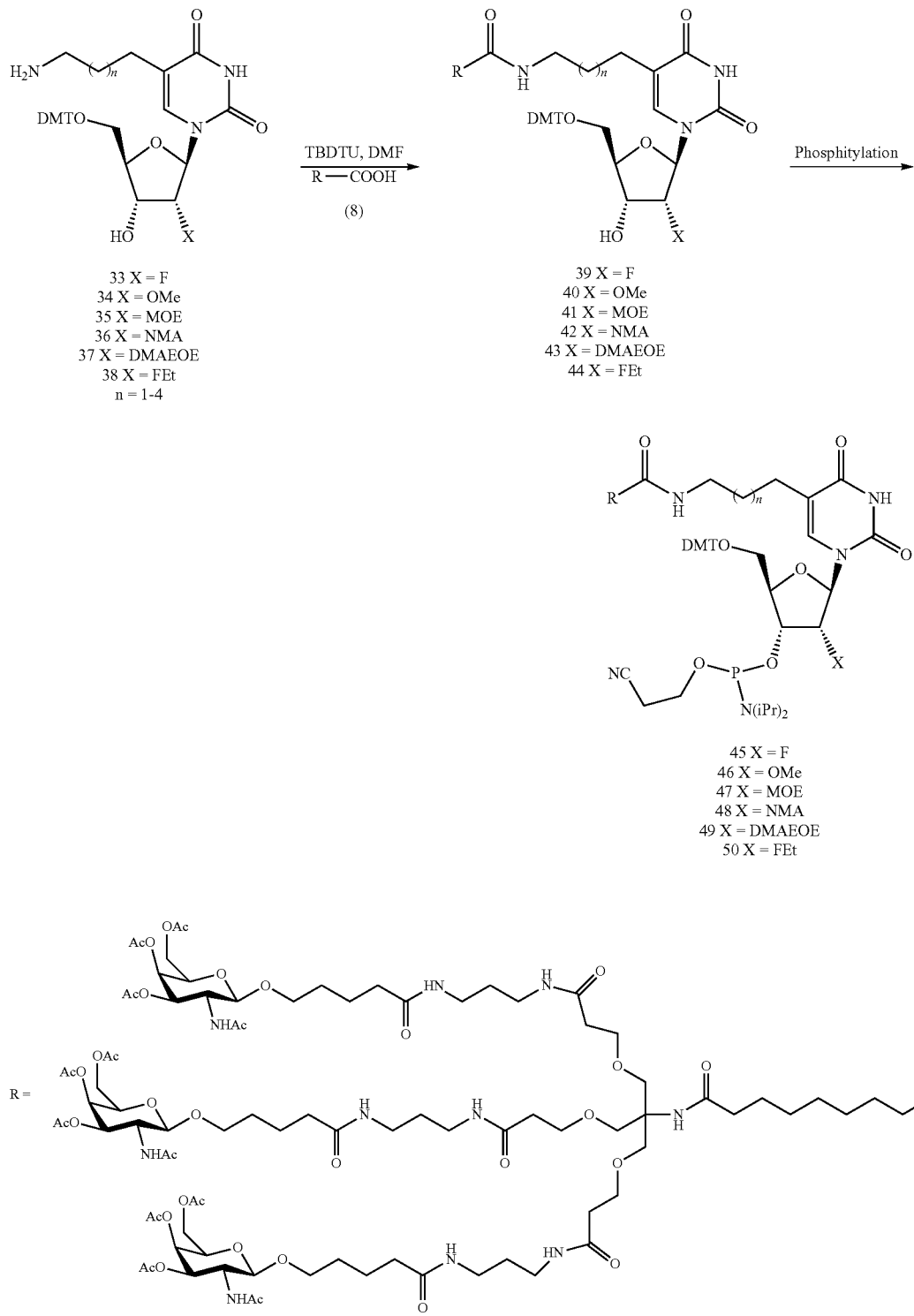
Compounds 33-38 are prepared using similar procedures as illustrated in Example 42. Compound 8 is prepared according to the procedures published by Rensen et al., *J. Med. Chem.*, 2004, 47, 5798-5808.

Example 33
Preparation of Compounds 63-68
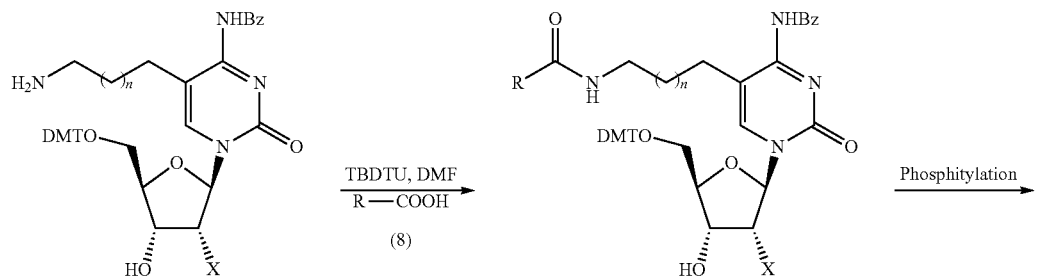
51 X = F
52 X = OMe
53 X = MOE
54 X = NMA
55 X = DMAEOE
56 X = FEt
n = 1-4
57 X = F
58 X = OMe
59 X = MOE
60 X = NMA
61 X = DMAEOE
62 X = FEt
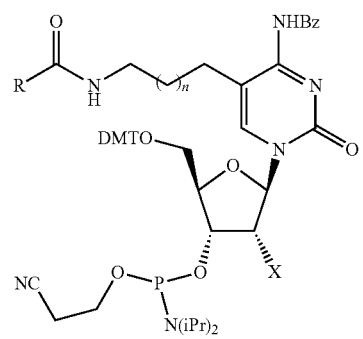
63 X = F
64 X = OMe
65 X = MOE
66 X = NMA
67 X = DMAEOE
68 X = FEt
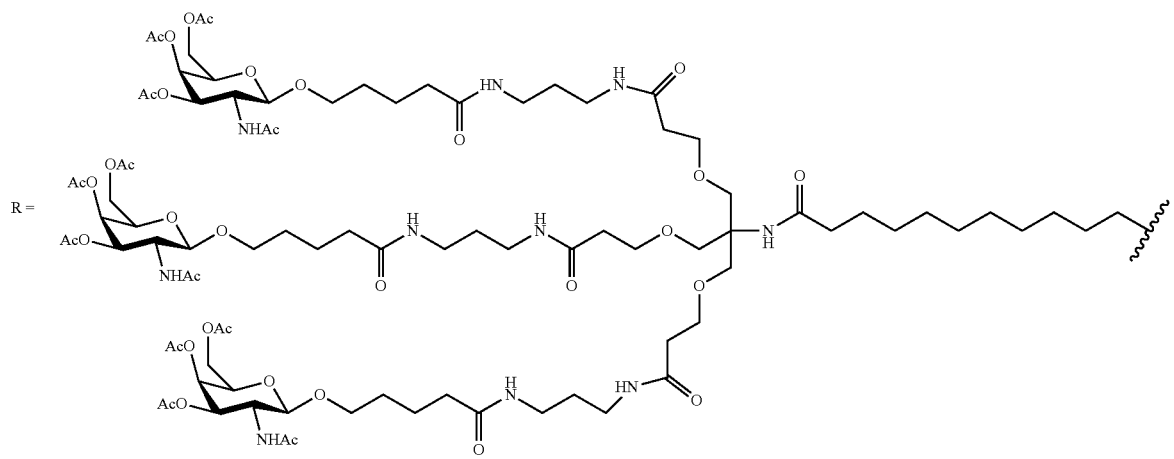
8
Compounds 51-56 are prepared using similar procedures as illustrated in Example 42. Compound 8 is prepared according to the procedures published by Rensen et al., *J. Med. Chem.*, 2004, 47, 5798-5808.

Example 34
Preparation of Compound 71
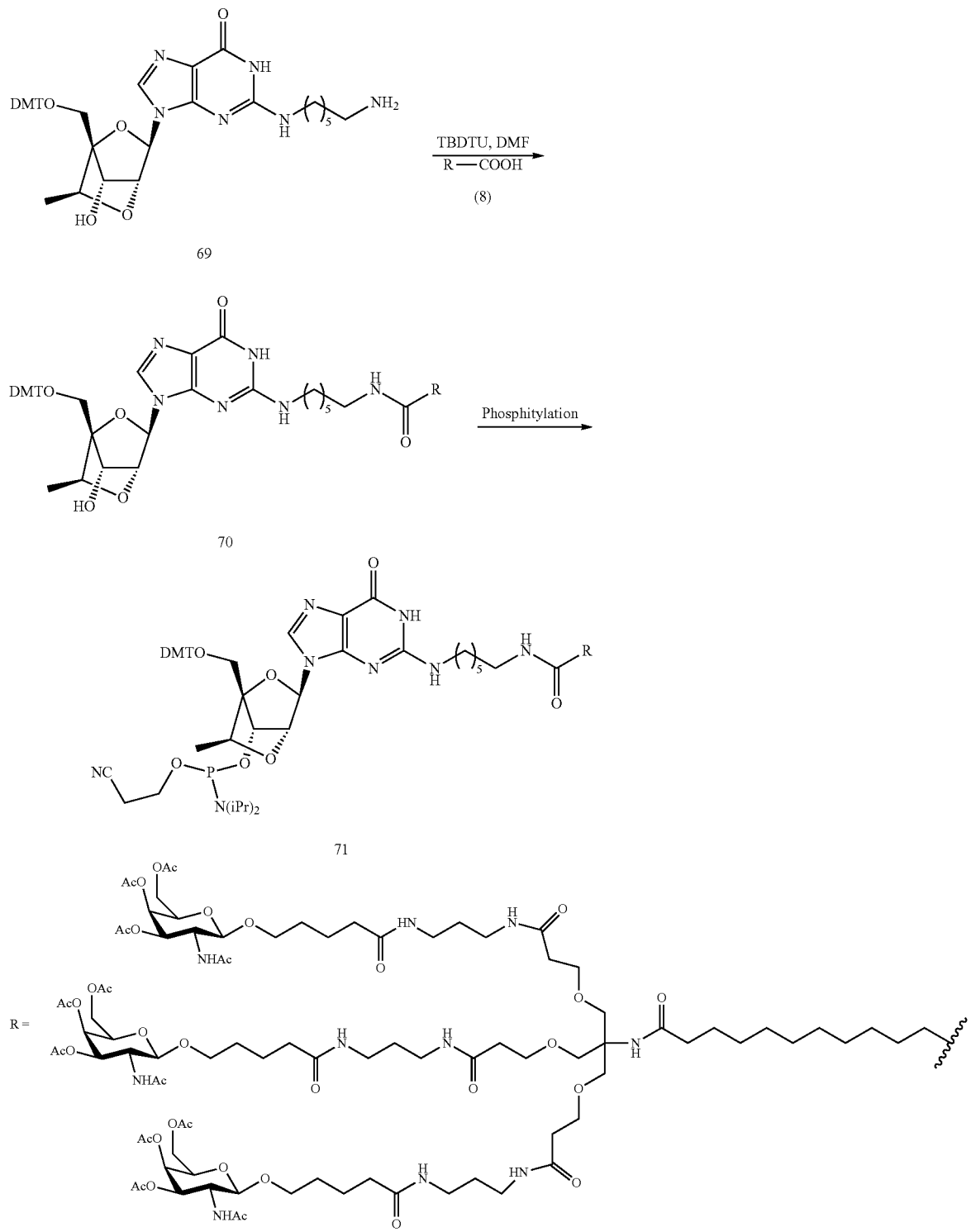
Compound 69 is prepared using similar procedures as illustrated in Example 40. Compound 8 is prepared according to the procedures published by Rensen et al., *J. Med. Chem.*, 2004, 47, 5798-5808.

Example 35
Preparation of Compound 74
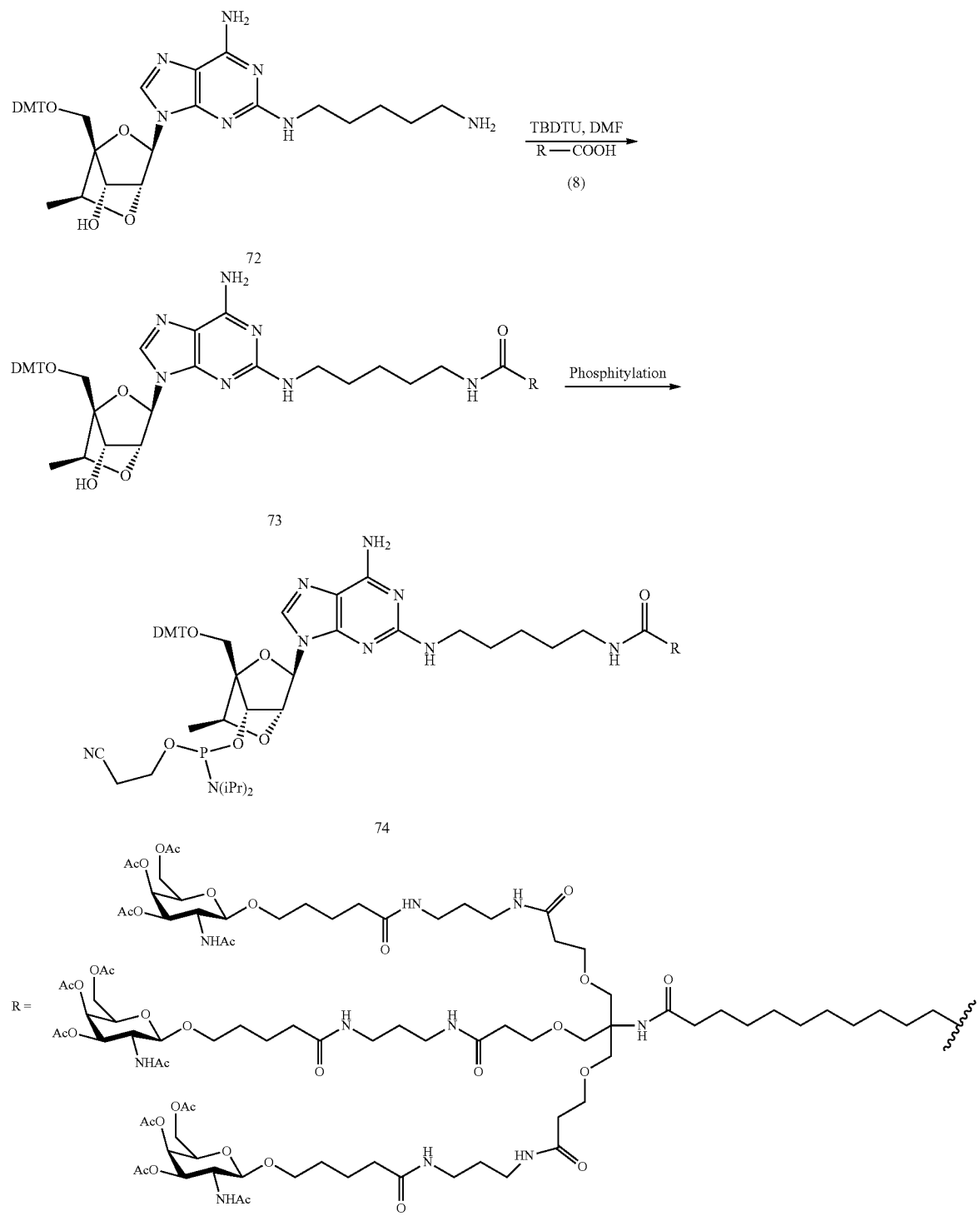
Compound 72 is prepared using similar procedures as illustrated in Example 40. Compound 8 is prepared according to the procedures published by Rensen et al., *J. Med. Chem.*, 2004, 47, 5798-5808.

Example 36
Preparation of Compound 76
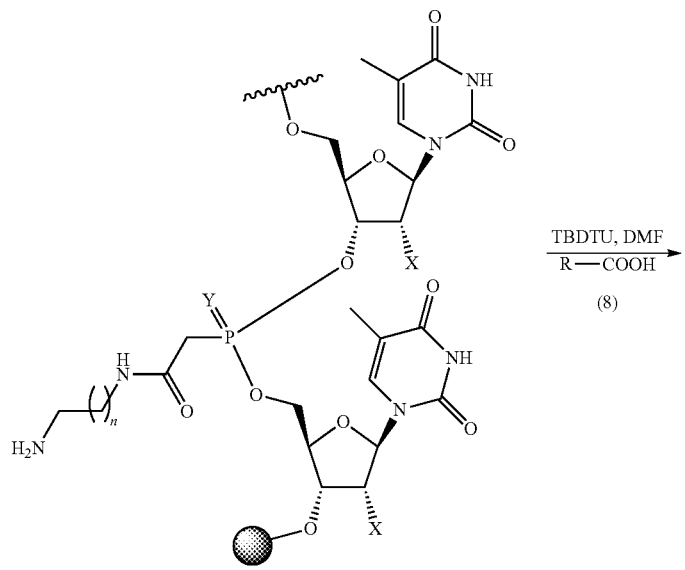
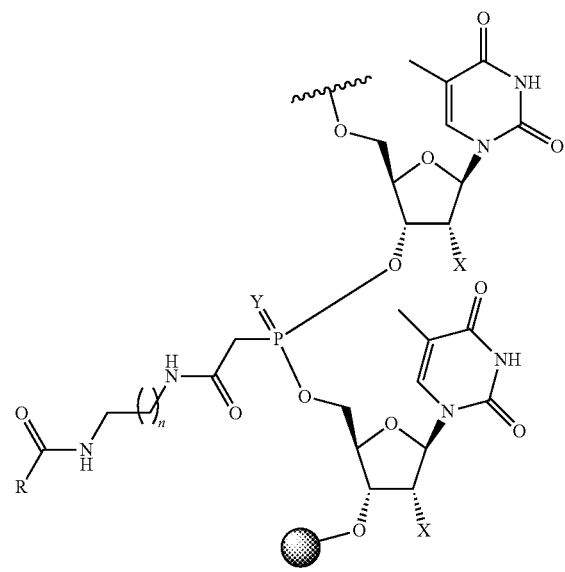

R = 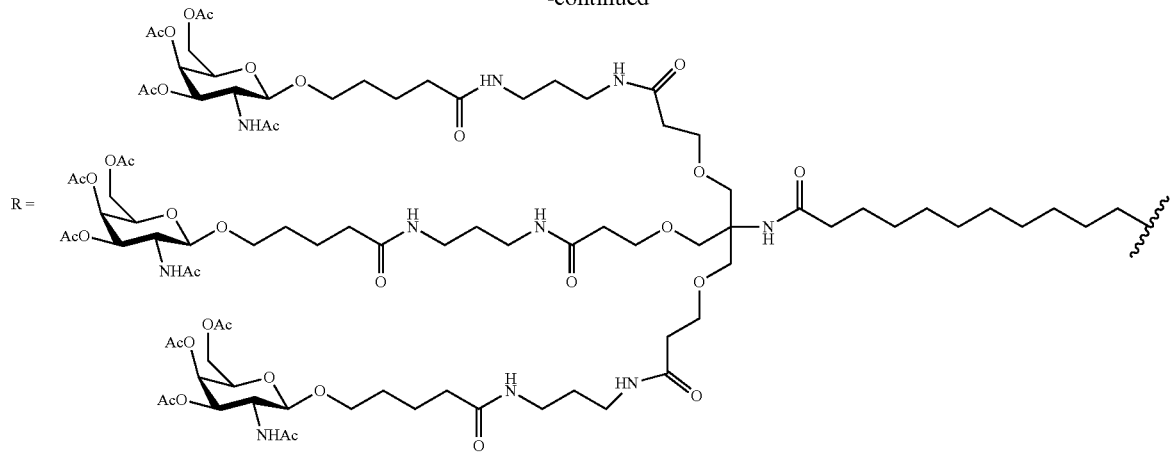
8
Y = S or O
X = sugar substituent group
n = 1-5
⬤—⋛ = solid support
Compound 75 is prepared as per the procedures illustrated in Example 17. Compound 8 is prepared according to the procedures published by Rensen et al., *J. Med. Chem.*, 2004, 47, 5798-5808.
Example 37
Preparation of Compound 78
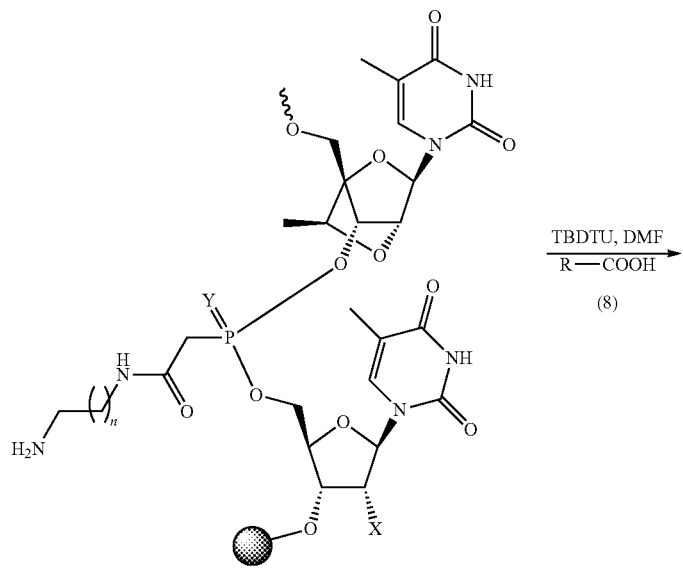
77

-continued
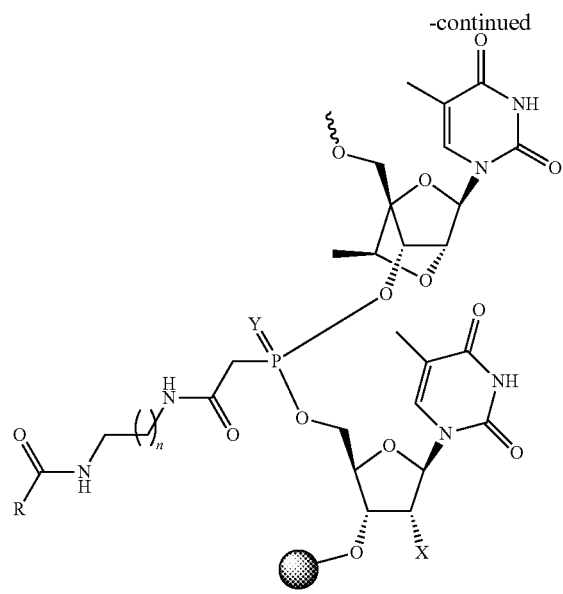
78
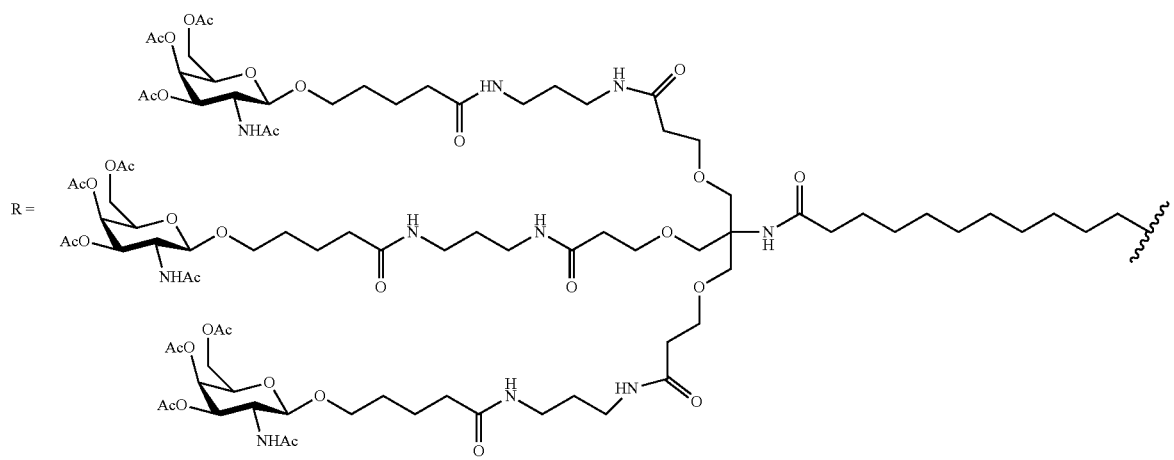
8
Y = S or O
X = sugar substituent group
n = 1-5
◯⁓ = solid support
Compound 77 is prepared as per the procedures illustrated in Examples 17, 43 and 44. Compound 8 is prepared according to the procedures published by Rensen et al., *J. Med. Chem.*, 2004, 47, 5798-5808.

Example 38
Preparation of Compound 80
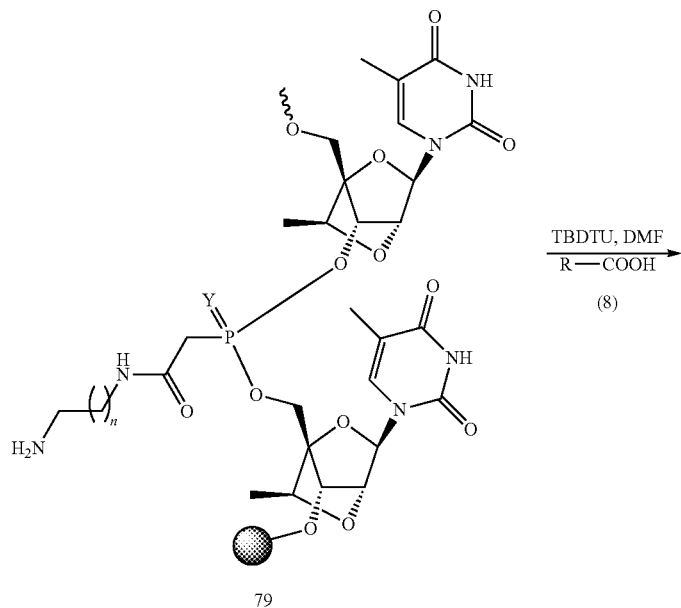
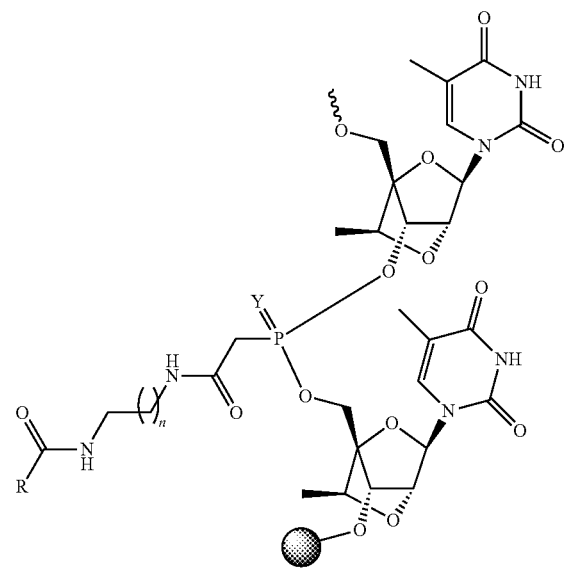

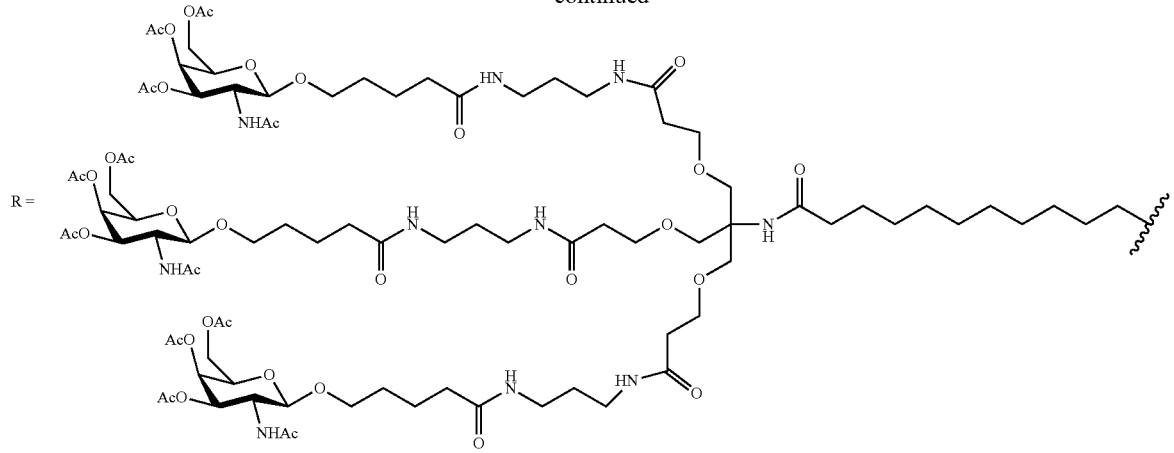
8
Y = S or O
n = 1-5
= solid support
Compound 79 is prepared as per the procedures illustrated in Examples 17, 43 and 44. Compound 8 is prepared according to the procedures published by Rensen et al., *J. Med. Chem.*, 2004, 47, 5798-5808.
Example 39
Preparation of Compound 83
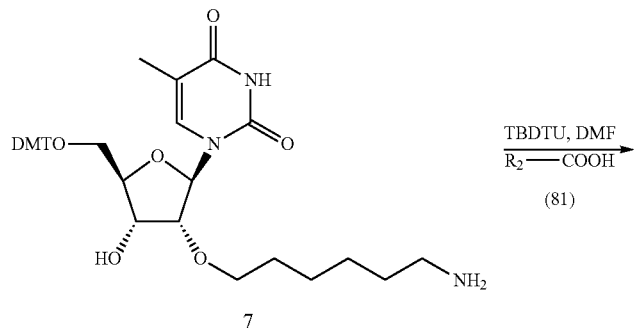
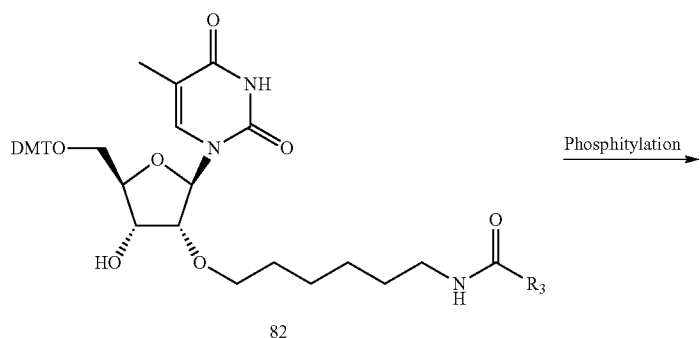

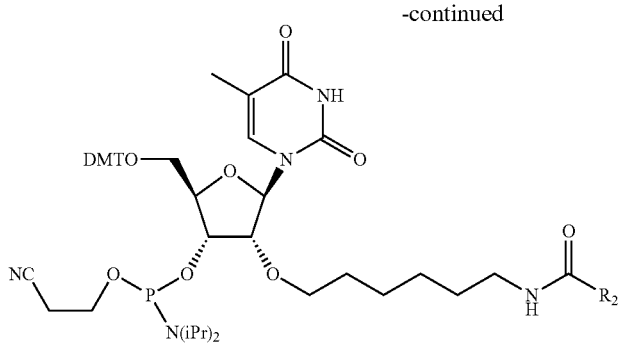
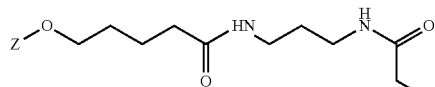
83
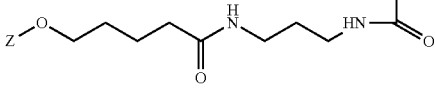
R₂ =
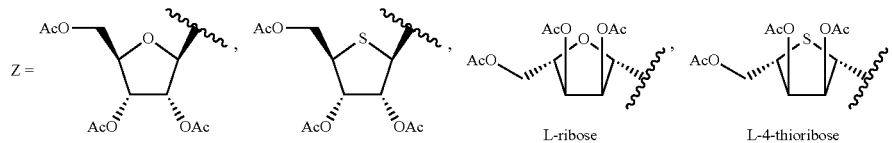
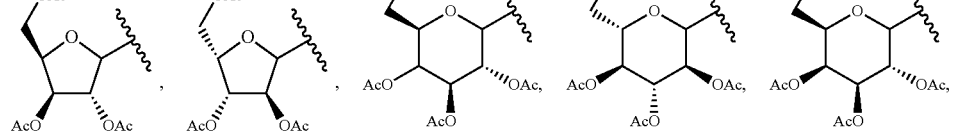
81
Z =
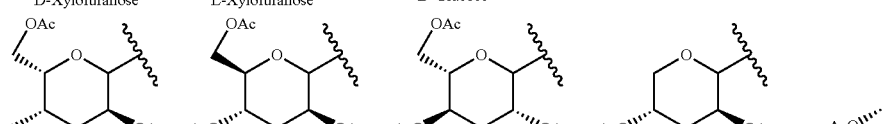
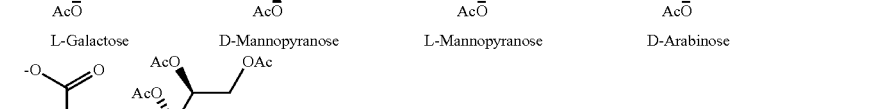
85
Compound 7 is prepared according to the procedures published in WO 2000/14048 or by Manoharan et al., *J. Org. Chem.*, 1999, 64, 6468-6472. Compound 81 is prepared using similar procedures according to Rensen et al., *J. Med. Chem.*, 2004, 47, 5798-5808.

Example 40
Preparation of Compound 85
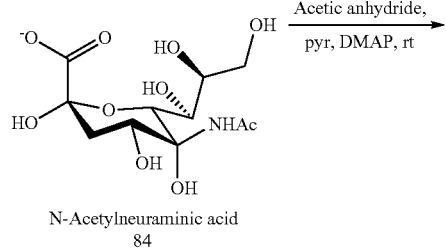
N-Acetylneuraminic acid
84
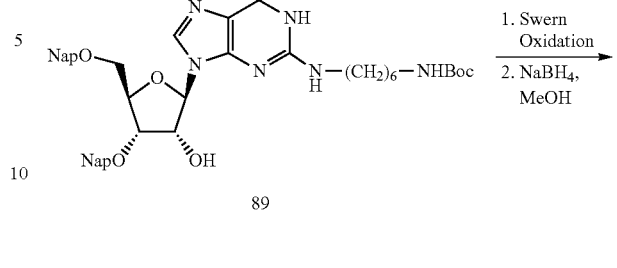
89
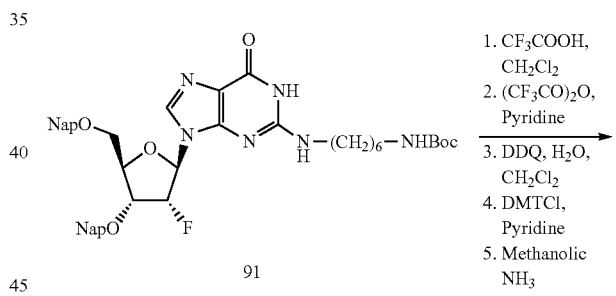
90
Compound 84, N-Acetylneuraminic acid is commercially available from various sources.
Example 41
Preparation of Compound 15
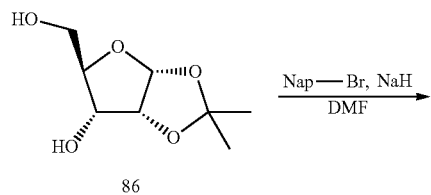
86
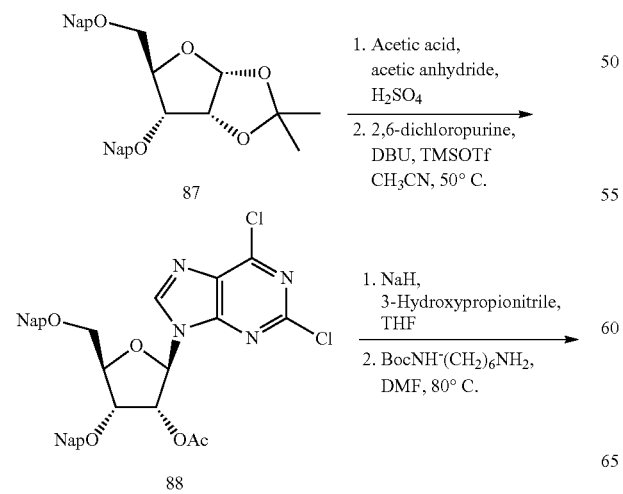
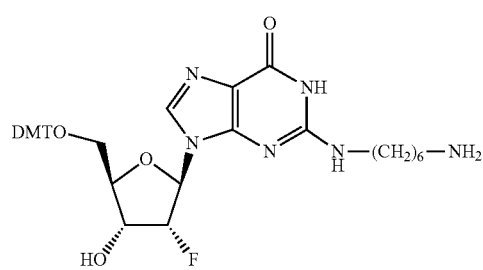
91
15
Compound 86, 1,2-O-isopropylidene-α-D-ribofuranose is commercially available from various sources.

Example 42
Preparation of Compounds 16-20
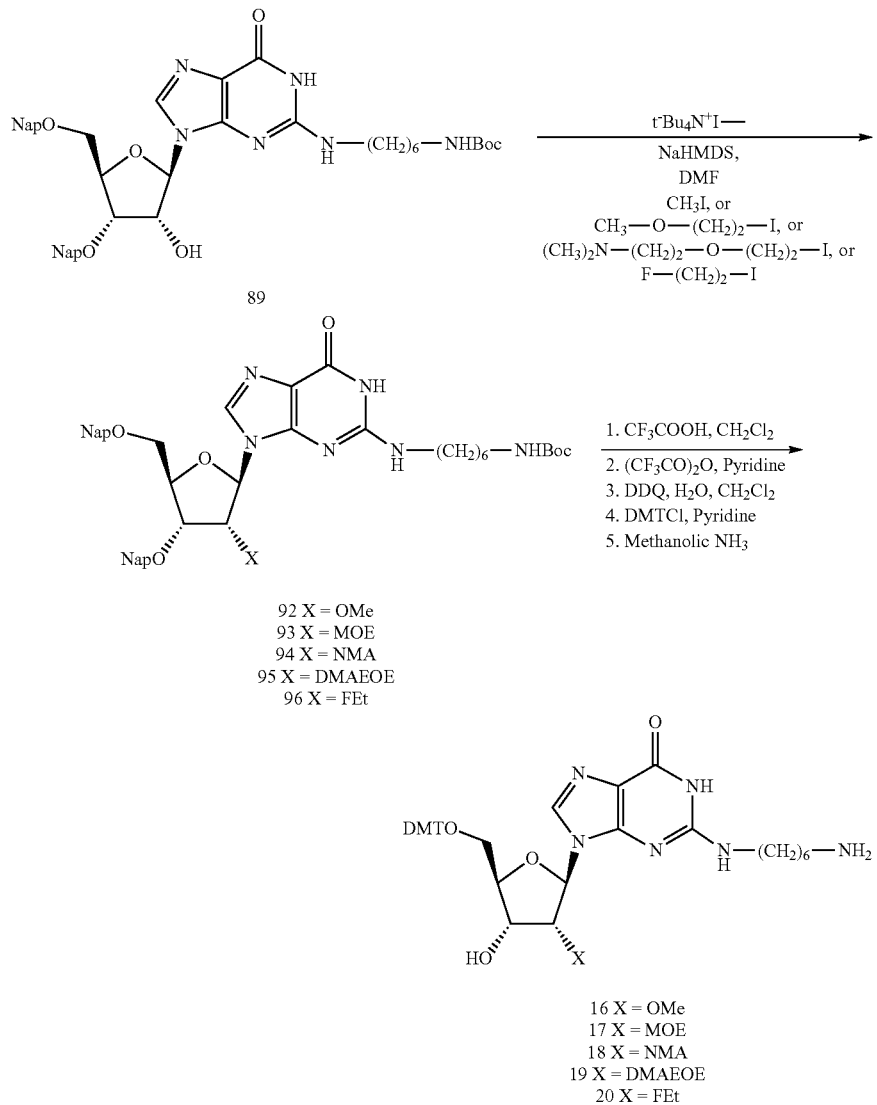
Compound 89 is prepared as per the procedures illustrated in Example 40.
Example 43
Preparation of Compound 33
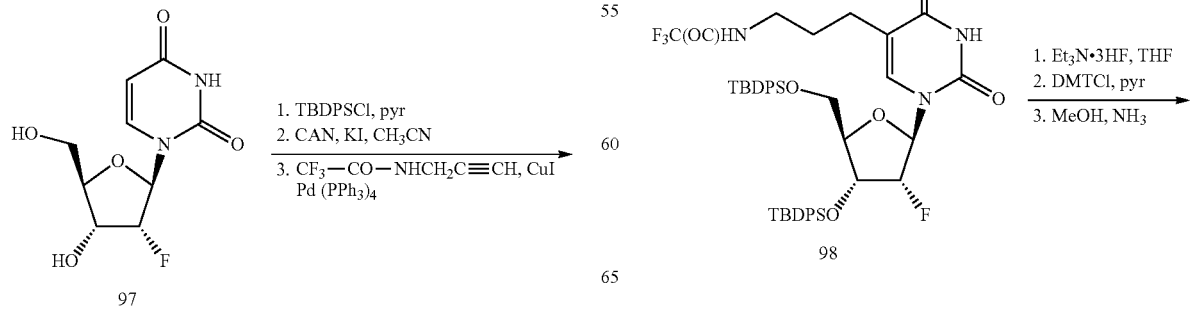

-continued

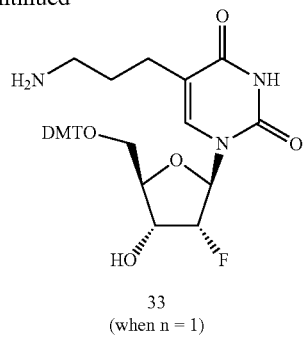

33
(when n = 1)

Compound 97 is commercially available from various sources.

Example 44

General Procedure for the Preparation of Compound 103

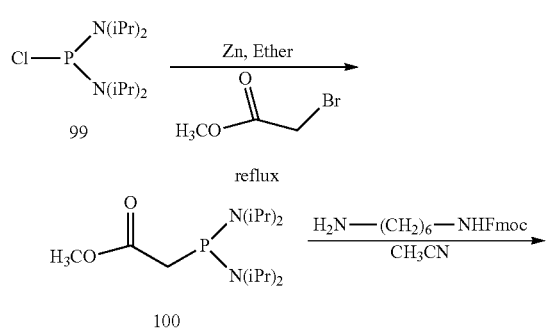

-continued

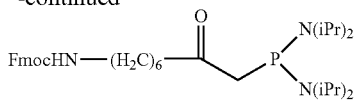

101

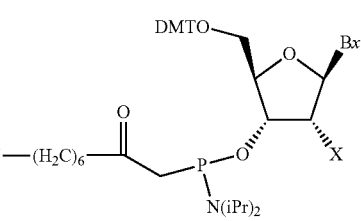

102

Compound 101
────────────→
DMF, tetrazole, NMI

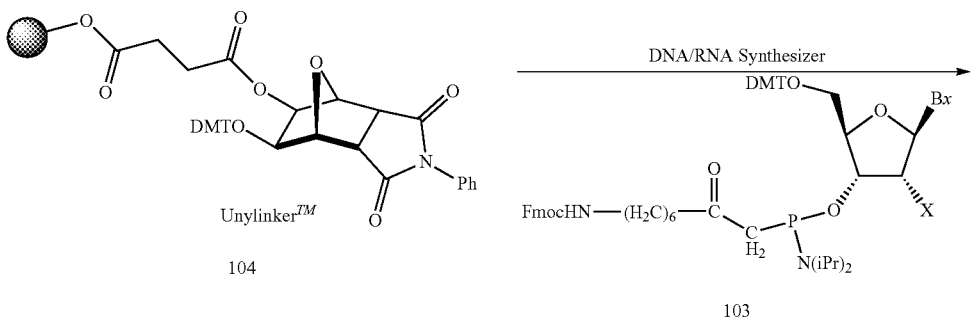

103

X = sugar substituent group
Bx = heterocyclic base moiety

Compound 99 is commercially available from various sources. Compound 100 is prepared according to the procedures published by Dellinger et al., *J. Am. Chem. Soc.*, 2003, 125, 940-950.

Example 45

General Procedure for the Preparation of Compound 106

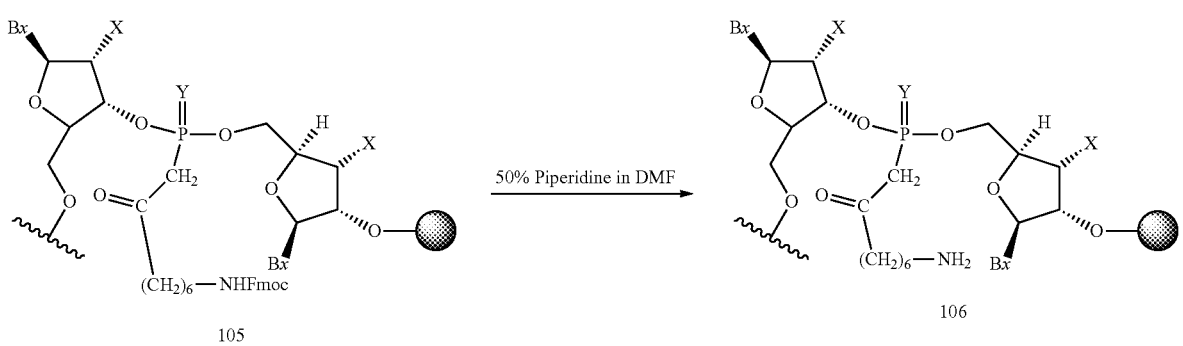

50% Piperidine in DMF
───────────→

$B_x$ = heterocyclic base moiety
X = sugar substituent group
Y = O or S

The Unylinker™ 104 is commercially available. Conjugated oligomeric Compound 103 is prepared as per the procedures illustrated in Example 43.

Example 46

Modified Oligonucleotides Comprising C10, C16 or C22 Conjugate at Position 1 or 8 Targeting PTEN In Vitro Study Several conjugated oligonucleotides from Tables 5 and 9 were selected and evaluated for their effects on PTEN mRNA expression level in vitro. These oligonucleotides were designed by introducing a C10, C16 or C22 conjugate at position 1 or 8, as counted from the 5'-terminus. ISIS 522247 lacking a conjugate group was included in the study for comparison.

The conjugated modified oligonucleotides were tested in vitro using two transfection methods. Hepatocytes at a density of 12,000 cells per well were transfected using LIPOFECTAMINE™ 2000 (Lipo) with 0.27, 0.82, 2.46, 7.40, 22.2, 66.67 and 200 nM concentrations or at a density of 35,000 cells per well using electroporation (Electro) with 0.027, 0.08, 0.25, 0.74, 2.20, 6.67 and 20 μM concentrations of conjugated oligonucleotides. After a treatment period of approximately 24 hours, RNA was isolated from the cells and PTEN mRNA levels were measured by quantitative real-time PCR. Primer probe set RTS186 was used to measure mRNA levels. PTEN mRNA levels were adjusted according to total RNA content, as measured by RIBOGREEN.

The half maximal inhibitory concentration ($IC_{50}$) of each oligonucleotide is presented in Table 17 and was calculated by plotting the concentrations of oligonucleotides used versus the percent inhibition of PTEN mRNA expression achieved at each concentration, and noting the concentration of oligonucleotide at which 50% inhibition of PTEN mRNA expression was achieved compared to the control. As illustrated in Table 17, the oligonucleotide with a 5'-phosphate and a C16 conjugate at position 1 (ISIS 549166) showed comparable potency in inhibiting PTEN mRNA levels as ISIS 522247 by both transfection methods.

TABLE 17

Comparison of inhibition of PTEN mRNA levels of C10, C16 or C22 conjugated oligonucleotides with ISIS 522247

| ISIS NO. | Conjugate | Conjugate position counted from 5' | 5'-Chemistry | Hepato/Lipo $IC_{50}$ (nM) | Heptato/Electro $IC_{50}$ (μM) |
|---|---|---|---|---|---|
| 522247 | No conjugate | N/A | (E)—(PO(OH)$_2$(CH=CH)— | 1.5 | 2 |
| 549621 | C10 | 1 | (E)—(PO(OH)$_2$(CH=CH)— | ND | 1.5 |
| 549166 | C16 | 1 | (PO(OH)$_2$)— | 1.2 | 2 |
| 551908 | C22 | 1 | (PO(OH)$_2$)— | 8 | 15 |
| 543911 | C16 | 8 | (E)—(PO(OH)$_2$(CH=CH)— | 1.2 | 20 |
| 551906 | C22 | 8 | (E)—(PO(OH)$_2$(CH=CH)— | 8 | >20 |

N/A = Not Applicable;
ND = no data

Example 47

Modified Oligonucleotides Comprising C16 Conjugate at Various Positions Targeting PTEN In Vitro Study A series of conjugated oligonucleotides was designed based on the parent oligomeric compound lacking the conjugate group, ISIS 522247. The conjugated oligonucleotides comprising a 5'-(E)-vinylphosphonate were created with a C16 conjugate group shifted slightly upstream or downstream (i.e. "microwalk") of the oligonucleotide. The newly designed conjugated oligonucleotides were tested and evaluated for their effects on PTEN mRNA levels in vitro. ISIS 522247 was included in the study for comparison.

The conjugated oligonucleotides were prepared using similar procedures as illustrated in Examples 12 and 17 and are described in Table 18. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, (PO(OH)$_2$(CH=CH—). Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. Nucleosides with a subscript "C16" are shown below. Underlined nucleosides indicate the conjugate position.

The conjugated modified oligonucleotides were tested in vitro using two transfection methods. Hepatocytes at a density of 12,000 cells per well were transfected using LIPOFECTAMINE™ 2000 (Lipo) with 0.27, 0.82, 2.46, 7.40, 22.2, 66.67 and 200 nM concentrations or at a density of 35,000 cells per well using electroporation (Electro) with 0.027, 0.08, 0.25, 0.74, 2.20, 6.67 and 20 μM concentrations of conjugated oligonucleotides. After a treatment period of approximately 24 hours, RNA was isolated from the cells and PTEN mRNA levels were measured by quantitative real-time PCR. Primer probe set RTS186 was used to measure mRNA levels. PTEN mRNA levels were adjusted according to total RNA content, as measured by RIBOGREEN.

The $IC_{50}$ of each oligonucleotide was calculated using the method described previously and the results are presented in Table 19. As illustrated, all but one conjugated oligonucleotides showed comparable potency in inhibiting PTEN mRNA levels by Lipofectamine as compared to ISIS 522247 lacking the conjugate.

TABLE 19

Comparison of inhibition of PTEN mRNA levels of C16-conjugated oligonucleotides with ISIS 522247

| ISIS NO. | Lipo $IC_{50}$ (nM) | Electro $IC_{50}$ (μM) | C16 conjugate position counted from 5'-terminus | SEQ ID NO |
|---|---|---|---|---|
| 522247 | 1 | 1 | No conjugate | 6 |
| 580933 | 1.5 | 4 | 1 | 6 |
| 576803 | 1.5 | 10 | 4 | 6 |
| 576798 | 1 | 8 | 5 | 6 |
| 576797 | 1 | 8 | 6 | 6 |
| 571032 | 1 | >20 | 8 | 6 |
| 576796 | 7 | >20 | 14 | 6 |
| 579694 | 0.9 | 10 | 15 | 6 |
| 576794 | 0.9 | 6 | 19 | 6 |
| 576793 | 1.5 | >20 | 20 | 6 |
| 576792 | 0.9 | 7 | 21 | 6 |

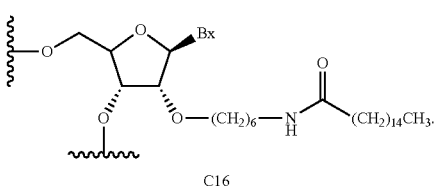

C16

TABLE 18

Modified oligonucleotides comprising C16 conjugate

| ISIS NO. | Composition (5' to 3') | C16 conjugate position counted from 5'-terminus | SEQ ID NO. |
|---|---|---|---|
| 522247 | Pv-T$_{es}$U$_{fs}$A$_m$U$_{fs}$C$_m$U$_{fs}$A$_m$U$_{fs}$A$_m$A$_{fs}$ U$_m$G$_{fs}$A$_m$U$_{fs}$C$_{ms}$A$_{fs}$G$_{ms}$G$_{fs}$U$_{ms}$A$_{es}$A$_e$ | No conjugate | 6 |
| 580933 | Pv-T$_{\underline{C16s}}$U$_{fs}$A$_m$U$_{fs}$C$_m$U$_{fs}$A$_m$U$_{fs}$A$_m$A$_{fs}$ U$_m$G$_{fs}$A$_m$U$_{fs}$C$_{ms}$A$_{fs}$G$_{ms}$G$_{fs}$U$_{ms}$A$_{es}$A$_e$ | 1 | 6 |
| 576803 | Pv-T$_{es}$U$_{fs}$A$_m$U$_{\underline{C16s}}$C$_m$U$_{fs}$A$_m$U$_{fs}$A$_m$A$_{fs}$ U$_m$G$_{fs}$A$_m$U$_{fs}$C$_{ms}$A$_{fs}$G$_{ms}$G$_{fs}$U$_{ms}$A$_{es}$A$_e$ | 4 | 6 |
| 576798 | Pv-T$_{es}$U$_{fs}$A$_m$U$_{fs}$C$_{\underline{C16}}$U$_{fs}$A$_m$U$_{fs}$A$_m$A$_{fs}$ U$_m$G$_{fs}$A$_m$U$_{fs}$C$_{ms}$A$_{fs}$G$_{ms}$G$_{fs}$U$_{ms}$A$_{es}$A$_e$ | 5 | 6 |
| 576797 | Pv-T$_{es}$U$_{fs}$A$_m$U$_{fs}$C$_m$U$_{\underline{C16s}}$A$_m$U$_{fs}$A$_m$A$_{fs}$ U$_m$G$_{fs}$A$_m$U$_{fs}$C$_{ms}$A$_{fs}$G$_{ms}$G$_{fs}$U$_{ms}$A$_{es}$A$_e$ | 6 | 6 |
| 571032 | Pv-T$_{es}$U$_{fs}$A$_m$U$_{fs}$C$_m$U$_{fs}$A$_m$U$_{\underline{C16s}}$A$_m$A$_{fs}$ U$_m$G$_{fs}$A$_m$U$_{fs}$C$_{ms}$A$_{fs}$G$_{ms}$G$_{fs}$U$_{ms}$A$_{es}$A$_e$ | 8 | 6 |
| 576796 | Pv-T$_{es}$U$_{fs}$A$_m$U$_{fs}$C$_m$U$_{fs}$A$_m$U$_{fs}$A$_m$A$_{fs}$ U$_m$G$_{fs}$A$_m$U$_{\underline{C16s}}$C$_{ms}$A$_{fs}$G$_{ms}$G$_{fs}$U$_{ms}$A$_{es}$A$_e$ | 14 | 6 |
| 579694 | Pv-T$_{es}$U$_{fs}$A$_m$U$_{fs}$C$_m$U$_{fs}$A$_m$U$_{fs}$A$_m$A$_{fs}$ U$_m$G$_{fs}$A$_m$U$_{fs}$C$_{\underline{C16s}}$A$_{fs}$G$_{ms}$G$_{fs}$U$_{ms}$A$_{es}$A$_e$ | 15 | 6 |
| 576794 | Pv-T$_{es}$U$_{fs}$A$_m$U$_{fs}$C$_m$U$_{fs}$A$_m$U$_{fs}$A$_m$A$_{fs}$ U$_m$G$_{fs}$A$_m$U$_{fs}$C$_{ms}$A$_{fs}$G$_{ms}$G$_{fs}$U$_{\underline{C16s}}$A$_{es}$A$_e$ | 19 | 6 |
| 576793 | Pv-T$_{es}$U$_{fs}$A$_m$U$_{fs}$C$_m$U$_{fs}$A$_m$U$_{fs}$A$_m$A$_{fs}$ U$_m$G$_{fs}$A$_m$U$_{fs}$C$_{ms}$A$_{fs}$G$_{ms}$G$_{fs}$U$_{ms}$U$_{\underline{C16s}}$A$_e$ | 20 | 6 |
| 576792 | Pv-T$_{es}$U$_{fs}$A$_m$U$_{fs}$C$_m$U$_{fs}$A$_m$U$_{fs}$A$_m$A$_{fs}$ U$_m$G$_{fs}$A$_m$U$_{fs}$C$_{ms}$A$_{fs}$G$_{ms}$G$_{fs}$U$_{ms}$A$_{es}$U$_{\underline{C16}}$ | 21 | 6 |

Example 48

Modified Oligonucleotides Comprising Hexylamino (HA) at Position 1 or 8 Targeting PTEN

In Vitro Study

Additional conjugated oligonucleotides were designed based on the parent oligomeric compound lacking the conjugate group, ISIS 522247. The conjugated oligonucleotides were designed by introducing a hexylamino (HA) or C16 conjugate group at position 1 or 8 of the oligonucleotide. The newly designed conjugated oligonucleotides were tested and evaluated for their effects on PTEN mRNA levels in vitro. ISIS 522247 was included in the study for comparison.

The conjugated oligonucleotides were prepared using similar procedures as illustrated in Examples 12 and 17 and are described in Table 20. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH-))$. A "Po" at the 5'-end indicates a 5'-phosphate group, $(PO(OH)_2-)$. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. Nucleosides with a subscript "C16" or HA are shown below. Underlined nucleosides indicate the conjugate position.

The conjugated modified oligonucleotides were tested in vitro using two transfection methods. Hepatocytes at a density of 12,000 cells per well were transfected using LIPOFECTAMINE™ 2000 (Lipo) with 0.27, 0.82, 2.46, 7.40, 22.2, 66.67 and 200 nM concentrations or at a density of 35,000 cells per well using electroporation (Electro) with 0.027, 0.08, 0.25, 0.74, 2.20, 6.67 and 20 µM concentrations of conjugated oligonucleotides. After a treatment period of approximately 24 hours, RNA was isolated from the cells and PTEN mRNA levels were measured by quantitative real-time PCR. Primer probe set RTS186 was used to measure mRNA levels. PTEN mRNA levels were adjusted according to total RNA content, as measured by RIBOGREEN.

The $IC_{50}$ of each oligonucleotide was calculated using the method described previously and the results are presented in Tables 21 and 22. As illustrated, incorporation of hexylamino at position 1 (ISIS 582081) or 8 (ISIS 576459) showed comparable potency in inhibiting PTEN mRNA levels while C16 conjugated oligonucleotides showed reduction in potency as compared to the parent compound, ISIS 522247.

TABLE 20

Modified oligonucleotides comprising hexylamino (HA) or C16 conjugate

| ISIS NO | Composition (5' to 3') | Conjugate | Conjugate position counted from 5' | 5'-Chemistry | SEQ ID NO. |
|---|---|---|---|---|---|
| 522247 | Pv-$T_{es}U_{fs}A_mU_{fs}C_mU_{fs}A_mU_{fs}A_mA_{fs}$ $U_mG_{fs}A_mU_{fs}C_{ms}A_{fs}G_{ms}G_{fs}U_{ms}A_{es}A_e$ | No conjugate | N/A | (E)-(PO(OH)$_2$(CH=CH)- | 6 |
| 580933 | Pv-$T_{C16s}U_{fs}A_mU_{fs}C_mU_{fs}A_mU_{fs}A_mA_{fs}U_m$ $G_{fs}A_m\overline{U_{fs}}C_{ms}A_{fs}G_{ms}G_{fs}U_{ms}A_{es}A_e$ | C16 | 1 | (E)-(PO(OH)$_2$(CH=CH)- | 6 |
| 582081 | Po-$U_{HAs}U_{fs}A_mU_{fs}C_mU_{fs}A_mU_{fs}A_mA_{fs}U_m$ $G_{fs}A_m\overline{U_{fs}}C_{ms}A_{fs}G_{ms}G_{fs}U_{ms}A_{es}A_e$ | HA | 1 | (PO(OH)$_2$- | 6 |
| 571032 | Pv-$T_sU_{fs}A_mU_{fs}C_mU_{fs}A_mU_{C16s}A_mA_{fs}U_m$ $G_{fs}A_mU_{fs}C_{ms}A_{fs}G_{ms}G_{fs}U_{ms}\overline{A_{es}}A_e$ | C16 | 8 | (E)-(PO(OH)$_2$(CH=CH)- | 6 |
| 576459 | Pv-$T_sU_{fs}A_mU_{fs}C_mU_{fs}A_mU_{HAs}A_mA_{fs}U_m$ $G_{fs}A_mU_{fs}C_{ms}A_{fs}G_{ms}G_{fs}U_{ms}\overline{A_{es}}A_e$ | HA | 8 | (E)-(PO(OH)$_2$(CH=CH)- | 6 |

N/A = Not Applicable

TABLE 21

Comparison of inhibition of PTEN mRNA levels of hexylamino (HA) or C16 conjugated oligonucleotides at position 1 with ISIS 522247

| ISIS NO. | Conjugate | Conjugate position counted from 5' | 5'-Chemistry | $IC_{50}$ (µM) |
|---|---|---|---|---|
| 522247 | No conjugate | N/A | (E)-(PO(OH)$_2$(CH=CH)- | 0.57 |
| 580933 | C16 | 1 | (E)-(PO(OH)$_2$(CH=CH)- | 3.3 |
| 582081 | HA | 1 | (PO(OH)$_2$- | 0.94 |

TABLE 22

Comparison of inhibition of PTEN mRNA levels of hexylamino (HA) or C16 conjugated oligonucleotides at position 8 with ISIS 522247

| ISIS NO. | Conjugate | Conjugate position counted from 5' | 5'-Chemistry | IC$_{50}$ (µM) |
|---|---|---|---|---|
| 522247 | No conjugate | N/A | (E)-(PO(OH$_2$(CH=CH)- | 0.82 |
| 571032 | C16 | 8 | (E)-(PO(OH$_2$(CH=CH)- | 7.8 |
| 576459 | HA | 8 | (E)-(PO(OH$_2$(CH=CH)- | 1.1 |

N/A = Not Applicable

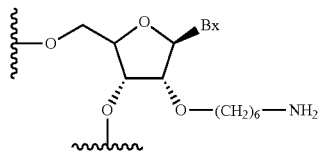

Hexylamino (HA)

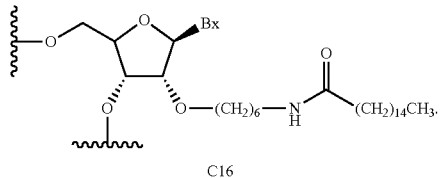

C16

Example 49

Modified Oligonucleotides Comprising C16 Conjugate Targeting PTEN

In Vivo Study

ISIS 543911 comprising a 5'-(E)-vinylphosphonate and C16 conjugate at position 8, as counted from the 5'-terminus was selected from the previous examples and evaluated for inhibition of PTEN mRNA levels in vivo. ISIS 522247 lacking a conjugate group and 5-10-5 MOE gapmer, ISIS 116847 were included in the study for comparison.

Six week old BALB/C mice (Jackson Laboratory, Bar Harbor, Me.) were injected subcutaneously once a day for one day with ISIS 116847 or 543911 at 3, 10 and 30 mg/kg or with saline treated control. Another group of mice was injected subcutaneously twice a day for two days at 25 mg/kg (100 mg/kg total) with ISIS 116847, 522247 or 543911. Each treatment group consisted of 4 animals. The mice were sacrificed 48 hrs following last administration. Liver tissues were homogenized and mRNA levels were quantitated using real-time PCR and normalized to RIBOGREEN as described herein. The results in Table 23 are presented as percent of PTEN mRNA expression, relative to untreated control levels and is denoted as "% UTC". As illustrated, inhibition of PTEN mRNA levels was achieved in a dose-dependent manner with the conjugated oligonucleotide. In addition, ISIS 543911 comprising a C16 conjugate at position 8 showed an increase in potency at 100 mg/kg as compared to the parent compound lacking a conjugate group, ISIS 522247.

TABLE 23

Comparison of inhibition of PTEN mRNA levels of C16 conjugated oligonucleotides at position 8 with ISIS 522247 and 5-10-5 MOE gapmer, ISIS 116847

| ISIS NO | Dosage (mg/kg) | % UTC | Conjugate/position counted from 5' |
|---|---|---|---|
| Saline | 0 | 100 | N/A |
| 116847 | 3 | 95.77 | 5-10-5 |
| | 10 | 76.48 | MOE gapmer |
| | 30 | 44.74 | |
| | 100 | 21.46 | |
| | 100 (25 mg/kg twice a day for 2 days) | 15.63 | |
| 522247 | 100 (25 mg/kg twice a day for 2 days) | 45.59 | No conjugate |
| 543911 | 3 | 92.79 | C16, pos 8 |
| | 10 | 86.84 | |
| | 30 | 72.73 | |
| | 100 (25 mg/kg twice a day for 2 days) | 24.42 | |

N/A = Not Applicable

Example 50

Modified Oligonucleotides Comprising C16 Conjugate Targeting PTEN

In Vivo Study

ISIS 571032 comprising a 5'-(E)-vinylphosphonate and C16 conjugate at position 8, as counted from the 5'-terminus was selected from the previous examples and evaluated for inhibition of PTEN mRNA levels in vivo. ISIS 522247 lacking a conjugate group and 5-10-5 MOE gapmer, ISIS 116847 were included in the study for comparison.

Six week old BALB/C mice (Jackson Laboratory, Bar Harbor, Me.) were injected subcutaneously once a day for one day with ISIS 116847 at 10, 30 and 100 mg/kg or 571032 at 7, 18, 44 and 110 mg/kg or with saline treated control. Another group of mice was injected subcutaneously twice a day for two days at 25 mg/kg (100 mg/kg total) with ISIS 522247. Each treatment group consisted of 4 animals. The mice were sacrificed 48 hrs following last administration. Liver tissues were homogenized and mRNA levels were quantitated using real-time PCR and normalized to GAPDH. The results in Table 24 are presented as percent of PTEN mRNA expression, relative to untreated control levels and is denoted as "% UTC". As illustrated, inhibition of PTEN mRNA levels was achieved in a dose-dependent manner with the conjugated oligonucleotide.

TABLE 24

Comparison of inhibition of PTEN mRNA levels of C16 conjugated oligonucleotide with ISIS 522247 and 5-10-5 MOE gapmer, ISIS 116847

| ISIS NO | Dosage (mg/kg) | % UTC | Conjugate/position counted from 5' |
|---|---|---|---|
| Saline | 0 | 100 | N/A |
| 116847 | 10 | 83.48 | 5-10-5 |
| | 30 | 35.22 | MOE gapmer |
| | 100 | 15.20 | |
| 522247 | 100 (25 mg/kg twice a day for 2 days) | 59.12 | No conjugate |

TABLE 24-continued

Comparison of inhibition of PTEN mRNA levels of C16 conjugated oligonucleotide with ISIS 522247 and 5-10-5 MOE gapmer, ISIS 116847

| ISIS NO | Dosage (mg/kg) | % UTC | Conjugate/position counted from 5' |
|---|---|---|---|
| 571032 | 7 | 82.05 | C16, pos 8 |
|  | 18 | 73.32 |  |
|  | 44 | 54.74 |  |
|  | 110 | 32.95 |  |

N/A = Not Applicable

Example 51

Modified Oligonucleotide Comprising C16 Conjugate Targeting PTEN

In Vivo Multiple Dose Response Study

ISIS 571032 comprising a 5'-(E)-vinylphosphonate and C16 conjugate at position 8, as counted from the 5'-terminus was selected from the previous example and evaluated for multiple dose response study in vivo targeting PTEN. ISIS 522247 lacking a conjugate group and 5-10-5 MOE gapmer, ISIS 116847 were included in the study for comparison.

Six week old BALB/C mice (Jackson Laboratory, Bar Harbor, Me.) were injected subcutaneously twice a week for three weeks with the conjugated oligonucleotide at dosage presented in Table 24 or with saline treated control. One group of mice was injected subcutaneously twice a day for two days at 25 mg/kg (100 mg/kg/wk total) with ISIS 522247. Each treatment group consisted of 4 animals. The mice were sacrificed 48 hrs following last administration. Liver tissues were homogenized and mRNA levels were quantitated using real-time PCR and normalized to Cyclophilin as described herein. The results in Table 25 are presented as percent of PTEN mRNA expression, relative to untreated control levels and is denoted as "% UTC". As illustrated, inhibition of PTEN mRNA levels was achieved in a dose-dependent manner with the conjugated oligonucleotide.

TABLE 25

Comparison of inhibition of PTEN mRNA levels of C16 conjugated oligonucleotide with ISIS 522247 and 5-10-5 MOE gapmer, ISIS 116847

| ISIS NO | Dosage (mg/kg/wk total) | % UTC | Conjugate/position counted from 5' |
|---|---|---|---|
| Saline | 0 | 100 | — |
| 116847 | 3 | 60.44 | 5-10-5 |
|  | 10 | 35.90 | MOE gapmer |
|  | 30 | 17.90 |  |
| 522247 | 100 | 49.35 | No conjugate |
| 571032 | 3 | 100.32 | C16, pos 8 |
|  | 7 | 84.30 |  |
|  | 18 | 67.76 |  |
|  | 44 | 32.00 |  |

Example 52

Modified Oligonucleotide Comprising C16 Conjugate Targeting PTEN

In Vivo Multiple Dose Response Study

ISIS 571032 comprising a 5'-(E)-vinylphosphonate and C16 conjugate at position 8, as counted from the 5'-terminus was selected from the previous example and evaluated for multiple dose response study in vivo targeting PTEN. ISIS 116847, a 5-10-5 MOE gapmer was included in the study for comparison.

Six week old BALB/C mice (Jackson Laboratory, Bar Harbor, Me.) were injected intravenously twice a week for three weeks with ISIS 116847 or 571032 at the dosage presented in Table 26 or with saline treated control. Each treatment group consisted of 4 animals. The mice were sacrificed 48 hrs following last administration. Liver tissues were homogenized and mRNA levels were quantitated using real-time PCR and normalized to Cyclophilin as described herein. The results in Table 26 are presented as percent of PTEN mRNA expression, relative to untreated control levels and is denoted as "% UTC". As illustrated, inhibition of PTEN mRNA levels was achieved in a dose-dependent manner with the conjugated oligonucleotide.

TABLE 26

Comparison of inhibition of PTEN mRNA levels of C16 conjugated oligonucleotide with ISIS 522247 and 5-10-5 MOE gapmer, ISIS 116847

| ISIS NO | Dosage (mg/kg/wk) | % UTC | Conjugate/position counted from 5' |
|---|---|---|---|
| Saline | 0 | 100 | — |
| 116847 | 6 | 79.21 | 5-10-5 |
|  | 20 | 42.45 | MOE gapmer |
|  | 60 | 21.67 |  |
| 571032 | 6 | 93.43 | C16, pos 8 |
|  | 14 | 81.55 |  |
|  | 36 | 48.79 |  |
|  | 88 | 23.44 |  |

Example 53

Modified Oligonucleotide Comprising C16 Conjugate Targeting PTEN

In Vivo Study

ISIS 571032 comprising a 5'-(E)-vinylphosphonate and C16 conjugate at position 8, as counted from the 5'-terminus was selected from the previous example and further evaluated for its effect in PTEN mRNA level in adipose tissue in vivo.

Six week old BALB/C mice (Jackson Laboratory, Bar Harbor, Me.) were treated twice a week for three weeks with ISIS 571032 at 44 mg/kg (88 mg/kg/wk total) by tail vein injection or with saline treated control. Each treatment group consisted of 4 animals. The mice were sacrificed 48 hrs following last administration. Liver tissues were homogenized and mRNA levels were quantitated using real-time PCR and normalized to Cyclophilin as described herein. The results in Table 27 are presented as the average percent of PTEN mRNA levels for each treatment group, normalized to PBS-treated control and is denoted as "% UTC". As illustrated, inhibition of PTEN mRNA level in adipose tissue was achieved with the conjugated oligonucleotide.

TABLE 27

Effect of C16 conjugated oligonucleotide on PTEN mRNA level in adipose tissue

| ISIS NO | Dosage (mg/kg/wk) | % UTC | Conjugate/position counted from 5' |
|---|---|---|---|
| Saline | 0 | 100 | — |
| 571032 | 88 | 41.19 | C16 |

Example 54

Modified Oligonucleotide Comprising C16 Conjugate Targeting PTEN

In Vivo Study

ISIS 571032 and 580933 comprising a 5'-(E)-vinylphosphonate and C16 conjugate at position 8 or 1, as counted from the 5'-terminus was selected from previous examples and evaluated for their effect on PTEN mRNA in vivo.

Six week old BALB/C mice (Jackson Laboratory, Bar Harbor, Me.) were treated subcutaneously with ISIS 571032 at 27.5 mg/kg twice a day for two days (110 mg/kg total). One group of mice was treated with ISIS 580933 at 2.8, 7, 18 and 44 mg/kg once a day for one day and 27.5 mg/kg twice a day for two days (110 mg/kg total). Another group of mice was treated with ISIS 116847 at 30 mg/kg once a day for one day. Each treatment group consisted of 3 animals. The mice were sacrificed 48 hrs following last administration. Liver tissues were homogenized and mRNA levels were quantitated using real-time PCR and normalized to RIBOGREEN as described herein. The results in Table 28 are presented as the average percent of PTEN mRNA levels for each treatment group, normalized to PBS-treated control and is denoted as "% UTC". As illustrated, incorporation of C16 conjugate at position 8 showed comparable potency as position 1 at 110 mg/kg.

TABLE 28

Effect of C16 conjugated oligonucleotides on PTEN mRNA level

| ISIS NO | Dosage (mg/kg total) | UTC (%) | Conjugate |
|---|---|---|---|
| Saline | 0 | 100 | — |
| 571032 | 110 | 22.05 | C16, pos 8 |
| 580933 | 2.8 | 109.57 | C16, pos 1 |
|  | 7 | 101.95 |  |
|  | 18 | 83.90 |  |
|  | 44 | 53.07 |  |
|  | 110 | 20.65 |  |
| 116847 | 30 | 44.06 | 5-10-5 MOE gapmer |

Example 55

Modified Oligonucleotides Comprising C16 Conjugate Targeting PTEN

In Vivo Study

An additional conjugated oligonucleotide was designed based on the parent oligomeric compound lacking the conjugate group, ISIS 522247. Since hydrolysis was observed at the amide bond between the alkyl linking group and the conjugate, the new conjugated oligonucleotide comprising a 5'-(E)-vinylphosphonate was designed by introducing a C16 conjugate group via a more stable carbamate linker at position 8 of the oligonucleotide. The newly designed conjugated oligonucleotide was tested and evaluated for their effects on PTEN mRNA levels in vivo. ISIS 522247 lacking a conjugate group and ISIS 571032 with a C16 conjugate group linked via an amide bond were included in the study for comparison.

The conjugated oligonucleotides were prepared using similar procedures as illustrated in Examples 12 and 17 and are described in Table 29. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH—)$. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. Nucleosides with a subscript "C16" or "C16x" are shown below. Underlined nucleosides indicate the conjugate position. "NA" indicates not applicable.

Six week old BALB/C mice (Jackson Laboratory, Bar Harbor, Me.) were treated with ISIS 522247 at 25 mg/kg twice a day for two days (100 mg/kg total). Another group of mice was treated with ISIS 571032 or 589269 at 6, 14, 36 and 88 mg/kg once a day for one day. Each treatment group consisted of 4 animals. The mice were sacrificed 48 hrs following last administration. Liver tissues were homogenized and mRNA levels were quantitated using real-time PCR and normalized to RIBOGREEN as described herein. The results in Table 29 are presented as the average percent of PTEN mRNA levels for each treatment group normalized to PBS-treated control and is denoted as "% UTC". As illustrated, treatment with the newly designed conjugated oligonucleotides showed an increase in potency in PTEN mRNA reduction as compared to treatment with the parent compound lacking a conjugate, ISIS 522247. In addition, incorporation of C16 conjugate at position 8 with a more stable carbamate linker exhibited comparable potency as compared to the amide linker.

The modified oligonucleotides were also evaluated for in vivo stability at dosage presented in Table 30. The tissue samples were collected and prepared using the same technique described in Example 25. Quantitative analysis of the oligonucleotides standard were performed by extracted ion chromatograms in the most abundant charge state (−4) using Chemstation software. The liver concentration (μg/g) of full length oligonucleotides comprising a 5'-terminal phosphonate group was measured by LC/MS and the results are presented below.

Figure 2:
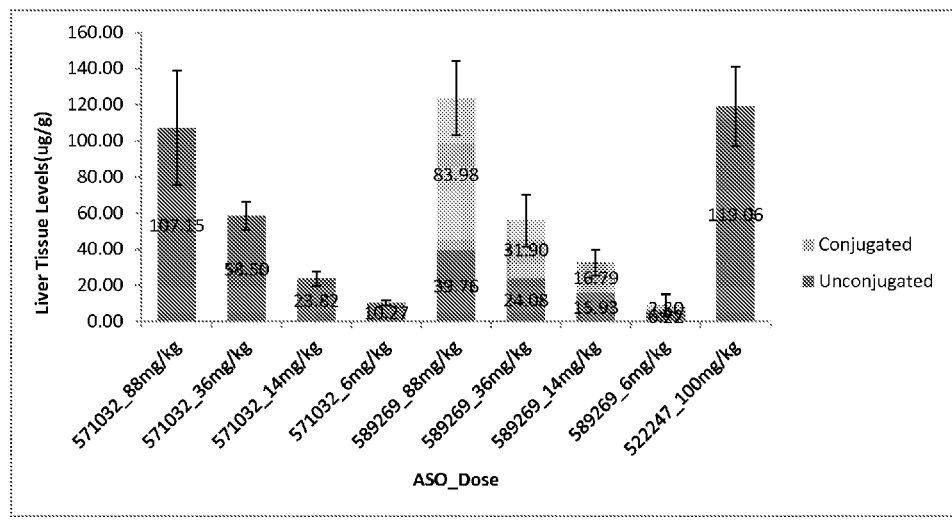
FIG. 2 illustrates the accumulation of C16 conjugated ASOs and ASOs without conjugates in the liver.

As illustrated in Table 30 and in FIG. 2, C16 conjugation increases liver accumulation of full-length oligonucleotides in a dose-dependent manner (ISIS 571032 and 589269). While the amide-linked C16 (ISIS 571032) hydrolyzed from the oligonucleotide, some fractions of carbamate-linked C16 conjugate, ISIS 589269 remained intact.

TABLE 28

Modified oligonucleotides comprising a C16
conjugate via an amide or a carbamate linker

| ISIS NO | Composition (5' to 3') | Conjugate/position counted from 5' | SEQ ID NO. |
|---|---|---|---|
| 522247 | Pv-$T_{es}U_{fs}A_mU_{fs}C_mU_{fs}A_mU_{fs}A_mA_{fs}$ $U_mG_{fs}A_mU_{fs}C_{ms}A_{fs}G_{ms}G_{fs}U_{ms}A_{es}A_e$ | No conjugate | 6 |
| 571032 | Pv-$T_{es}U_{fs}A_mU_{fs}C_mU_{fs}A_mU_{C16s}A_mA_{fs}$ $U_mG_{fs}A_mU_{fs}C_{ms}A_{fs}G_{ms}G_{fs}U_{ms}A_{es}A_e$ | C16 with amide linker, pos 8 | 6 |
| 589269 | Pv-$T_{es}U_{fs}A_mU_{fs}C_mU_{fs}A_mU_{C16xs}A_mA_{fs}$ $U_mG_{fs}A_mU_{fs}C_{ms}A_{fs}G_{ms}G_{fs}U_{ms}A_{es}A_e$ | C16 with carbamate linker, pos 8 | 6 |

TABLE 29

Effect of modified oligonucleotides comprising a C16 conjugate via an amide or a carbamate linker on PTEN mRNA level

| ISIS NO | Dosage (mg/kg total) | UTC (%) | Conjugate/position counted from 5' | SEQ ID NO. |
|---|---|---|---|---|
| Saline | 0 | 100 | — | — |
| 522247 | 100 | 58.99 | No conjugate | 6 |
| 571032 | 6 | 102.27 | C16 with amide linker, pos 8 | 6 |
|  | 14 | 89.58 |  |  |
|  | 36 | 65.53 |  |  |
|  | 88 | 35.09 |  |  |
| 589269 | 6 | 101.69 | C16 with carbamate linker, pos 8 | 6 |
|  | 14 | 102.76 |  |  |
|  | 36 | 70.29 |  |  |
|  | 88 | 46.31 |  |  |

Example 56

Hybridization-Dependent Nuclease ELISA Protocol

Liver samples (10-100 mg) were digested with 500 uL proteinase K digestion buffer (5U proteinase K (Sigma, St. Louis, Mo.)/1 mL Buffer G2 (Qiagen, Hilden, Germany)) for about 1 hour at 40° C. Standard curves were prepared with each analyte at 0.01 µM-5 µM in 500 µL control tissue homogenate (100 mg control liver/mL proteinase K digestion buffer) and digested 1 hr at 40° C. along with study samples. Study samples and standard curves were diluted 1:100 in blank liver digest and 25 uL hybridized with 475 uL 3 nM complementary hybridization probe that included a 5' digoxigenin and 3' biotin for 2 hrs at room temperature. 200 uL hybridization mix was added to NeutrAvidin-coated

TABLE 30

Comparison of full-length modified oligonucleotides comprising a C16 conjugate via an amide or a carbamate linker in liver accumulation with ISIS 522247 in vivo

| ISIS NO | Dosage (mg/kg/wk total) | Liver conc. of full length ssRNA with loss of C16 (µg/g) | Liver conc. of full length ssRNA with C16 intact (µg/g) | Conjugate |
|---|---|---|---|---|
| Saline | 0 | N/A | N/A | — |
| 522247 | 100 | 119.06 | N/A | No conjugate |
| 571032 | 6 | 10.27 | C16 conjugate completely hydrolyzed | C16 with an amide linker |
|  | 14 | 23.82 |  |  |
|  | 36 | 58.50 |  |  |
|  | 88 | 107.15 |  |  |
| 589269 | 6 | 6.22 | 2.8 | C16 with a carbamate linker |
|  | 14 | 15.93 | 16.79 |  |
|  | 36 | 24.08 | 31.9 |  |
|  | 88 | 39.76 | 83.98 |  |

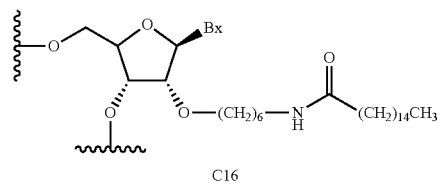

C16

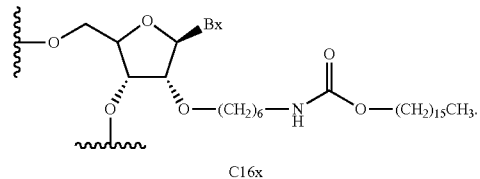

C16x 96-well plates (Thermo, Rockford, Ill.) and incubated at room temperature for 1-2 hrs. NeutrAvidin plates were washed with 0.2% Tween 20 in Tris-buffered saline (TBST) and 300 uL 50-300 U/mL S1 nuclease (Life Technologies, Carlsbad, Calif.) was added and incubated at room temperature for 2 hrs. NeutrAvidin plates were washed with TBST and 200 uL 1:2000 anti-Digoxigenin-AP (Roche, Mannheim, Germany) was added and incubated for 1 hr. at room temperature. NeutrAvidin plates were washed with TBST and 200 uL Attophos (Promega, Madison Wis.) was added and fluorescence monitored (excitation 450/50, emission 580/50) using a SpectraMax Gemini microplate reader (Molecular Devices, Sunnyvale, Calif.). Catalysis of Attophos was stopped by addition of 100 uL saturated solution of disodium phosphate (25% $Na_2HPO_4$) before final quantitation of fluorescence on microplate reader.

Example 57

Modified Oligonucleotide Comprising C16 Conjugate Targeting PTEN

In Vivo Study

ISIS 522247 and 543911 comprising a 5'-(E)-vinylphosphonate and C16 conjugate at position 8, as counted from the 5'-terminus was selected from the previous example and further evaluated for liver accumulation targeting PTEN in vivo.

Figure 3:
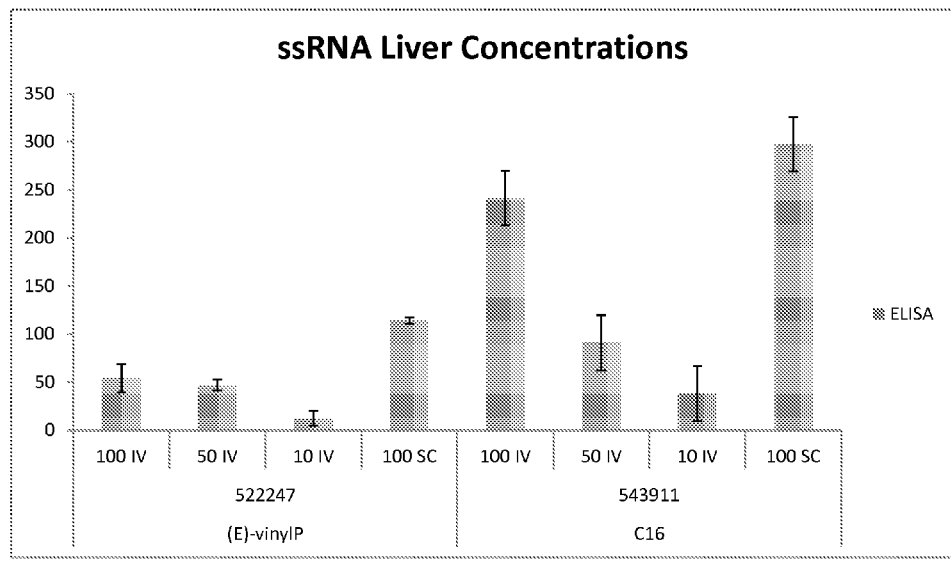
FIG. 3 illustrates the accumulation of C16 conjugated ASOs and ASOs without conjugates in the liver as determined by ELISA.

Six week old BALB/C mice (Jackson Laboratory, Bar Harbor, Me.) were treated once a day for one day with ISIS 522247 or 543911 at 10, 50 or 100 mg/kg by intravenous (IV) injection. Another group of mice was treated with ISIS 522247 or 543911 twice a day for two days at 25 mg/kg (100 mg/kg total) by subcutaneous (SC) injection. Each treatment group consisted of 4 animals. The mice were sacrificed 48 hrs following last administration. Liver tissues were homogenized and analyzed using hybridization-dependent nuclease ELISA protocol as exemplified in Example 57 to determine the concentration of the conjugated oligonucleotide in the liver. The results are presented in Table 32 and FIG. 3. As illustrated, total concentration determined by ELISA showed more oligonucleotide in liver accumulation for C16 conjugate as compared to the parent oligonucleotide lacking the conjugate, ISIS 522247.

TABLE 32

Comparison of full-length modified oligonucleotides comprising a C16 conjugate in liver accumulation with ISIS 522247 in vivo

| ISIS NO | Dosage (mg/kg/wk total) | Mode of administration | Liver conc. of full length ssRNA (µg/g) | SEQ ID NO. |
|---|---|---|---|---|
| 522247 | 10 | IV | 10.4 ± 10.1 | 6 |
|  | 50 |  | 47.09 ± 10.1 |  |
|  | 100 |  | 54.21 ± 14.6 |  |
|  | 100 | SC | 128.7 ± 21.0 |  |
| 543911 | 10 | IV | 35.8 ± 6.3 | 18 |
|  | 50 |  | 91.2 ± 28.4 |  |
|  | 100 |  | 241.82 ± 28.6 |  |
|  | 100 | SC | 297.47 ± 28.4 |  |

We claim:

1. A compound comprising an oligonucleotide consisting of 10-30 linked nucleosides and at least one conjugate group, wherein the 5'-terminal nucleoside of the oligonucleotide has Formula IV:

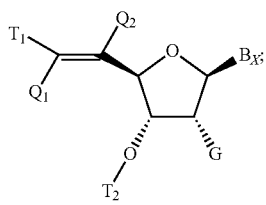

wherein:

$T_1$ is

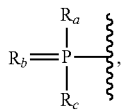

wherein:
- $R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and
- $R_b$ is O or S;
- $T_2$ is an internucleoside linking group linking the compound of Formula IV to the remainder of the oligonucleotide;
- $Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;
- each $R_3$ and $R_4$ is, independently, H, $C_1$-$C_6$ alkyl or substituted $C_1$-$C_6$ alkyl;
- Bx is a heterocyclic base moiety;
- G is H, OH, halogen, a conjugate group, or O—[C($R_8$)($R_9$)]$_n$—[(C=O)$_m$—$X_1$]$_j$—Z;
- each $R_8$ and $R_9$ is, independently, H, halogen, $C_1$-$C_6$ alkyl or substituted $C_1$-$C_6$ alkyl;
- $X_1$ is O, S or N($E_1$);
- Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
- $E_1$, $E_2$ and $E_3$ are each, independently, H, $C_1$-$C_6$ alkyl or substituted $C_1$-$C_6$ alkyl;
- n is from 1 to about 6;
- m is 0 or 1;
- j is 0 or 1;
- each substituted group comprises one or more optionally protected substituent groups independently selected from halogen, $OJ_1$, $N(J_1)(J_2)$, =$NJ_1$, $SJ_1$, $N_3$, CN, OC(=$X_2$)$J_1$, OC(=$X_2$)—$N(J_1)(J_2)$ and C(=$X_2$)$N(J_1)(J_2)$;
- $X_2$ is O, S or $NJ_3$;
- each $J_1$, $J_2$ and $J_3$ is, independently, H or $C_1$-$C_6$ alkyl; and
- provided that when j is 1 then Z is other than halogen or $N(E_2)(E_3)$.

2. The compound of claim 1, wherein the conjugate group is covalently attached to the oligonucleotide at a nucleoside at position 1, 2, 3, 4, 6, 7, 8, 9, 18, 19, 20, or 21 from the 5'-end of the oligonucleotide or at position 1, 2, 3, 12, 13, 4, 15, 17, 18, 19, 20, or 21 from the 3'-end of the oligonucleotide.

3. The compound of claim 2, wherein the conjugate group is covalently attached to any of the 1 to 4 5'-most terminal nucleosides of the oligonucleotide.

4. The compound of claim 2, wherein the conjugate group is covalently attached to the 5'-terminal nucleoside of the oligonucleotide.

5. The compound of claim 2, wherein the conjugate group is covalently attached to the 8$^{th}$ nucleoside from the 5'-terminal end of the oligonucleotide.

6. The compound of claim 2, wherein the conjugate group is covalently attached to the 6$^{th}$ nucleoside from the 5'-terminal end of the oligonucleotide.

7. The compound of claim 2, wherein the conjugate group comprises $C_{20}$ alkyl.

8. The compound of claim 2, wherein the conjugate group comprises $C_{16}$ alkyl.

9. The compound of claim 2, wherein the conjugate group comprises $C_{10}$ alkyl.

10. The compound of claim 2, wherein the conjugate group comprises a steroid.

11. The compound of claim 2, wherein the conjugate group comprises cholesterol.

12. The compound of claim 2, wherein the conjugate group comprises a carbohydrate.

13. The compound of claim 2, wherein the conjugate group comprises N-acetylgalactosamine.

14. The compound of claim 2, wherein each nucleoside is a modified nucleoside.

15. The compound of claim 2, comprising at least one 2'-substituted nucleoside.

16. The compound of claim 2, wherein the compound is single-stranded.

17. The compound of claim 2, wherein each of the 6 to 9 3'-most terminal internucleoside linkages is a phosphorothioate linkage and each of the other internucleoside linkages is a phosphodiester linkage.

18. The compound of claim 2, wherein each of the 6 to 9 3'-most terminal internucleoside linkages is a phosphorothioate linkage and each of the other internucleoside linkages is a phosphodiester or a phosphorothioate linkage.

19. The compound of claim 2, wherein the conjugate group comprises $C_{10}$ to $C_{22}$ alkyl.

20. The compound of claim 2, wherein the conjugate group comprises $C_{10}$ to $C_{22}$ alkenyl.

21. The compound of claim 2, wherein the conjugate group comprises $C_{22}$ alkyl.

* * * * *

SEQUENCE LISTING

```
<160> NUMBER OF SEQ ID NOS: 26

<210> SEQ ID NO 1
<211> LENGTH: 3160
<212> TYPE: DNA
<213> ORGANISM: Homo sapiens
<220> FEATURE:
<221> NAME/KEY: CDS
<222> LOCATION: (1035)..(2246)

<400> SEQUENCE: 1 cctccctcg cccggcgcgg tcccgtccgc ctctcgctcg cctcccgcct ccctcggtc      60 ttccgaggcg cccgggctcc cggcgcggcg gcggaggggg cgggcaggcc ggcgggcggt    120
gatgtggcag gactctttat gcgctgcggc aggatacgcg ctcggcgctg ggacgcgact    180
gcgctcagtt ctctcctctc ggaagctgca gccatgatgg aagtttgaga gttgagccgc    240
tgtgaggcga ggccgggctc aggcgaggga gatgagagac ggcggcggcc gcggcccgga    300
gcccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcggcggcgg cggcacctcc cgctcctgga gcgggggga gaagcggcg      540 cggcggcggc cgcggcgggct gcagctccag ggaggggtc tgagtcgcct gtcaccattt    600
ccagggctgg gaacgccgga gagttggtct ctccccttct actgcctcca acacggcggc    660
ggcggcggcg gcacatccag ggacccgggc cggttttaaa cctcccgtcc gccgccgccg    720 cacccccgt ggcccgggct ccggaggccg ccggcggagg cagccgttcg gaggattatt      780
```

-continued

```
cgtcttctcc ccattccgct gccgccgctg ccaggcctct ggctgctgag gagaagcagg      840
cccagtcgct gcaaccatcc agcagccgcc gcagcagcca ttacccggct gcggtccaga      900
gccaagcggc ggcagagcga ggggcatcag ctaccgccaa gtccagagcc atttccatcc      960
tgcagaagaa gccccgccac cagcagcttc tgccatctct ctcctccttt ttcttcagcc     1020
```

```
acaggctccc agac atg aca gcc atc atc aaa gag atc gtt agc aga aac      1070
             Met Thr Ala Ile Ile Lys Glu Ile Val Ser Arg Asn
               1               5                   10 aaa agg aga tat caa gag gat gga ttc gac tta gac ttg acc tat att      1118
Lys Arg Arg Tyr Gln Glu Asp Gly Phe Asp Leu Asp Leu Thr Tyr Ile
        15                  20                  25 tat cca aac att att gct atg gga ttt cct gca gaa aga ctt gaa ggc      1166
Tyr Pro Asn Ile Ile Ala Met Gly Phe Pro Ala Glu Arg Leu Glu Gly
    30                  35                  40 gta tac agg aac aat att gat gat gta gta agg ttt ttg gat tca aag      1214
Val Tyr Arg Asn Asn Ile Asp Asp Val Val Arg Phe Leu Asp Ser Lys
45                  50                  55                  60 cat aaa aac cat tac aag ata tac aat ctt tgt gct gaa aga cat tat      1262
His Lys Asn His Tyr Lys Ile Tyr Asn Leu Cys Ala Glu Arg His Tyr
                65                  70                  75 gac acc gcc aaa ttt aat tgc aga gtt gca caa tat cct ttt gaa gac      1310
Asp Thr Ala Lys Phe Asn Cys Arg Val Ala Gln Tyr Pro Phe Glu Asp
            80                  85                  90 cat aac cca cca cag cta gaa ctt atc aaa ccc ttt tgt gaa gat ctt      1358
His Asn Pro Pro Gln Leu Glu Leu Ile Lys Pro Phe Cys Glu Asp Leu
        95                  100                 105 gac caa tgg cta agt gaa gat gac aat cat gtt gca gca att cac tgt      1406
Asp Gln Trp Leu Ser Glu Asp Asp Asn His Val Ala Ala Ile His Cys
    110                 115                 120 aaa gct gga aag gga cga act ggt gta atg ata tgt gca tat tta tta      1454
Lys Ala Gly Lys Gly Arg Thr Gly Val Met Ile Cys Ala Tyr Leu Leu
125                 130                 135                 140 cat cgg ggc aaa ttt tta aag gca caa gag gcc cta gat ttc tat ggg      1502
His Arg Gly Lys Phe Leu Lys Ala Gln Glu Ala Leu Asp Phe Tyr Gly
                145                 150                 155 gaa gta agg acc aga gac aaa aag gga gta act att ccc agt cag agg      1550
Glu Val Arg Thr Arg Asp Lys Lys Gly Val Thr Ile Pro Ser Gln Arg
            160                 165                 170 cgc tat gtg tat tat tat agc tac ctg tta aag aat cat ctg gat tat      1598
Arg Tyr Val Tyr Tyr Tyr Ser Tyr Leu Leu Lys Asn His Leu Asp Tyr
        175                 180                 185 aga cca gtg gca ctg ttg ttt cac aag atg atg ttt gaa act att cca      1646
Arg Pro Val Ala Leu Leu Phe His Lys Met Met Phe Glu Thr Ile Pro
    190                 195                 200 atg ttc agt ggc gga act tgc aat cct cag ttt gtg gtc tgc cag cta      1694
Met Phe Ser Gly Gly Thr Cys Asn Pro Gln Phe Val Val Cys Gln Leu
205                 210                 215                 220 aag gtg aag ata tat tcc tcc aat tca gga ccc aca cga cgg gaa gac      1742
Lys Val Lys Ile Tyr Ser Ser Asn Ser Gly Pro Thr Arg Arg Glu Asp
                225                 230                 235 aag ttc atg tac ttt gag ttc cct cag ccg tta cct gtg tgt ggt gat      1790
Lys Phe Met Tyr Phe Glu Phe Pro Gln Pro Leu Pro Val Cys Gly Asp
            240                 245                 250 atc aaa gta gag ttc ttc cac aaa cag aac aag atg cta aaa aag gac      1838
Ile Lys Val Glu Phe Phe His Lys Gln Asn Lys Met Leu Lys Lys Asp
        255                 260                 265 aaa atg ttt cac ttt tgg gta aat aca ttc ttc ata cca gga cca gag      1886
Lys Met Phe His Phe Trp Val Asn Thr Phe Phe Ile Pro Gly Pro Glu
    270                 275                 280
```

```
gaa acc tca gaa aaa gta gaa aat gga agt cta tgt gat caa gaa atc    1934
Glu Thr Ser Glu Lys Val Glu Asn Gly Ser Leu Cys Asp Gln Glu Ile
285                 290                 295                 300 gat agc att tgc agt ata gag cgt gca gat aat gac aag gaa tat cta    1982
Asp Ser Ile Cys Ser Ile Glu Arg Ala Asp Asn Asp Lys Glu Tyr Leu
                305                 310                 315 gta ctt act tta aca aaa aat gat ctt gac aaa gca aat aaa gac aaa    2030
Val Leu Thr Leu Thr Lys Asn Asp Leu Asp Lys Ala Asn Lys Asp Lys
        320                 325                 330 gcc aac cga tac ttt tct cca aat ttt aag gtg aag ctg tac ttc aca    2078
Ala Asn Arg Tyr Phe Ser Pro Asn Phe Lys Val Lys Leu Tyr Phe Thr
                335                 340                 345 aaa aca gta gag gag ccg tca aat cca gag gct agc agt tca act tct    2126
Lys Thr Val Glu Glu Pro Ser Asn Pro Glu Ala Ser Ser Ser Thr Ser
350                 355                 360 gta aca cca gat gtt agt gac aat gaa cct gat cat tat aga tat tct    2174
Val Thr Pro Asp Val Ser Asp Asn Glu Pro Asp His Tyr Arg Tyr Ser
365                 370                 375                 380 gac acc act gac tct gat cca gag aat gaa cct ttt gat gaa gat cag    2222
Asp Thr Thr Asp Ser Asp Pro Glu Asn Glu Pro Phe Asp Glu Asp Gln
                385                 390                 395 cat aca caa att aca aaa gtc tga attttttttt atcaagaggg ataaaacacc   2276
His Thr Gln Ile Thr Lys Val
                400 atgaaaataa acttgaataa actgaaaatg gacctttttt tttttaatgg caataggaca  2336 ttgtgtcaga ttaccagtta taggaacaat tctcttttcc tgaccaatct tgttttaccc  2396 tatacatcca cagggttttg acacttgttg tccagttgaa aaaaggttgt gtagctgtgt  2456 catgtatata cctttttgtg tcaaaaggac atttaaaatt caattaggat taataaagat  2516 ggcactttcc cgttttattc cagttttata aaaagtggag acagactgat gtgtatacgt  2576 aggaattttt tccttttgtg ttctgtcacc aactgaagtg gctaaagagc tttgtgatat  2636 actggttcac atcctacccc tttgcacttg tggcaacaga taagtttgca gttggctaag  2696 agaggtttcc gaaaggtttt gctaccattc taatgcatgt attcgggtta gggcaatgga  2756 ggggaatgct cagaaaggaa ataatttat gctggactct ggaccatata ccatctccag   2816 ctatttacac acacctttct ttagcatgct acagttatta atctggacat tcgaggaatt  2876 ggccgctgtc actgcttgtt gtttgcgcat ttttttttaa agcatattgg tgctagaaaa  2936 ggcagctaaa ggaagtgaat ctgtattggg gtacaggaat gaaccttctg caacatctta  2996 agatccacaa atgaagggat ataaaaataa tgtcataggt aagaaacaca gcaacaatga  3056 cttaaccata taaatgtgga ggctatcaac aaagaatggg cttgaaacat tataaaaatt  3116 gacaatgatt tattaaatat gttttctcaa ttgtaaaaaa aaaa                   3160

<210> SEQ ID NO 2
<211> LENGTH: 26
<212> TYPE: DNA
<213> ORGANISM: Artificial sequence
<220> FEATURE:
<223> OTHER INFORMATION: Primer

<400> SEQUENCE: 2
aatggctaag tgaagatgac aatcat                                          26

<210> SEQ ID NO 3
<211> LENGTH: 25
<212> TYPE: DNA
```

```
<213> ORGANISM: Artificial sequence
<220> FEATURE:
<223> OTHER INFORMATION: Primer

<400> SEQUENCE: 3
tgcacatatc attacaccag ttcgt                                              25

<210> SEQ ID NO 4
<211> LENGTH: 30
<212> TYPE: DNA
<213> ORGANISM: Artificial sequence
<220> FEATURE:
<223> OTHER INFORMATION: Probe

<400> SEQUENCE: 4
ttgcagcaat tcactgtaaa gctggaaagg                                         30

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 5
tugucucugg uccuuacuua a                                                  21

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)

<400> SEQUENCE: 6
tuaucuauaa ugaucaggua a                                                  21

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(21)

<400> SEQUENCE: 7
tgaacauugg aauaguuuca a                                                  21

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ctgctagcct ctggatttga                                                    20
```

```
<210> SEQ ID NO 9
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(18)
<220> FEATURE:
<221> NAME/KEY: misc_feature
<222> LOCATION: (20)..(22)

<400> SEQUENCE: 9
tugucucugg uccuuacutc aa                                                22

<210> SEQ ID NO 10
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(14)
<220> FEATURE:
<221> NAME/KEY: misc_feature
<222> LOCATION: (16)..(22)

<400> SEQUENCE: 10
tugucucugg uccutcacuu aa                                                22

<210> SEQ ID NO 11
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(10)
<220> FEATURE:
<221> NAME/KEY: misc_feature
<222> LOCATION: (12)..(22)

<400> SEQUENCE: 11
tugucucugg tcccuuacuu aa                                                22

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(5)
<220> FEATURE:
<221> NAME/KEY: misc_feature
<222> LOCATION: (7)..(22)

<400> SEQUENCE: 12
tuguctccug guccuuacuu aa                                                22

<210> SEQ ID NO 13
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: misc_feature
<222> LOCATION: (2)..(20)
<220> FEATURE:
<221> NAME/KEY: misc_feature
<222> LOCATION: (22)..(22)

<400> SEQUENCE: 13
tugucucugg uccuuacuua tc                                              22

<210> SEQ ID NO 14
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(22)

<400> SEQUENCE: 14
tcuaucuaua augaucaggu aa                                              22

<210> SEQ ID NO 15
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(20)
<220> FEATURE:
<221> NAME/KEY: misc_feature
<222> LOCATION: (22)..(22)

<400> SEQUENCE: 15
tuaucuauaa ugaucaggua tc                                              22

<210> SEQ ID NO 16
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(18)
<220> FEATURE:
<221> NAME/KEY: misc_feature
<222> LOCATION: (20)..(22)

<400> SEQUENCE: 16
tuaucuauaa ugaucaggtc aa                                              22

<210> SEQ ID NO 17
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(10)
<220> FEATURE:
<221> NAME/KEY: misc_feature
<222> LOCATION: (12)..(22)

<400> SEQUENCE: 17
tuaucuauaa tcgaucaggu aa                                              22
```

```
<210> SEQ ID NO 18
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(7)
<220> FEATURE:
<221> NAME/KEY: misc_feature
<222> LOCATION: (9)..(22)

<400> SEQUENCE: 18
tuaucuatca augaucaggu aa                                                    22

<210> SEQ ID NO 19
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(5)
<220> FEATURE:
<221> NAME/KEY: misc_feature
<222> LOCATION: (7)..(22)

<400> SEQUENCE: 19
tuauctcaua augaucaggu aa                                                    22

<210> SEQ ID NO 20
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(3)
<220> FEATURE:
<221> NAME/KEY: misc_feature
<222> LOCATION: (5)..(22)

<400> SEQUENCE: 20
tuatccuaua augaucaggu aa                                                    22

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
gctgattaga gagaggtccc                                                       20

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(7)
<220> FEATURE:
<221> NAME/KEY: misc_feature
<222> LOCATION: (9)..(21)
```

<400> SEQUENCE: 22
tuaucuataa ugaucaggua a                                          21

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(5)
<220> FEATURE:
<221> NAME/KEY: misc_feature
<222> LOCATION: (7)..(21)

<400> SEQUENCE: 23
tuauctauaa ugaucaggua a                                          21

<210> SEQ ID NO 24
<211> LENGTH: 27
<212> TYPE: DNA
<213> ORGANISM: Artificial sequence
<220> FEATURE:
<223> OTHER INFORMATION: Primer

<400> SEQUENCE: 24
gcgtttgctc ttcttcttgc gtttttt                                    27

<210> SEQ ID NO 25
<211> LENGTH: 21
<212> TYPE: DNA
<213> ORGANISM: Artificial sequence
<220> FEATURE:
<223> OTHER INFORMATION: Primer

<400> SEQUENCE: 25
ttgtctctgg tccttacttt t                                          21

<210> SEQ ID NO 26
<211> LENGTH: 21
<212> TYPE: DNA
<213> ORGANISM: Artificial sequence
<220> FEATURE:
<223> OTHER INFORMATION: Probe

<400> SEQUENCE: 26
ttgtctctgg tccttactta a                                          21